US012709624B2

(12) United States Patent
Dong et al.

(10) Patent No.: US 12,709,624 B2
(45) Date of Patent: Aug. 18, 2026

(54) MODULAR SYNTHESIS OF 1,2-AZABORINES VIA RING-OPENING BN-ISOSTERE BENZANNULATION

(71) Applicant: The University of Chicago, Chicago, IL (US)

(72) Inventors: Guangbin Dong, Chicago, IL (US); Hairong Lyu, Chicago, IL (US); Zhijie Chen, Chicago, IL (US); Yifei Wu, Chicago, IL (US); Shinyoung Choi, Chicago, IL (US)

(73) Assignee: The University of Chicago, Chicago, IL (US)

( * ) Notice: Subject to any disclaimer, the term of this patent is extended or adjusted under 35 U.S.C. 154(b) by 367 days.

(21) Appl. No.: 18/473,518

(22) Filed: Sep. 25, 2023

(65) Prior Publication Data

US 2024/0174698 A1 May 30, 2024

Related U.S. Application Data

(60) Provisional application No. 63/376,889, filed on Sep. 23, 2022.

(51) Int. Cl.
*C07F 5/02* (2006.01)
*C07F 7/08* (2006.01)
*C07J 43/00* (2006.01)

(52) U.S. Cl.
CPC ............ *C07F 5/027* (2013.01); *C07F 7/0812* (2013.01); *C07F 7/0832* (2013.01); *C07J 43/003* (2013.01)

(58) Field of Classification Search
CPC ...... C07F 5/027; C07F 7/0812; C07F 7/0832; C07J 43/003
USPC .......................................................... 546/13
See application file for complete search history.

(56) References Cited

U.S. PATENT DOCUMENTS

2011/0021735 A1* 1/2011 Liu .......................... C07F 5/02 546/10
2011/0021818 A1* 1/2011 Liu .......................... C01B 3/22 564/10
2017/0081347 A1* 3/2017 Liu ...................... C07D 213/71

OTHER PUBLICATIONS

Giustra et al (The State of the Art in Azaborine Chemistry: New Synthetic Methods and Applications, Journal of the American Chemical Society, 2018, 140, 1184-1194) (Year: 2018).*
Subbaiah, M. A. M. et al. "Bioisosteres of the Phenyl Ring: Recent Strategic Applications in Lead Optimization and Drug Design" J. Med. Chem., vol. 64 (Sep. 30, 2021), pp. 14046-14128.
Campbell, P. G. et al. "Recent Advances in Azaborine Chemistry" Angew. Chem. Int. Ed., vol. 51 (May 29, 2012), pp. 6074-6092.
Giustra, Z. X. et al. "The State of the Art in Azaborine Chemistry: New Synthetic Methods and Applications" J. Am. Chem. Soc., vol. 140 (Jan. 9, 2018), pp. 1184-1194.
Bhattacharjee, A. et al. "Selectivity in the Elaboration of Bicyclic Borazarenes" Adv. Synth. Catal., vol. 363 (Jan. 7, 2021), pp. 2256-2273.
Abengózar, A. et al. "Recent developments in the chemistry of BN-aromatic hydrocarbons" Advances in Heterocyclic Chemistry, vol. 135 (Mar. 2, 2021), pp. 197-259.
Liu, Z. et al. "B—N versus C—C: How Similar Are They?" Angew. Chem. Int. Ed., vol. 47 (Dec. 19, 2007), pp. 242-244.

(Continued)

*Primary Examiner* — James H Alstrum-Acevedo
*Assistant Examiner* — Sahar Inam
(74) *Attorney, Agent, or Firm* — McDonnell Boehnen Hulbert & Berghoff LLP

(57) ABSTRACT

The present disclosure relates generally to 1,2-azaborines and methods of making the same.

17 Claims, 10 Drawing Sheets

(56) References Cited

OTHER PUBLICATIONS

Zhao, P. et al. "Medicinal Chemistry Profiling of Monocyclic 1,2-Azaborines" ChemMedChem, vol. 12 (Feb. 8, 2017), pp. 358-361.
Baldock, C. et al. "A Mechanism of Drug Action Revealed by Structural Studies of Enoyl Reductase" Science, vol. 274 (Dec. 20, 1996), pp. 2107-2110.
Davis, M. C. et al. "Synthesis and Evaluation of Benzodiazaborine Compounds Against M. Tuberculosis H37RV in vitro" Bioorganic & Medicinal Chemistry Letters, vol. 8 (May 18, 1998), pp. 843-846.
Grassberger, M. A. et al. "Preparation and Antibacterial Activities of New 1,2,3-Diazaborine Derivatives and Analogues" Journal of Medicinal Chemistry, vol. 27 (Aug. 1, 1984), pp. 947-953.
Baker, S. J. et al. "Therapeutic Potential of Boron-Containing Compounds" Future Med. Chem., vol. 1 (Oct. 21, 2009), pp. 1275-1288.
Vlasceanu, A. et al. "BN/CC isosterism in borazaronaphthalenes towards phosphodiesterase 10A (PDE10A) inhibitors" Bioorg. Med. Chem., vol. 23 (Aug. 1, 2015), pp. 4453-4461.
Liu, L. et al. "Boron Mimetics: 1,2-Dihydro-1,2-azaborines Bind inside a Nonpolar Cavity of T4 Lysozyme" Angew. Chem. Int. Ed., vol. 48 (Aug. 26, 2009), pp. 6817-6819.
Rombouts, F. J. R. et al. "Benzazaborinines as Novel Bioisosteric Replacements of Naphthalene: Propranolol as an Example" J. Med. Chem., vol. 58 (Nov. 13, 2015), pp. 9287-9295.
Lamm, A. N. et al. "How stable are 1,2-dihydro-1,2-azaborines toward water and oxygen?" Mol. BioSyst., vol. 5 (Aug. 10, 2009), pp. 1303-1305.
Abbey, E. R. et al. "Protecting Group-Free Synthesis of 1,2-Azaborines: A Simple Approach to the Construction of BN-Benzenoids" J. Am. Chem. Soc., vol. 135 (Aug. 6, 2013), pp. 12908-12913.
Dewar, M. J. S. et al. "A Derivative of Borazarene" J. Am. Chem. Soc., vol. 84 (Oct. 1, 1962), p. 3782.
White, D. G. "2-Phenyl-2, 1-borazarene and Derivatives of 1,2-Azaboracycloalkanes" J. Am. Chem. Soc., vol. 85 (Nov. 1, 1963), pp. 3634-3636.
Ashe, A. J. et al. "A Synthesis of Aromatic Five- and Six-Membered B—N Heterocycles via Ring Closing Metathesis" Org. Lett., vol. 2 (Jun. 17, 2000), pp. 2089-2091.
Baggett, A. W. et al. "Late-Stage Functionalization of 1,2-Dihydro-1,2-azaborines via Regioselective Iridium-Catalyzed C—H Borylation: The Development of a New N, N-Bidentate Ligand Scaffold" J. Am. Chem. Soc., vol. 137 (Apr. 14, 2015), pp. 5536-5541.
Braunschweig, H. et al. "Antiaromaticity to Aromaticity: From Boroles to 1,2-Azaborinines by Ring Expansion with Azides" Chem. Eur. J., vol. 20 (Jun. 25, 2014), pp. 9858-9861.
Schäfer M. et al. "Regioselective Catalytic and Stepwise Routes to Bulky, Functional-Group-Appended, and Luminescent 1,2-Azaborinines" Chem. Eur. J., vol. 22 (May 16, 2016), pp. 8603-8609.
Heß, M. et al. "Rhodium-Mediated Stoichiometric Synthesis of Mono-, Bi-, and Bis-1,2-Azaborinines: 1-Rhoda-3,2-azaboroles as Reactive Precursors" Chem. Eur. J., vol. 27 (Jul. 2, 2021), pp. 9503-9507.
Lyu, H. et al. "Boron insertion into alkyl ether bonds via zinc/nickel tandem catalysis" Science, vol. 372 (Apr. 9, 2021), pp. 175-182.
Fumagalli, G. et al. "Recent Methodologies That Exploit C—C Single-Bond Cleavage of Strained Ring Systems by Transition Metal Complexes" Chem. Rev., vol. 117 (Jan. 11, 2017), pp. 9404-9432.
Mcconnell, C. R. et al. "Late-stage functionalization of BN-heterocycles" Chem. Soc. Rev., vol. 48 (Mar. 28, 2019), pp. 3436-3453.
Pan, J. et al. "Electrophilic Aromatic Substitution Reactions of 1,2-Dihydro-1,2-azaborines" Org. Lett., vol. 9 (Jan. 24, 2007), pp. 679-681.
Abengózar, A. et al. "Synthesis, Optical Properties, and Regioselective Functionalization of 4a-Aza-10a-boraphenanthrene" Org. Lett., vol. 19 (Jun. 13, 2017), pp. 3458-3461.
Compton, J. S. et al. "3-Boryl-2,1-borazaronaphthalene: Umpolung Reagents for Diversifying Naphthalene Isosteres" J. Org. Chem., vol. 83 (Jul. 10, 2018), pp. 9484-9491.
Guzik, K. et al. "Development of the Inhibitors That Target the PD-1/PD-L1 Interaction—A Brief Look at Progress on Small Molecules, Peptides and Macrocycles" Molecules, vol. 24 (May 30, 2019), p. 2071.
Ying, J. et al. "Convenient Palladium-Catalyzed Reductive Carbonylation of Aryl Bromides Under Gas-Free Conditions" Eur. J. Org. Chem., vol. 2018 (Mar. 30, 2018), pp. 2780-2783.
Hougard, J.-M. et al. "Bifenthrin: A Useful Pyrethroid Insecticide for Treatment of Mosquito Nets" Journal of Medical Entomology, vol. 39 (May 1, 2002), pp. 526-533.
Liu, Y. et al. "The Versatile Reaction Chemistry of an Alpha-Boryl Diazo Compound" J. Am. Chem. Soc., vol. 143 (Aug. 24, 2021), pp. 14059-14064.
Baggett, A. W. et al. "A Boron Protecting Group Strategy for 1,2-Azaborines" J. Am. Chem. Soc., vol. 139 (Oct. 2, 2017), pp. 15259-15264.
Stevens, R. V. "General Methods of Alkaloid Synthesis" Acc. Chem. Res., vol. 10 (Jun. 1, 1977), pp. 193-198.
Dewar, M. J. S. et al. "New heteroaromatic compounds. Part III. 2,1-Borazaro-naphthalene (1,2-dihydro-1-aza-2-boranaphthalene)" J. Chem. Soc., 1959, pp. 2728-2730.
Davies, G. H. M. et al. "Method for Accessing Nitrogen-Containing, B-Heteroaryl-Substituted 2,1-Borazaronaphthalenes" J. Org. Chem., vol. 82 (Dec. 14, 2016), pp. 549-555.
Liu, X. et al. "Synthesis of 1,2-Borazaronaphthalenes from Imines by Base-Promoted Borylation of C—H bond" J. Org. Chem., vol. 80 (Feb. 24, 2015), pp. 3737-3744.
Beaudry, C. M. et al. "Biosynthetic and Biomimetic Electrocyclizations" Chemical Reviews, vol. 105 (Nov. 23, 2005), pp. 4757-4778.
Qin, P. et al. "Transition-Metal Catalysis of Triene 6-pi Electrocyclization: The pi-Complexation Strategy Realized" Angew. Chem. Int. Ed., vol. 59 (Jun. 8, 2020), pp. 17958-17965.
Yu, T.-Q. et al. "How to Promote Sluggish Electrocyclization of 1,3,5-Hexatrienes by Captodative Substitution" J. Org. Chem., vol. 71 (Jun. 20, 2006), pp. 6157-6164.
Epiotis, N. D. et al. "The Theory of Pericyclic Reactions" Angew. Chem. Int. Ed., vol. 13 (Dec. 1974), pp. 751-780.
Woodward, R. B. et al. "Stereochemistry of Electrocyclic Reactions" J. Am. Chem. Soc., vol. 87 (Jan. 1, 1965), pp. 395-397.
Kukier, G. A. et al. "Violations. How Nature Circumvents the Woodward-Hoffmann Rules and Promotes the Forbidden Conrotatory 4n + 2 Electron Electrocyclization of Prinzbach's Vinylogous Sesquifulvalene" J. Am. Chem. Soc., vol. 143 (Dec. 16, 2021), pp. 21694-21704.

* cited by examiner

1n, 1.0 g

3n' 1.06 g, 80%, easier
B–N torsion

TS1

θ (C1-N-B-Br) = 13.5° s-*cis* 9

θ (C1-N-B-Br) = 52.2°

$\Delta E_{torsion}$ = 8.8 kcal/mol $d$(Br···H) = 2.45 Å

*reduced steric repulsions*

$\Delta G^‡$ = 20.8 kcal/mol

TS3 s-*cis* 11

TS1
6π-disrotatory

TS2
6π-conrotatory

HOMO coefficients of
s-*cis* 9

HOMO coefficients of
TS1 s-trans-11 s-cis-11

IM2

12

ΔG‡ = 20.8 kcal/mol
TS1

ΔG‡ = 21.1 kcal/mol
TS2

ΔG‡ = 34.9 kcal/mol
TS3 s-*cis*-9 s-*cis*-11

MODULAR SYNTHESIS OF 1,2-AZABORINES VIA RING-OPENING BN-ISOSTERE BENZANNULATION

CROSS-REFERENCE TO RELATED APPLICATIONS

This application claims the benefit of priority of U.S. Provisional Patent Application No. 63/376,889, filed Sep. 23, 2022, which is hereby incorporated herein by reference in its entirety.

STATEMENT REGARDING FEDERALLY SPONSORED RESEARCH OR DEVELOPMENT

This invention was made with government support under GM144048 awarded by the National Institutes of Health. The government has certain rights in the invention.

BACKGROUND OF THE DISCLOSURE

1. Field of Invention

The present disclosure relates generally to 1,2-azaborines and methods of making the same.

2. Technical Background

Due to the prevalence of arenes in small-molecule drugs, incorporating arene isosteres or bioisosteres has become an emerging strategy in medicinal chemistry for identifying candidates of enhanced performance without substantially altering structures of lead compounds. 1,2-Azaborines, a class of boron-nitrogen heterocycles with substantial aromaticity, and showed in the schematic below, are viewed as unique BN-isosteres of benzene.

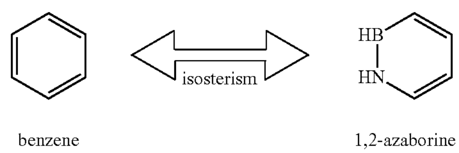

benzene 1,2-azaborine

They are generally more polar than benzene, leading to more localized electron distributions and better aqueous solubility. Compared to the original carbonaceous compounds, improved biological activity and bioavailability have been observed with their 1,2-azaborine analogues. For example, as shown in a 2017 report by Liu (Zhao, P., Nettleton, D. O., Karki, R. G., Zécri, F. J. & Liu, S.-Y. Medicinal chemistry profiling of monocyclic 1,2-azaborines. *ChemMedChem* 12, 358-361 (2017)), the replacement of a phenyl group with a simple 1,2-azaborine moiety in a CDK2 inhibitor led to 2-4-fold increase of efficacy. Similarly, Janssen Pharmaceuticals (Rombouts, F. J., Tovar, F., Austin, N., Tresa ern, G. & Trabanco, A. A. Benzazaborinines as Novel Bioisosteric Replacements of Naphthalene: Propranolol as an Example. *J. Med. Chem.* 58, 9287-9295 (2015)) disclosed systematic in vitro and in vivo profiling of 1,2-azaborine analogues of several drug candidates, in which comparable or even better biological activity and ADMET (absorption, distribution, metabolism, excretion and toxicity) properties have been observed. These studies further suggest that 1,2-azaborines are stable under physiological, mildly basic, or oxidative conditions, serving as viable pharmacophores.

Despite the great promise of using 1,2-azaborines as arene bioisosteres in drug discovery, only a limited number of bioactive BN-analogues have been reported to date, because it is still not a trivial task to access multi-substituted 1,2-azaborines. In particular, unlike those in a fused polyaromatic system, preparation of monocyclic 1,2-azaborines remains a substantial challenge. The state-of-art synthesis employed allyl Molander salt and allyl amine as substrates to access B-alkoxy-1,2-azaborines in 25% yield over four steps, featured by a ring-closing metathesis with Schrock's catalyst and a Pd-catalyzed dehydrogenative aromatization. This reaction scheme is shown below:

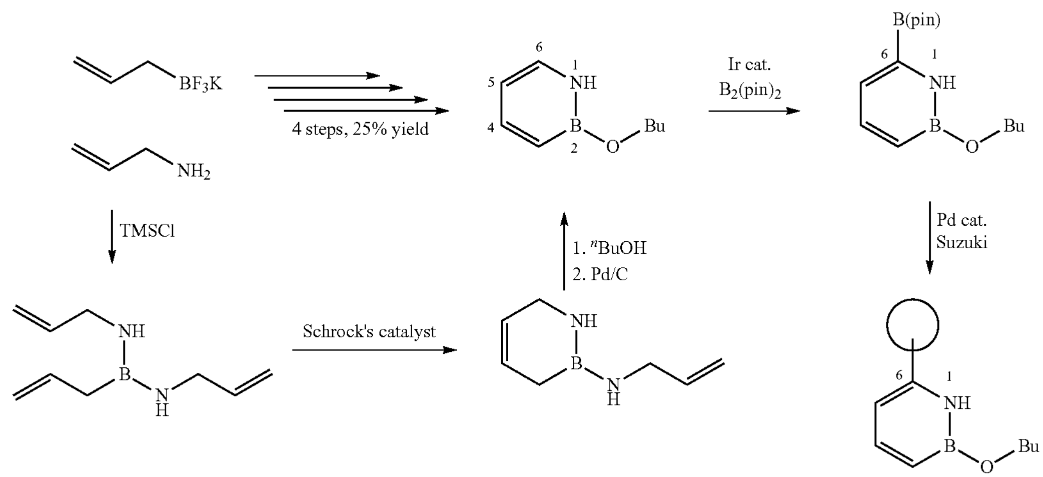

While this represents a remarkable improvement from the prior approaches, extension of this strategy to directly prepare C-substituted 1,2-azaborines has been elusive. For instance, synthesis of C6-substituted 1,2-azaborines required an overall six-step sequence. Alternatively, Braunschweig et al. (Braunschweig, H., Hörl, C., Mailänder, L., Radacki, K. & Wahler, J. Antiaromaticity to aromaticity: from boroles to 1, 2-azaborinines by ring expansion with azides. Chem.—Eur. J. 20, 9858-9861 (2014)).disclosed a distinct approach to access poly-substituted 1,2-azaborines through either insertion of a nitrene into boroles (generated from a divinyl lithium intermediate), as shown below, or via a Rh-catalyzed/mediated cyclization between iminoboranes and alkynes.

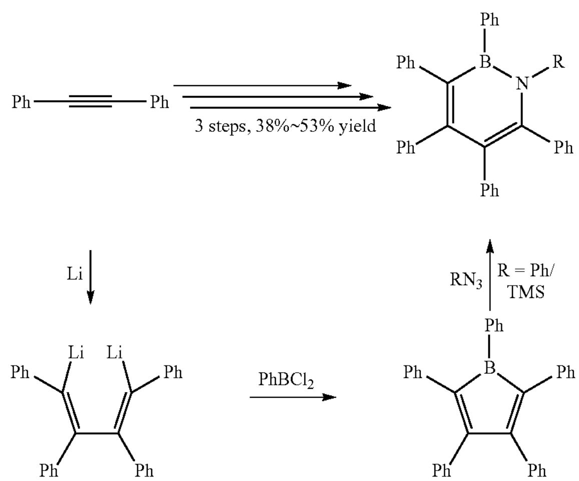

These reactions show limited scopes with moderate yield. To harness the full potential of the BN/CC isomerism for medicinal chemistry research, it is necessary to conceive of a more direct BN-benzannulation strategy to access monocyclic 1,2-azaborines. Ideally, this strategy can 1) use easily accessible substrates, 2) operate under mild conditions, 3) tolerate a broad range of functional groups, 4) give good overall yield, 5) avoid expensive noble metals, 6) be easily scalable, and 7) be modular to access multi-substituted 1,2-azaborines with diverse structures in a straightforward manner. Accordingly, there is a need in the art for improved 1,2-azaborine synthesis methods.

SUMMARY OF THE DISCLOSURE

In one aspect, the present disclosure provides a compound having the structure

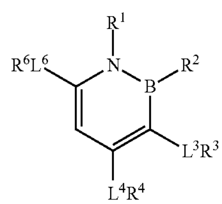

or a pharmaceutically-acceptable salt thereof, or a solvate thereof, wherein $R^1$ is a carbon-linked substituent having no more than 40 non-H atoms;

$R^2$ is a carbon-linked substituent having no more than 40 non-H atoms;

$R^3$ is H or a substituent having no more than 40 non-H atoms, and $L^3$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{1-2}NR^7$— and —$NR^7S(O)_{1-2}$—, or -$L^3$-$R^3$ is halo (e.g., chloro, fluoro or bromo), nitro, or cyano;

$R^4$ is H or a substituent having no more than 40 non-H atoms, and $L^4$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{1-2}NR^7$— and —$NR^7S(O)_{1-2}$—, or -$L^4$-$R^4$ is halo (e.g., chloro, fluoro or bromo), nitro, or cyano;

$R^6$ is H or a substituent having no more than 40 non-H atoms, and $L^6$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{1-2}NR^7$— and —$NR^7S(O)_{1-2}$—, or -$L^6$-$R^6$ is halo (e.g., chloro, fluoro or bromo), nitro, or cyano;

wherein each $R^6$ is independently selected from the group consisting of hydrogen, $C_1$-$C_3$ alkyl and —C(O)($C_1$-$C_3$ alkyl).

Another aspect of the present disclosure provides a method for making a 1,2-disubstituted azaborine. The method includes combining a Lewis acid, an N-substituted 1-cyclopropyl imine, and a B-substituted dihaloborane and allowing them to react to form an B-substituted, N-substituted, 1-halo-N-(6-halohex-3-enyl)boranamine; then treating the B-substituted, N-substituted, 1-halo-N-(6-halohex-3-enyl)boranamine with a base to provide the 1,2-disubstituted azaborine.

Another aspect of the present disclosure provide compounds as described herein prepared by the methods as described herein.

BRIEF DESCRIPTION OF FIGURES

The accompanying drawings are included to provide a further understanding of the methods and compositions of the disclosure, and are incorporated in and constitute a part of this specification. The drawings illustrate one or more embodiment(s) of the disclosure, and together with the description serve to explain the principles and operation of the disclosure.

Figure 1:
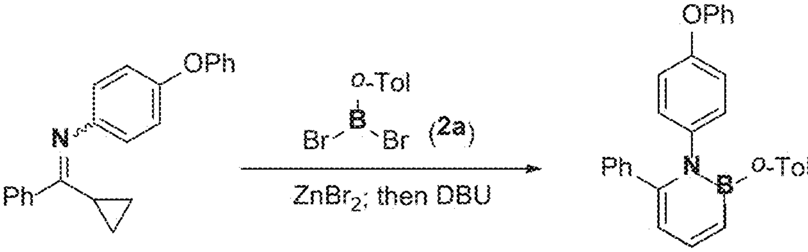
FIG. 1 is a schematic of the synthesis as described herein.
Figure 1:
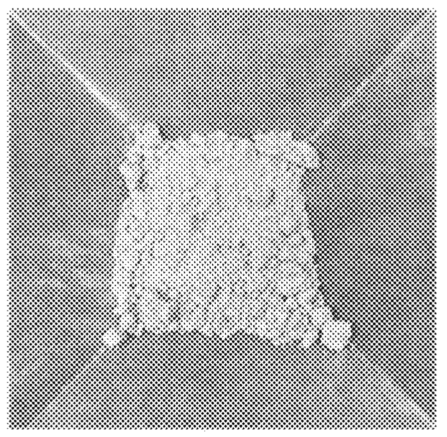

DETAILED DESCRIPTION 1,2-Azaborines represent a unique class of benzene isosteres that holds great potential for various applications. However, it remains a long-standing challenge to prepare monocyclic 1,2-azaborines in an efficient and modular manner. The present disclosure provides a straightforward method to directly access diverse multi-substituted 1,2-azaborines from readily available cyclopropyl imines/ketones and dibromoboranes under relatively mild conditions. The scheme below shows a general 1,2-azaborine synthesis method described herein.

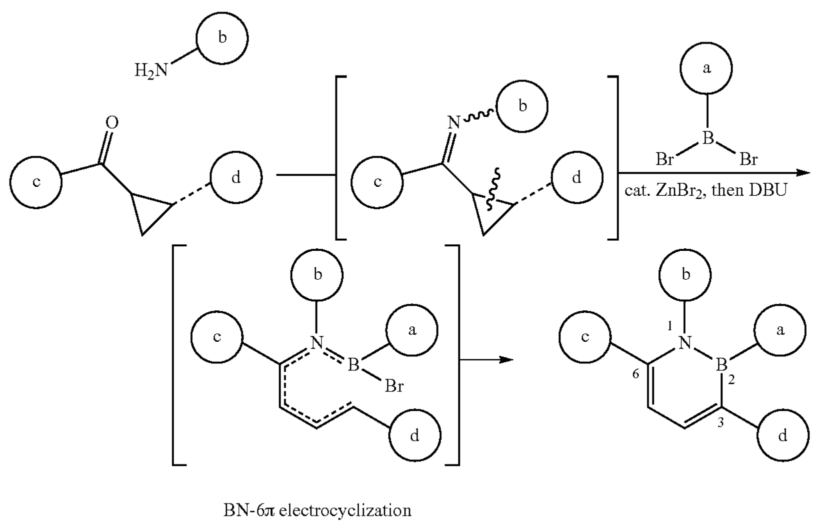

The reaction is scalable and versatile in that it has a broad substrate scope, and tolerates a range of functional groups. It can be modular, and can be run in one pot or in two separate steps. This method can also be used to provide various 1,2-azaborine compounds, as described herein.

Thus, one aspect of the disclosure provides a compound having the structure

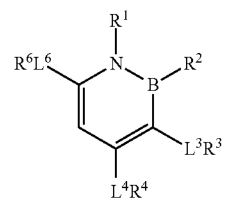

or a pharmaceutically-acceptable salt thereof, or a solvate thereof, wherein $R^1$ is a carbon-linked substituent having no more than 40 non-H atoms;

$R^2$ is a carbon-linked substituent having no more than 40 non-H atoms;

$R^3$ is H or a substituent having no more than 40 non-H atoms, a d $L^3$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —$OS(O)_{1-2}$—, —$S(O)_{1-2}NR^7$— and —$NR^7S(O)_{1-2}$—, or -$L^3$-$R^3$ is halo (e.g., chloro, fluoro or bromo), nitro, or cyano;

$R^4$ is H or a substituent having no more than 40 non-H atoms, and $L^4$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —$OS(O)_{1-2}$—, —$(O)_{1-2}NR^7$— and —$NR^7S(O)_{1-2}$—, or -$L^4$-$R^4$ is halo (e.g., chloro, fluoro or bromo), nitro, or cyano;

$R^6$ is H or a substituent having no more than 40 non-H atoms, and $L^6$ is selected from the group consisting of a bond, —C(O)—, —S—, —$O(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)

S—, —SC(O)—, —C(S)O—, —OC(S)—, —C(S)S—, —SC(S)—, —$S(O)_{1-2}O$—, —$OS(O)_{1-2}$—, —$S(O)_{1-2}NR^7$— and —$NR^7S(O)_{1-2}$—, or -$L^6$-$R^6$ is halo (e.g., chloro, fluoro or bromo), nitro, or cyano;

wherein each $R^6$ is independently selected from the group consisting of hydrogen, $C_1$-$C_3$ alkyl and —C(O)($C_1$-$C_3$ alkyl).

As described above, $R^1$ is a carbon-linked substituent having no more than 40 non-H atoms. For example, in some embodiments, $R^1$ is a carbon-linked substituent having no more than 30, no more than 20, or no more than 10 non-H atoms. The carbon-linked substituent may be selected from a variety of carbon-containing substituents. In some embodiments as described herein, $R^1$ is an optionally-substituted alkyl, optionally-substituted alkenyl, or optionally-substituted alkynyl. For example, in various embodiments, $R^1$ is an optionally-substituted $C_1$-$C_{24}$ alkyl (e.g., $C_1$-$C_{18}$ alkyl, $C_1$-$C_{12}$ alkyl, or $C_1$-$C_6$ alkyl), n optionally-substituted $C_2$-$C_{24}$ alkenyl (e.g., $C_2$-$C_{18}$ alkenyl, $C_2$-$C_{12}$ alkenyl, or $C_2$-$C_6$ alkenyl), or an optionally-substituted $C_1$-$C_{24}$ alkynyl (e.g., $C_1$-$C_{18}$ alkynyl, $C_1$-$C_{12}$ alkynyl, or $C_1$-$C_6$ alkynyl). In some embodiments as described herein, $R^1$ is an optionally-substituted aryl, optionally-substituted heteroaryl, optionally-substituted cycloalkyl, or optionally-substituted heterocycloalkyl. For example, in various embodiments, $R^1$ is an optionally-substituted $C_6$-$C_{24}$ aryl (e.g., $C_6$-$C_{18}$ aryl or $C_6$-$C_{12}$ aryl) or an optionally-substituted $C_5$-$C_{24}$ heteroaryl (e.g., $C_5$-$C_{18}$ heteroaryl or $C_5$-$C_{12}$ heteroaryl). In some embodiments, $R^1$ is an optionally-substituted $C_3$-$C_{24}$ cycloalkyl (e.g., $C_3$-$C_{18}$ cycloalkyl, $C_3$-$C_{12}$ cycloalkyl, or $C_3$-$C_6$ cycloalkyl) or an optionally-substituted $C_3$-$C_{24}$ heterocycloalkyl (e.g., $C_3$-$C_{18}$ heterocycloalkyl, $C_3$-$C_{12}$ heterocycloalkyl, or $C_3$-$C_6$ heterocycloalkyl).

As described above, $R^2$ is a carbon-linked substituent having no more than 40 non-H atoms. For example, in some embodiments, $R^2$ is a carbon-linked substituent having no more than 30, no more than 20, or no more than 10 non-H atoms. The carbon-linked substituent may be selected from a variety of carbon-containing substituents. In some embodiments as described herein, $R^2$ is an optionally-substituted alkyl, optionally-substituted alkenyl, or optionally-substituted alkynyl. For example, in various embodiments, $R^2$ is an optionally-substituted $C_1$-$C_{24}$ alkyl (e.g., $C_1$-$C_{18}$ alkyl, $C_1$-$C_{12}$ alkyl, or $C_1$-$C_6$ alkyl), an optionally-substituted $C_2$-$C_{24}$ alkenyl (e.g., $C_2$-$C_{18}$ alkenyl, $C_2$-$C_{12}$ alkenyl, or $C_2$-$C_6$ alkenyl), or an optionally-substituted $C_1$-$C_{24}$ alkynyl (e.g., $C_1$-$C_{18}$ alkynyl, $C_1$-$C_{12}$ alkynyl, or $C_1$-$C_6$ alkynyl). In some embodiments as described herein, $R^2$ is an optionally-substituted aryl, optionally-substituted heteroaryl, optionally-substituted cycloalkyl, or optionally-substituted heterocycloalkyl. For example, in various embodiments, $R^2$ is an optionally-substituted $C_6$-$C_{24}$ aryl (e.g., $C_6$-$C_{18}$ aryl or $C_6$-$C_{12}$ aryl) or an optionally-substituted $C_5$-$C_{24}$ heteroaryl (e.g., $C_5$-$C_{18}$ heteroaryl or $C_5$-$C_{12}$ heteroaryl). In some embodiments, $R^2$ is optionally-substituted $C_3$-$C_{24}$ cycloalkyl (e.g., $C_3$-$C_{18}$ cycloalkyl, $C_3$-$C_{12}$ cycloalkyl, or $C_3$-$C_6$ cycloalkyl) or an optionally-substituted $C_3$-$C_{24}$ heterocycloalkyl (e.g., $C_3$-$C_{18}$ heterocycloalkyl, $C_3$-$C_{12}$ heterocycloalkyl, or $C_3$-$C_6$ heterocycloalkyl).

In some embodiments as described herein, $R^1$ and $R^2$ are different carbon-linked substituent.

As described above, $R^3$ is H or a substituent having no more than 40 no-H atoms. In some embodiments as described herein, $R^3$ is H. In other embodiment-, $R^3$ is a carbon-linked substituent having no more than 30, no more than 20, or no more than 10 non-H atoms. The carbon-linked substituent may be selected from a variety of carbon-containing substituents. In other embodiments, $R^3$ is an optionally-substituted alkyl, optionally-substituted alkenyl, or optionally-substituted alkynyl. For example, in various embodiments, $R^3$ is an optionally-substituted $C_1$-$C_{24}$ alkyl (e.g., $C_1$-$C_{18}$ alkyl, $C_1$-$C_{12}$ alkyl, or $C_1$-$C_6$ alkyl), an optionally-substituted $C_2$-$C_{24}$ alkenyl (e.g., $C_2$-$C_{18}$ alkenyl, $C_2$-$C_{12}$ alkenyl, or $C_2$-$C_6$ alkenyl), or an optionally-substituted $C_1$-$C_{24}$ alkynyl (e.g., $C_1$-$C_{18}$ alkynyl, $C_1$-$C_{12}$ alkynyl, or $C_1$-$C_6$ alkynyl). In some embodiments as described herein, $R^3$ is an optionally-substituted aryl, optionally-substituted heteroaryl, optionally substituted cycloalkyl, or optionally-substituted heterocycloalkyl. For example, in various embodiments, $R^3$ is an optionally-substituted $C_6$-$C_{24}$ aryl (e.g., $C_6$-$C_{18}$ aryl or $C_6$-$C_{12}$ aryl) or an optionally-substituted $C_5$-$C_{24}$ heteroaryl (e.g., $C_5$-$C_{18}$ heteroaryl or $C_5$-$C_{12}$ heteroaryl). In some embodiments as described herein, $R^3$ is optionally-substituted $C_3$-$C_{24}$ cycloalkyl (e.g., $C_3$-$C_{18}$ cycloalkyl, $C_3$-$C_{12}$ cycloalkyl, or $C_3$-$C_6$ cycloalkyl) or an optionally-substituted $C_3$-$C_{24}$ heterocycloalkyl (e.g., $C_3$-$C_{18}$ heterocycloalkyl, $C_3$-$C_{12}$ heterocycloalkyl, or $C_3$-$C_6$ heterocycloalkyl).

As described above, $L^3$ may be selected from the group consisting of a bond, —C(O)—, —S—, —$S(O)_{1-2}$—, —O—, —$NR^7$—, —$C(O)NR^7$—, —$NR^7C(O)$—, —$C(S)NR^7$—, —$NR^7C(S)$—, —C(O)O—, —OC(O)—, —C(O)S—, —SC(O)—, —C(S)O—, —OC(S)—, —C(S)S—, —SC(S)—, —$S(O)_{1-2}O$—, —$OS(O)_{1-2}$—, —$S(O)_{1-2}NR^7$— and —$NR^7S(O)_{1-2}$—. For example, in certain embodiments, $L^3$ is a bond. In other embodiments as described herein, $L^3$ is selected from the group consisting of a bond, —C(O)—, —S—, —$S(O)_{1-2}$—, —O—, and —$NR^7$—.

Alternatively, in other embodiments, the 1,2-azaborines may be directly substituted with a halo, nitro, or cyano. As such, in certain other embodiments, -$L^3$-$R^3$ is halo, nitro, or cyano. In some embodiments, -$L^3$-$R^3$ is halo. For example, in some embodiments, -$L^3$-$R^3$ is selected from chloro, fluoro, or bromo. In some embodiments, -$L^3$-$R^3$ is nitro. In other embodiments, -$L^3$-$R^3$ is cyano.

As described above, $R^4$ is H or a subsistent having no more than 40 non-H atoms. For example, in some embodiments as described herein, $R^4$ is H. In other embodiments, $R^4$ is a carbon-linked substituent having no more than 30, no more than 20, or no more than 10 non-H atoms. The carbon-linked substituent may be selected from a variety of carbon-containing substituents. In other embodiments, $R^4$ is an optionally-substituted alkyl, optionally-substituted alkenyl, or optionally-substituted alkynyl. For example, in various embodiments as described herein, $R^4$ is an optionally-substituted $C_1$-$C_{24}$ alkyl (e.g., $C_1$-$C_{18}$ alkyl, $C_1$-$C_{12}$ alkyl, or $C_1$-$C_6$ alkyl), an optionally-substituted $C_2$-$C_{24}$ alkenyl (e.g., $C_2$-$C_{18}$ alkenyl, $C_2$-$C_{12}$ alkenyl, or $C_2$-$C_6$ alkenyl), or an optionally-substituted $C_1$-$C_{24}$ alkynyl (e.g., $C_1$-$C_{18}$ alkynyl $C_1$-$C_{12}$ alkynyl, or $C_1$-$C_6$ alkynyl). In some embodiments, $R^4$ is an optionally-substituted aryl, optionally-substituted heteroaryl, optionally-substituted cycloalkyl, or optionally-substituted heterocycloalkyl. For example, in various embodiments, $R^4$ is an optionally-substituted $C_6$-$C_2$ aryl (e.g., $C_6$-$C_{18}$ aryl or $C_6$-$C_{12}$ aryl) or an optionally-substituted $C_5$-$C_{24}$ heteroaryl (e.g., $C_5$-$C_{18}$ eteroaryl or $C_5$-$C_{12}$ heteroaryl). In other embodiments, $R^4$ is optionally-substituted $C_3$-$C_{24}$ cycloalkyl (e.g., $C_3$-$C_{18}$ cycloalkyl, $C_3$-$C_{12}$ cycloalkyl, or $C_3$-$C_6$ cycloalkyl) or an optionally-substituted $C_3$-$C_{24}$ heterocycloalkyl (e.g., $C_3$-$C_{18}$ heterocycloalkyl, $C_3$-$C_{12}$ heterocycloalkyl, r $C_3$-$C_6$ heterocycloalkyl).

As described above, $L^4$ may be selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{12}NR^7$— and —$NR^7S(O)_{1-2}$—. In certain embodiments, $L^4$ is a bond. In other embodiments as described herein, $L^4$ is selected from the group consisting of a bond, —C(O)—, —S—, —$S(O)_{1-2}$—, —O—, and —$NR^7$—.

Alternatively, in other embodiments, the 1,2-azaborines may be directly substituted with a halo, nitro, or cyano. As such, in certain other embodiments, -$L^4$-$R^4$ is halo, nitro, or cyano. In some embodiments, -$L^4$-$R^4$ is halo. For example, in some embodiments, -$L^4$-$R^4$ chloro, fluoro, or bromo. In some embodiments, -$L^4$-$R^4$ is nitro. In other embodiments, -$L^4$-$R^4$ is cyano.

As described above, $R^6$ is H or a substituent having no more than 40 non-H atoms. For example, in some embodiments, $R^6$ is H. In other embodiments, $R^6$ is a carbon-linked substituent having no more than 30, no more than 20, or no more than 10 non-H atoms. The carbon-linked substituent may be selected from a variety of carbon-containing substituents. In some embodiments as described herein, $R^6$ is an optionally-substituted alkyl, optionally-substituted alkenyl, or optionally-substituted alkynyl. For example, in various embodiments, $R^6$ is an optionally-substituted $C_1$-$C_{24}$ alkyl (e.g., $C_1$-$C_{18}$ alkyl, $C_1$-$C_{12}$ alkyl, or $C_1$-$C_6$ alkyl), an optionally-substituted $C_2$-$C_{24}$ alkenyl (e.g., $C_2$-$C_{18}$ alkenyl, $C_2$-$C_{12}$ alkenyl, or $C_2$-$C_6$ alkenyl), or an optionally-substituted $C_1$-$C_{24}$ alkynyl (e.g., $C_1$-$C_{18}$ alkynyl, $C_1$-$C_{12}$ alkynyl, or $C_1$-$C_6$ alkynyl). In some embodiments as described herein, $R^6$ is an optionally-substituted aryl, optionally-substituted heteroaryl, optionally-substituted cycloalkyl, or an optionally)-substituted heterocycloalkyl. For example, in various embodiments, $R^6$ is an optionally-substituted $C_6$-$C_{24}$ aryl (e.g., $C_6$-$C_{18}$ aryl or $C_6$-$C_{12}$ aryl) or an optionally-substituted $C_5$-$C_{24}$ heteroaryl (e.g., $C_5$-$C_{18}$ heteroaryl or $C_5$-$C_{12}$ heteroaryl). In some embodiments as described herein, $R^6$ is optionally-substituted $C_3$-$C_{24}$ cycloalkyl (e.g., $C_3$-$C_{18}$ cycloalkyl, $C_3$-$C_{12}$ cycloalkyl, $C_3$-$C_6$ cycloalkyl) or an optionally-substituted $C_3$-$C_{24}$ heterocycloalkyl (e.g., $C_3$-$C_{18}$ heterocycloalkyl, $C_3$-$C_{12}$ heterocycloalkyl, or $C_3$-$C_6$ heterocycloalkyl). In other embodiments, each $R^6$ is independently selected from the group consisting of hydrogen, $C_1$-$C_3$ alkyl and —C(O)($C_1$-$C_3$ alkyl).

As described herein, $L^6$ may be selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —C(S)—, —C(S)S—, —SC(S)—, —$S(O)_{1-2}$O—, —O$S(O)_{1-2}$—, —$S(O)_{1-2}NR^7$— and —$NR^7S(O)_{1-2}$—. For example, in certain embodiments, $L^6$ is a bond. In some embodiments as described herein, $L^6$ is selected from the group consisting of a bond, —C(O)—, —S—, —$S(O)_{1-2}$—, —O—, and —$NR^7$—.

Alternatively, in other embodiments, the 1,2-azaborines may be directly substituted with a halo, nitro, or cyano. As such, in certain other embodiments, -$L^6$-$R^6$ is halo, nitro, or cyano. In some embodiments, -$L^6$-$R^6$ is halo. For example, in some embodiments, -$L^6$-$R^6$ chloro, fluoro, or bromo. In some embodiments, -$L^6$-$R^6$ is nitro. In other embodiments, -$L^6$-$R^6$ is cyano.

In some embodiments as described herein, $R^3$, $R^4$, and $R^6$ are different substituents.

As described above, $R^1$, $R^2$, $R^3$, $R^4$, and $R^6$ can be selected from optionally-substituted groups. The optionally-substituted groups are independently optionally-substituted by one or more of each $R^7$. For example, $R^7$ may be independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^8$, —($C_0$-$C_6$ alkyl)-$NR^{10}R^9$, —($C_0$-$C_6$ alkyl)-$OR^{11}$, —($C_0$-$C_6$ alkyl)-C(O)$R^{11}$, —($C_0$-$C_6$ alkyl)-$S(O)_{0-2}R^{11}$, -halogen, —$NO_2$ and —CN. In some embodiments, L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —S C(S)$NR^9$—, —$NR^9$C(S)—, —C(S)$NR^9$—, —SC(O)$NR^9$—, —$NR^9$C(S)—, —$S(O)_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(s)O—, —OC(S)S—, —$NR^9$C($NR^2$)$NR^9$—, —$NR^9SO_2$—, —$SO_2NR^9$— and —$NR^9SO_2NR^9$—. In some embodiments, each $R^8$, $R^{10}$ and $R^{11}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl). In some embodiments, each $R^9$ is independently selected from —H, —($C_1$-$C_4$ alkyl), —C(O)—($C_1$-$C_4$ alkyl) and —C(O)O—($C_1$-$C_4$ alkyl). As used herein, Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Methods of Preparation

Methods of Preparing 1,2-disubstituted azaborines

As described above, it remains a challenge to prepare monocyclic 1,2-azabornines in efficient and modular manner. In particular, it is challenging to provide-substituted 1,2-azaborines. Here, the present disclosure provides a modular, noble metal free, and versatile synthesis method for 1,2-azaborines, such as the compounds as described herein. The method includes combining a Lewis acid, an N-substituted 1-cyclopropyl imine, and a B-substituted dihaloborane and allowing them to react to form an B-substituted, N-substituted, 1-halo-N-(6-halohex-3-enyl)boranamine; then treating the B-substituted, N-substituted, 1-halo-N-(6-halohex-3-enyl)boranamine with a base to provide the 1,2-disubstituted azaborirre.

The method of the present disclosure advantageously does not include noble metal catalysts. Rather, a Lewis acid can be used to react the N-substituted 1-cyclopropyl imine and the B-substituted dihaloborane. In some embodiments as described herein, the Lewis acid is $ZnBr_2$, $Zn(OTf)_2$ or $BF_3$. In some embodiments as described herein, the Lewis acid is present in amount of 10 mol % of the N-substituted 1-cyclopropyl imine and the B-substituted dihaloborane, whichever is provided in lesser molar amount.

The N-substituted 1-cyclopropyl imine provides the nitrogen and carbon atoms that ultimately form the ring structure of the azaborine. In some embodiments as described herein, the N-substituted 1-cyclopropyl imine has the structure

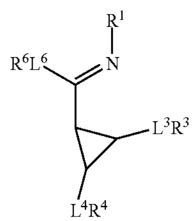

wherein $R^1$, $R^3$, $R^4$, $R^6$, $L^3$, $L^4$, and $L^6$, are as described herein.

The reaction also includes a B-substituted dihaloborane to provide the boron to the azaborine. The dihaloborane may be selected form dibromoborane or dichloroborane. In some embodiments as described herein, the dihaloborane is a dibromoborane. For example, in some embodiments, the B-substituted dihaloborane has the structure

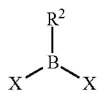

wherein $R^2$ is as described herein, and X is halo. For example, X may be selected from Cl or Br. In some embodiments as described herein, the B-substituted dihaloborane is generated (e.g., in situ) by reaction of a trihaloborane (e.g., triboroborane) with a substituted silane.

The combination of the Lewis acid, the N-substituted 1-cyclopropyl imine, and the B-substituted dihaloborane react to form an B-substituted, N-substituted, 1-halo-N-(6-halohex-3-enyl)boranamineB-substituted, N-substituted, 1-halo-N-(6-halohex-3-enyl)boranamine. In some embodiments as described herein, the B-substituted, N-substituted, 1-halo-N-(6-halohex-3-enyl)boranamineB-substituted, N-substituted, 1-halo-N-(6-halohex-3-enyl)boranamine has the structure

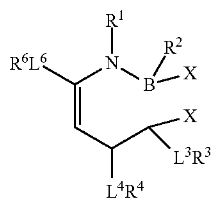

wherein the $R^1$, $R^2$, $R^3$, $R^4$, $R^6$, $L^3$, $L^4$, and $L^6$ are as described herein.

In some embodiments as described herein, a molar ratio of the B-substituted dihaloborane to the N-substituted 1-cyclopropyl imine is in the range of 0.7-1.5, e.g., 0.8-1.25, or 0.9-1.1. For example, in various embodiments, the molar ratio of the B-substituted dihaloborane to the N-substituted 1-cyclopropyl imine is in the range of 0.95-1.5, e.g., 0.95-1.25, or 0.95-1.15, or 1.05-1.5, or 1.05-1.25, or 1.05-1.15.

In some embodiments as described herein, the Lewis acid, the N-substituted 1-cyclopropyl imine and the B-substituted dihaloborane are allowed to react at a temperature in the range of 40-100° C., e.g., 40-80° C., or 40-70° C., or 40-65° C., or 50-100° C., or 50-80° C., or 50-70° C., or 50-65° C., or 55-100° C., or 55-80° C., or 55-70° C., or 55-65° C.

The Lewis acid, the N-substituted 1-cyclopropyl imine and the B-substituted dihaloborane are allowed to react for a sufficient time to provide an B-substituted, N-substituted, 1-halo-N-(6-halohex-3-enyl)boranamineB-substituted, N-substituted, 1-halo-N-(6-halohex-3-enyl)boranamine. In some embodiments as described herein, the Lewis acid, the N-substituted 1-cyclopropyl imine and the B-substituted dihaloborane are allowed to react for a time of at least 1 h, e.g., at least 2 h, or at least 3 h.

The reaction of the Lewis acid, the N-substituted 1-cyclopropyl imine, and the B-substituted dihaloborane may be performed in a solvent, as known in the art. In some embodiments as described herein, the reaction is performed in a solvent. For example, in some embodiments, the solvent is chlorobenzene.

To provide the disubstituted 1,2-azaborine, the B-substituted, N-substituted, 1-halo-N-(6-halohex-3-enyl)boranamineB-substituted, N-substituted, 1-halo-N-(6-halohex-3-enyl)boranamine is reacting with a base. In some embodiments as described herein, the base is an amine base. In some embodiments as described herein, the base is a hindered amine base As would be known to the skilled person, a hindered amine base is a sterically hindered base that is a poor nucleophile (e.g., a non-nucleophile base). In some embodiments as described herein, the amine base has a conjugate acid pKa in water of at least 12, e.g., at least 12.5 or at least 13. In some embodiments, the amine base is 1,8-diazabicyclo(5.4.0)undec-7-ene (DBU).

The method of the disclosure may be conducted in two steps or a one pot process. For example, the reaction of a Lewis acid, an N-substituted 1-cyclopropyl imine, and a B-substituted dihaloborane and the treating of an B-substituted, N-substituted, 1-halo-N-(6-halohex-3-enyl)boranamineB-substituted, N-substituted, 1-halo-N-(6-halohex-3-enyl)boranamine can be carried out as two steps. Alternatively, a one-pot method can be used. Accordingly, in some embodiments as described herein, the B-substituted, N-substituted, 1-halo-N-(6-halohex-3-enyl)boranamineB-substituted, N-substituted, 1-halo-N-(6-halohex-3-enyl)boranamine is treated with the amine base in the reaction mixture of the previous step.

In some embodiments as described herein, the 1,2-disubstituted azaborine is a compound as described herein. As such, another aspect of the present disclosure provides the compounds as described herein prepared by the methods as described herein.

Methods of Preparing 3-halo-1,2-disubstituted azaborines

Another aspect of the present disclosure provide a method for making a 3-halo-1,2-disubstituted azaborine. To prepare the 3-halo-1,2-disubstituted azaborines, the method of making the 1,2-disubstituted azaborine described above maybe used to provide a 1,2-disubstituted azaborine. This 1,2-disubstituted azaborine may then be halogenated. As such, in some embodiments, the method includes combining a Lewis acid, an N substituted 1-cyclopropyl imine, and a B-substituted dihaloborane and allowing them to react to form an B-substituted, N-substituted, 1-halo-N-(6-halohex-3-enyl) boranamine; then treating the B-substituted, N-substituted, 1-halo-N-(6-halohex-3-enyl)boranamine with a base to provide the 1,2-disubstituted azaborine; and then halogenating the 1,2-disquieted azaborine to provide a 3-halo-1,2-disubstituted azaborine, wherein N-substituted 1-cyclopropyl imine has the structure:

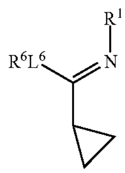

wherein $L^6$ and $R^6$ are as described herein.

The halogenating may including contacting the 1,2-azaborine with a halogenating agent. For example, in some embodiments the halogenating agent is selected from a brominating agent of an iodinating reagent. In some embodiments as escribed herein, the halogenating agent is bromine. In other embodiments as described herein, the halogenating agent is 1,3-Diiodo-5,5-Dimethylhydantoin (DIH). The halogenating may be performed in a solvent. For example, in some embodiments, the solvent is dichloromethane.

The halogenating may be conducted at a temperate and for a time sufficient to provide the 3-halo-1,2-disubstituted azaborine. For example, in some embodiments as described herein, the halogenating is conducted at a temperature in the range of 0° C. to 60° C. In various embodiments as described herein, the halogenating is conducted at a temperature., in the range of 10-60° C., or 10-50° C., or 10-40° C., or 20-60° C., or 20-50° C., or 20-40° C. In various embodiments as described herein, the halogenating is conducted for at least 1 hour, at least 2 hours, at least 3 hours, or at least 4 hours.

In some embodiments as described herein, the 3-halo-1,2-disubstituted azaborine is a compound as described herein. As such, another aspect of the present disclosure provides the compounds as described herein prepared by the methods as described herein.

In some embodiments of the method for making 3-halo-1,2-disubstituted azaborine, the method further includes cross coupling the 3-halo-1,2-disubstituted azaborine to provide a 1,2,3-trisubstituted azaborine. For the cross-coupling reaction, in some embodiments as described herein, the 3-halo-1,2-disubstituted azaborine is a 3-bromo-1,2-disubstituted azaborine. For example, the 3-halo-1,2-disubstituted may have the structure:

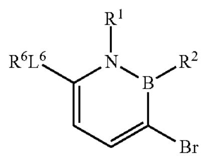

wherein the substituents are as described herein.

In some embodiments as described herein, the 1,2,3-trisubstituted azaborine is a compound as described herein. As such, another aspect of the present disclosure provides the compounds as described herein prepared by the methods as described herein.

Method of Preparing 1,2,3,4,6-pentasubstituted azaborine

Another aspect of the present disclosure provide a method for making a 1,2,3,4,6-pentasubstituted azaborine. The method includes providing a 3-halo-1,2-disubstituted azaborine; and combining the 3-halo-1,2-disubstituted azaborine, a bromo-containing compound, and a vinyl or alkyne reagent in the presence of palladium catalyst system, a carboxamide, a pyridinol, and a base and allowing them to react to form the 1,2,3,4,6-pentasubstituted azaborine.

In some embodiments as described herein, the 3-halo-1,2-disubstituted azaborine is a 3-iodo-1,2-disubstituted azaborine. For example, in some embodiments, the 3-halo-1,2-disubstituted azaborine has the structure:

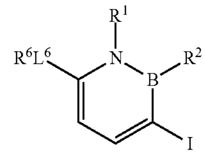

wherein the substituents are as described herein. In some embodiments as described herein, the 3-halo-1,2-disubstituted azaborine is prepared by the method as described herein.

As described above, the method includes combining the 3-halo-1,2-disubstituted azaborine with a bromo-containing compound. In some embodiments Is described herein, the bromo-containing compound is an optionally substituted aryl-bromo compound or an optionally substituted alkyl-bromo compound. For example, in some embodiment as described herein, the bromo-containing compound has the structure Br-$L^4R^4$, wherein $L^4$ and $R^4$ are as described herein.

The method also including combining the 3-halo-1,2-disubstituted azaborine and bromo-containing compound with a vinyl reagent or an alkyne reagent. In some embodiments, the 3-halo-1,2-disubstituted azaborine and a bromo-containing compound are combined with a vinyl reagent. In other embodiments, the 3-halo-1,2-disubstituted azaborine and a bromo-containing compound are combined with an alkyne reagent. In various embodiments as described herein, the vinyl reagent is selected from vinyl containing substituents as described by $R^3$ herein. In various embodiments as described herein, the alkynyl reagent is selected from vinyl containing substituents as described by $R^3$ herein.

As described above, the method also includes combining the 3-halo-1,2-disubstituted azaborine, a bromo-containing compound, and a vinyl or alkyne reagent in the presence of palladium catalyst system, a carboxamide, a pyridinol, and a base. In some embodiments as described herein, the palladium catalyst system comprises $Pd(TFA)_2$ and 2-(Dicyclohexylphosphino)$_{3,6}$-dimethoxy-2',4',6'-triisopropyl-1,1'-biphenyl (BrettPhos reagent). In some embodiments as described herein, the carboxamide the carboxamide is (1S,4R)-N-methylbicyclo[2.2.1]hept-2-ene-2-carboxamide. In some embodiments as described herein, the pyridinol is 3,5-bis(trifluoromethyl)pyridin-2-ol. In some embodiments as described herein, the base is selected from a hydroxide, carbonate, or phosphate. In some embodiments, the base is a carbonate, for example, potassium carbonate.

In some embodiments as described herein, the 3-halo-1,2-disubstituted azaborine, a bromo-containing compound, and a vinyl or alkyne reagent are present in a molar ratio of at least 1:1:1, or at least 1:1:1.05. In various embodiments as described Herein, the palladium catalyst system is present in an amount of at least 10 mol %, or at least 20 mol %, or at least 30 mol %. In various embodiments as described herein, the carboxamide and 3-halo-1,2-disubstituted azaborine are present in molar ratio of at least 1:1, at leas: 1.5:1, or at least 2:1. In some embodiments as described herein, the pyridinol is present in an amount of at least 5 mol % or at least 10 mol %. In various embodiments as described herein, the base and 3-halo-1,2-disubstituted azaborine present in a molar ratio of at least 1:1, or at least 2:1, or at least 3:1, or at least 4:1.

In some embodiments as described herein, the reaction is performed in a solvent. The solvent may be selected from those known in the art. For example in some embodiments as described herein, the solvent is a mixture of toluene and dimethyl ether in a volume ratio of 1:1.

The reaction may be conducted at a temperate and for a time sufficient to provide the 1,2,3,4,6-pentasubstituted azaborine. For example, in various embodiments as described herein, the 3-halo-1,2-disubstituted azaborine, a bromo-containing compound, and a vinyl or alkyne reagent in the presence of palladium catalyst system, a carboxamide, a pyridinol, and a base are allowed to react at a temperature in the range of 100-150° C., or 100-140° C., or 100-130° C., or 100-120° C., or 110-150° C., or 110-140° C., or 110-130° C., or 110-120° C. In various embodiments as described herein. In various embodiments as described herein, the 3-halo-1,2-disubstituted azaborine, a bromo-containing compound, and a vinyl or alkyne reagent in the presence of palladium catalyst system, a carboxamide, a pyridinol, and a base are allowed to react for a time of at least 12 hours, at least 14 hours, at least 16 hours or at least 18 hours.

In some embodiments as described herein, the 1,2,3,4,6-pe tasubstituted azaborine is a compound as described herein. As such, another aspect of the present disclosure provides the compounds as described herein prepared by the methods as described herein.

Compounds as described herein can be purified by any of the means known in the art, including chromatographic means, such as HPLC, preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry," Plenum Press, London and New York 1973, in T. W. Greene and P. G. M. Wuts "Protective Groups in Organic Synthesis," Third edition, Wiley, New York 1999, in "The Peptic es"; Volume 3 (editors: E. Gross and J. Meienhofer), Academic Press, London and New York 1981, in "Methoden der organischen Chemie," Houben-Weyl, 4.sup.th edition, Vol. 15/I, Georg Thieme Verlag, Stuttgart 1974, in H.-D. Jakubke and H. Jescheit, "Aminosauren, Peptide, Protide," Verlag Chemie, Weinheim, Deerfield Beach, and Basel 1982, and/or in Jochen Lehmann, "Chemie der Kohlenhydrate: Monosaccharide and Derivate," Georg Thieme Verlag, Stuttgart 1974. The protecting groups may be removed at a convenient subsequent stage using methods known from the art.

The methods described herein are useful for the preparation of a wide variety of 1,2-azaborine compounds, including 1,2-azaborine analogs of known aryl-containing compounds and derivatives thereof, for use in mechanistic studies, therapeutic lead identification, and therapy. Non-limiting examples of such 1,2-azaborine compounds described below with respect to the Examples, including especially compounds 3ar, 3as, 3at, 3au, 3av and 3aw.

Definitions

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" (i.e., the attachment is via the last portion of the name) unless a dash indicates otherwise. For example, $C_1$-$C_6$alkoxycarbonyloxy and —OC(O)$C_1$-$C_6$alkyl indicate the same functionality; similarly arylalkyl and -alkylaryl indicate the same functionality.

When difunctional radicals are written left-to-right, the left-hand part of the radical is bound at a position more proximal to the azaborine core than is the right-hand part of the radical.

For simplicity, chemical moieties are defined and referred to throughout primarily as univalent chemical moieties (for example, alkyl, aryl, etc.). Nevertheless, such terms are also used to convey corresponding multivalent moieties under the appropriate structural circumstances clear to those skilled in the art. For example, while an "alkyl" moiety can refer to a monovalent radical (for example $CH_3$—$CH_2$—), in some circumstances a bivalent linking moiety can be "alkyl," in which case those skilled in the art will understand the alkyl to be a divalent radical (for example the $C_2$ alkylene —$CH_2$—$CH_2$— may be described as a $C_2$ alkyl group), which is equivalent to the term "alkylene." (Similarly, in circumstances in which a divalent moiety is required and is stated as being "aryl," those skilled in the art will understand that the term "aryl" refers to the corresponding divalent moiety, arylene). All atoms are understood to have their normal number of valences for bond formation (i.e., 4 for carbon, 3 for N, 2 for 0, and 2, 4, or 6 for S, depending on the oxidation state of the S). Nitrogens in the presently disclosed compounds can be hypervalent, for example, an N-oxide or tetrasubstituted ammonium salt. On occasion a moiety may be defined, for example, as $(A)_a$-B-, wherein a is 0 or 1. In such instances, when a is 0 the moiety is B- and when a is 1 the moiety is A-B-.

As used herein, the term "alkyl" includes alkyl, alkenyl and alynyl groups of a designed number of carbon atoms, desirably from 1 to about 24 carbons (i.e., inclusive of 1 and 12). The term "$C_m$-$C_n$ alkyl" means an alkyl group having from m to n carbon atoms (i.e., inclusive of m and n). The term "$C_m$-$C_n$ alkyl" means an alkyl group having from m to n carbon atoms. For example, "$C_6$-$C_6$ alkyl" is an alkyl group having from one to six carbon atoms. Alkyl and alkyl groups may be straight or branched and depending on context, may be a monovalent radical or a divalent radical (i.e., an alkylene group). In the case of an alkyl or alkyl group having zero carbon atoms (i.e., "$C_0$ alkyl"), the group is simply a single covalent bond if it is a divalent radical or is a hydrogen atom if it is a monovalent radical. For example, the moiety "—($C_0$-$C_6$ alkyl)-Ar" signifies connection of an optionally substituted aryl through a single bond or an alkylene bridge having from 1 to 6 carbons. Examples of "alkyl" include, for example, methyl, ethyl, propyl, isopropyl, butyl, iso-, sec- and tert-butyl, pentyl, hexyl, heptyl, 3-ethylbutyl, 3-hexenyl and propargyl. If the number of carbon atoms is not specified, the subject "alkyl" or "alkyl" moiety has from 1 to 24 carbons.

The term "haloalkyl" is an alkyl group substituted with one or more halogen atoms, for example F, Cl, Br and I. A more specific term, for example, "fluoroalkyl" is an alkyl group substituted with one or more fluorine atoms. Examples of "fluoroalkyl" include fluoromethyl, difluoromethyl, trifluoromethyl, pentafluoroethyl, hexafluoroisopropyl and the like. In certain embodiments of the compounds disclosed herein, each haloalkyl is a fluoroalkyl.

The term "aryl" represents an aromatic carbocyclic ring system having a single ring (for example, phenyl) which is optionally fused to other aromatic hydrocarbon rings or non-aromatic hydrocarbon rings. "Aryl" includes ring systems having multiple condensed rings and in which at least one is aromatic, (for example, 1,2,3,4-tetrahydronaphthyl, naphthyl). Examples of aryl groups include phenyl, 1-naphthyl, 2-naphthyl, indanyl, indenyl, dihydronaphthyl, fluorenyl, tetralinyl, 2,3-dihydrobenzofuranyl and 6,7,8,9-tetrahydro-5H-benzo[a]cycloheptenyl. The aryl groups herein are unsubstituted or, when specified as "optionally substituted", can unless stated otherwise be substituted in one or more substitutable positions with various groups, as described below.

The term "heteroaryl" refers to an aromatic ring system containing at least one heteroatom selected from nitrogen, oxygen and sulfur in an aromatic ring. The heteroaryl may be fused to one or more cycloalkyl or heterocycloalkyl rings. Examples f heteroaryl groups include, for example, pyridyl, pyrimidinyl, quinolinyl, benzothienyl, indolyl, indolinyl, pyridazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, benzo[1,4]oxazinyl, trizolyl, tetrazolyl, isothiazolyl, naphthyridinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indoliziyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyralyl S-oxide, benzothiopyranyl S,S-dioxide. Preferred heteroaryl groups include pyridyl, pyrimidyl, quinolinyl, indolyl, pyrrolyl, furanyl, thienyl and imidazolyl, pyrazolyl, indazolyl, thia olyl and benzothiazolyl. In certain embodiments, each heteroaryl is selected from pyridyl, pyrimidinyl, pyridazinyl, pyrazinyl, imidazolyl, isoxazolyl, pyrazolyl, oxazolyl, thiazolyl, furanyl, thienyl, pyrrolyl, oxadiazolyl, thiadiazolyl, triazolyl, tetrazolyl, isothiazolyl, pyridinyl-N-oxide, pyrrolyl N-oxide, pyrimidinyl N-oxide, pyridazinyl N-oxide, pyrazinyl N-oxide, imidazolyl N-oxide, isoxazolyl N-oxide, oxazolyl N-oxide, thiazolyl N-oxide, pyrrolyl N-oxide, oxadiazolyl N-oxide, thiadiazolyl N-oxide, triazolyl N-oxide, and tetrazolyl N-oxide. Preferred heteroaryl groups include pyridyl, pyrimidyl, quinolinyl, indolyl, pyrrolyl, furanyl, thienyl, imidazolyl, pyrazoly, indazolyl, thiazolyl and benzothiazolyl. The heteroaryl groups herein are unsubstituted or, when specified as "optionally substituted", can unless stated otherwise be substituted in one or more substitutable positions with various groups, as described below.

The term "heterocycloalkyl" refers to a non-aromatic ring or ring system containing at least one heteroatom that is preferably selected from nitrogen, oxygen and sulfur, wherein said heteroatom is in a non-aromatic ring. The heterocycloalkyl may be saturated (i.e., a heterocycloalkyl) or partially unsaturated (i.e., a heterocycloalkenyl). The heterocycloalkyl ring is optionally fused to other heterocycloalkyl rings and/or non-aromatic hydrocarbon rings and/or phenyl rings. In certain embodiments, the heterocycloalkyl groups have from 3 to 7 members in a single ring. In other embodiments, heterocycloalkyl groups have 5 or 6 members in a single ring. Examples of heterocycloalkyl groups include, for example, azabicyclo[2.2.2]octyl (in each case also "quinuclidinyl" or a quinuclidine derivative), azabicyclo[3.2.1]octyl, morpholinyl, thiomorpholinyl, thiomorpholinyl S-oxide, thiomorpholinyl S,S-dioxide, 2-oxazolidonyl, piperazinyl, homopiperazinyl, piperazinonyl, pyrrolidinyl, azepanyl, azetinyl, pyrrolinyl, tetrahydropyranyl, piperidinyl, tetrahydrofuranyl, tetrahydrothienyl, 3,4-dihydroisoquinolin-2(1H)-yl, isoindolindionyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, imidazolidonyl, tetrahydrothienyl S-oxide, tetrahydrothinyl S,S-dioxide and homothiomorpholinyl S-oxide. Especially desirable heterocycloalkyl groups include morpholinyl, 3,4-dihydroisoquinolin-2(1H)-yl, tetrahydropyranyl, piperidinyl, aza-bicyclo[2.2.2]octyl, γ-butyrolactonyl (i.e., an oxo-substituted tetrahydrofuranyl), γ-butryolactamyl (i.e., an oxo-substituted pyrrolidine), pyrrolidinyl, piperazinyl, azepanyl, azetidinyl, thiomorpholinyl, thiomorpholinyl S,S-dioxide, 2-oxazolidonyl, imidazolidonyl, isoindolindinyl, piperazinonyl. The heterocycloalkyl groups herein are unsubstituted or, when specified as "optionally substituted", can unless stated otherwise be substituted in one or more substitutable positions with various groups, as described below.

The term "cycloalkyl" refers to a non-aromatic carbocyclic ring or ring system, which may be saturated (i.e., a cycloalkyl) or partially unsaturated (i.e., a cycloalkenyl). The cycloalkyl ring optionally fused to or otherwise attached (for example, bridged systems) to other cycloalkyl rings. Preferred cycloalkyl groups have from 3 to 7 members in a single ring. More preferred cycloalkyl groups have 5 or 6 members in a single ring. Examples of cycloalkyl groups include, for example, cyclohexyl, cyclopentyl, cyclobutyl, cyclopropyl, tetrahydroraphthyl and bicyclo[2.2.1]heptane. The cycloalkyl groups herein are unsubstituted or, when specified as "optionally substituted", may be substituted in one or more substitutable positions with various groups.

The term "oxa" means a divalent oxygen radical in a chain, sometimes designated as —O—.

The term "oxo" means a doubly bonded oxygen, sometimes designated as =O or for example in describing a carbonyl "C(O)" may be used to show an oxo substituted carbon.

The term "electron withdrawing group" means a group that withdraws electron density from the structure to which it is attached than would a similarly attached hydrogen atom. For example, electron withdrawing groups can be selected from the group consisting of halo, cyano, —($C_1$-$C_4$ fluoroalkyl), —O—($C_1$-$C_4$ fluoroalkyl), —C(O)—($C_0$-$C_4$ alkyl), —C(O)O—($C_0$-$C_4$ alkyl), —C(O)N($C_0$-$C_4$ alkyl)($C_0$-$C_4$ alkyl), —$S(O)_2$O—($C_0$-$C_4$ alkyl), —$SF_5$, NO and —C(O)—Hca in which the Hca includes a nitrogen atom to which the —C(O)— is bound, in which no alkyl, fluoroalkyl or heterocycloalkyl is substituted with an aryl, heteroaryl, cycloalkyl or heterocycloalkyl-containing group.

The term "substituted," when used to modify a specified group or radical, means that one or more hydrogen atoms of the specified group or radical are each, independently of one another, replaced with the same or different substituent groups as defined below.

Substituent groups for substituting for hydrogens on saturated carbon atoms in the specified group or radical are, unless otherwise specified, —$R^{60}$, halo, —$O^-M^+$, =O, —$OR^{70}$, —$SR^{70}$, —$S^-M^+$, =S, —$NR^{80}R^{80}$, =$NR^{70}$, =N—$OR^{70}$, trihalomethyl, —$CF_3$, —CN, —OCN, —SCN, —NO, —$NO_2$, =$N_2$, —$N_3$, —$SO_2R^{70}$, —$SO_2O^-M^+$, —$SO_2OR^{70}$, —$OSO_2R^{70}$, —$OSO_2$O—$M^+$, —$OSO_2OR^{70}$, —P(O)$(O^-)_2(M^+)_2$, —P(O)($OR^{70}$)$O^-M^+$, —P(O)$(OR^{70})_2$, —C(O)$R^{70}$, —C(S)$R^{70}$, —C($NR^{70}$)$R^{70}$, —C(O)$O^-M^+$, —C(O)$OR^{70}$, —C(S)$OR^{70}$, —C(O)$NR^{80}R^{80}$, —C($NR^{70}$)$NR^{80}R^{80}$, —OC(O)$R^{70}$, —O(S)$R^{70}$, —OC(O)$O^-M^+$, —OC(O)$OR^{70}$, —OC(S)$OR^{70}$, —$NR^{70}$C(O)$R^{70}$, —$NR^{70}$C(S)$R^{70}$, —$NR^{70}CO_2$ $M^+$, —$NR^{70}CO_2R^{70}$, —$NR^{70}$C(S) $OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$. Each $R^{60}$ is independently selected from the group consisting of alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{71}$, —$SR^{71}$, —$S^-M^+$, =S, —$NR^{81}R^{81}$, =$NR^{71}$, =N—$OR^{71}$, trihalomethyl, —$CF_3$, —CN, —OCN, —SCN, —NO, —$NO_2$, =$N_2$, —$N_3$, —$SO_2R^{71}$, —$OSO^-M^+$, —$SO_2OR^{71}$, —$OSO_2R^{71}$, —$OSO_2O^-M^+$, —$OSO_2OR^{71}$, —P(O)$(O^-)_2(M^+)_2$, —P(O)($OR^{71}$)$O^-M^+$, —P(O)$(OR^{71})_2$, —C(O)$R^{71}$, —C(S)$R^{71}$, —C($NR^{71}$)$R^{71}$, —C(O)$O^-M^+$, —C(O)$OR^{71}$, —C(S)$OR^{71}$, —C(O)$NR^{81}R^{81}$, —C($NR^{74}$)N $R^{81}R^{81}$, —OC(O)$R^{71}$, —OC(S)$R^{71}$, —OC(O)$O^-M^+$, —OC(O)$OR^{71}$, —OC(S)$OR^{71}$, —$NR^{71}$C(O)$R^{71}$, —$NR^{71}$C(S)$R^{71}$, —$NR^{71}CO_2^-M^+$, —$NR^{71}CO_2R^{71}$, —$NR^{71}$C(S)$OR^{71}$, —$NR^{71}$C(O)$NR^{81}R^{81}$, —$NR^7$C($NR^{71}$)$R^7$1 and —$NR^{71}$C($NR^{71}$)$NR^{81}R^{81}$. Each $R^{70}$ is independently hydrogen or $R^{60}$; each $R^{80}$ is independently $R^{70}$ or alternatively, two $R^{80}$'s, taken together with the nitrogen atom to which they are bonded, form a 5-, 6- or 7-membered heterocycloalkyl which may optionally include from 1 to 4 of the same or different additional heteroatoms selected from the group consisting of 0, N and S, of which N may have —H or $C_1$-$C_3$ alkyl substitution; and each $M^+$ is a counter ion with a net single positive charge. Each $R^{71}$ is independently hydrogen or $R^{61}$, in which $R^{61}$ is alkyl, heteroalkyl, cycloalkyl, heterocycloalkyl, heterocycloalkylalkyl, cycloalkylalkyl, aryl, arylalkyl, heteroaryl and heteroarylalkyl, each of which is optionally substituted with 1, 2, 3, 4 or 5 groups selected from the group consisting of halo, —$O^-M^+$, =O, —$OR^{72}$, —$SR^{72}$, —$S^-M^+$, =S, —$NR^{82}R^{82}$, =$NR^{72}$, =N—$OR^{72}$, trihalomethyl, —$CF_3$, —CN, —OCN, —SCN, —NO, —$NO_2$, =$N_2$, —$N_3$, —$SO_2R^{71}$, $SO_2O^-M^+$, —$SO_2OR^{72}$, —$OSO_2R^{72}$, —$OSO_2$O—$M^+$, —$OSO_2OR^{72}$, —P(O)$(O)_2(M^+)_2$, —P(O)($OR^{72}$)$O^-M^+$, —P(O)$(OR^{72})_2$, —C(O)$R^{72}$, —C(S)$R^{72}$, —C($NR^{72}$)$R^{72}$, —C(O)$O^-M^+$, —C(O)$OR^{72}$, C(S)$OR^{72}$, —C(O)$NR^{82}R^{82}$, —C($NR^{72}$)$NR^{82}R^{82}$, —OC(O)$R^{72}$, —OC(S)$R^{72}$, —OC(O)$O^-M^+$, —OC(O)$OR^{72}$, —OC(S)$OR^{72}$, —$NR^{72}$C(O)$R^{72}$, —$NR^{72}$C(S)$R^{72}$, —$NR^{72}CO_2^-M^+$, —$NR^{72}CO_2R^{72}$, —$NR^{72}$C(S)$OR^{72}$, —$NR^{72}$C(O)$NR^{82}R^{82}$, —$NR^{72}$C($NR^{72}$)$R^{72}$ and —$NR^{72}$C($NR^{72}$)$NR^{82}R^{82}$; and each $R^{81}$ is independently $R^{71}$ or alternatively, two $R^{81}$s, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution. Each $R^{72}$ is independently hydrogen, ($C_1$-$C_6$ alkyl) or ($C_1$-$C_6$ fluoroalkyl); each $R^{82}$ is independently $R^{72}$ or alternative y, two $R^{82}$s, taken together with the nitrogen atom to which they are bonded, form a 5-, 6- or 7-membered heterocycloalkyl which may optionally include 1, 2, 3 or 4 of the same or different additional heteroatoms selected from the group consisting of O, N and S, of which N may have —H or $C_1$-$C_3$ alkyl substitution. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means for example that one of the counter ions for such divalent alkali earth ions can be an ionized form of a presently disclosed compound and the other a typical counter ion such as chloride, or two ionized presently disclosed molecules can serve as counter ions for such divalent alkali earth ions, or a doubly ionized compound can serve as the counter ion for such divalent alkali earth ions). As specific examples, —$NR^{80}R^{80}$ is meant to include —$NH_2$, —NH-alkyl, N-pyrrolidinyl, N-piperazinyl, 4-methyl-piperazin-1-yl and N-morpholinyl. In certain embodiments, each $R^{60}$ is H or (unsubstituted $C_1$-$C_6$ alkyl). In certain embodiments, each $R^{70}$ is H or (unsubstituted $C_1$-$C_6$ alkyl). In certain embodiments, each $R^{80}$ is H or (unsubstituted $C_1$-$C_6$ alkyl).

Substituent groups for hydrogens on unsaturated carbon atoms in "substituted" alkene, alkyne, aryl and heteroaryl groups are, unless otherwise specified, —$R^{60}$, halo, —$O^-M^+$, —$OR^{70}$, —$SR^{70}$, —$S^-M^+$, —$NR^{80}R^{80}$, trihalomethyl, —$CF_3$, —CN, —OCN, —SCN, —NO, —$NO_2$, —$N_3$, —$SO_2R^{70}$, —$SO_3^-M^+$, —$SO_3R^{70}$, —$OSO_2R^{70}$, —$OSO_3^-M^+$, —$OSO_3R^{70}$, —$PO_3$-2$(M^+)_2$, —P(O)($OR^{70}$)$O^-M^+$, —P(O)$(OR^{70})_2$, —C(O)$R^{70}$, —C(S)$R^{70}$, —C($NR^{70}$)$R^{70}$, —$CO_2$ $M^+$, —$CO_2R^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2^-M^+$, —$OCO_2R^{70}$, —OC(S)$OR^{70}$, —$NR^{70}$C(O)$R^{70}$, —$NR^{70}$C(S)$R^{70}$, —$NR^{70}CO_2^-M^+$, —$NR^{70}CO_2R^{70}$, —$NR^{70}$C(S)O 70, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined.

Substituent groups for hydrogens on nitrogen atoms in "substituted" heteroalkyl and heterocycloalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —$S(O)_2R^{70}$, —$S(O)_2O^-M^+$, —$S(O)_2OR^{70}$, —$OS(O)_2R^{70}$, —$OS(O)_2O^-M^+$, —$OS(O)_2OR^{70}$, —P(O)$(O^-)_2(M^+)_2$, —P(O)($OR^{70}$)$O^-M^+$, —P(O)($OR^{70}$)($OR^{70}$), —C(O)$R^{70}$, —C(S)$R^{70}$, —C($NR^{70}$)$R^{70}$, —C(O)$OR^{70}$, —C(S)$OR^{70}$, —C(O)$NR^8OR^{80}$, —C($NR^{70}$)$NR^{80}R^{80}$, —OC(O)$R^{70}$, —OC(S)$R^{70}$, —OC(O)$OR^{70}$, —OC(S)$OR^{70}$, —$NR^{70}$C(O)$R^{70}$, —$NR^{70}$C(S)$R^{70}$, —$NR^{70}$C(O)$OR^{70}$, —$NR^{70}$C(S)$OR^{70}$, —$NR^{70}$C(O)$NR^{80}R^{80}$, —$NR^{70}$C($NR^{70}$)$R^{70}$ and —$NR^{70}$C($NR^{70}$)$NR^{80}R^{80}$, where $R^{60}$, $R^{70}$, $R^{80}$ and $M^+$ are as previously defined.

In certain embodiments as described above, the substituent groups on carbon atoms can also or alternatively be —$SF_5$.

In certain embodiments of the compounds disclosed herein, a group that is substituted has 1, 2, 3, or 4 substituents, 1, 2, or 3 substituents, 1 or 2 substituents, or 1 substituent.

In certain embodiments, an "optionally substituted alkyl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N (unsubstituted $C_1$-$C_4$ alkyl)$_2$, —C(O)OH, C(O)O (unsubstituted $C_1$-$C_6$ alkyl), —$(NH)_{0.1}SO_2R^{33}$, —$(NH)_{0-1}COR^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted alkyl" is also or alternatively optionally substituted with —$N_3$ or —$SF_5$.

In certain embodiments, an "optionally substituted aryl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(sunsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N (unsubstituted $C_1$-$C_4$ alkyl)$_2$, —C(O)OH, C(O)O (unsubstituted $C_1$-$C_6$ alkyl), —$(NH)_{0.1}SO_2R^{33}$, —$(NH)_{0-1}COR^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted aryl" is also or alternatively optionally substituted with —$N_3$ or —$SF_5$.

In certain embodiments, an "optionally substituted heteroaryl," unless otherwise specified, is substituted with halogen (e.g., F, Cl), unsubstituted ($C_1$-$C_6$ alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$-$C_6$ haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N (unsubstituted $C_1$-$C_4$ alkyl)$_2$, —C(O)OH, C(O)O (unsubstituted $C_1$—C alkyl), —$(NH)_{0.1}SO_2R^{33}$, —$(NH)_{0.1}COR^{33}$, heterocycloalkyl optionally substituted with an (unsubstituted $C_1$-$C_6$ alkyl) and heteroaryl optionally substituted with an (unsubstituted $C_1$-$C_6$ alkyl), in which each $R^{33}$ is (unsubstituted $C_1$—C alkyl), ($C_1$—C haloalkyl(unsubstituted $C_3$-$C_8$ cycloalkyl) or ($C_3$-$C_5$ heterocycloalkyl) optionally substituted with an (unsubstituted $C_1$-$C_6$ alkyl). In certain embodiments, "optionally substituted heteroaryl" is also or alternatively optionally substituted with —$N_3$ or —$SF_5$.

In certain embodiments, an "optionally substituted cycloalkyl" unless otherwise specified, is substituted with halogen (e.g., F, Cl), unsubstituted ($C_1$-$C_6$ alkoxy) (e.g., methoxy, ethoxy), —($C_1$—C haloalkoxy) (e.g., trifluoromethoxy), —SH, —S(unsubstituted $C_1$—C alkyl), —S($C_1$-$C_6$ haloalkyl), —OH, —CN, —$NO_2$, —$NH_2$, —NH (unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N (unsubstituted $C_1$-$C_4$ alkyl)$_2$, —C(O)OH, C(O)O (unsubstituted $C_1$—C alkyl), —$(NH)_{0.1}SO_2R^{33}$, —$(NH)_{0.1}COR^{33}$, heterocycloalkyl optionally substituted with an (unsubstituted $C_1$—C alkyl) and heteroaryl optionally substituted with an (unsubstituted $C_1$-$C_6$ alkyl), in which each 33 is (unsubstituted $C_1$-$C_6$alkyl), ($C_1$-$C_6$ haloalkyl(unsubstituted $C_3$—C cycloalkyl) or ($C_3$-$C_5$ heterocycloalkyl) optionally substituted with an (unsubstituted $C_1$—C alkyl). In certain embodiments, "optionally substituted cycloalkyl" is also or alternatively optionally substituted with —$N_3$ or —SFS.

In certain embodiments, an "optionally substituted heterocycoalkyl," unless otherwise specified, is substituted with halogen (e.g., F, Cl), unsubstituted ($C_1$—C-alkoxy) (e.g., methoxy, ethoxy), —($C_1$-$C_6$ haloalkoxy) (e.g., trifluoromethoxy), —SH, —S(unsubstituted $C_1$-$C_6$ alkyl), —S($C_1$—C haloalkyl), —OH, —CN, —$NO_2$, —$NH_2$, —NH(unsubstituted $C_1$-$C_4$ alkyl), —N(unsubstituted $C_1$-$C_4$ alkyl)$_2$, —C(O)—$NH_2$, C(O)NH(unsubstituted $C_1$-$C_4$ alkyl), C(O)N (unsubstituted $C_1$-$C_4$ alkyl)$_2$, —C(O)OH, C(O)O (unsubstituted $C_1$—C alkyl), —$(NH)_{0.1}SO_2R^{33}$, —$(NH)_{0.1}COR^{33}$, heterocycloalkyl optionally substituted with an (unsubstituted $C_6$-$C_6$ alkyl) and heteroaryl optionally substituted with an (unsubstituted $C_1$-$C_6$ alkyl), in which each $R^{33}$ is (unsubstituted $C_1$-$C_6$ alkyl), ($C_1$-$C_6$ haloalkyl(unsubstituted $C_3$-$C_8$ cycloalkyl) or ($C_3$-$C_8$ heterocycloalkyl) optionally substituted with an (unsubstituted $C_1$-$C_6$ alkyl). In certain embodiments, "optionally substituted heterocycloalkyl" is also or alternatively optionally substituted with —$N_3$ or —$SF_5$.

The term "unsaturated" as used herein means the referenced chemical structure contains at least one multiple carbon-carbon bond, but is not aromatic. For example, a unsaturated cycloalkyl group as defined herein includes cyclohexenyl, cyclopentenyl, cyclohexadienyl, and the like.

It will be apparent to one skilled in the art that certain compounds of this disclosure may exist in tautomeric forms, all such tautomeric forms of the compounds being within the scope of the disclosure. Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the disclosure. Both the R and the S stereochemical isomers, as well as all mixtures thereof, are included within the scope of the disclosure.

EXAMPLES

The preparation of the compounds of the disclosure is illustrated further by the following examples, which are not to be construed as limiting the disclosure in scope or spirit to the specific procedures and compounds described in them. The utility of the method disclosed is demonstrated in the concise syntheses of BN isosteres of a PD-1/PD-L1 inhibitor and pyrethroid insecticide bifenthrin. Combined experimental and computational mechanistic studies suggest that the reaction pathway involves boron-mediated cyclopropare ring-opening and base-mediated elimination, followed by an unusual low-barrier 6π-electrocyclization accelerated by the BN/CC isomerism.

Example 1: Strategies for the Synthesis of 1,2-Azaborines and Condition Optimization From the outset, it was questioned whether 1,2-azaborines could be synthesized from readily available cyclopropyl imines and a boron electrophile via a "ring-opening-then-rebound" strategy. It was initially hypothesized that a tandem boron-mediated C—C bond cleavage/reductive C—B bond formation should generate the six-membered BN-heterocycle, which then gives the 1,2-azaborines after oxidative aromatization, as shown below.

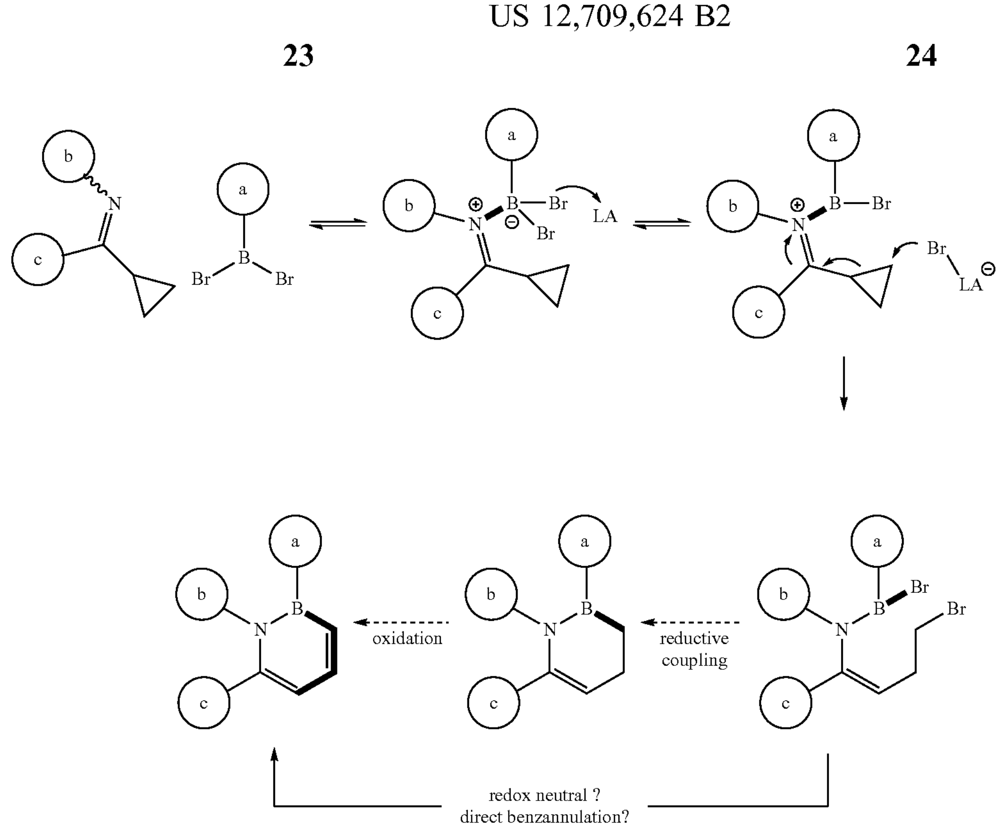

As such, the original strategy involves a tandem Lewis acid-catalyzed boron-mediated C—C bond cleavage/reductive C—B bond formation, followed by an oxidative aromatization, as described in the schematic below:

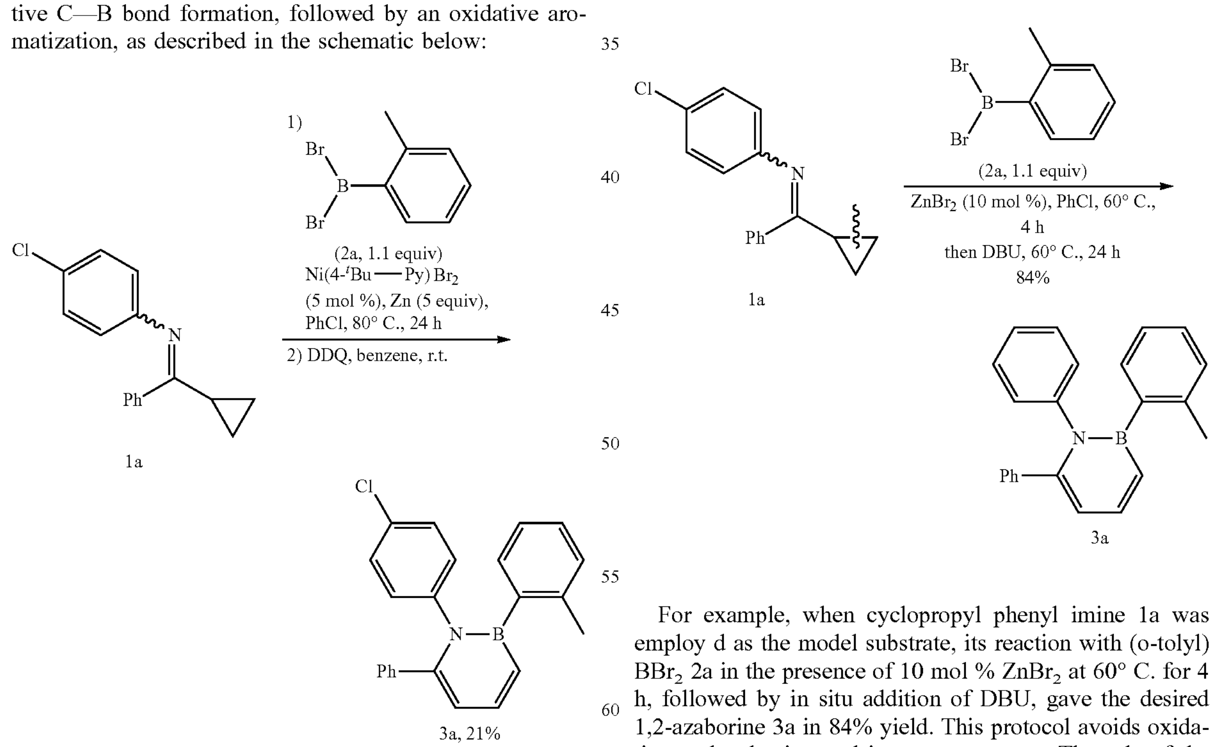

1a 3a, 21%

1a

3a

While this proposal was indeed feasible, a more straightforward and redox-neutral method to prepare 1,2-azaborines was realized simply by treating the ring-opened intermediate with a base in a one-pot manner, as shown below:

For example, when cyclopropyl phenyl imine 1a was employ d as the model substrate, its reaction with (o-tolyl) $BBr_2$ 2a in the presence of 10 mol % $ZnBr_2$ at 60° C. for 4 h, followed by in situ addition of DBU, gave the desired 1,2-azaborine 3a in 84% yield. This protocol avoids oxidation and reduction and is easy to operate. The role of the Lewis acid was likely to activate the imine/dibromoborane adduct in order to promote the cyclopropane ring-opening. Among various Lewis acids examined, $ZnBr_2$ proved to be optimal, as shown in Table 1. While $Zn(OTf)_2$ and $BF_3$ also offered good yield, other Lewis acids were less efficient. On the other hand, DBU was found to be the most suitable base; in contrast, weaker amines or inorganic bases were not effective for this transformation, as shown in Table 1. The reactions were conducted on a 0.1 mmol scale in 0.5 mL of solvent in a closed reaction vial and the yields were determined by $^1H$ NMR with dibromomethane as internal standard.

TABLE 1

| No. | Lewis Acid | Base | Yield of 3a (%) |
|---|---|---|---|
| 1 | None | DBU | 84 |
| 2 | $AlCl_3$ | DBU | 39 |
| 3 | $Sc(OTf)_3$ | DBU | 53 |
| 4 | $Zn(OTf)_3$ | DBU | 77 |
| 5 | LiCl | DBU | 54 |
| 6 | $VBr_3$ | DBU | 47 |
| 7 | $BF_3$•$Et_2l$ | DBU | 70 |
| 8 | $ZnBr_2$ | $Et_3N$ | 20 |
| 9 | $ZnBr_2$ | TMEDA | Trace |
| 10 | $ZnBr_2$ | DIPEA | Trace |
| 11 | $ZnBr_2$ | DABOC | Trace |
| 12 | $ZnBr_2$ | $Na_2CO_3$ | Trace |
| 13 | $ZnBr_2$ | $(Bu)_3N$ | Trace |

Example 2: Synthesis of 1,2-azaborines

Given that (a) cyclopropyl imines/ketones are readily accessible from the corresponding carboxylic acid derivatives and (b) dibromoboranes can be in situ generated from $BBr_3$ and silanes, the scope of the reaction appears to be quite broad. The following schematic shows a variety of compounds prepared.

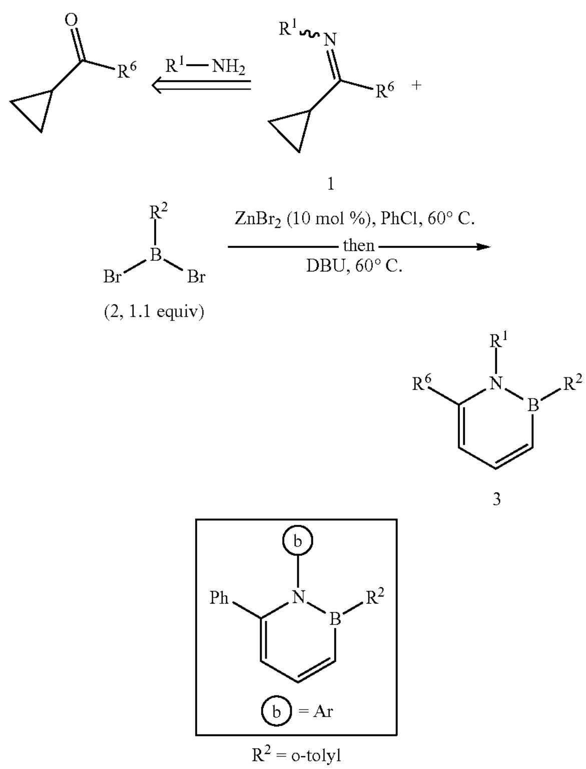

-continued

3a

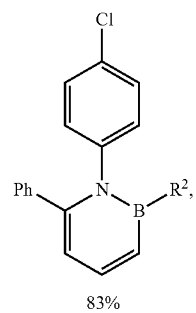

83%

3b

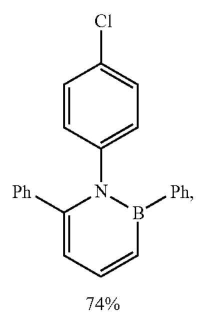

74%

3c

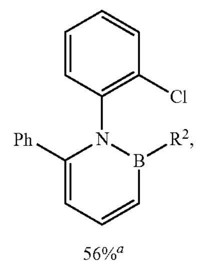

56%[a]

3d

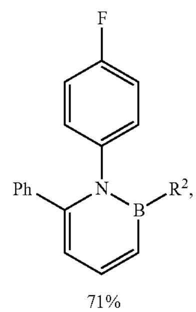

71%

3e

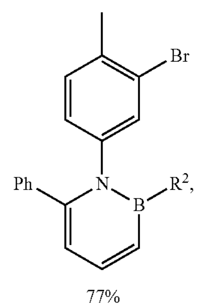

77%

-continued
3f
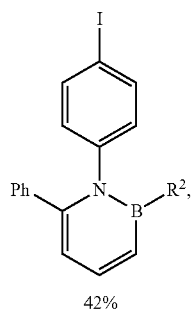
42%
3g
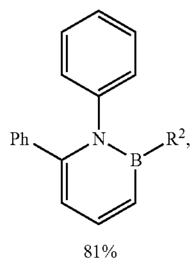
81%
3h
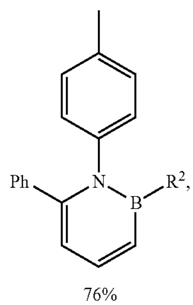
76%
3i
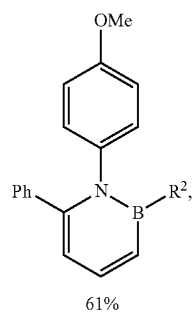
61%
3j
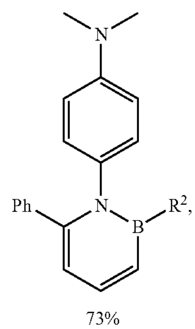
73%
-continued
3k
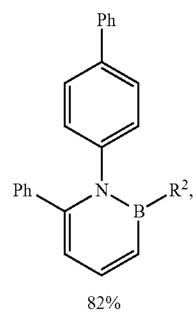
82%
3l
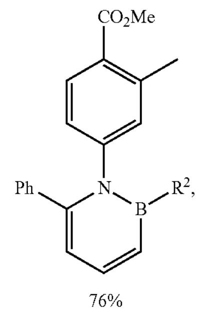
76%
3m
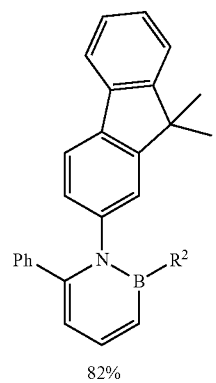
82%
3n
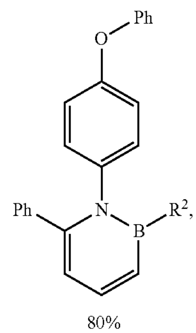
80%

-continued
3o
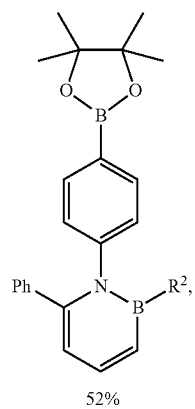
52%
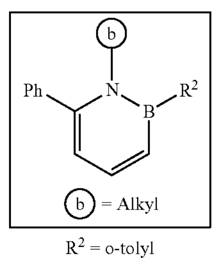
$R^2$ = o-tolyl
3p
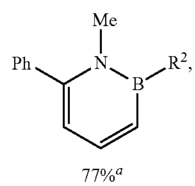
77%[a]
3q
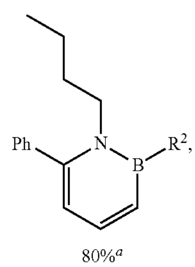
80%[a]
3r
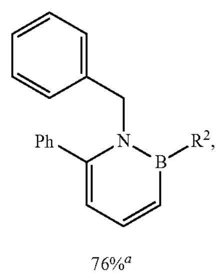
76%[a]
-continued
3s
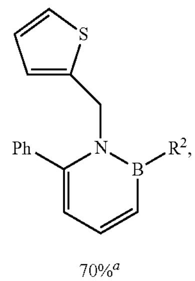
70%[a]
3t
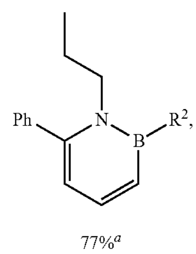
77%[a]
3u
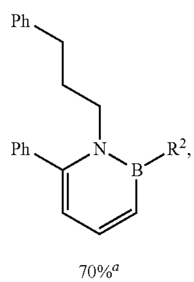
70%[a]
3v
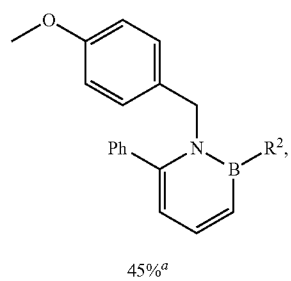
45%[a]
3w
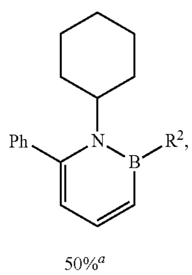
50%[a]
3x
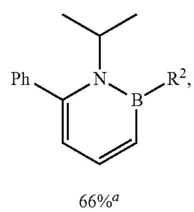
66%[a]

-continued
3y
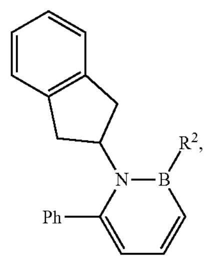
36%[a]
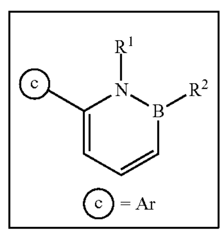
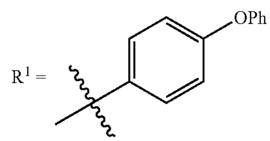
$R^2$ = o-tolyl
3z
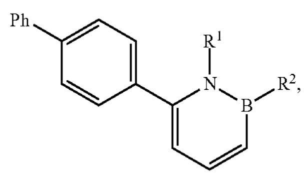
79%
3aa
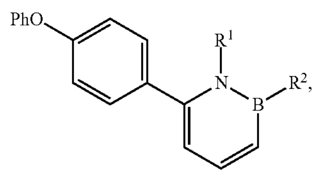
72%
3ab
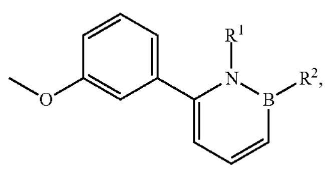
49%
3ac
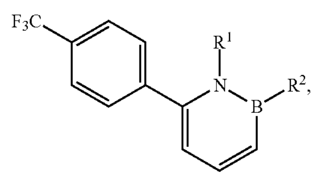
82%
-continued
3ad
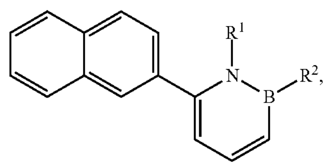
55%
3ae
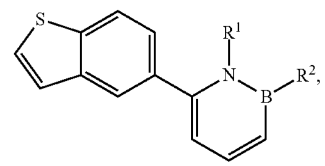
53%
3af
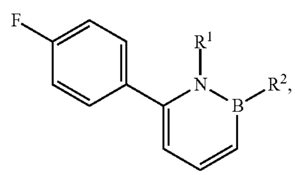
79%
3ag
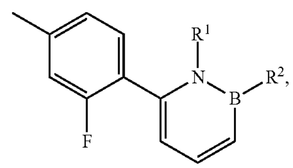
57%[a]
3ah
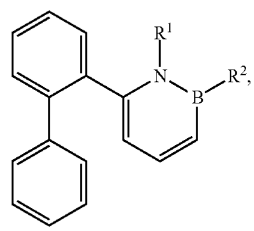
51%[a]
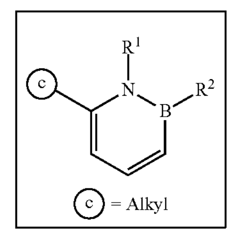
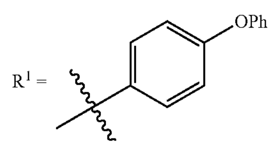
$R^2$ = o-tolyl -continued
3ai
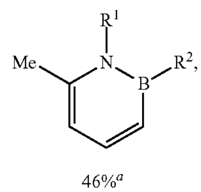
46%[a]
3aj
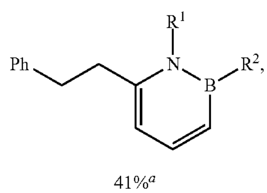
41%[a]
3ak
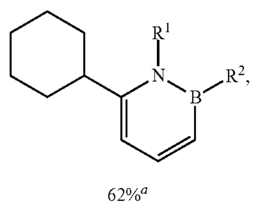
62%[a]
3al
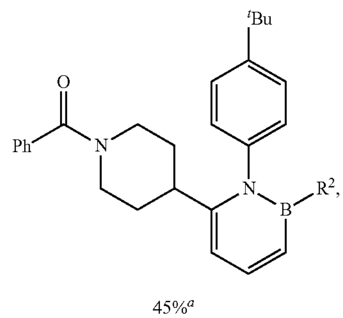
45%[a]
3am
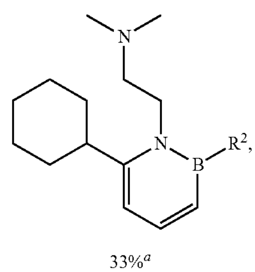
33%[a]
3an
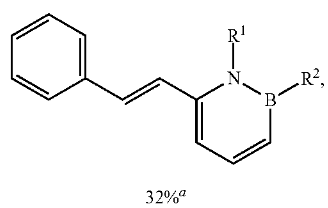
32%[a]
-continued
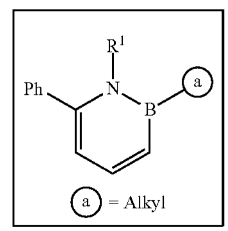
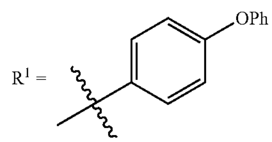
3ao
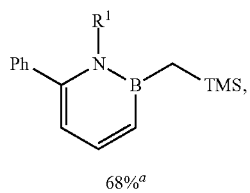
68%[a]
3ap
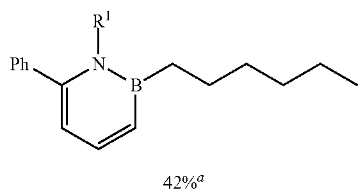
42%[a]
3aq
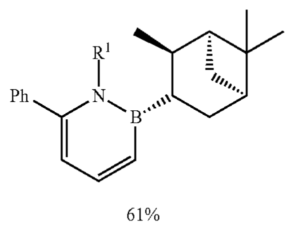
61%
drug molecule and natural product derivatives $R^2$ = o-tolyl
3ar
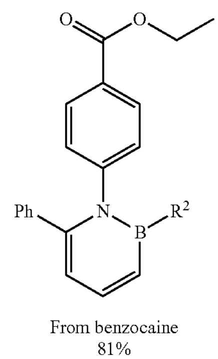
From benzocaine
81%

-continued

3as

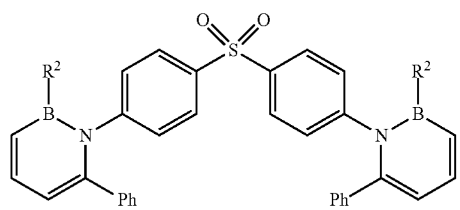

From dapsone
20%[a]

3at

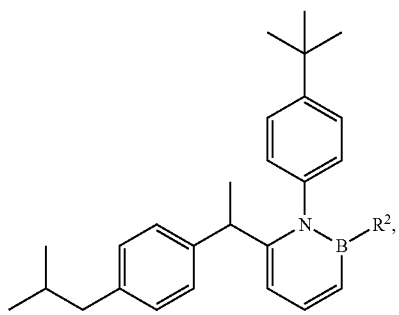

From ibuprofen
48%[a]

3au

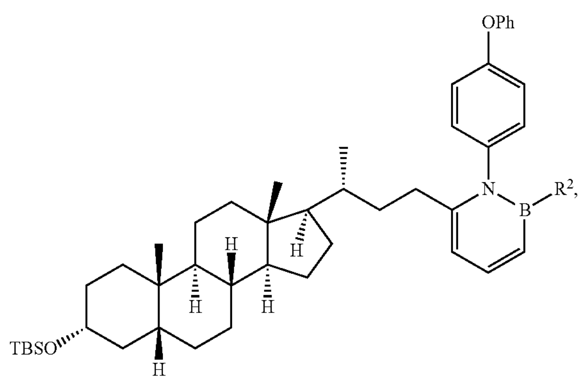

From lithocholic acid
28%[a]

3av

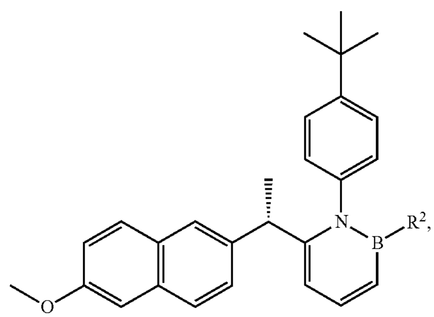

From naproxen
25%[a]

-continued

3aw

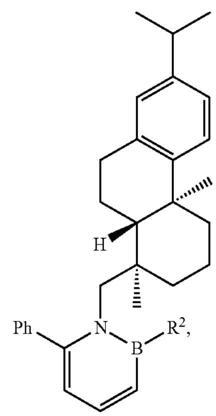

From leelamine
71%[a]

Preparation of monocyclic 1,2-azaborines 3a-3o, 3t-3aw (a representative procedure A)

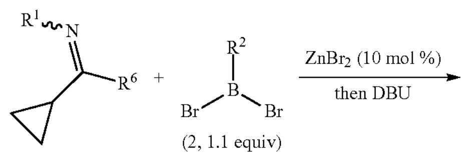

1

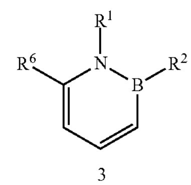

3

An oven-dried 4 mL vial was charged with imine 1 (0.2 mmol, 1 equiv) and $ZnBr_2$ (4.5 mg, 0.02 mmol, 10 mol %) in a nitrogen-filled glovebox. Dry chlorobenzene (1 mL) was then added. After dibromoborane 2 (0.22 mmol, 1.1 equiv) was added, the vial was tightly sealed and stirred on a pie-block preheated to 60° C. or 80° C. under nitrogen for 4 h. 1,8-Diazabicyclo(5.4.0)undec-7- ene (DBU, 90 μL, 0.6 mmol, 3 equiv) was then added and the reaction mixture was stirred at the same temperature for 24 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/20) to give azaborine 3. For air-sensitive 1,2-azaborines 3ah-3aj, flash column chromatography was conducted in a nitrogen-filled glovebox using 1-3% ether in pentane as the eluent. For the reactions marked with an "a", the reaction was run at 80° C. and trimethylsilyl (TMS).

Preparation of monocyclic 1,2-azaborines 3p-3s and 3az (a representative procedure

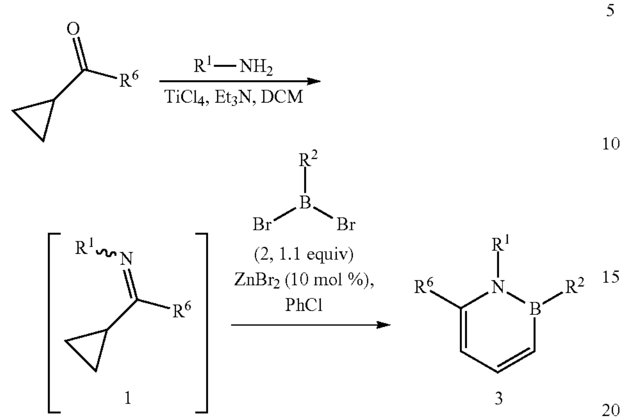

An oven-dried 10 mL Schlenk flask was charged with the corresponding ketone (0.2 mmol, 1 equiv), amine (0.22 mmol, 1.1 equiv), triethylamine (56 μL, 0.4 mmol, 2 equiv) and dry dichloromethane (1 mL). $TiCl_4$ (0.1 mL, 1M solution in DCM, 0.1 mmol, 0.5 equiv) was then added dropwise under nitrogen at 0° C. over a period of 5 min. After being stirred at 0° C. for 0.5 h, the reaction mixture was warmed to room temperature and stirred for 12 h. Upon completion, the reaction mixture was filtered through a pad of Celite, washed with hexane and concentrated to dryness under vacuum. The crude product was redissolved with hexane and filtered through a pad of Celite and concentrated to dryness again. The obtained imine 1 was directly used in the next step without further purification.

In a nitrogen-filled glovebox, the obtained crude imine 1 was dissolved in dry chlorobenzene (1 mL) and transferred into an oven-dried 4 mL vial. After $ZnBr_2$ (4.5 mg, 0.02 mmol, 10 mol %) and dibromoborane 2 (0.22 mmol, 1.1 equiv) were added, the vial was tightly sealed and stirred on a pie-block preheated to 80° C. under nitrogen for 4 h. 1,8-Diazabicyclo(5.4.0)undec-7-ene (DBU, 90 μL, 0.6 mmol, 3 equiv) was then added and the reaction mixture was stirred at the same temperature for 24 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/20) to give azabrine 3. For the reactions marked with an "a", the reaction was run at 80° C. and trimethylsilyl (TMS).

Characterization

Below are the details of the characterization of compounds 3a-3ax.

3a

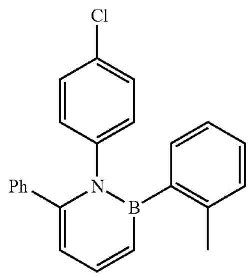

3a: Yield: 83%. Light brown oil. $R_f$=0.7 (hexane/ethyl acetate=9:1). $^1H$ NMR (400 MHz, $C_6D_6$): δ 7.66 (dd, J=11.0, 6.7 Hz, 1H), 7.14-7.09 (m, 2H), 7.05-7.00 (m, 1H), 6.99-6.92 (m, 4H), 6.89-6.82 (m, 3H), 6.58-6.48 (m, 4H), 6.45 (dd J=6.7, 1.5 Hz, 1H) (aryl CH), 2.22 (s, 3H) ($CH_3$). $^{13}C$ NMR (101 MHz, $C_6D_6$): δ 148.5, 143.7, 139.3, 138.9, 132.7, 131.8, 130.5, 129.9, 129.2, 128.0, 127.9, 127.6, 127.5, 124.7, 114.7 (aryl C), 23.2 ($CH_3$). $^{11}B$ NMR (128 MHz, $C_6D_6$): δ 38.0 (br, 1B). IR (KBr, $cm^{-1}$): ν 3060, 3003, 2922, 1592, 1522, 1489, 1446, 1414, 1402, 1384, 1358, 1241, 1087, 1016. HRMS (ESI): Calcd for $C_{23}H_{20}BClN^+$ $[M+H]^+$: 356.1372, found: 356.1373.

3b

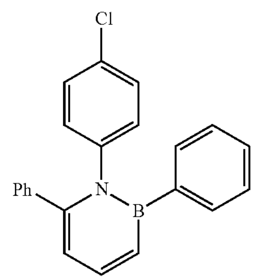

3b: Yield: 74%. Pale yellow solid. M.p.=145-147° C. $R_f$=0.65 (hexane/ethyl acetate=9:1). $^1H$ NMR (400 MHz, $C_6D_6$): δ 7.71 (dd, J=11.1, 6.7 Hz, 1H), 7.32-7.24 (m, 3H), 7.15-7.07 (m, 3H), 6.92-6.82 (m, 5H), 6.62-6.56 (m, 2H), 6.44 (dd, J=6.7, 1.5 Hz, 1H), 6.40-6.33 (m, 2H) (aryl CH). $^{13}C$ NMR (101 MHz, $C_6D_6$): δ 148.4, 144.1, 143.5, 138.8, 134.1, 132.1, 131.1, 123.0, 128.3, 127.8, 127.7, 127.7, 127.6, 114.5 (aryl C). $^{11}B$ NMR (128 MHz, $C_6D_6$): δ 36.9 (br, 1B). IR (KBr, $cm^{-1}$): ν 1594, 1570, 1523, 1488, 1447, 1432, 1413, 1401, 1384, 1363, 1287, 1272, 1235, 1195, 1164, 1087, 1027, 1016. HRMS (ESI): Calcd for $C_{22}H_{18}BClN^+$ $[M^+ H]^+$: 342.1215, found: 342.1219.

3c

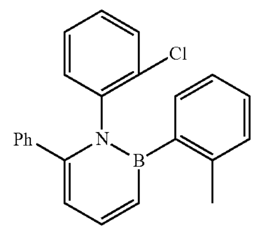

3c: Yield: 56%. Pale yellow solid. M.p.=119-121° C. $R_f$=0.7 (hexane/ethyl acetate=9:1). $^1H$ NMR (500 MHz, $C_6D_6$): δ 7.69 (dd, J=11.1, 6.7 Hz, 1H), 7.23-7.18 (m, 3H), 7.05 (d, J=7.6 Hz, 1H), 7.00 (t, J=7.4 Hz, 1H), 6.94-6.83 (m, 5H), 6.68 (d, J=8.0 Hz, 1H), 6.48 (d, J=6.7 Hz, 1H), 6.42 (t, J=7.6 Hz, 1H), 6.31 (t, J=7.7 Hz, 1H) (aryl CH), 2.49 (s, 3H) ($CH_3$). $^{13}C$ NMR (126 MHz, $C_6D_6$): δ 148.8, 143.8, 143.0, 140.0, 138.6, 132.4, 132.4, 129.8, 129.5, 129.3, 128.4, 127.8, 127.6, 127.5, 126.2, 124.4, 114.3 (aryl C), 23.4 ($CH_3$). $^{11}B$ NMR (128 MHz, $C_6D_6$): δ 37.8 (br, 1B). IR (KBr, $cm^{-1}$): ν 3061, 3004, 2919, 2855, 1593, 1577, 1522, 1490, 1477, 1458, 1438, 1411, 1384, 1359, 1290, 1264, 238, 1158, 1094, 1066, 1030. HRMS (ESI): Calcd for $C_{23}H_{20}BClN^+[M^+ H]^+$: 356.1372, found: 356.1375.

3d

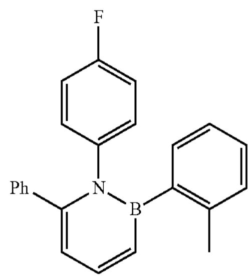

3d: Yield: 71%. Light brown oil. $R_f$=0.6 (hexane/ethyl acetate=9:1). $^1H$ NMR (400 MHz, $C_6D_6$): δ 7.68 (dd, J=11.0, 6.7 Hz, 1H), 7.15-7.10 (m, 2H), 7.05-6.94 (m, 5H), 6.91-6.83 (m, 3H), 6.57-6.51 (m, 2H), 6.47 (dd, J=6.7, 1.5 Hz, 1H), 6.29-6.19 (m, 2H) (aryl CH), 2.24 (s, 3H) ($CH_3$). $^{13}C$ NMR (101 MHz, $C_6D_6$): δ 160.7 (d, $^1J_{C-F}$=245.7 Hz), 148.8, 143.7, 141.2 (d, $^4J_{C-F}$=3.3 Hz), 139.2 (d, $^2J_{C-F}$=26.6 Hz), 132.7, 130.6 (d, $^3J_{C-F}$=8.3 Hz), 123.0, 129.2, 127.9, 127.5, 127.4, 124.7, 114.7, 114.6, 114.5 (aryl C), 23.3 ($CH_3$). $^{11}B$ NMR (128 MHz, $C_6D_6$): δ 37.9 (br, 1B). $^{11}F$ NMR (377 MHz, $CDCl_3$): δ −116.0 (m, 1F). IR (KBr, $cm^{-1}$): v 3003, 2963, 2920, 2857, 1591, 1522, 1505, 1488, 1444, 1407, 1384, 1357, 1289, 1234, 1220, 1179, 1153, 1095, 1073, 1028, 1016. HRMS (ESI): Calcd for $C_{22}H_{17}BFNNa^+$ $[M^+Na]^+$: 348.1330, found: 348.1368.

3e

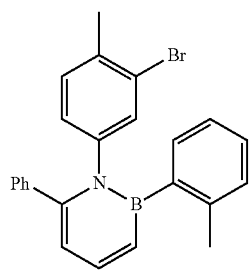

3e: Yield: 77%. Light brown oil. $R_f$=0.7 (hexane/ethyl acetate=9:1). $^1H$ NMR (400 MHz, $C_6D_6$): δ 7.67 (dd, J=11.0, 6.7 Hz, 1H), 7.21-7.18 (dd, J=6.6, 2.2 Hz, 1H), 7.16-7.09 (m, 2H), 7.04-6.96 (m, 5H), 6.91-6.80 (m, 3H), 6.57 (d, J=8.0, 2.2 Hz, 1H), 6.45 (dd, J=6.7, 1.5 Hz, 1H), 6.34-6.27 (m, 1H) (aryl CH), 2.26 (s, 3H), 1.72 (s, 3H) ($CH_3$). $^{13}C$ NMR (101 MHz, $C_6D_6$): δ 146.5, 142.0, 141.8, 137.2, 137.0, 33.6, 131.2, 130.6, 127.9, 127.8, 127.2, 125.9, 125.6, 125.5, 122.7, 121.5, 112.6 (aryl C), 21.2, 20.0 ($CH_3$). $^{11}B$ NMR (128 MHz, $C_6D_6$): δ 38.1 (br, 1B). IR (KBr, $cm^{-1}$): v 3060, 3003, 2921, 2857, 1593, 1566, 1522, 1490, 1446, 1412, 1384, 1359, 1281, 1265, 1240, 1199, 1157, 1090, 1038. HRMS (ESI): Calcd for $C_{24}H_{22}BBrN^+$ $[M^+H]^+$: 414.1023, found: 414.1024.

3f

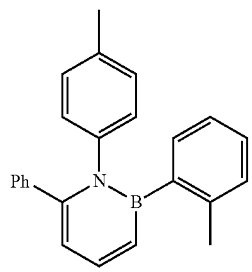

3f: Yield: 42%. Light brown oil. $R_f$=0.7 (hexane/ethyl acetate=9:1). $^1H$ NMR (400 MHz, $C_6D_6$): δ 7.65 (dd, J=11.0, 6.7 Hz, 1H), 7.14-7.07 (m, 2), 7.04-6.88 (m, 7H), 6.88-6.80 (m, 3H), 6.45 (dd, J=6.8, 1.5 Hz, 1H), 6.36-6.30 (m, 2H) (aryl CH), 2.21 (s, 3H) ($CH_3$). $^{13}C$ NMR (101 MHz, $C_6D_6$): δ 148.3, 144.9, 143.7, 139.3, 138.8, 137.0, 132.7, 131.1, 129.9, 129.2, 127.9, 127.6, 127.6, 124.7, 114.8, 91.0 (aryl C), 23.2 ($CH_3$). $^{11}B$ NMR (128 MHz, $C_6D_6$): δ 37.8 (br, 1B). IR (KBr, $cm^{-1}$): v 3064, 3001, 2926, 2853, 1593, 1522, 1483, 1412, 1384, 1357, 1240, 1010. HRMS (ESI): Calcd for $C_{23}H_{20}BIN^+$ $[M^+H]^+$: 448.0728, found: 448.0725.

3g

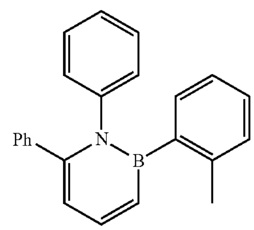

3g: Yield: 81%. Light brown oil. Rf=0.7 (hexane/ethyl acetate=9:1). $^1H$ NMR (400 MHz, $C_6D_6$): δ 7.71 (dd, J=11.0, 6.7 Hz, 1H), 7.21-7.15 (m, 2H), 7.07-6.95 (m, 5H), 6.91-6.82 (m, 3H), 6.81-6.75 (m, 2H), 6.66-6.59 (m, 2H), 6.59-6.53 (m, 1H), 6.50 (dd, J=6.7, 1.5 Hz, 1H) (aryl CH), 2.29 (s, 3H) ($CH_3$). $^{13}C$ NMR (101 MHz, $C_{66}$): δ 148.8, 145.2, 143.6, 139.4, 139.3, 132.8, 123.0, 129.3, 129.1, 127.8, 127.4, 127.3, 126.0, 124.6, 114.6 (aryl C), 23.3 ($CH_3$). $^{11}B$ NMR (128 MHz, $C_6D_6$): δ 38.2 (br, 1B). IR (KBr, $cm^{-1}$): v 3060, 3040, 3003, 2920, 1591, 1572, 1522, 1490, 1445, 1409, 1359, 1289, 1265, 1239, 1028.

HRMS (ESI): Calcd for $C_{23}H_{21}BN^+$ $[M^+H]^+$: 322.1762, found: 322.1764.

3h

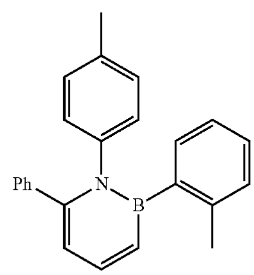

3h: Yield: 76%. Light brown oil. Rf=0.7 (hexane/ethyl acetate=9:1). $^1H$ NMR (500 MHz, $C_6D_6$): δ 7.72 (dd, J=11.0, 6.7 Hz, 1H), 7.28-7.22 (m, 1H), 7.17 (dd, J=10.9, 1.5 Hz, 1H), 7.11-7.06 (m, 2H), 7.02 (t, J=6.2 Hz, 3H), 6.90 (dd, J=8.3, 6.8 Hz, 2H), 6.86-6.82 (m, 1H), 6.71 (d, J=7.9 Hz, 2H), 6.51 (dd, J=6.7, 1.5 Hz, 1H), 6.45 (d, J=7.9 Hz, 2H) (aryl CH), 2.31 (s, 3H), 1.67 (s, 3H) ($CH_3$). $^{13}C$ NMR (126 MHz, $C_6D_6$): δ 149.1, 143.6, 142.7, 139.6, 139.4, 135.4, 132.8, 130.01, 129.1, 129.0, 128.6, 127.8, 127.4, 127.3, 124.6, 114.6 (aryl C), 23.4, 20.6, ($CH_3$). $^{11}B$ NMR (160 MHz, $C_6D_6$): δ 38.0 (br, 1B). IR (KBr, $cm^{-1}$): v 3060, 3030, 3002, 2954, 2921, 2861, 1592, 1522, 1509, 1489, 1445, 1412, 1383, 1360, 1289, 1265, 1240, 1179, 1156, 1109, 1090, 1075, 1029. HRMS (ESI): Calcd for $C_{24}H_{23}BN^+$ $[M^+H]^+$: 336.1918, found: 336.1921.

3i

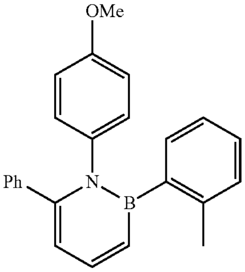

3i: Yield: 61%. Light brown oil. $R_f$=0.55 (hexane/ethyl acetate=9:1). $^1$H NMR (400 MHz, $C_6D_6$): δ 7.73 (dd, J=11.0, 6.7 Hz, 1H), 7.30-7.21 (m, 1H), 7.19 (s, 1H), 7.11-7.07 (m, 2H), 7.03 (dd, J=4.6, 1.5 Hz, 3H), 6.95-6.83 (m, 3H), 6.74-6.67 (m, 2H), 6.52 (dd, J=6.7, 1.5 Hz, 1H), 6.27-6.18 (m, 2H) (aryl CH), 2.90 (s, 3H) ($O_{c-3}$), 2.31 (s, 3H) ($CH_3$). $^{13}$C NMR (101 MHz, $C_6D_6$): b 157.6, 149.3, 143.6, 139.6, 139.4, 138.1, 132.9, 130.0, 129.1, 127.8, 127.4, 127.3, 124.7, 114.6, 113.1 (aryl C), 54.4 ($OCH_3$), 23.4 ($CH_3$). $^{11}$B NMR (128 MHz, $C_6D_6$): δ 38.2 (br, 1B). IR (KBr, $cm^{-1}$): v 3057, 3042, 3000, 2960, 2931, 2916, 2837, 1611, 1592, 1571, 1522, 1509, 1490, 1443, 1408, 1384, 1361, 1298, 1246, 1181, 1171, 1157, 1107, 1089, 1034. HRMS (ESI): Calcd for $C_{24}H_{23}BNO^+$ [$M^+$ H]$^+$: 352.1867, found: 352.1874.

3j

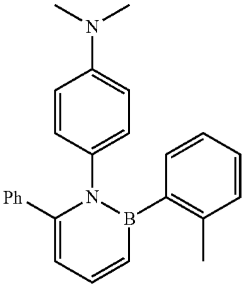

3j: Yield: 73%. Light brown oil. $R_f$=0.3 (hexane/ethyl acetate=9:1). $^1$H NMR (400 MHz, $C_6D_6$): δ 7.75 (dd, J=10.9, 6.7 Hz, 1H), 7.38-7.32 (m, 1H), 7.21-7.16 (m, 3H), 7.06-7.00 (m, 3H), 6.96-6.90 (m, 2H), 6.86-6.82 (m, 1H), 6.78-6.73 (m, 2H), 6.55 (dd, J=6.7, 1.5 Hz, 1H), 6.01 (d, J=8.9 Hz, 2H) (aryl CH), 2.36 (s, 3H), 2.14 (s, 6H) ($CH_3$). $^{13}$C NMR (101 MHz, $C_6D_6$): δ 149.7, 148.1, 143.4, 140.0, 139.4, 134.5, 133.0, 130.0, 129.6, 129.1, 127.8, 127.2, 127.1, 124.7, 114.6, 111.1 (aryl C), 39.6, 23.4 ($CH_3$). $^{11}$B NMR (128 MHz, $C_6D_6$): δ 38.4 (br, 1B). IR (KBr, $cm^{-1}$): v 3060, 3043, 2999, 2917, 2888, 2859, 2803, 1613, 1591, 1571, 1521, 1489, 1445, 1409, 1384, 1353, 1290, 1240, 1190, 1167, 1089. HRMS (SI): Calcd for $C_{25}H_{26}BN^+$ [$M^+$ H]$^+$: 365.2184, found: 365.2196.

3k

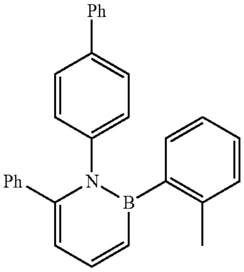

3k: Yield: 82%. Light brown oil. $R_f$=0.65 (hexane/ethyl acetate=9:1). $^1$H NMR (400 MHz, $C_6D_6$): δ 7.73 (dd, J=11.0, 6.7 Hz, 1H), 7.26 (dd, J=7.6, 2.0 Hz, 1H), 7.19 (dd, J=11.0, 1.5 Hz, 1H), 7.12-7.08 (m, 2H), 7.06-7.00 (m, 8H), 6.94-6.81 (m, 7H), 6.54 (dd, J=6.7, 1.5 Hz, 1H) (aryl CH), 2.33 (s, 3H) ($CH_3$). $^{13}$C NMR (101 MHz, $C_6D_6$): δ 148.8, 144.4, 143.7, 140.2, 139.5, 139.4, 138.7, 132.9, 130.0, 129.6, 129.2, 128.8, 127.9, 127.5, 127.4, 127.3, 127.1, 126.4, 124.7 (aryl C), 23.4 ($CH_3$). $^{11}$B NMR (128 MHz, $C_6D_6$): δ 38.5 (br, 1B). IR (KBr, $cm^{-1}$): v3058, 3032, 3003, 2918, 2859, 1719, 1592, 1571, 1522, 1487, 1446, 1412, 1384, 1359, 1265, 1240, 1179, 1157, 1110, 1076, 1029, 1009. HRMS (ESI): Calcd for $C_{29}H_{25}BN^+$ [$M^+$ H]$^+$: 398.2075, found: 398.2074.

31

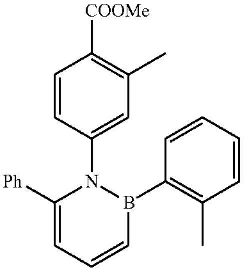

31: Yield: 76%. Light brown oil. $R_f$=0.45 (hexane/ethyl acetate=9:1). $^1$H NMR (400 MHz, $C_6D_6$): δ 7.68 (dd, J=11.0, 6.7 Hz, 1H), 7.50 (d, J=8.3 Hz, 1H), 7.19-7.11 (m, 3H), 7.02-6.92 (m, 5H), 6.88-6.77 (m, 3H), 6.69-6.59 (m, 2H), 6.47 (dd, J=6.7, 1.5 Hz, 1H) (aryl CH), 3.23 (s, 3H) ($COOCH_3$), 2.27 (d, J=13.9 Hz, 6H) ($CH_3$). $^{13}$C NMR (101 MHz, $C_6D_6$): δ 166.5 ($COOCH_3$), 148.3, 148.2, 143.8, 140.7, 139.3, 139.0, 132.8, 132.6, 130.8, 129.8, 129.1, 127.9, 127.7, 127.5, 127.2, 126.6, 124.7, 114.7 (aryl C), 51.0 ($COOCH_3$), 23.2, 21.7 ($CH_3$). $^{11}$B NMR (160 MHz, $C_6D_6$): δ 38.1 (br, 1B). IR (KBr, $cm^{-1}$): v3058, 3001, 2950, 2928, 2861, 1719, 1654, 1593, 1572, 1522, 1490, 1437, 1413, 1384, 1358, 1255, 1192, 1142, 1084, 1029. HRMS (ESI): Calcd for $C_{26}H_{25}BNO^+$ [$M^+$ H]$^+$: 394.1973, found: 394.1975.

3m

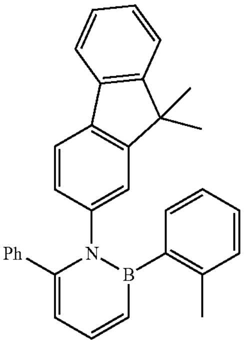

3m: Yield: 82%. Light brown oil. $R_f$=0.7 (hexane/ethyl acetate=9:1). $^1$H NMR (400 MHz, $C_6D_6$): δ 7.77 (dd, J=11.0, 6.7 Hz, 1H), 7.32-7.19 (m, 3H), 7.12-7.01 (m, 5H), 7.01-6.93 (m, 4H), 6.87-6.74 (m, 5H), 6.57 (dd, J=6.8, 1.5 Hz, 1H) (aryl CH), 2.27 (s, 3H), 1.08 (d, J=4.9 Hz, 6H) ($CH_3$). $^{13}$C NMR (101 MHz, $C_6D_6$): δ 153.9, 153.4, 149.0, 144.3, 143.7, 139.5, 139.4, 138.9, 133.0, 130.0, 129.1, 127.8, 127.3, 127.3, 127.3, 127.2, 124.6, 124.3, 122.7, 120.5, 119.2, 114.5 (aryl C), 46.6 ($CMe_2$), 26.8, 26.7, 23.3 ($CH_3$). $^{11}B$ NMR (160 MHz, $C_6D_6$): δ 38.2 (br, 1B). IR (KBr, $cm^{-1}$): v 3060, 3042, 3015, 2959, 2921, 2859, 1592, 1522, 1490, 1472, 1460, 1448, 1409, 1383, 1359, 1280, 1265, 1244, 1156, 1090, 1076, 1028, 1008. HRMS (ESI): Calcd for $C_{32}H_{29}BN^+$ [$M^+$ H]$^+$: 438.2388, found: 438.388.

3n

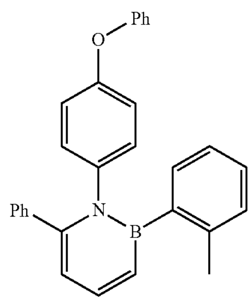

3n: Yield: 80%. Pale yellow solid. M.p.=96-98° C. $R_f$=0.65 (hexanelethyl acetate=9:1). $^1H$ NMR (400 MHz, $C_6D_6$): δ 7.71 (dd, J=11.0, 6.7 Hz, 1H), 7.18 (d, J=1.4 Hz, 1H), 7.15 (d, J=1.5 Hz, 1H), 7.09-6.96 (m, 7H), 6.95-6.88 (m, 3H), 6.83-6.76 (m, 1H), 6.68-6.60 (m, 4H), 6.50 (dd, J=6.7, 1.5 Hz, 1H), 6.41-6.34 (m, 2H) (aryl CH), 2.30 (s, 3H) ($CH_3$). $^{13}C$ NMR (101 MHz, $C_6D_6$): δ 158.0, 155.0, 148.9, 143.7, 140.7, 39.4, 139.3, 132.9, 130.5, 130.1, 129.9, 129.1, 127.8, 127.4, 127.3, 124.6, 123.1, 118.8, 118.6, 114.4 (aryl C), 23.4 ($CH_3$). $^{11}B$ NMR (128 MHz, $C_6D_6$): δ 38.6 (br, 1B). IR (KBr, $cm^{-1}$): v 3060, 3041, 3001, 2918, 2859, 1591, 1522, 1502, 1489, 1445, 1408, 1384, 1360, 1290, 1231, 1199, 1164, 1100, 1075, 1027. HRMS (ESI): Calcd for $C_{29}H_{25}BNO^+$ [$M^+$ H]$^+$: 414.2024, found: 414.2029.

3o

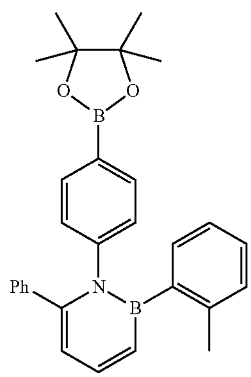

3o: Yield: 52%. Light brown oil. $R_f$=0.5 (hexane/ethyl acetate=9:1). $^1H$ NMR (400 MHz, $C_6D_6$): δ 7.72-7.63 (m, 3H), 7.20 (dd, J=6.9, 2.0 Hz, 1H), 7.15-7.11 (m, 1H), 7.04-6.99 (m, 2H), 6.97-6.90 (m, 3H), 6.88-6.73 (m, 5H), 6.48 (dd, J=6.7, 1.5 Hz, 1H) (aryl CH), 2.24 (s, 3H), 0.92 (s, 12H) ($CH_3$). $^{13}C$ NMR (101 MHz, $C_6D_6$): δ 148.7, 148.0, 143.6, 139.3, 139.2, 134.7, 132.7, 129.9, 129.1, 129.0, 127.8, 127.5, 127.4, 124.6, 114.7 (aryl C), 83.6 ($CMe_2$), 24.9, 23.3 ($CH_3$). $^{11}B$ NMR (128 MHz, $C_6D_6$): δ 38.0 (br, 1B), 31.2 (br, 1B). IR (KBr, $cm^{-1}$): v 3062, 2995, 2978, 2924, 1604, 1591, 1566, 1522, 1490, 1458, 1446, 1399, 1384, 1359, 1320, 1266, 1239, 1213, 1143, 1086, 1021. HRMS (ES): Calcd for $C_{29}H_{32}B_2NO^+$ [$M^+$ H]$^+$: 448.2614, found: 448.2622.

3p

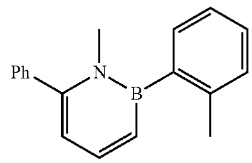

3p: Yield: 77%. Light brown oil. $R_f$=0.7 (hexane/ethyl ac tate=9:1). $^1H$ NMR (400 MHz, $C_6D_6$): δ 7.63 (dd, J=10.9, 6.7 Hz, 1H), 7.48 (dd, J=6.8, 2.0 Hz, 1H), 7.25-7.19 (m, 3H), 7.10-7.02 (m, 6H), 6.31 (dd, J=6.7, 1.6 Hz, 1H) (aryl CH), 3.03 (s, 3H) ($NCH_3$), 2.32 (s, 3H) ($CH_3$). $^{13}C$ NMR (101 MHz, $C_6D_6$): δ 150.2, 143.2, 139.7, 139.3, 132.6, 129.6, 129.3, 128.5, 125.5, 114.2 (aryl C), 39.5 ($NCH_3$), 22.9 ($CH_3$). $^{11}B$ NMR (128 MHz, $C_6D_6$): δ 37.7 (br, 1B). IR (KBr, $cm^1$): v 3060, 3007, 2945, 2922, 1683, 1589, 1527, 1492, 1445, 1412, 1359, 1282, 1218, 1182, 1032, 1016, 1001. HRMS (ESI): Calcd for $C_{18}H_{19}BN^+$ [$M^+$ H]$^+$: 260.1605, found: 260.1611.

3q

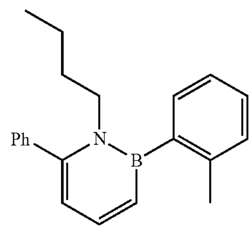

3q: Yield: 80%. Colorless oil. $R_f$=0.7 (hexane/ethyl acetate=9:1). $^1H$ NMR (500 MHz, $C_6D_6$): δ 7.62 (dd, J=10.9, 6.6 Hz, 1H), 7.52 (dd, J=5.5, 2.4 Hz, 1H), 7.22 (d, J=3.9 Hz, 5H), 7.10-7.02 (m, 4H), 6.30 (d, J=6.6 Hz, 1H) (aryl CH), 3.80 (dd, J=11.4, 5.1 Hz, 1H), 3.65-3.59 (m, 1H) ($NCH_2$), 2.40 (s, 3H) (CH3), 1.34-1.20 (m, 2H), 0.67-0.62 (m, 2H) ($CH_2$), 0.35 (t, J=7.3 Hz, 3H) ($CH_3$). $^{13}C$ NMR (126 MHz, $C_6D_6$): δ 149.6, 143.0, 139.4, 139.3, 132.5, 129.6, 129.5, 127.7, 125.3, 114.8 (aryl C), 49.7, 34.8, 23.1, 19.9, 13.3 (tBu, Me). $^{11}B$ NMR (128 MHz, $C_6D_6$): δ 37.9 (br, 1B). IR (KBr, $cm^{-1}$): v 3059, 3001, 2959, 2930, 1872, 2861, 1685, 1637, 1589, 1527, 1490, 1444, 1415, 1384, 1356, 1280, 1225, 1195, 1177, 1142, 1114, 1074, 1026. HRMS (ESI): Calcd for $C_{21}H_{25}BN^+$ [$M^+$ H]$^+$: 302.2075, found: 302.2076.

3r

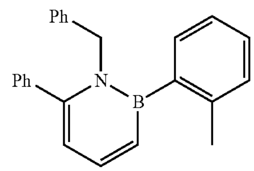

3r: Yield: 76%. Light brown oil. $R_f$=0.7 (hexane/ethyl acetate=9:1). $^1H$ NMR (400 MHz, $C_6D_6$): δ 7.64 (dd, J=10.9, 6.6 Hz, 1H), 7.53-7.46 (m, 1H), 7.16-7.14 (m, 2H), 7.12-7.08 (m, 2H), 6.99-6.88 (m, 5H), 6.85 (dt, J=4.6, 1.6 Hz, 3H), 6.54-6.48 (m, 2H), 6.32 (dd, J=6.6, 1.6 Hz, 1H) (aryl CH), 4.91 (s, 2H) ($CH_2$), 2.33 (s, 3H) ($CH_3$). $^{13}C$ NMR (101 MHz, $C_6D_6$): δ 150.1, 143.4, 140.3, 139.7, 138.9, 132.4, 129.5, 129.4, 128.2, 127.9, 127.9, 126.7, 125.3, 115.1 (aryl C), 53.9 ($CH_2$), 23.0 ($CH_3$). $^{11}B$ NMR (128 MHz, $C_6D_6$): δ 38.5 (br, 1B). IR (KBr, $cm^{-1}$): v 3061, 3005, 2950, 2857, 1590, 1527, 1490, 1452, 1414, 1384, 1346, 1329, 1288, 1230, 1157, 1126, 1074, 1029. HRMS (ESI): Calcd for $C_{24}H_{23}BN^+$ [$M^+$ H]$^+$: 336.1918, found: 336.1922.

3s

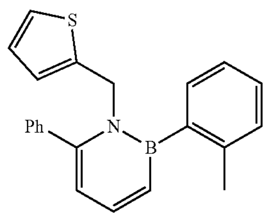

3s: Yield: 70%. Colorless oil. $R_f$=0.7 (hexane/ethyl acetate=9:1). $^1H$ NMR (400 MHz, $C_6D_6$): δ 7.63-7.55 (m, 2H), 7.21-7.17 (m, 3H), 7.07-6.99 (T, 6H), 6.61 (dd, J=5.1, 1.3 Hz, 1H), 6.42 (dd, J=5.1, 3.5 Hz, 1H), 6.28 (dd, J=6.6, 1.6 Hz, 1H), 6.01-5.96 (m, 1H) (aryl CH), 5.10-4.90 (m, 2H) ($CH_2$), 2.34 (s, 3H) ($CH_3$). $^{13}C$ NMR (101 MHz, $C_6D_6$): δ 149.5, 143.6, 143.5, 139.9, 138.7, 132.6, 129.6, 129.5, 128.0, 128.0, 126.3, 125.3, 125.0, 124.4, 115.3 (aryl C), 49.2 ($CH_2$), 23.0 ($CH_3$). $^{11}B$ NMR (128 MHz, $C_6D_6$): δ 38.4 (br, 1B). IR (KBr, $cm^{-1}$): v 3059, 3022, 3003, 2947, 2920, 2859, 1590, 1527, 1489, 1443, 1414, 1384, 1357, 1335, 1288, 1226, 1155, 1122, 1075, 1028. HRMS (ESI): Calcd or $C_{22}H_{21}BNS^+$ [$M^+$ H]$^+$: 342.1482, found: 342.1486.

3t, 6-phenyl-1-propyl-2-(o-tolyl)-1,2-dihydro-1,2-azaborinine, was made by procedure A, described above.

3u, 6-phenyl-1-(3-phenylpropyl)-2-(o-tolyl)-1,2-dihydro-1,2-azaborinine, was made by procedure A, described above.

3v, 1-(4-methoxybenzyl)-6-phenyl-2-(o-tolyl)-1,2-dihydro-1,2 azaborinine, was made by procedure A, described above.

3w, 1-cyclohexyl-6-phenyl-2-(o-tolyl)-1,2-dihydro-1,2-azaborinine, was made by procedure A, described above.

3x, 1-isopropyl-6-phenyl-2-(o-tolyl)-1,2-dihydro-1,2-azaborinine, was made by procedure A, described above.

3y, 1-(2,3-dihydro-1H-inden-2-yl)-6-phenyl-2-(o-tolyl)-1,2-dihydro-1,2-azaborinine, was made by procedure A, described above.

3z

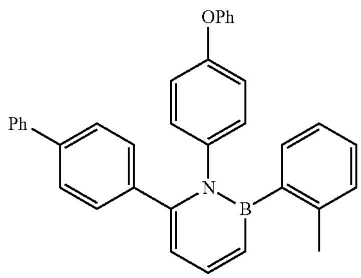

3z: Yield: 79%. Light brown oil. $R_f$=0.65 (hexane/ethyl acetate=9:1). $^1H$ NMR (400 MHz, $C_6D_6$): δ 7.75 (dd, J=11.0, 6.7 Hz, 1H), 7.36-7.30 (m, 2H), 7.24-7.18 (m, 4H), 7.16-7.14 (m, 2H), 7.13-7.00 (m, 6H), 6.95-6.88 (m, 2H), 6.78-6.71 (m, 1H), 6.71-6.61 (m, 4H), 6.57 (dd, J=6.7, 1.5 Hz, 1H), 6.43-6.36 (m, 2H) (aryl CH), 2.32 (s, 3H) ($CH_3$). $^{13}C$ NMR (101 MHz, $C_6D_6$): δ 158.1, 155.0, 148.7, 143.7, 140.8, 140.7, 140.4, 139.5, 138.2, 132.9, 130.6, 129.9, 129.2, 129.1, 127.7, 127.3, 127.3, 126.6, 124.6, 123.1, 119.0, 118.5, 114.5 (aryl C), 23.4 ($CH_3$). $^{11}B$ NMR (128 MHz, $C_6D_6$): δ 39.1 (br, 1B). IR (KBr, $cm^{-1}$): v 3003, 2918, 2853, 1591, 1488, 1408, 1384, 1357, 1290, 1264, 1230, 1199, 1164, 1099, 1023, 1008. HRMS (ESI): Calcd for $C_{35}H_{29}BNO^+$ [$M^+$ H]$^+$: 490.2337, found: 40.2341.

3aa

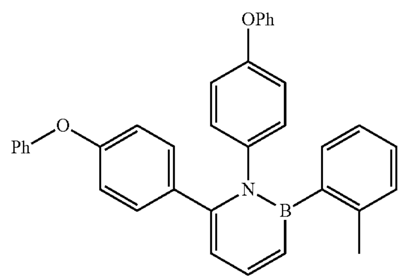

3aa: Yield: 72%. Light brown oil. $R_f$=0.65 (hexane/ethyl acetate=9:1). $^1H$ NMR (400 MHz, $C_6D_6$): δ 7.72 (dd, J=11.0, 6.7 Hz, 1H), 7.21-7.14 (m, 3H), 7.10-6.98 (m, 7H), 6.95-6.90 (m, 2H), 6.88-6.84 (m, 2H), 6.83-6.78 (m, 1H), 6.74-6.66 (m, 4H), 6.64-6.58 (m, 2H), 6.51 (dd, J=6.7, 1.5 Hz, 1H), 6.45-6.39 (m, 2H) (aryl CH), 2.31 (s, 3H) ($CH_3$).

$^{13}C$ NMR (101 MHz, $C_6D_6$): δ 158.1, 157.3, 157.2, 155.1, 148.4, 143.7, 140.7, 139.4, 134.0, 132.9, 131.6, 130.6, 130.1, 129.9, 129.1, 127.3, 124.6, 123.8, 123.2, 119.5, 118.8, 118.6, 118.0, 114.2 (aryl C), 23.4 ($CH_3$). $^{11}B$ NMR (128 MHz, $C_6D_6$): δ 38.2 (b r, 1B). IR (KBr, $cm^{-1}$): v 3060, 3040, 3004, 2917, 2859, 1589, 1489, 1407, 1384, 1359, 1331, 1234, 1200, 1167, 1103, 1072, 1015. HRMS (ESI): Calcd for $C_{35}H_{29}BNO^+$ [$M^+$ H]$^+$: 506.2286, found: 506.2290.

3ab

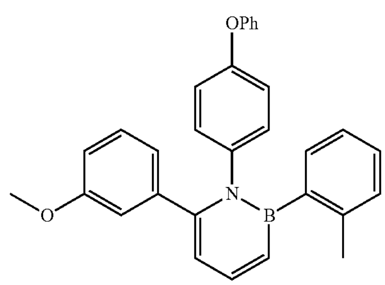

3ab: Yield: 49%. Light brown oil. $R_f$=0.5 (hexane/ethyl acetate=9:1). $^1H$ NMR (500 MHz, $C_6D_6$): δ 7.71 (dd, J=11.0, 6.7 Hz, 1H), 7.21-7.14 (m, 2H), 7.10-6.96 (m, 5H), 6.88 (t, J=7.9 Hz, 1H), 6.83-6.76 (m, 1H), 6.76-6.63 (m, 6H), 6.61-6.54 (m, 2H), 6.42-6.36 (m, 2H) (aryl CH), 3.18 (s, 3H) ($OCH_3$), 2.30 (s, 3H) ($CH_3$). $^{13}C$ NMR (126 MHz, $C_6D_6$): δ 159.4, 158.2, 155.0, 148.8, 143.7, 140.9, 140.5, 139.5, 132.9, 130.5, 129.9, 129.1, 129.0, 127.3, 124.6, 123.1, 122.6, 118.9, 118.5, 115.8, 114.3, 113.5 (aryl C), 54.7 ($OCH_3$), 23.4 ($CH_3$). $^{11}B$ NMR (160 MHz, $C_6D_6$): δ 38.4 (br, 1B). IR (KBr, $cm^{-1}$): v3060, 3042, 3003, 2957, 2934, 2916, 2833, 1590, 1577, 1522, 1503, 1488, 1406, 1384, 1357, 1318, 1288, 1228, 1165, 1098, 1048. HRMS (ESI): Calcd for $C_{30}H_{27}BNO_2^+$ $[M^+ H]^+$: 444.2129, found: 444.2132.

3ac

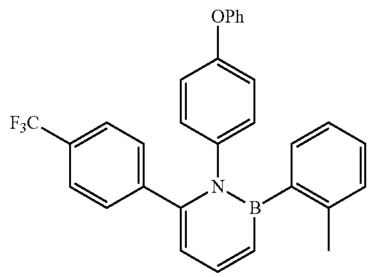

3ac: Yield: 82%. Light brown oil. $R_f$=0.65 (hexane/ethyl acetate=9:1). 1H NMR (400 MHz, $C_6D_6$): δ 7.67 (dd, J=11.0, 6.7 Hz, 1H), 7.19 (d, J=1.5 Hz, 1H), 7.14 (d, J=1.3 Hz, 1H), 7.11-6.99 (m, 7H), 6.85 (d, J=8.1 Hz, 2H), 6.83-6.77 (m, 1H), 6.62 (dd, J=8.7, 1.1 Hz, 2H), 6.52-6.47 (m, 2H), 6.35-6.32 (m, 3H) (aryl CH), 2.28 (s, 3H) ($CH_3$). $^{13}C$ NMR (126 MHz, $C_6D_6$): δ 157.9, 155.3, 147.3, 143.4, 142.7, 140.1, 139.4, 132.8, 130.3, 129.9, 129.4 (q, $^2J_{C\text{-}CF3}$=32.4 Hz), 129.2, 127.5, 124.7 (q, $^3J_{C\text{-}CF3}$=3.9 Hz) (aryl C), 124.7 (q, $1J_{C\text{-}CF3}$=272.9 Hz) (CF3), 124.7, 123.3, 119.0, 118.5, 114.6 (aryl C), 23.3 ($CH_3$). $^{11}B$ NMR (128 MHz, $C_6D_6$): δ 38.1 (br, 1B). $^{11}F$ NMR (377 MHz, $C_6D_6$): δ −62.3 (m, 3F) ($CF_3$). IR (KBr, $cm^{-1}$): ν 1598, 1527, 1502, 1489, 1406, 1384, 1325, 1231, 1166, 1126, 1109, 1068, 1018. HRMS (ESI): Calcd for $C_{30}H_{24}BF_3NO^+$ $[M^+ H]^+$: 482.1898, found: 482.1903.

3ad

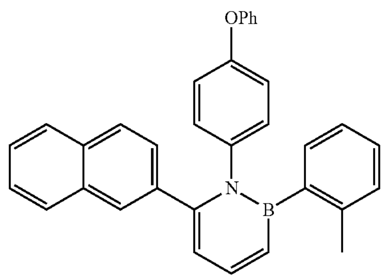

3ad: Yield: 55%. Light brown oil. $R_f$=0.65 (hexane/ethyl acetate=9:1). $^1H$ NMR (500 MHz, $C_6D_6$): δ 7.76 (dd, J=11.0, 6.7 Hz, 1H), 7.59 (s, 1H), 7.56 (d, J=7.9 Hz, 1H), 7.48 (d, J=7.8 Hz, 1H), 7.31 (d, J=8.5 Hz, 1H), 7.24-7.17 (m, 4H), 7.10-7.02 (m, 4H), 6.92 (t, J=7.7 Hz, 2H), 6.76 (t, J=7.4 Hz, 1H), 6.65 (d, J=8.7 Hz, 2H), 6.60 (d, J=6.7 Hz, 1H), 6.57-6.48 (m, 2H), 6.28 (d, J=8.7 Hz, 2H) (aryl CH), 2.33 (s, 3H) ($CH_3$). $^{13}C$ NMR (101 MHz, $C_6D_6$): δ 158.2, 154.9, 148.9, 143.7, 140.7, 139.5, 136.9, 133.3, 133.0, 132.7, 130.6, 129.8, 129.4, 129.2, 127.9, 127.8, 127.4, 127.2, 126.6, 126.6, 124.6, 122.9, 119.0, 118.4, 114.9 (aryl C), 23.4 ($CH_3$). $^{11}B$ NMR (128 MHz, $C_6D_6$): δ 38.2 (br, 1B). IR (KBr, $cm^{-1}$): ν 3044, 3003, 2920, 2857, 1618, 1598, 1527, 1503, 1489, 1406, 1384, 1363, 1325, 1290, 1230, 1166, 1126, 1109, 1068, 1018. HRMS (ESI): Calcd for $C_{33}H_{27}BNO^+$ $[M^+ H]^+$: 464.2180, found: 464.2188.

3ae

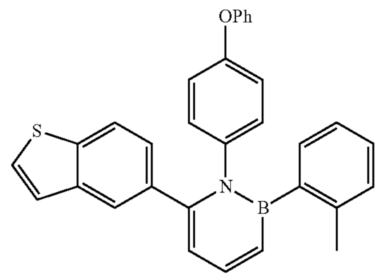

3ae: Yield: 53%. Light brown oil. $R_f$=0.55 (hexane/ethyl acetate=9:1). $^1H$ NMR (500 MHz, $C_6D_6$): δ 7.76 (dd, J=11.0, 6.7 Hz, 1H), 7.46 (d, J=1.6 Hz, 1H), 7.26 (d, J=8.4 Hz, 1H), 7.23-7.18 (m, 2H), 7.09-7.01 (m, 4H), 6.96 (t, J=7.8 Hz, 2H), 6.90-6.83 (m, 3H), 6.78 (t, J=7.3 Hz, 1H), 6.62 (d, J=8.6 Hz, 2H), 6.55 (t, J=6.5 Hz, 2H), 6.30 (d, J=8.6 Hz, 2H) (aryl CH), 2.33 (s, 3H) ($CH_3$). $^{13}C$ NMR (101 MHz, $C_6D_6$): δ 158.2, 154.8, 149.0, 143.7, 140.8, 139.5, 139.5, 139.1, 135.5, 132.9, 130.5, 129.8, 129.2, 127.3, 127.3, 126.4, 125.2, 124.6, 124.0, 122.9, 121.7, 119.1, 118.3, 114.8 (aryl C), 23.4 ($CH_3$). $^{11}B$ NMR (128 MHz, $C_6D_6$): δ 38.8 (br, 1B). IR (KBr, $cm^{-1}$): ν 3005, 2922, 2854, 1590, 1522, 1502, 1488, 1458, 1438, 1420, 1405, 1384, 1360, 1330, 1289, 1230, 1164, 1092, 1049, 1023, 1002. HRMS (ESI): Calcd for $C_{31}H_{25}BNOS^+$ $[M^+ H]^+$: 470.1744, found: 470.1745.

3af

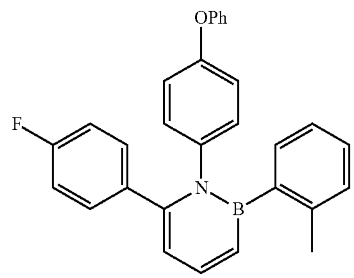

3af: Yield: 79%. Light brown oil. $R_f$=0.65 (hexane/ethyl acetate=9:1). $^1H$ NMR (400 MHz, $C_6D_6$): δ 7.68 (dd, J=11.0, 6.7 Hz, 1H), 7.16 (t, J=1.5 HZ, 1H), 7.15-7.15 (m, 1H), 7.09-6.96 (m, 5H), 6.81-6.77 (m, 3H), 6.66-6.64 (m, 2H), 6.57-6.53 (m, 4H), 6.42-6.35 (m, 3H) (aryl CH), 2.30 (s, 3H) ($CH_3$). $^{13}C$ NMR (101 MHz, $C_6D_6$): δ 162.3 (d, $^1J_{C\text{-}F}$=247.5 Hz), 157.9, 155.2, 147.8, 143.6, 140.5, 139.4, 135.2 (d, $^4J_{C\text{-}F}$=3.7 Hz), 132.8, 131.8 (d, $^3J_{C\text{-}F}$=8.1 Hz), 130.4, 129.9, 129.2, 127.4, 124.6, 123.3, 118.8, 118.6, 114.8 (d, $^2J_{C\text{-}F}$=21.5 Hz), 114.3 (aryl C), 23.3 ($CH_3$). $^{11}B$ NMR (128 MHz, $C_6D_6$): δ 38.4 (br, 1B). $^{19}F$ NMR (377 MHz, $C_6D_6$): δ −114.05 (m, 1F). IR (KBr, $cm^{-1}$): ν 3003, 2920, 2855, 1598, 1525, 1502, 1489, 1406, 1384, 1361, 1290, 1232, 1159, 1098, 1015. HRMS (ESI): Calcd for $C_{29}H_{24}BFNO^+$$[M^+ H]^+$: 432.1929, found: 432.1922.

3ag

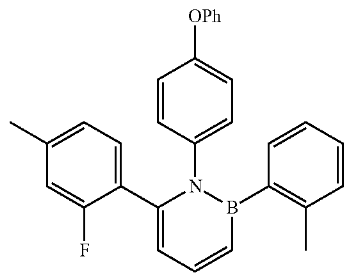

3ag: Yield: 57%. Light brown oil. $R_f$=0.65 (hexane/ethyl acetate=9:1). $^1$H NMR (400 MHz, $C_6D_6$): δ 7.70 (dd, J=11.0, 6.7 Hz, 1H), 7.19 (dd, J=11.0, 0.4 Hz, 1H), 7.14 (d, J=1.5 Hz, 1H), 7.07-6.94 (m, 5H), 6.86 (t, J=7.7 Hz, 1H), 6.78 (t, J=7.4 Hz, 1H), 6.60 (d, J=8.4 Hz, 2H), 6.50-6.46 (m, 2H), 6.45-6.38 (m, 3H) (aryl CH), 2.31 (i, 3H), 1.79 (s, 3H) ($CH_3$). $^{13}$C NMR (101 MHz, $C_6D_6$): δ 159.5 (d, $^1J_{C-F}$=246.4 Hz), 158.0, 155.3, 143.4, 140.8 (d, $^3J_{C-F}$=8.0 Hz), 140.6, 139.5, 132.9, 131.7 (d, $^4J_{C-F}$=3.3 Hz), 130.1, 129.8, 129.1, 127.3, 124.6, 124.5, 124.4, 124.3, 123.1, 118.6, 116.0 (d, $^2J_{C-F}$=21.9 Hz), 114.7 (aryl C), 23.3, 20.8 ($CH_3$). $^{11}$B NMR (128 MHz, $C_6D_6$): δ 38.5 (br, 1B). $^{11}$ F NMR (377 MHz, $C_6D_6$): δ −112.02 (m, 1F). IR (KBr, cm$^{-1}$): v3062, 3042, 3004, 2920, 2857, 1628, 1599, 1571, 1524, 1502, 1489, 1438, 1410, 1384, 1362, 1331, 1285, 1265, 1231, 1199, 1165, 1132, 1099, 1080, 1016. HRMS (ESI): Calcd for $C_{30}H_{26}BFNO^+$[$M^+$ H]$^+$: 446.2086, found: 446.2092.

3ah

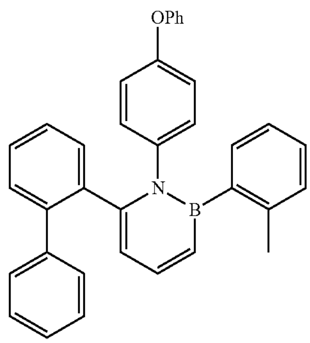

3ah: Yield: 51%. Light brown oil. $R_f$=0.65 (hexane/ethyl acetate=9:1). $^1$H NMR (400 MHz, $C_6D_6$): δ 7.67 (dd, J=11.0, 6.7 Hz, 1H), 7.34 (dd, J=7.6, 1.8 Hz, 1H), 7.12 (dd, J=11.0, 1.5 Hz, 1H), 7.07-6.87 (m, 14H), 6.83-6.77 (m, 1H), 6.70-6.64 (m, 2H), 6.56 (dd, J=6.7, 1.5 Hz, 1H), 6.50 (dd, J=8.6, 2.6 Hz, 1H), 6.38 (dd, J=8.6, 2.8 Hz, 1H), 6.12 (dd, J=8.6, 2.8 Hz, 1H), 5.49 (d, J=8.6 Hz, 1H) (aryl CH), 2.24 (s, 3H) ($CH_3$). $^{13}$C NMR (101 MHz, $C_0D_6$): δ 158.3, 154.6, 148.7, 143.1, 140.9, 140.5, 139.6, 137.8, 132.4, 131.9, 130.4, 130.0, 129.9, 129.8, 129.0, 128.9, 128.2, 127.3, 127.0, 127.0, 124.5, 123.0, 118.4, 118.2, 117.9, 115.7 (aryl C), 23.2 ($CH_3$). $^{11}$B NMR (128 MHz, $C_6D_6$): δ 38.4 (br, 1B). IR (KBr, cm$^{-1}$): v 3059, 3005, 2922, 2855, 1591, 1522, 1502, 1489, 1476, 1458, 1449, 1433, 1406, 1384, 1362, 1290, 1230, 1199, 1165, 1085, 1016. HRMS (ESI): Calcd for $C_{35}H_{29}BNO^+$ [$M^+$ H]$^+$: 490.2337, found: 490.2337.

3ai

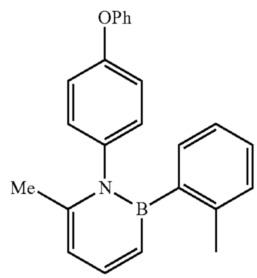

3ai: Yield: 46%. Light brown oil. $R_f$=0.65 (hexane/ethyl acetate=9:1). $^1$H NMR (400 MHz, $C_6D_6$): δ 7.64 (dd, J=11.0, 6.7 Hz, 1H), 7.13-7.09 (m, 1H), 7.07-6.93 (m, 6H), 6.87-6.79 (m, 1H), 6.78-6.70 (m, 2H), 6.57 (m, 4H), 6.27-6.19 (m, 1H) (aryl CH), 2.29 (s, 3H), 1.83 (s, 3H) ($CH_3$). $^{13}$C NMR (101 MHz, $C_6D_6$): δ 157.8, 155.9, 144.9, 144.0, 140.4, 139.3, 132.8, 130.0, 129.2, 129.0, 127.1, 124.4, 123.4, 119.0, 119.0, 112.1 (aryl C), 23.4, 22.2 ($CH_3$).

$^{11}$B NMR (128 MHz, $C_6D_6$): δ 37.7 (br, 1B). IR (KBr, cm$^{-1}$): v 3209, 3041, 3004, 2921, 2852, 1701, 1685, 1654, 1637, 1602, 1522, 1505, 1489, 1437, 1411, 1384, 1369, 1287, 1227, 1198, 1164, 1100, 1073, 1034. HRMS (ESI): Calcd for $C_{24}H_{23}BNO^+$ [$M^+$ H]$^+$: 352.1867, found: 352.1872.

3aj

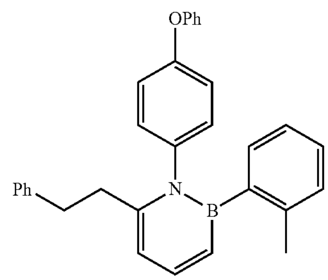

3aj: Yield: 41%. Light brown oil. $R_f$=0.65 (hexane/ethyl acetate=9:1). $^1$H NMR (400 MHz, $C_6D_6$): δ 7.68 (dd, J=11.0, 6.8 Hz, 1H), 7.12-6.96 (m, 10H), 6.86-6.81 (m, 3H), 6.78-6.72 (m, 2H), 6.62 (d, J=8.7 Hz, 2H), 6.56 (d, J=8.7 Hz, 2H), 6.28 (dd, J=6.8, 1.4 Hz, 1H) (aryl CH), 2.62 (m, 4H) ($CH_2$), 2.29 (s, 3H) ($CH_3$). $^{13}$C NMR (10 MHz, $C_6D_6$): δ 155.8, 148.1, 144.0, 141.4, 139.8, 139.2, 132.7, 130.0, 129.0, 128.8, 128.6, 127.1, 126.5, 124.4, 123.3, 119.2, 118.8, 111.7 (aryl C), 36.8, 36.6 ($CH_2$), 23.5 ($CH_3$). $^{11}$B NMR (128 MHz, $C_6D_6$): δ 38.3 (br, 1B). IR (KBr, cm$^{-1}$): v 3366, 3061, 3038, 3027, 2921, 2852, 1709, 1670, 1637, 1600, 1522, 1506, 1489, 1454, 1411, 1384, 1284, 1233, 1164, 1101, 1073, 1024. HRMS (ESI): Calcd for $C_{31}H_{29}BNO^+$ [$M^+$ H]$^+$: 442.2337, found: 442.2333.

3ak

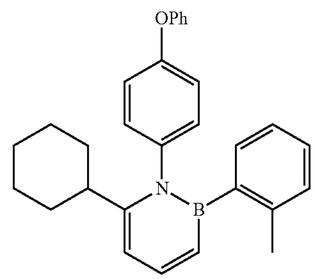

3ak: Yield: 62%. Light brown oil. $R_f$=0.7 (hexane/ethyl acetate=9:1). $^{1}$H NMR (400 MHz, $C_6D_6$): δ 7.77 (dd, J=10.9, 7.0 Hz, 1H), 7.10-7.06 (m, 1), 7.05-6.97 (m, 6H), 6.85-6.76 (m, 3H), 6.75-6.68 (m, 2H), 6.61 (d, J=8.7 Hz, 2H), 6.37 (dd, J=7.0, 1.4 Hz, 1H) (aryl CH), 2.49-2.40 (m, 1H) (CH), 2.28 (s, 3H) ($CH_3$), 1.86-1.79 (m, 2H), 1.59-1.54 (m, 2H), 1.49-1.44 (m, 1H), 1.30-1.24 (m, 2H), 1.08-1.01 (m, 1H), 0.95-0.89 (m, 2H) ($CH_2$). $^{13}$C NMR (126 MHz, $C_6D_6$): δ 158.1, 155.8, 154.3, 144.2, 140.0, 139.2, 132.7, 130.0, 128.9, 126.9, 124.3, 123.3, 119.2, 118.8, 108.8 (aryl C), 41.2, 34.4, 27.0, 26.2, 23.5 (Cyclohexyl and Me). $^{11}$B NMR (128 MHz, $C_6D_6$): δ 37.7 (br, 1B). IR (KBr, $cm^{-1}$): v 2927, 2853, 1600, 1522, 1503, 1489, 1449, 1412, 1384, 1349, 1230, 1164, 1097, 1071, 1023. HRMS (ESI): Calcd for $C_{29}H_{31}BNO^+$ [$M^+$ H]$^+$: 420.2493, found: 420.2494.

3al

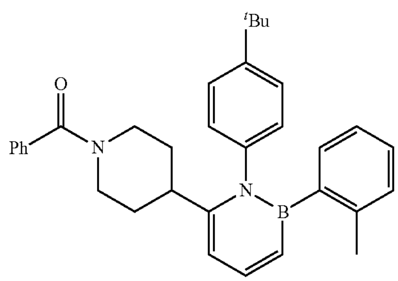

3al: Yield: 45%. Light brown oil. $R_f$=0.3 (hexane/ethyl acetate=3:1). $^{1}$H NMR (400 MHz, $C_6D_6$): δ 7.73-7.68 (m, 1H), 7.36-7.32 (m, 2H), 7.12-7.04 (m, 5H), 7.02-6.94 (m, 5H), 6.83 (d, J=8.0 Hz, 2H), 6.18 (d, J=7.0 Hz, 1H) (aryl CH), 4.81 (s, 2H), 3.42 (s, 2H) ($NCH_2$), 2.51-2.45 (m, 1H), 2.32-2.24 (m, 4H), 2.09-2.01 (m, 3H) (CH, $CH_3$ and $NCH_2$), 1.04 (s, 9H) ($^t$Bu). $^{13}$C NMR (101 MHz, $C_6D_6$): δ 169.7, 151.9, 149.9, 143.9, 141.7, 139.1, 137.1, 132.6, 129.6, 129.0, 128.5, 127.6, 127.0, 125.3, 124.3 (aryl C), 39.4, 34.4, 31.2, 23.5 (alkyl C). $^{11}$B NMR (128 MHz, $C_6D_6$): δ 38.9 (br, 1B). IR (KBr, $cm^{-1}$): v3058, 3001, 2961, 2919, 2862, 1636, 1601, 1577, 1522, 1508, 1458, 1431, 1384, 1312, 1276, 1245, 1207, 1146, 1096, 1070, 1026. HRMS (ESI): Calcd for $C_{33}H_{38}BN_2O^+$ [$M^+$ H]$^+$: 489.3072, fo nd: 489.3075.

3am, 2-(6-cyclohexyl-2-(o-tolyl)-1,2-azaborinin-1(2H)-yl)-N,N-dimethylethan-1-amine, was made by procedure A, described above.

3an

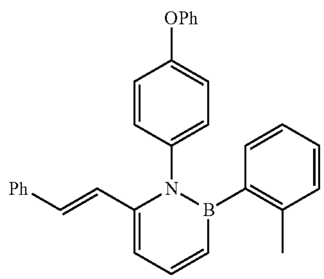

3an: Yield: 32%. Light brown oil. $R_f$=0.65 (hexane/ethyl acetate=9:1). $^{1}$H NMR (400 MHz, $C_6D_6$): δ 7.73 (dd, J=10.9, 6.9 Hz, 1H), 7.16-7.12 (m, 4H), 7.09-6.89 (m, 10H), 6.84-6.78 (m, 2H), 6.75-6.70 (m, 4H), 6.55 (d, J=8.7 Hz, 2H) (aryl CH and alkenyl CH), 2.29 (s, 3H) ($CH_3$). $^{13}$C NMR (101 MHz, $C_6D_6$): δ 155.9, 145.9, 143.7, 140.0, 139.4, 137.2, 132.8, 131.7, 123.0, 129.9, 129.1, 127.0, 125.4, 124.5, 123.3, 119.2, 118.8, 110.4 (aryl C and alkenyl C), 23.4 ($CH_3$). $^{11}$B NMR (128 MHz, $C_6D_6$): δ 37.3 (br, 1B). IR (KBr, $cm^{-1}$): v 3059, 3028, 2957, 2918, 2850, 1654, 1637, 1618, 1589, 1560, 1502, 1489, 1458, 1438, 1410, 1384, 1230, 1163, 1084, 1023. HRMS (ESI): Calcd for $C_{31}H_{27}BNO^+$ [M H]$^+$: 440.2180, found: 440.2187.

3ao

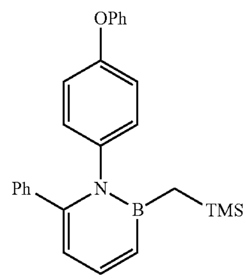

3ao: Yield: 68%. Light yellow oil. $R_f$=0.7 (hexane/ethyl acetate=9:1). $^{1}$H NMR (500 MHz, $C_6D_6$): δ 7.58 (dd, J=11.1, 6.6 Hz, 1H), 7.11-6.74 (m, 11H), 6.70 (d, J=8.7 Hz, 2H), 6.61 (d, J=8.7 Hz, 2H), 6.30 (dd, J=6.6, 1.5 Hz, 1H) (aryl CH), 0.71 (s, 2H) ($CH_2$), 0.06 (s, 9H) ($CH_3$). $^{13}$C NMR (126 MHz, $C_6D_6$): δ 158.0, 155.4, 149.1, 141.9, 140.9, 139.8, 131.0, 130.1, 130.0, 127.7, 127.2, 123.3, 119.0, 118.9, 112.3 (aryl C), 1.18 ($CH_3$). $^{11}$B NMR (160 MHz, $C_6D_6$): δ 38.7 (br, 1B). IR (KBr, $cm^{-1}$): v 2952, 2923, 1595, 1523, 1503, 1489, 1445, 1413, 1384, 1234, 1210, 1156, 1096, 1052, 1016. HRMS (ESI): Calcd for $C_{26}H_{29}BNOSi^+$ [$M^+$ H]$^+$: 410.2106, found: 410.2099.

3ap

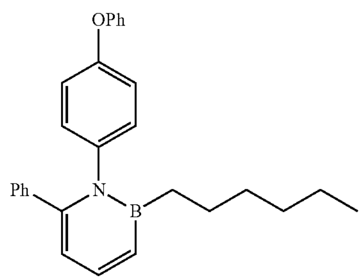

3ap: Yield: 42%. Colorless oil. $R_f$=0.7 (hexane/ethyl acetate=9:1). $^{1}$H NMR (500 MHz, $C_6D_6$): δ 7.74-7.68 (m, 1H), 7.18 (d, J=11.3 Hz, 1H), 7.02-6.98 (m, 4H), 6.94-6.88 (m, 3H), 6.84-6.74 (m, 3H), 6.60 (s, 4H), 6.39 (dd, J=6.6, 1.6 Hz, 1) (aryl CH), 1.78-1.69 (m, 2H), 1.44-1.39 (m, 2H), 1.34-1.28 (m, 4H), 1.20 (t, J=8.0 Hz, 2H) ($CH_2$), 0.93-0.85 (m, 3H) ($CH_3$). $^{13}$C NMR (126 MHz, $C_6D_6$): δ 157.8, 155.6, 149.0, 143.2, 140.6, 139.5, 130.3, 130.2, 130.0, 127.7, 127.3, 123.4, 119.0, 118.8, 112.7 (aryl C), 33.0, 32.4, 27.5, 23.1, 14.4 ($CH_2$ and $CH_3$). $^{11}$B NMR (160 MHz, $C_6D_6$): δ 39.6 (br, 1B). IR (KBr, c rr): v2957, 2925, 2856, 1607, 1594, 1523, 1503, 1489, 1424, 1384, 1283, 1236, 1164, 1086, 1015. HRMS (ESI): Calcd for $C_{28}H_{31}BNO^+$ [$M^+$ H]$^+$: 408.2493, found: 408.2494.

3aq

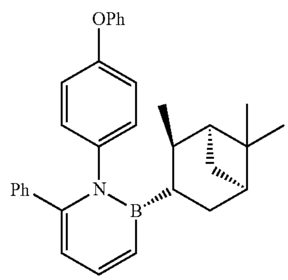

3aq: Yield: 61%. Colorless oil. $R_f$=0.7 (hexane/ethyl acetate=9:1). $^1$H NMR (500 MHz, $C_6D_6$): δ 7.74 (dd, J=11.3, 6.6 Hz, 1H), 7.21 (d, J=11.2 Hz, 1H), 7.06-6.98 (m, 4H), 6.95-6.87 (m, 4H), 6.84-6.78 (m, 2H), 6.77-6.72 (m, 2H), 6.64-6.58 (m, 2H), 6.37 (d, J=6.6 Hz, 1H) (aryl CH), 2.64-2.50 (m, 2H), 2.04-1.91 (m, 4H), 1.58-1.53 (m, 1H), 1.31-1.29 (m, 1H), 1.26 (s, 3H), 1.02-0.97 (m, 6H) (alkyl CH). $^{13}$C NMR (126 MHz, $C_6D_6$): δ 155.4, 148.2, 144.0, 141.0, 130.8, 130.6, 130.2, 130.0, 127.7, 127.3, 123.2, 119.5, 119.2, 118.5, 112.6 (aryl C), 49.2, 42.4, 41.8, 39.4, 35.5, 33.1, 29.1, 23.5, 22.6 (alkyl C). $^{11}$B NMR (160 MHz, $C_6D_6$): δ 40.6 (br, 1B). IR (KBr, $cm^{-1}$): ν 2957, 2923, 2852, 1589, 1508, 1488, 1445, 1384, 1234, 1205, 1163, 1097, 1073, 1024. HRMS (ESI): Calcd for $C_{32}H_{35}BNO^+$ $[M^+ H]^+$: 460.2806, found: 460.2753.

3ar

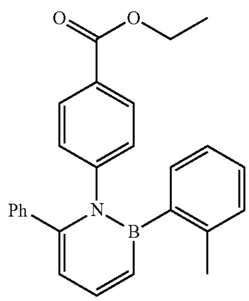

3ar: Yield: 81%. Light brown oil. Rf=0.45 (hexane/ethyl acetate=9:1). $^1$H NMR (500 MHz, $C_6D_6$): δ 7.71-7.60 (m, 3H), 7.15-7.10 (m, 2H), 7.01-6.93 (m, 5H), 6.86-6.78 (m, 3H), 6.76 (d, J=8.2 Hz, 2H), 6.47 (dd, J=6.7, 1.4 Hz, 1H) (aryl CH), 3.85 (q, J=7.1 Hz, 2H) ($CH_2$), 2.24 (s, 3H), 0.81 (t, J=7.1 Hz, 3H) ($CH_3$). $^{13}$C NMR (126 MHz, $C_6D_6$): δ 165.3 (carbonyl C), 149.2, 148.3, 143.8, 139.3, 138.8, 132.7, 129.9, 129.4, 129.2, 128.6, 127.9, 127.7, 127.6, 124.7, 114.8 (aryl C), 60.7 ($CH_2$), 23.2, 14.0 ($CH_3$). $^{11}$B NMR (160 MHz, $C_6D_6$): δ 38.2 (br, 1B). IR (KBr, $cm^{-1}$): ν 3061, 3001, 2981, 2919, 2851, 1718, 1603, 1546, 1522, 1507, 1490, 1477, 1445, 1407, 1384, 1358, 1306, 1274, 1172, 1158, 101, 1021. HRMS (ESI): Calcd for $C_{26}H_{25}BNO^+$ $[M^+ H]^+$: 394.1973, found: 394.1978.

3as

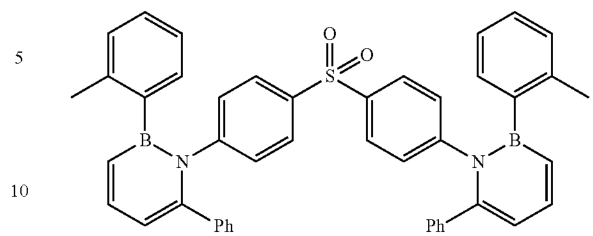

3as: Yield: 20%. Light brown oil. $R_f$=0.65 (hexane/ethyl acetate=3:1). $^1$H NMR (400 MHz, $C_6D_6$): δ 7.95 (s, 2H), 7.75 (dd, J=11.1, 6.8 Hz, 2H), 7.50 (dd, J=7.0, 1.8 Hz, 2H), 7.29-7.14 (m, 18H), 7.08-7.06 (m, 6H), 6.55-6.25 (m, 2H) (aryl CH), 2.46 (s, 6H) ($CH_3$).

$^{13}$C NMR (101 MHz, $C_6D_6$): δ 145.0, 144.8, 141.1, 138.6, 133.7, 129.9, 129.3, 128.7, 128.7, 126.2, 125.7, 109.6 (aryl C), 23.1 ($CH_3$). $^{11}$B NMR (128 MHz, $C_6D_6$): δ 36.0 (br, 1B). IR (KBr, $cm^{-1}$): ν3380, 3059, 3024, 3003, 2919, 2855, 1637, 1597, 1572, 1545, 1522, 1491, 1447, 1414, 1400, 1384, 1357, 1320, 1295, 1240, 1154, 1106, 1075, 1037. HRMS (ESI): Calcd for $C_{46}H_{39}B_2N_2O_2S^+$$[M^+ H]^+$: 705.2913, found: 705.2915.

3at

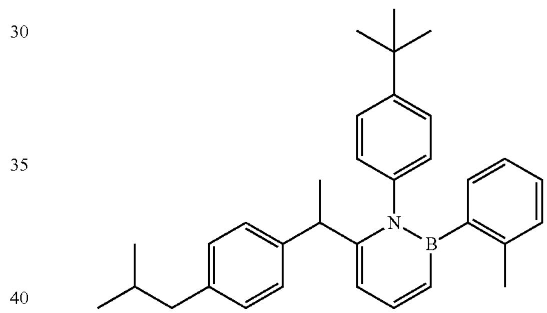

3at: Yield: 48%. Light brown oil. $R_f$=0.7 (hexane/ethyl acetate=9:1). $^1$H NMR (500 MHz, $C_6D_6$): δ 7.79 (dd, J=10.9, 6.9 Hz, 1H), 7.12-7.08 (m, 2H), 7.00 (dd, J=8.3, 2.3 Hz, 1H), 6.94-6.87 (m, 4H), 6.87-6.82 (m, 2H), 6.73 (d, J=8.1 Hz, 2H), 6.68 (dd, J=8.3, 2.3 Hz, 1H), 6.56 (dd, J=6.9, 1.4 Hz, 1H), 6.38 (dd, J=8.3, 2.3 Hz, 1H) (ayl CH), 4.06 (q, J=7.1 Hz, 1H) (CH), 2.32-2.29 (m, 5H) ($CH_2$ and $CH_3$), 1.72 (hept, J=6.8 z, 1H) (CH), 1.38 (d, J=7.1 Hz, 3H), 1.04 (s, 9H), 0.83 (dd, J=6.6, 4.7 Hz, 6H) ($CH_3$). $^{13}$C NMR (126 MHz, $C_6D_6$): δ 152.0, 143.6, 143.0, 141.6, 139.5, 139.0, 132.6, 129.3, 128.9, 127.5, 126.9, 124.9, 124.7, 124.3, 110.3 (aryl C), 45.2, 42.2, 34.3, 31.2, 30.5, 23.5, 23.2, 22.5, 22.4 ($^t$Bu and Me). $^{11}$B NMR (160 MHz, $C_6D_6$): δ 38.0 (br, 1B). IR (KBr, $cm^{-1}$): ν 3084, 3048, 3004, 2963, 2924, 2868, 1600, 1523, 1508, 1460, 1437, 1413, 1384, 1366, 1308, 1268, 1243, 1206, 1160, 1113, 1080, 1020. HRMS (ESI): Calcd for $C_{33}H_{41}BN^+$ $[M^+ H]^+$: 462.3327, found: 462.3321.

3au

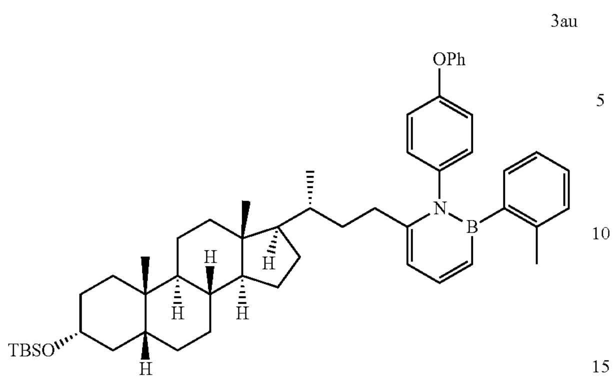

3au: Yield: 28%. Light brown oil. $R_f$=0.7 (hexane/ethyl acetate=9:1). $^1$H NMR (500 MHz, $C_6D_6$): δ 7.75 (dd, J=11.0, 6.7 Hz, 1H), 7.14 (d, J=7.8 Hz, 1H), 7.09-7.00 (m, 6H), 6.85 (t, J=7.3 Hz, 1H), 6.82-6.73 (m, 4H), 6.63 (d, J=8.0 Hz, H), 6.43 (dd, J=6.8, 1.4 Hz, 1H) (aryl CH), 3.68-3.62 (m, 1H), 2.61-2.65 (m, 1H), 2.41-2.30 (m, 4H), 2.03-1.97 (m, 1H), 1.82-1.77 (m, 2H), 1.74-1.71 (m, 1H), 1.67-1.59 (m, 3H), 1.58-1.46 (m, 4H), 1.34-1.20 (m, 10H), 1.12 (d, J=9.6 Hz, 1H), 1.06 (s, 9H), 0.9-0.91 (m, 3H), 0.89 (s, 3H), 0.78 (d, J=6.4 Hz, 3H), 0.74-0.70 (m, 1H), 0.54 (s, 3H), 0.15 (m, J=2.7 Hz, 6H) (alkyl CH). $^{13}$C NMR (126 MHz, $C_6D_6$): δ 144.2, 132.8, 123.0, 129.9, 124.4, 119.2, 119.1, 118.9, 111.5 (aryl C), 73.0, 56.2, 55.9, 42.9, 42.5, 40.6, 40.2, 37.4, 36.9, 36.1, 36.1, 35.9, 34.7, 31.6, 31.4, 28.5, 27.7, 26.6, 26.2, 24.4, 23.6, 23.5, 21.2, 18.8, 18.4, 12.2, −4.3, −4.3 (alkyl C). $^{11}$B NMR (160 MHz, $C_6D_6$): δ 37.6 (br, 1B). IR (KBr, cm$^{-1}$): v 2884, 2860, 1601, 1522, 1504, 1489, 1472, 1449, 1411, 1384, 1235, 1095, 1081. HRMS (ESI): Calcd for $C_{52}H_{73}BNO_2Si^+$[M$^+$ H]$^+$: 782.5498, found: 782.5500.

3av

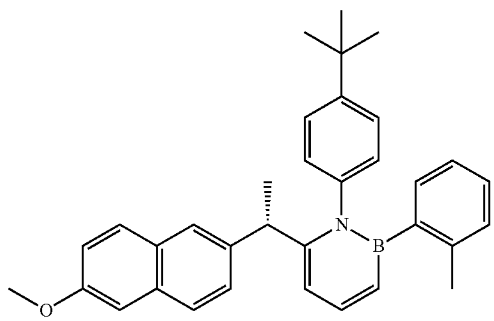

3av: Yield: 25%. Light brown oil. $R_f$=0.65 (hexane/ethyl acetate=9:1). $^1$H NMR (400 MHz, $C_6D_6$): δ 7.82 (dd, J=10.9, 6.9 Hz, 1H), 7.49 (d, J=8.5 Hz, 1H), 7.38 (d, J=8.9 Hz, 1H), 7.17 (s, 1H), 7.14 (dd, J=3.8, 1.9 Hz, 1H), 7.11-7.07 (m, 2H), 7.04-6.99 (m, 2H), 6.97-6.87 (m, 5H), 6.62 (dd, J=7.0, 1.4 Hz, 1H), 6.48 (dd, J=8.4, 2.3 Hz, 1H), 6.30 (dd, J=8.3, 2.3 Hz, 1H) (aryl CH), 4.21 (q, J=7.1 Hz, 1H) ($CHCH_3$), 3.38 (s, 3H) ($OCH_3$), 2.30 (s, 3H) ($CH_3$), 1.46 (d, J=7.1 Hz, 3H) ($CHCH_3$), 1.02 (s, 9H) ($^t$Bu). $^{13}$C NMR (01 MHz, $C_6D_6$): δ 158.1, 151.8, 149.4, 143.7, 141.5, 140.6, 133.9, 132.6, 129.6, 129.5, 128.8, 127.1, 127.0, 126.9, 126.2, 124.9, 124.8, 124.2, 119.2, 110.4, 106.0 (aryl C), 54.83, 42.51, 34.27, 31.25, 23.51, 22.99 (alkyl C). $^{11}$B NMR (128 MHz, $C_6D_6$): δ 38.6 (br, 1B). IR (Br, cm$^{-1}$): v 3055, 3001, 2965, 2932, 2902, 2870, 1635, 1603, 1522, 1507, 1483, 1462, 1438, 1413, 1385, 1265, 1242, 1229, 1212, 1162, 1120, 1078, 1034. HRMS (ESI): Calcd for $C_{34}H_{37}BNO^+$ [M$^+$ H]$^+$: 486.2963, found: 486.2963.

3aw

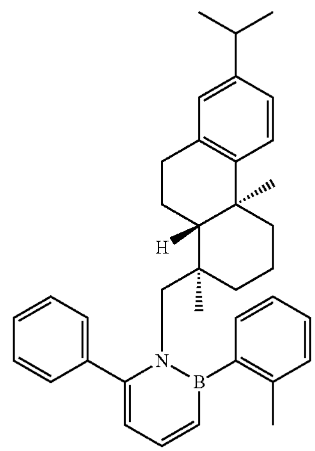

3aw: Yield: 71%. Colorless oil. $R_f$=0.7 (hexane/ethyl acetat=9:1). $^1$H NMR (400 MHz, $C_6D_6$, a mixture of atropisomers in ~1.5:1 ratio): δ 7.76-7.34 (m, 3H), 7.33-7.17 (m, 4H), 7.14-6.95 (m, 5H), 6.93-6.89 (m, 1H), 6.77-6.75 (m, 1H), 6.33-6.27 (m, 1H), 4.64 (dd, J=74.3, 13.1 Hz, 0.4H), 4.37-4.23 (m, 0.6H), 4.17-4.03 (m, 0.6H), 3.85 (dd, J=118.0, 13.5 Hz, 0.4H), 2.73-2.19 (m, 6H), 1.92 (d, J=12.6 Hz, 1H), 1.44-1.33 (m, 3H), 1.24-1.17 (m, 7H), 1.07-0.77 (m, 7H), 0.60-0.49 (m, 3H). $^{13}$C NMR (101 MHz, $O_6D_6$): δ 152.2, 151.2, 150.9, 147.7, 145.6, 143.6, 143.4, 142.3, 142.1, 141.4, 141.3, 140.7, 140.5, 140.4, 140.2, 138.7, 138.2, 135.5, 134.8, 133.3, 130.6, 130.2, 129.5, 129.1, 127.0, 125.6, 125.4, 125.2, 124.2, 123.9, 116.5, 116.1, 115.7, 115.5, 60.6, 60.3, 59.4, 47.5, 47.3, 46.3, 40.2, 38.6, 38.3, 38.1, 37.8, 37.7, 37.2, 34.0, 34.0, 30.2, 30.1, 29.5, 25.8, 25.7, 25.6, 24.5, 24.4, 24.3, 23.3, 22.3, 19.3, 18.9, 18.7, 18.6. $^{11}$B NMR (128 MHz, $C_6D_6$): δ 39.7 (br, 1B). IR (KBr, cm$^{-1}$): v2958, 2280, 1589, 1524, 1489, 1456, 1414, 1378, 1288, 1265, 1231, 1149, 1119, 1075, 1028. HRMS (ESI): Calcd for $C_{37}H_{45}BN^+$ [M$^+$ H]$^+$: 514.3640, found: 514.3657. $[\alpha]_D^{22}$=−32.7 (c=5.6, $CH_2Cl_2$).

3ax

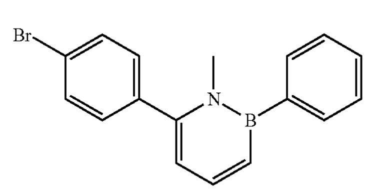

3ax: Yield: 51%. Light brown oil. $R_f$=0.7 (hexane/ethyl acetate=9:1). $^1$H NMR (500 MHz, $C_6D_6$): δ 7.69-7.64 (m, 2H), 7.61 (dd, J=10.9, 6.6 Hz, 1H), 7.36 (dd, J=8.1, 6.7 Hz, 2H), 7.30-7.24 (m, 1H), 7.17 (d, J=8.3 Hz, 2H), 7.11 (dd, J=10.9, 1.6 Hz, 1H), 6.66 (d, J=8.3 Hz, 2H), 6.18-6.09 (m, 1H) (aryl CH), 3.00 (s, 3H) ($CH_3$). $^{13}$C NMR (126 MHz, $C_6D_6$): δ 148.9, 143.2, 137.8, 133.6, 131.6, 130.8, 128.1, 122.6, 114.2 (aryl C), 39.8 ($CH_3$). $^{11}$B NMR (160 MHz, $C_6D_6$): δ 37.1 (br, 1B). IR (KBr, cm$^{-1}$): v 3008, 2923, 2852, 1618, 1599, 1585, 1560, 1529, 1485, 1458, 1431, 1412, 1384, 1282, 1214, 1181, 1142, 1102, 1071, 1010.

HRMS (ESI): Calcd for $C_{17}H_{16}BBrN^+$ [$M^+$ H]$^+$: 324.0554, found: 324.0556.

Preparation of 1,2,3,6-tetrasubstituted 1,2-azaborines 3ay and 3az

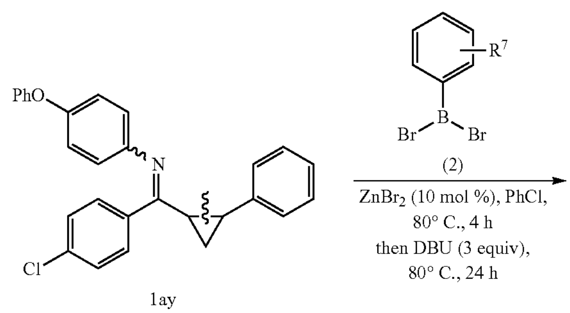

1ay

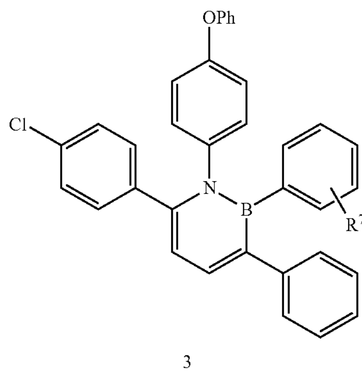

3

$R^7$ = o-Tol, 3ay
p-Cl, 3az

An oven-dried 4 mL vial was charged with imine lay (84.6 mg, 0.2 mmol, 1 equiv) and $ZnBr_2$ (4.5 mg, 0.02 mmol, 10 mol %) in a nitrogen-filled glovebox. Dry chlorobenzene (1 mL) was then added. After dibromoborane 2 (0.22 mmol, 1.1 equiv) was added, the vial was tightly sealed and stirred on a pie-block preheated to 80° C. under nitrogen for 4 h. 1,8-Diazabicyclo(5.4.0)undec-7-ene (DBU, 90 μL, 0.6 mmol, 3 equiv) was then added and the reaction mixture was stirred at the same temperature for 24 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/20) to give azaborine 3ay or 3az.

Characterization

Below are the details of the characterization of compounds 3ay and 3az.

3ay

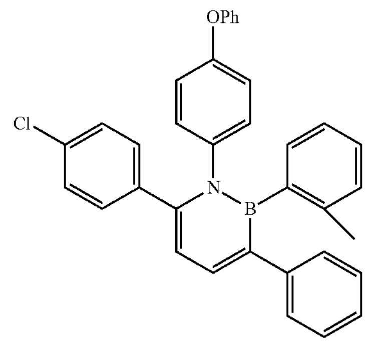

3ay: Yield: 30%. Light yellow solid. M.p.=95-97° C. $R_f$=0.65 (hexane/ethyl acetate=9:1). $^1H$ NMR (400 MHz, $CDCl_3$): δ 7.92 (d, J=7.2 Hz, 1H), 7.42-7.34 (m, 3H), 7.32-7.27 (m, 4H), 7.26-7.19 (m, 4H), 7.16-7.09 (m, 3H), 7.03-6.99 (m, 1H), 6.97-6.91 (m, 2H), 6.83 (dd, J=8.5, 2.6 Hz, 1H), 6.80-6.73 (m, 4H), 6.69 (dd, J=8.5, 2.7 Hz, 1H) (aryl CH), 2.04 (s, 3H) ($CH_3$). $^{13}C$ NMR (101 MHz, $CDCl_3$): δ 158.0, 154.5, 146.9, 144.7, 141.7, 140.6, 139.2, 137.1, 133.6, 132.9, 131.2, 130.7, 129.7, 129.6, 128.6, 128.3, 128.0, 127.9, 126.7, 125.7, 124.1, 122.9, 119.4, 119.2, 117.9, 113.8 (aryl C), 22.6 ($CH_3$). $^{11}B$ NMR (128 MHz, $CDCl_3$): δ 38.5 (br, 1B). IR (KBr, $cm^{-1}$): v3055, 3001, 2969, 2918, 2851, 1588, 1561, 1529, 1503, 1489, 1444, 1401, 1384, 1343, 1228, 1199, 1165, 1093, 1015. HRMS (ESI): Calcd for $C_{35}H_{28}BClNO^+$[$M^+$ H]$^+$: 524.1947, found: 524.1955.

3az

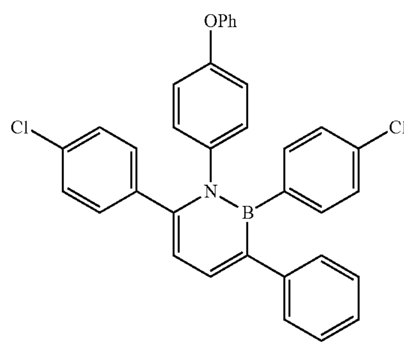

3az: Yield: 29%. Pale yellow solid. M.p.=172-174° C. $R_f$=0.6 (hexane/ethyl acetate=9:1). $^1H$ NMR (500 MHz, $C_6D_6$): δ 7.77 (d, J=7.2 Hz, 1H), 7.35-7.27 (m, 2H), 7.17 (d, J=4.9 Hz, 2H), 7.14 (s, 1H), 7.12-7.06 (m, 3H), 6.98-6.94 (m, 2H), 6.90-6.81 (m, 5H), 6.75-6.67 (m, 4H), 6.42 (d, J=7.2 Hz, 1H), 6.35 (d, J=8.8 Hz, 2H), 6.29 (d, J=8.8 Hz, 2H) (aryl CH). $^{13}C$ NMR (126 MHz, $C_6D_6$): δ 158.1, 155.4, 147.0, 145.0, 143.0, 134.0, 137.1, 135.4, 133.9, 133.2, 131.4, 130.9, 130.1, 129.4, 128.5, 127.6, 126.3, 123.4, 119.4, 118.4, 114.2 (aryl C). $^{11}B$ NMR (160 MHz, $C_6D_6$): δ 37.1 (br, 1B). IR (KBr, $cm^{-1}$): v 2924, 2853, 1588, 1529, 1502, 1489, 1458, 1384, 1343, 1275, 1229, 1165, 1089, 1014. HRMS (ESI): Calcd for $C_{34}H_{25}BCl_2NO^+$ [$M^+$ H]$^+$: 544.1401, found: 544.1387.

DISCUSSION

Diverse anilines can efficiently condense with cyclopropyl ketones, which all generated the desired 1,2,6-trisubstituted 1,2-azaborines in good yields The reaction temperature was increased to 80° C. for some challenging substrates to enhance the overall efficiency. In addition, alkylamine-derived products can also be produced efficiently (3p-3y and 3aw). Moreover, both aryl and alkyl-substituted dibromoboranes, including the one derived from α-pinene (3aq), were suitable coupling partners. Notably, a B-silylmethyl 1,2-azaborine (3ao) was effectively obtained and the silyl group could serve as a handle for further functionalization. Furthermore, various $C_6$-substitutents, including aryl, alkenyl, and alkyl groups, can be installed. It is noteworthy that the 1,2-azaborine with alkyl substituents at both CE and N1 positions (3am) can be obtained. Finally, complex substrates derived from drug molecu es, e.g., benzocaine, dapsone, ibuprofen and naproxen, as well as natural products (lithocholic acid and leelamine) smoothly underwent the BN-isostere benzannulation reaction to deliver the desired products 3ar-3aw in moderate to good yields. It is attractive that a range of functional groups were tolerated with this method. In particular, moieties reactive under various transition-metal catalysis conditions, such as halogens (—F, —Cl, —Br and —I, 3α-3f) and pinacol boronate (3o), remained intact. Electrophilic groups, such as esters (31 and 3ar), amid (3al), and sulfones (3as), as well as Lewis basic groups, such as ethers (3i, 3n, 3v and 3ab), tertiary amines (3j and 3am) and silyl ethers (3au), were also compatible.

Interestingly, apart from simple cyclopropyl, (3-phenyl-substituted cyclopropyl imines were also competent substrates, delivering 1,2,3,6-tetrasubstituted azaborines 3ay or 3az in moderate yield with complete selectivity of cleaving the more substituted C—C bond. This reaction scheme is shown below:

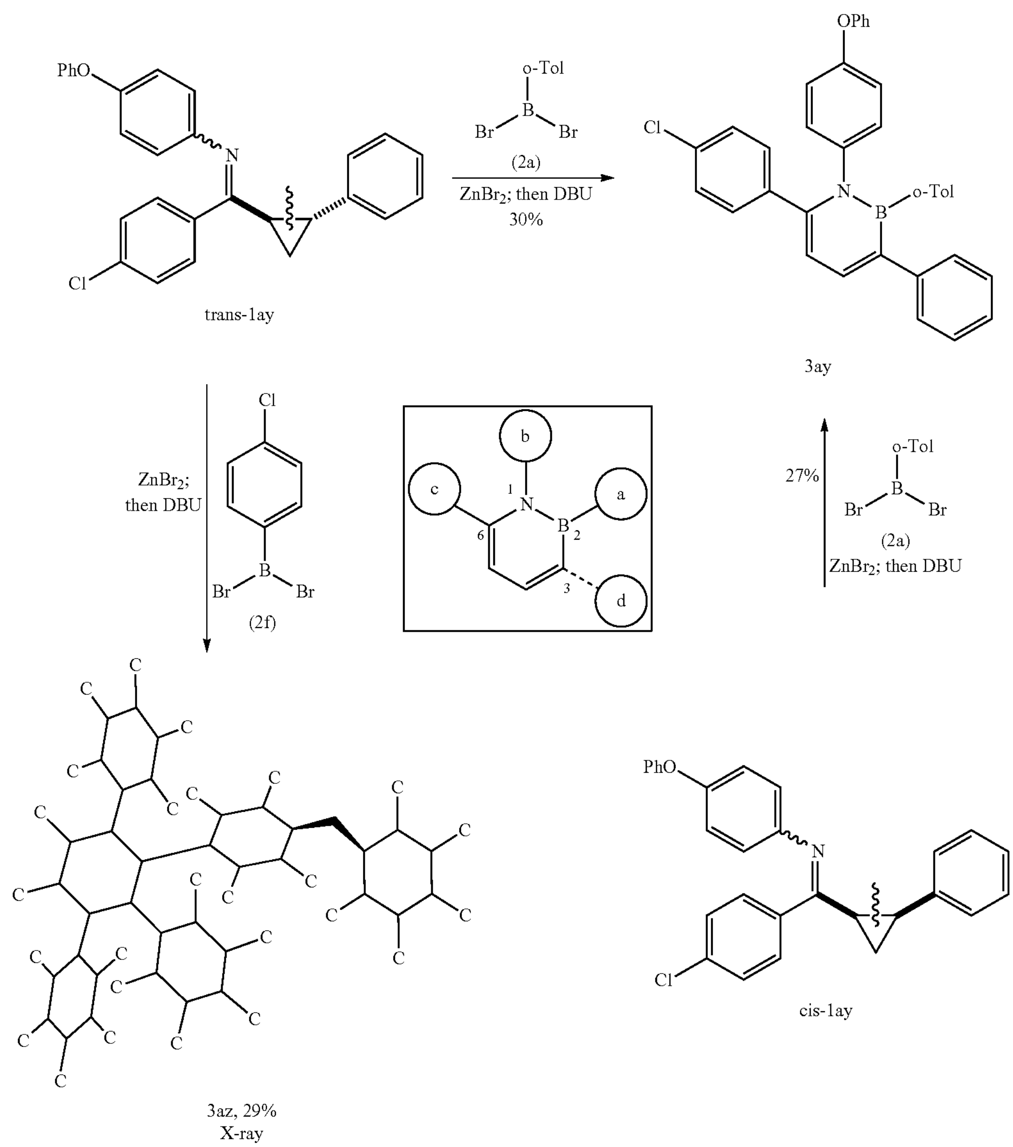

trans-1ay

3ay

3az, 29%
X-ray cis-1ay

Both the trans and cis isomers of the substrates (lay) gave the same product (3ay) in comparable yield, suggesting that the reactivity is not significantly affected by the cyclopropane stereochemistry. The relatively low yield was likely due to the steric hindrance of the P-phenyl group during the annulation process. The structure of 3az was further confirmed by X-ray crystallography.

Preparation of mesityl protected monocyclic 1,2-azaborines 3a'-3q' (a representative procedure C)

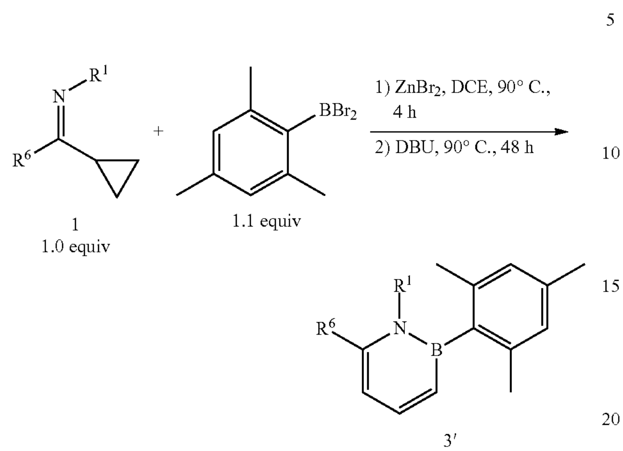

1
1.0 equiv 1.1 equiv

3'

In a nitrogen-filled glovebox, the obtained crude imine 1 was dissolved in dry 1,2-dichloroethane (DCE, 1 mL) and transferred into an oven-dried 4 mL vial. After $ZnBr_2$ (4.5 mg, 0.02 mmol, 10 mol %) and dibromoborane 2 (0.22 mmol, 1.1 equiv) were added, the vial was tightly sealed and stirred on a pie-block preheated to 90° C. under nitrogen for 4 h. 1,8-Diazabicyclo(5.4.0)undec-7-ene (DBU, 90 µL, 0.6 mmol, 3 equiv) was then added and the reaction mixture was stirred at the same temperature for 48 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/20) to give azaborine 3'.

Characterization

Below are the details of the characterization of compounds 3a'-3g'

3a'

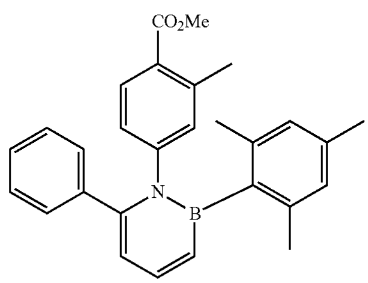

3a': Yield: 51% (mixture of 1:1 rotamers). Colorless oil. Rr: 0.4 (hexane/ethyl acetate=9:1). $^1$H NMR (400 MHz, $CDCl_3$): δ 7.77-7.73 (m, 1H), 7.49 (d, J=8.0 Hz, 1H), 7.13 (m, 5H), 6.86 (d, J=10.3 Hz, 1H), 6.68 (s, 1H), 6.67 (d, J=8.3 Hz, 1H), 6.63 (s, 2H), 6.52 (d, J=6.6 Hz, 1H), 3.76 (s, 3H), 2.26 (s, 3H), 2.18 (s, 3H), 2.07 (s, 3H), 2.05 (s, 3H). $^{13}$C NMR (101 MHz, $CDCl_3$): δ 167.49, 148.26, 148.20, 143.36, 140.11, 138.72, 136.58, 131.71, 130.25, 129.52, 127.82, 127.45, 126.88, 126.84, 126.46, 125.54, 114.47, 51.76, 23.21, 23.17, 21.52, 21.21. $^{11}$B NMR (128 MHz, $CDC_3$): δ 39.33. IR (KBr, $cm^{-1}$): 2951, 2921, 2857, 1723, 1605, 1594, 1573, 1522, 1490, 1411, 1376, 1357, 1256, 1191, 1171, 1143, 1083, 1030, 982, 915, 875, 849, 808, 780, 756, 730, 700, 664 $cm^{-1}$. HRMS (ESI): m/z calcd for $C_{28}H_{29}BNO_2^+$ [$M^+$ $H^+$]: 422.2286. Found: 422.2290.

3b'

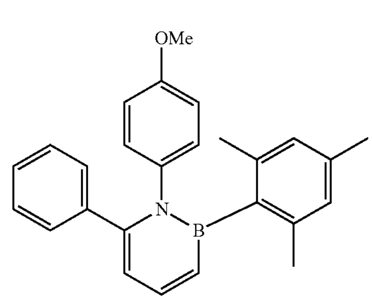

3b': Yield: 37%. Off-white oil. Rr: 0.6 (hexane/ethyl acetate=9:1). $^1$H NMR (400 MHz, $CDCl_3$): δ 7.76-7.73 (m, 1H), 7.13 (m, 5H), 6.84 (d, J=11.0 Hz, 1H), 6.71 (d, J=7.4 Hz, 2H), 6.65 (s, 2H), 6.50 (d, J=6.7 Hz, 1H), 6.41 (d, J=6.8 Hz, 2H), 3.6 (s, 3H), 2.19 (s, 3H), 2.08 (s, 6H). $^{93}$C NMR (101 MHz, $CDCl_3$): δ 157.14, 149.16, 143.09, 139.23, 138.80, 138.22, 136.25, 129.68, 128.95, 127.67, 127.08, 126.78, 114.12, 112.61, 55.22, 23.27, 21.25. $^1$B NMR (128 MHz, $CDC_3$): δ 39.82. IR (KBr, $cm^{-1}$): 2909, 1572, 1609, 1522, 1508, 1490, 1460, 1443, 1408, 1359, 1298, 1245, 1179, 1150, 1107, 1088, 1034, 989, 848, 832, 805, 782, 770, 757, 699 $cm^{-1}$. HRMS (ESI): m/z calcd for $C_{26}H_{27}BNO^+$ [$M^+$ $H^+$]: 380.2180. Found: 380.2187.

3c'

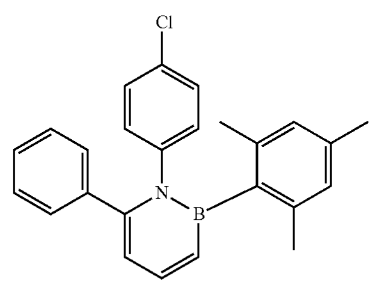

3c': Yield: 42%. Yellow oil. Rr: 0.65 (hexane/ethyl acetate=9:1). $^1$H NMR (400 MHz, $CDCl_3$): δ 7.75 (dd, J=11.0, 6.6 Hz, 1H), 7.17-7.15 (m, 3H), 7.1-7.09 (m, 2H), 6.88 (d, J=3.2 Hz, 1H), 6.85 (d, J=6.2 Hz, 2H), 6.73 (d, J=8.8 Hz, 2H), 6.66 (s, 2H), 6.52 (d, J=7.1 Hz, 1H), 2.20 (s, 3H), 2.06 (s, 6H). $^{13}$C NMR (101 MHz, $CDCl_3$): δ 148.44, 143.73, 143.36, 138.69, 136.63, 131.41, 129.64, 129.40, 127.87, 127.66, 127.42, 126.93, 114.46, 23.22, 21.25.

$^{11}$B NMR (128 MHz, $CDCl_3$): δ 38.35. IR (KBr, $cm^1$): 2913, 2855, 1609, 1592, 1574, 1521, 1489, 1445, 1412, 1401, 1358, 1283, 1265, 1238, 1176, 1151, 1086, 1028, 1016, 988, 966, 849, 832, 763, 755, 714, 700 $cm^{-1}$. HRMS (ESI): m/z calcd for $C_{24}H_{25}BClN^+$[$+H^+$]: 384.1685. Found: 384.1683.

3d'

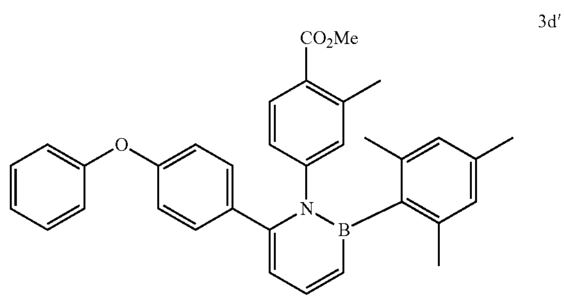 [SMILES: COC(=O)c1ccc(N2B(c3c(C)cc(C)cc3C)C=CC=C2c2ccc(Oc3ccccc3)cc2)cc1C]

3d': Yield: 30% (mixture of 1:1 rotamers). Off-white oil. $R_f$: 0.5 (hexane/ethyl acetate=9:1). $^1$H NMR (400 MHz, $CDCl_3$): δ 7.75 (dd, J=11.0, 6.7 Hz, 1H), 7.54 (d, J=8.9 Hz, 1H), 7.31 (t, J=7.8 Hz, 2H), 7.11-7.06 (m, 3H), 6.91-6.85 (m, 3H), 6.78 (d, J=8.5 Hz, 2H), 6.69 (d, J=6.8 Hz, 2H), 6.64 (s, 2H), 6.54 (d, J=6.7 Hz, 1H), 3.80 (s, 3H), 2.30 (s, 3H), 2.19 (s, 3H), 2.07 (d, J=4.9 Hz, 6H). $^{13}$C NMR (101 MHz, $CDCl_3$): δ 167.46, 157.12, 156.49, 148.31, 147.63, 143.38, 140.12, 138.72, 136.62, 133.82, 131.77, 131.03, 130.33, 129.88, 126.90, 126.87, 126.55, 125.60, 123.51, 118.91, 118.28, 114.26, 51.82, 23.26, 23.16, 21.58, 21.22. $^{11}$B NMR (128 MHz, $CDCl_3$): δ 39.46. IR (KBr, $cm^{-1}$): 2948, 2907, 1722, 1596, 1524, 1500, 1488, 1435, 1410, 1353, 1286, 1240, 1194, 1169, 1142, 1082, 1014, 982, 870, 848, 807, 775, 692 $cm^{-1}$. HRMS (ESI): m/z calcd for $C_{34}H_{33}BNO_3^+$ $[M^+ H^+]$: 514.2548. Found: 514.2552.

3e'

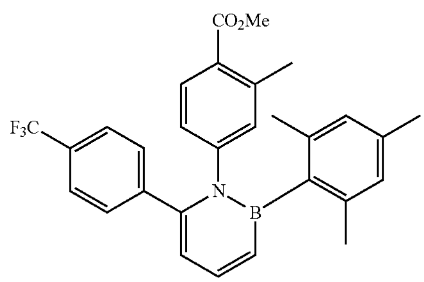

3e': Yield: 19% (mixture of 1:1 rotamers). Colorless oil. $R_f$: 0.45 (hexane/ethyl acetate=9:1). $^1$H NMR (400 MHz, $CDCl_3$): δ 7.75 (dd, J=11.0, 6.6 Hz, 1H), 7.52 (d, J=8.2 Hz, 1H), 7.41 (d, J=8.0 Hz, 2H), 7.25 (d, J=5.9 Hz, 2H), 6.92 (d, J=11.0 Hz, 1H), 6.68-6.63 (m, 4H), 6.52 (d, J=6.6 Hz, 1H), 3.77 (s, 3H), 2.27 (s, 3H), 2.18 (s, 3H), 2.07 (s, 3H), 2.03 (s, 3H).

$^{13}$C NMR (101 MHz, $CDC_3l$): δ 167.33, 147.75, 146.53, 143.23, 142.33, 140.44, 138.66, 136.80, 131.53, 130.54, 129.75, 126.96, 126.92, 125.43, 124.85 (d, J=$C_{F3}$=3.9 Hz), 115.05, 51.86, 23.17, 21.55, 21.21. $^{11}$B NMR (128 MHz, $CDCl_3$): δ 40.02. $^{19}$F NMR (470 MHz, $CDCl_3$): δ −62.62. IR (KBr, $cm^{-1}$): 2951, 1721, 1598, 1571, 1527, 1508, 1436, 1408, 1357, 1325, 1255, 1168, 1128, 1110, 1084, 1068, 1016, 983, 844, 775, 754, 728, 706, 671 $cm^{-1}$. HRMS (ESI): m/z calcd for $C_{29}H_{28}BF_3NO_2^+$$[M^+ H^+]$: 490.2160. Found: 490.2164.

3f'

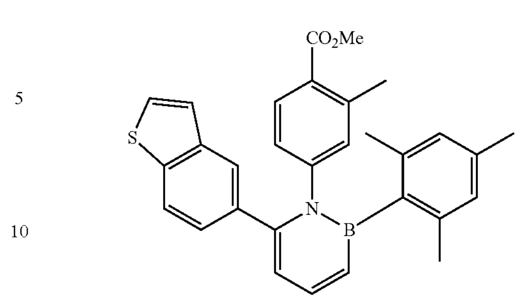

3f': Yield: 36% (mixture of 1:1 rotamers). Colorless oil. $R_f$: 0.4 (hexane/ethyl acetate=9:1). $^1$H NMR (400 MHz, $CDCl_3$): δ 7.77 (dd, J=11.0, 6.7 Hz, 1H), 7.71 (s, 1H), 7.58 (d, J=8.4 Hz, 1H), 7.47 (d, J=8.3 Hz, 1H), 7.41 (d, J=5.4 Hz, 1H), 7.24 (d, j=5.7 Hz, 1H), 7.01 (d, J=8.4 Hz, 1H), 6.89 (d, J=10.9 Hz, 1H), 6.75 (s, 1H), 6.71 (d, J=8.4 Hz, 1H), 6.66 (s, 1H), 6.63 (s, 1H), 6.58 (d, J=6.6 Hz, 1H), 3.74 (s, 3H), 2.24 (s, 3H), 2.19 (s, 3H), 2.12 (s, 3H), 2.04 (s, 3H). $^{13}$C NMR (101 MHz, $CDCl_3$): δ 167.43, 148.27, 148.20, 143.41, 140.17, 139.30, 138.89, 138.72, 136.60, 135.10, 131.65, 130.34, 127.16, 126.89, 126.85, 126.47, 125.76, 125.58, 124.53, 124.01, 121.69, 114.95, 51.74, 23.25, 23.19, 21.58, 21.22. $^{11}$B NMR (128 MHz, $CDCl_3$): δ 39.44. IR (KBr, $cm^1$): 2947, 1719, 1593, 1522, 1499, 1436, 1356, 1254, 1187, 1142, 1081, 1046, 988, 879, 848, 811, 759, 772, 737, 708, 669 $cm^{-1}$. HRMS (ESI): m/z calcd for $C_{30}H_{29}BNO_2S^+$ $[M^+ H^+]$: 478.2007. Found: 478.2012.

3g'

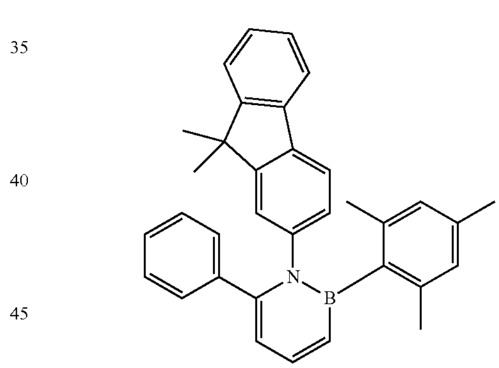

3g': Yield: 40% (mixture of 1:1 rotamers). Off-white solid, M.p.: 73-75° C. $R_f$: 0.7 (hexane/ethyl acetate=9:1). $^1$H NMR (500 MHz, $CDCl_3$): δ 7.80 (dd, J=11.0, 6.7 Hz, 1H), 7.53 (dd, J=6.4, 2.0 Hz, 1H), 7.33 (dd, J=6.5, 2.0 Hz, 1H), 7.28-7.23 (m, 3H), 7.19-7.17 (m, 2H), 7.12-7.06 (m, 3H), 6.93 (dd, J=11.0, 1.5 Hz, 1H), 6.81 (d, J=2.0 Hz, 1H), 6.77 (dd, J=8.0, 2.0 Hz, 1H), 6.63 (s, 2H), 6.59 (dd, J=6.7, 1.5 Hz, 1H), 2.14 (s, 3H), 2.12 (s, 6H), 1.14 (s, 3H), 1.13 (s, 3H). $^{13}$C NMR (126 MHz, $CDCl_3$): δ 153.78, 152.89, 148.94, 144.27, 143.17, 139.22, 138.90, 138.74, 136.39, 136.26, 129.70, 127.65, 127.11, 127.05, 127.01, 126.97, 126.81, 123.21, 122.67, 119.93, 118.83, 114.09, 46.50, 26.79, 26.40, 23.30, 23.17, 21.13. $^{11}$B NMR (128 MHz, $CDCl_3$): δ 40.56. IR (KBr, $cm^{-1}$): 3204, 3061, 3017, 2959, 2919, 2858, 1609, 1574, 1521, 1490, 1472, 1460, 1448, 1358, 1298, 1281, 1265, 1241, 1174, 1155, 1076, 1029, 1009, 979, 941, 912, 885, 849, 830, 780, 757, 738, 702, 655 $cm^1$. HRMS (ESI): m/z calcd for $C_{34}H_{33}BN^+$ $[M^+ H^+]$: 466.2701. Found: 466.2704.

Example 3: Synthesis of 1,2,3,6-tetrasubstituted 1,2-azaborines via the derivatization of 3-bromo-1,2,6-triarylated azaborine Note that synthesis of 1,2,3,6-tetrasubstituted azaborines has been very rare. It has been found that these compounds can be prepared more efficiently via site-selective bromination of trisubstituted azaborine 3b followed by cross couplings to introduce various functional groups at the $C_3$ position. This reaction scheme is shown below:

-continued

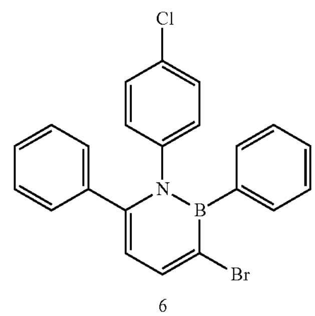

6

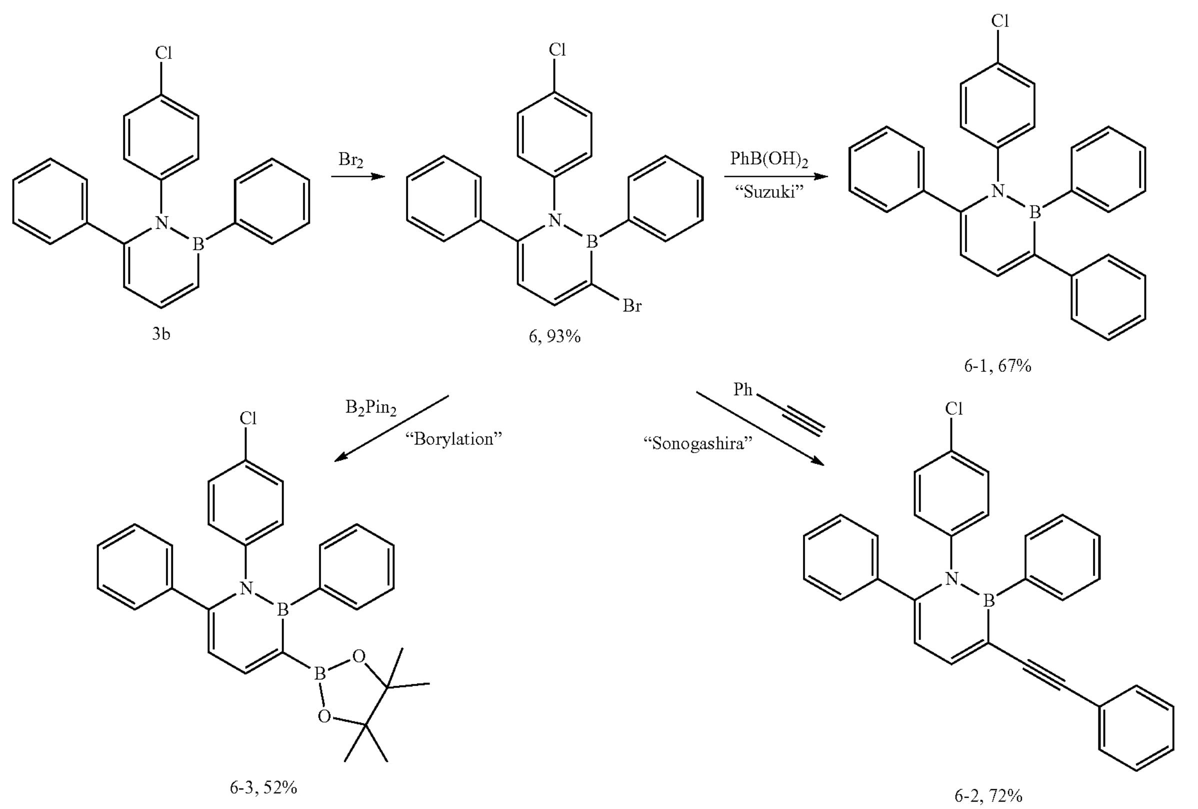

The synthesis of the tetrasubstituted azaborines is describe below.

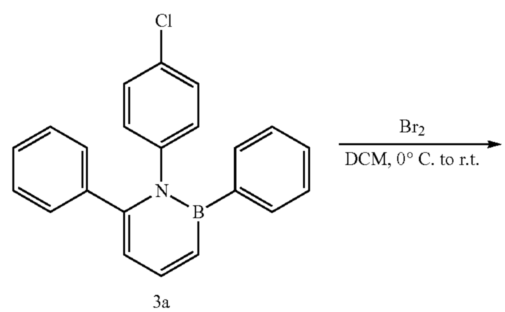

3a

Preparation of 3-bromo-1,2,6-triarylated azaborine 6

At 0° C., to a DCM (6 mL) solution of 3a (205 mg, 0.6 mmol) was slowly added bromine (6.6 mL, 1.1 equiv., 0.1 M in DCM). The resulting solution was allowed to warm to room temperature and stir for 1 hour. Upon completion, $Et_3N$ (167 μL, 2 equiv.) was added to the reaction mixture and all the volatiles were removed under vacuum. The crude product was subjected to flash column chromatography (EtOAc/hexane=1/100 to 1/20) to give 6 as a pale yellow solid (234 mg, 93%). M.p.=148-150° C. $R_f$=0.6 (hexane/ethyl acetate=9:1).

$^1H$ NMR (400 MHz, $C_6D_6$): δ 7.99 (d, J=7.6 Hz, 1H), 7.27-7.22 (m, 2H), 7.09 (dd, J=8.0, 6.4 Hz, 2H), 7.03 (d, J=7.3 Hz, 1H), 6.83-6.79 (m, 5H), 6.50 (d, J=8.6 Hz, 2H), 6.22 (d, J=8.6 Hz, 2H), 6.07 (d, J=7.6 Hz, 1H) (aryl CH). $^{11}C$ NMR (101 MHz, $C_6D_6$): δ 148.2, 146.0, 143.2, 137.9, 133.5, 132.2, 130.6, 129.7, 129.1, 127.9, 127.7, 127.3, 113.9 (aryl C). $^{11}B$ NMR (128 MHz, $C_6D_6$): δ 36.6 (br, 1B). IR (KBr, $cm^{-1}$): ν 3074, 3054, 3034, 2926, 2855, 1605, 1590, 1571, 1512, 1489, 1445, 1430, 1384, 1369, 1345, 1242, 1103, 1090, 1028, 1016. HRMS (ESI): Calcd for $C_{22}H_{17}BBrClN^+$ $[M^+ H]^+$: 420.0320, found: 420.0314.

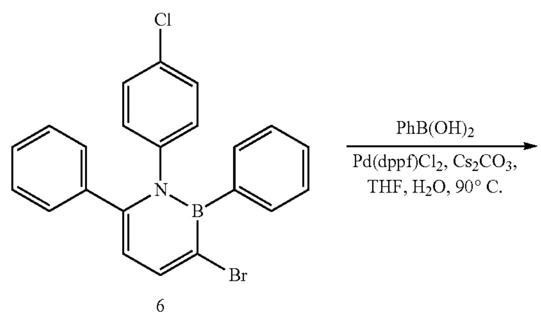

6

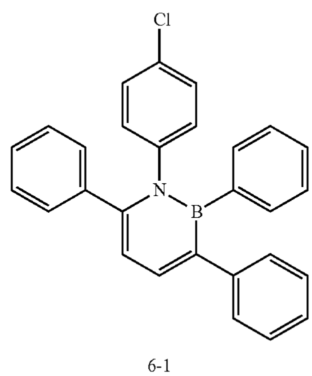

6-1

Synthesis of 6-1. 3-Bromo-1,2,6-triarylated azaborine 6 (41.9 mg, 0.1 mmol), phenyl boronic acid (36.6 mg, 0.3 mmol, 3 equiv), $Pd(dppf)Cl_2$ (3.7 mg, 0.005 mmol, 5 mol %) and $Cs_2CO_3$ (97.7 mg, 0.3 mmol, 3 equiv) were mixed in 1 mL THE in a vial under nitrogen atmosphere. After the addition of degassed H2O (12.5 μL, 0.7 mmol, 7 equiv.), the resulting mixture was stirred at 90° C. under nitrogen for 8 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/20) to give 6-1 as a yellow oil (28.0 mg, 67%). $R_f$=0.65 (hexane/ethyl acetate=9:1). $^1H$ NMR (400 MHz, $C_6D_6$): δ 7.60 (d, J=7.1 Hz, 1H), 7.19-7.14 (m, 2H), 6.96-6.93 (m, 2H), 6.88-6.85 (q, J=3.3, 2.1 Hz, 3H), 6.77'-6.73 (m, 5H), 6.72-6.62 (m, 3H), 6.37-6.33 (m, 3H), 6.17 (d, J=8.5 Hz, 2H) (aryl CH). $^3C$ NMR (101 MHz, $C_6D_6$): δ 147.9, 145.4, 143.7, 143.1, 138.7, 133.9, 131.9, 131.1, 130.0, 129.4, 127.9, 127.7, 127.4, 127.0, 126.0, 114.3 (aryl C). $^{11}B$ NMR (128 VHz, $C_6D_6$): δ 37.7 (br, 1B). IR (KBr, $cm^{-1}$): ν 3211, 3056, 3028, 2963, 2925, 2854, 1597, 1589, 1571, 1530, 1491, 1458, 1443, 1431, 1384, 1348, 1264, 1091, 1027, 1016. HRMS (ESI): Calcd for $C_{28}H_{22}BClN^+[M^+ H]^+$: 418.1528, found: 418.1520.

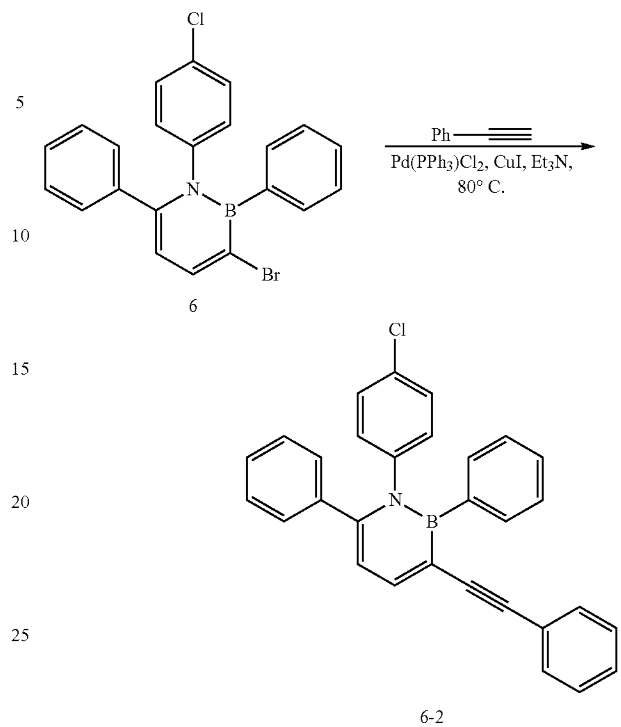

6

6-2

Synthesis of 6-2. 3-Bromo-1,2,6-triarylated azaborine 6 (41.9 mg, 0.1 mmol), PdCl2(PPh3)2 (3.5 mg, 0.005 mmol, 5 mol %), CuI (1.9 mg, 0.01 mmol, 10 mol %) and phenylacetylene (33 μL, 0.3 mmol, 3 equiv) were dissolved in triethylamine (0.4 mL) under nitrogen atmosphere. The resultant mixture was stirred at 80° C. under nitrogen for 24 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/20) to give 6-2 as a yellow oil (32.0 mg, 72%). $R_f$=0.6 (hexane/ethyl acetate=9:1). $^1H$ NMR (400 MHz, $C_6D_6$): δ 8.07 (d, J=7.3 Hz, 1H), 7.51-7.46 (m, 4H), 7.19-7.09 (m, 2H), 7.00-6.94 (m, 4H), 6.83 (s, 5H), 6.54 (d, J=8.6 Hz, 2H), 6.33 (d, J=7.2 Hz, 1H), 6.28 (d, J=8.6 Hz, 2H) (aryl CH).

$^{13}C$ NMR (101 MHz, $C_6D_6$): δ 148.8, 147.1, 143.2, 138.2, 134.3, 132.2, 131.8, 130.9, 129.8, 128.6, 128.2, 127.9, 127.7, 127.7, 127.2, 125.5, 114.5 (aryl C), 94.9, 94.6 (alkynyl C). $^{11}B$ NMR (128 MHz, $C_6D_6$): δ 38.1 (br, 1B). IR (KBr, $cm^1$): ν 3054, 2924, 1596, 1585, 1571, 1561, 1526, 1489, 1384, 1341, 1090, 1015. HRMS (ESI): Calcd for $C_{30}H_{22}BClN^+$ $[M^+ H]^+$: 442.1528, found: 442.1529.

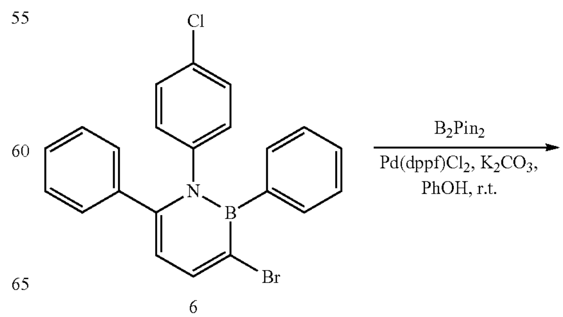

6

-continued

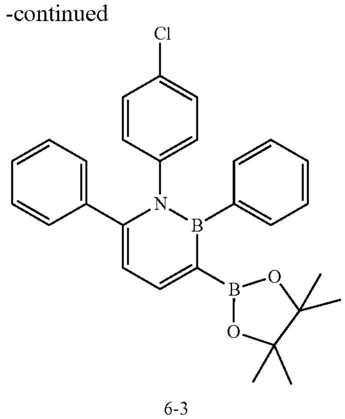

6-3

Synthesis of 6-3. 3-Bromo-1,2,6-triarylated azaborine 6 (41.9 mg, 0.1 mmol), Pd(dppf)Cl2 (3.7 mg, 0.005 mmol, 5 mol %), $B_2pin_2$ (27.9 mg, 0.11 mmol 1.1 equiv), $K_2CO_3$ (55.2 mg, 0.4 mmol, 4 equiv) and phenol (18.8 mg, 0.2 mmol, 2.0 equiv) were mixed in 0.8 mL THE in a vial under nitrogen atmosphere. The resulting mixture was stir-ed at room temperature under nitrogen for 8 h. Then, the reaction mixture was filtered through a pad of Celite, washed with ethyl acetate and concentrated to dryness in vacuo. The crude product was subjected to flash column chromatography (EtOAc/hexane=1/100 to 1/20) to give 6-3 as a yellow oil (24.5 mg, 52%). $R_f$=0.5 (hexane/ethyl acetate=9:1). $^1H$ NMR (400 MHz, $C_6D_6$): δ 8.62 (d, J=6.7 Hz, 1H), 7.35-7.31 (m, 2H), 7.15-7.10 (m, 3H), 6.89-6.87 (m, 2H), 6.83-6.81 (m, 3H), 6.56-6.50 (m, 3H), 6.33 (d, J=8.5 Hz, 2H) (aryl CH), 1.10 (s, 12H) ($CH_3$). $^{13}C$ NMR (101 MHz, $C_6D_6$): δ 152.5, 150.7, 143.5, 138.7, 133.9, 131.7, 131.1, 129.9, 129.4, 127.7, 126.7, 114.7 (aryl C), 82.9 ($CMe_2$), 24.9 ($CH_3$). $^{11}B$ NMR (128 MHz, $C_6D_6$): δ 39.1 (br, 1B) (BN), 33.7 (br, 1B) (Bpin). IR (KBr, $cm^{-1}$): v 2926, 2851, 1586, 1573, 1530, 1490, 1469, 1445, 1431, 1384, 1345, 1288, 1145, 1109, 1091, 1019. HRMS (ESI): Calcd for $C_{28}H_{29}B_2ClNO'$ $[M^+ H]^+$: 468.2067, found: 468.2069.

Example 4: Synthesis of 3-Iodo-1,2,6-Triarylated Azaborine

Note that synthesis of 1,2,3,6-tetrasubstituted azaborines has been very rare. Alternatively, such compounds can be prepared more efficiently via site-selective iodination of trisubstituted azaborine 3' (described above). This reaction scheme is shown below:

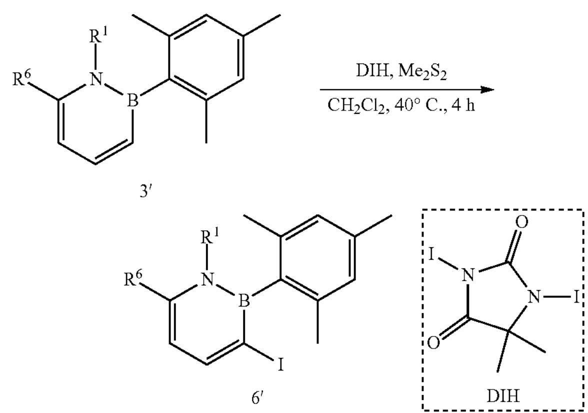

Preparation of mesityl protected monocyclic 1,2-azaborine iodides 6a'-6q' (a representative procedure D)

In a 4 mL vial, 3' (0.5 mmol) was dissolved in 1,2-dichloromethane (10 mL). 1,3-Diiodo-5,5-Dimethylhydantoin (DIH, 0.375 mmol, 142.5 mg) and $Me_2S_2$ (5 mol %, 2.4 mg) were added sequentially, then the vial was tightly sealed and stirred on a pie-block preheated to 40° C. (6e' required 0.75 mmol DIH and a reaction temperature of 60° C.). After 4 h, the reaction mixture was quenched with triethylamine (1 mmol, 0.14 mL) and the crude mixture was concentrated to dryness in vacuo. The crude product was subjected to flash column chromatography (EtOAc/hexane=1/100 to 1/20) to give azaborine iodide 6'.

Characterization

Below are the details of the characterization of compounds 6a'-6g'

6a'

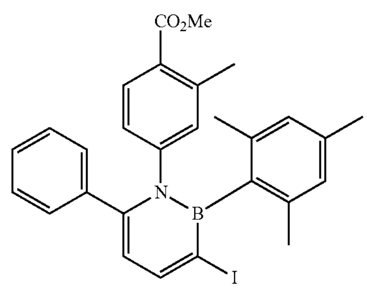

6a': Yield: 75% (mixture of 1:1 rotamers). Off-white solid. M.p.: 64-66° C. $R_f$: 0.3 (hexane/ethyl acetate=9:1). $^1H$ NMR (400 MHz, $CDCl_3$): δ 8.35 (d, J=7.4 Hz, 1H), 7.49 (d, J=8.1 Hz, 1H), 7.15-7.13 (m, 3H), 7.10-7.08 (m, 2H), 6.67 (s, 1H), 6.65 (d, J=2.4 Hz, 1H), 6.63 (d, J=6.4 Hz, 2H), 6.30 (d, J=7.4 Hz, 1H), 3.76 (s, 3H), 2.26 (s, 3H), 2.18 (s, 3H), 2.07 (s, 3H), 2.05 (s, 3H). $^{13}C$ NMR (101 MHz, $CDCl_3$): δ 167.27, 151.35, 148.86, 147.81, 140.25, 138.14, 138.13, 137.79, 137.06, 131.20, 130.35, 129.25, 127.94, 127.84, 126.93, 126.88, 125.08, 115.29, 51.79, 22.54, 21.48, 21.36. $^{11}B$ NMR (128 MHz, $CDCl_3$): δ 39.29. IR (KBr, $cm^{-1}$): 3025, 2948, 2913, 2855, 1722, 1866, 1608, 1589, 1572, 1506, 1488, 1445, 1435, 1361, 1339, 1257, 1191, 1169, 1142, 1105, 1084, 1023, 987, 966, 916, 884, 849, 819, 786, 763,737, 700 $cm^1$. HRMS (ESI): m/z calcd for $C_{28}H_{28}BINO_2^+$$[M^+ H^+]$: 548.1252. Found: 548.1256.

6b'

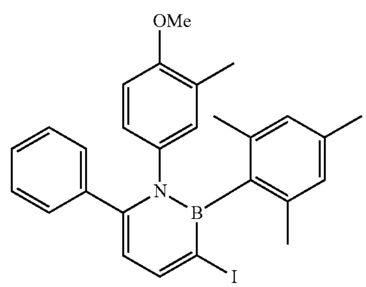

6b': Yield: 73%. Light yellow solid. M.p.: 168-170° C. $R_f$: 0.5 (hexane/ethyl acetate=9:1). $^1H$ NMR (400 MHz, $CDCl_3$): 8.33 (d, J=7.4 Hz, 1H), 7.15-7.13 (m, 3H), 7.11-

7.08 (m, 2H), 6.70 (d, J=8.8 Hz, 2H), 6.65 (s, 2H), 6.41 (d, J=8.8 Hz, 2H), 6.27 (d, J=7.4 Hz, 1H), 3.60 (s, 3H), 2.20 (s, 3H), 2.08 (s, 6H). $^{13}C$ NMR (101 MHz, $CDCl_3$): δ 157.41, 151.14, 149.85, 138.30, 138.19, 137.92, 136.72, 129.41, 128.48, 127.81, 127.48, 126.83, 114.99, 112.73, 55.20, 22.60, 21.40. $^{11}B$ NMR (128 MHz, $CDCl_3$): δ 39.91. IR (KBr, $cm^{-1}$): 2916, 2852, 1609, 1586, 1571, 1508, 1487, 1442, 1364, 1339, 1298, 1256, 1171, 1107, 1033, 979, 832, 763, 738, 699, 602 $cm^{-1}$. HRMS (ESI): m/z calcd for $C_{26}H_{27}BNO^+$ [$M^+$ $H^+$]: 506.1147. Found: 506.1153.

6c′

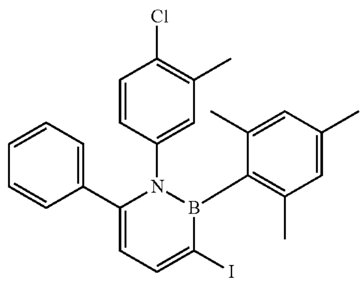

6c': Yield: 75%. Off-white solid. M.p.: 73-75° C. $R_f$: 0.55 (hexane/ethyl acetate=9:1). $^1H$ NMR (400 MHz, $CDC_3l$): 8.34 (d, J=7.4 Hz, 1H), 7.17-7.15 (m, 3H), 7.09-7.06 (m, 2H), 6.87 (d, J=8.6 Hz, 2H), 6.72 (d, J=8.7 Hz, 2H), 6.65 (s, 2H), 6.29 (d, J=7.3 Hz, 1H), 2.21 (s, 3H), 2.06 (s, 6H). $^{13}C$ NMR (101 MHz, $CDCl_3$): δ 151.40, 149.14, 143.44, 138.15, 137.84, 137.16, 131.93, 129.41, 128.96, 128.03, 127.84, 127.01, 115.30, 22.58, 21.43. $^{11}B$ NMR (128 MHz, $CDCl_3$): δ 40.15. IR (KBr, $cm^{-1}$): 3027, 2911, 2855, 1609, 1587, 1560, 1507, 1489, 1459, 1444, 1401, 1363, 1339, 1279, 1264, 1240, 1171, 1091, 1029, 1015, 980, 849, 833, 778, 762, 738, 715, 699 $cm^{-1}$. HRMS (ESI): m/z calcd for $C_{25}H_{23}BClN^+$[$M^+$ $H^+$]: 510.0651. Found: 510.0651.

6d′

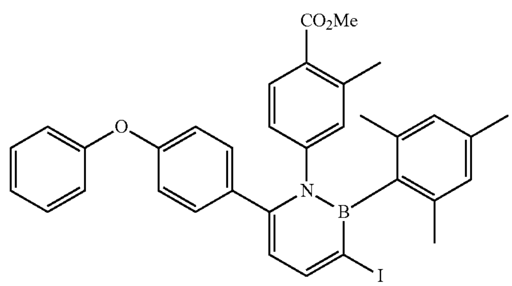

6d': Yield: 75% (mixture of 1:1 rotamers). Off-white solid. M.p.: 75-77° C. $R_f$: 0.4 (hexane/ethyl acetate=9:1). $^1H$ NMR (400 MHz, $CDC_3$): δ 8.35 (d, J=7.4 Hz, 1H), 7.54 (d, J=9.0 Hz, 1H), 7.33-7.29 (m, 2H), 7.10 (t, J=7.6 Hz, 1H), 7.05 (dd, J=8.7, 1.8 Hz, 2H), 6.89 (d, J=7.6 Hz, 2H), 6.77 (d, J=8.7 Hz, 2H), 6.70-6.64 (m, 4H), 6.31 (d, J=7.4 Hz, 1H), 3.80 (s, 3H), 2.31 (s, 3H), 2.19 (s, 3H), 2.07 (s, 6H). $^{13}C$ NMR (101 MHz, $CDCl_3$): δ 167.28, 156.88, 156.85, 151.38, 148.32, 147.89, 140.31, 138.15, 137.12, 132.78, 131.27, 130.83, 130.46, 129.92, 127.03, 126.97, 126.93, 125.16, 123.69, 119.05, 118.24, 115.13, 51.87, 22.60, 22.55, 21.55, 21.39. $^{11}B$ NMR (128 MHz, $CDCl_3$): δ 41.95. IR (KBr, $cm^{-1}$): 2948, 1722, 1608, 1589, 1512, 1488, 1434, 1360, 1336, 1241, 1192, 1168, 1142, 1104, 1085, 122, 870, 846, 811, 783, 749, 706, 693 $cm^{-1}$. HRMS (ESI): m/z calcd for $C_{34}H_{32}BINO_3^+$[$M^+$ $H^+$]: 640.1514. Found: 640.1512.

6e′

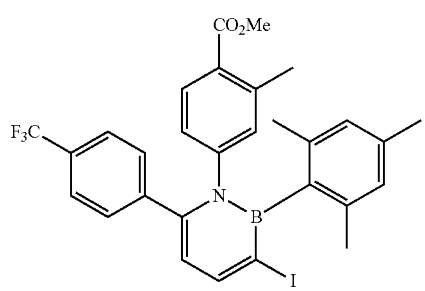

6e': Yield: 56% (mixture of 1:1 rotamers). White solid. M.p.: 168-170° C. Rr: 0.3 (hexane/ethyl acetate=9:1). $^1H$ NMR (400 MHz, $CDCl_3$): δ 8.37 (d, J=7.4 Hz, 1H), 7.52 (d, J=8.2 Hz, 1H), 7.41 (d, J=8.2 Hz, 2H), 7.24 (d, J=8.1 Hz, 2H), 6.69-6.12 (m, 4H), 6.29 (d, J=7.4 Hz, 1H), 3.78 (s, 3H), 2.27 (s, 3H), 2.19 (s, 3H), 2.08 (s, 3H), 2.03 (s, 3H). $^{13}C$ NMR (101 MHz, $CDCl_3$): δ 167.15, 151.26, 147.35, 147.12, 141.42, 140.62, 138.14, 138.11, 137.31, 131.05, 130.66, 129.56, 127.40, 127.04, 126.98, 125.01 (d, JC-CF3=4.0 Hz), 115.76, 51.91, 22.57, 22.54, 21.54, 21.38. $^{11}B$ NMR (128 MHz, $CDCl_3$): δ 40.33. $^{19}F$ NMR (376 MHz, $CDCl_3$): δ −62.71. IR (KBr, $cm^{-1}$): 2919, 1723, 1609, 1592, 1570, 1496, 1435, 1409, 1364, 1324, 1257, 1168, 1128, 1110, 1084, 1065, 1017, 885, 848, 816, 780, 757, 706, 678 $cm^{-1}$. HRMS (ESI): m/z calcd for $C_{29}H_{27}BF_3INO_2^+$[$M^+$ $H^+$]: 616.1126. Found: 616.1128.

6f′

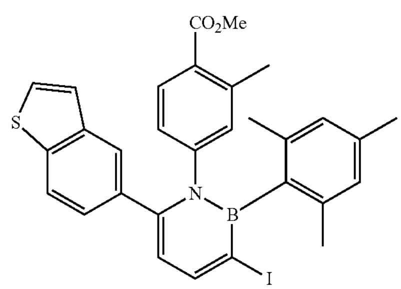

6f': Yield: 67% (mixture of 1:1 rotamers). White solid. M.p.: 88-90° C. Rr: 0.3 (hexane/ethyl acetate=9:1). $^1H$ NMR (500 MHz, $CDCl_3$): δ 8.36 (d, J=7.3 Hz, 1H), 7.67 (s, 1H), 7.58 (d, J=8.4 Hz, 1H), 7.46 (d, J=8.4 Hz, 1H), 7.42 (d, J=5.4 Hz, 1H), 7.24 (d, J=5.5 Hz, 1H), 6.98 (dd, J=8.4, 1.8 Hz, 1H), 6.74 (s, 1H), 6.69 (dd, J=8.4, 2.2 Hz, 1H), 6.65 (s, 1H), 6.61 (s, 1H), 6.35 (d, J=7.4 Hz, 1H), 3.73 (s, 3H), 2.24 (s, 3H), 2.19 (s, 3H), 2.12 (s, 3H), 2.04 (s, 3H). $^{13}C$ NMR (126 MHz, $CDCl_3$): δ 167.22, 151.39, 148.89, 147.85, 140.33, 139.29, 139.24, 138.18, 138.12, 137.09, 134.15, 131.17, 130.45, 127.44, 126.96, 126.94, 126.90, 125.33, 125.13, 124.33, 123.93, 121.87, 115.77, 51.77, 22.61, 22.54, 21.54, 21.38. $^{11}B$ NMR (160 MHz, $CDCl_3$): δ 39.48. IR (KBr, $cm^{-1}$): 2947, 1718, 1684, 1608, 1585, 1541, 1495, 1473, 1457, 1436, 1362, 1340, 1254, 1187, 1142, 1105, 1086, 1050, 1023, 997, 880, 848, 808, 782, 763, 737, 707, 682, 669 $cm^{-1}$. HRMS (ESI): m/z calcd for $C_{30}H_{28}BINO_2S^+$[$M^+$ $H^+$]: 604.0973. Found: 604.0974.

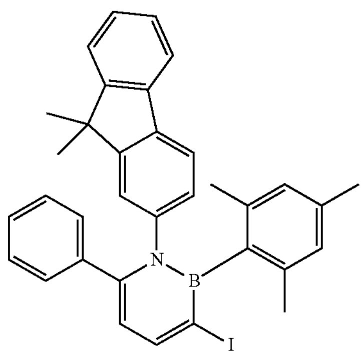

6g'

6g': Yield: 67% (mixture of 1:1 rotamers). White solid, M.p.: 136-138° C. $R_f$: 0.6 (hexane/ethyl acetate=9:1). $^1H$ NMR (500 MHz, $CDCl_3$): δ 8.37 (d, J=7.4 Hz, 1H), 7.50 (d, J=6.4 Hz, 1H), 7.32-7.30 (m, 1H), 7.26-7.22 (m, 3H), 7.15-7.13 (m, 2H), 7.09-7.06 (m, 3H), 6.78 (s, 1H), 6.72 (dd, J=8.0, 2.0 Hz, 1H), 6.61 (s, 1H), 6.59 (s, 1H), 6.34 (d, J=7.4 Hz, 1H), 2.12 (s, 3H), 2.12 (s, 3H), 2.09 (s, 3H), 1.14 (s, 3H), 1.12 (s, 3H). $^{13}C$ NMR (126 MHz, $CDCl_3$): δ 153.76, 153.04, 151.19, 149.64, 143.95, 138.69, 138.32, 138.15, 136.87, 136.74, 129.46, 127.80, 127.52, 127.23, 127.06, 126.88, 126.53, 122.70, 120.01, 118.9, 114.97, 46.55, 26.76, 26.38, 22.60, 22.58, 21.30. $^{11}B$ NMR (128 MHz, $CDCl_3$): δ 39.75. IR (KBr, $cm^{-1}$): 2958, 2919, 2856, 1610, 1586, 1571, 1506, 1488, 1472, 1459, 1448, 1421, 1361, 1339, 1297, 1279, 1171, 1155, 1101, 1075, 1028, 995, 847, 828, 761, 738, 698 $cm^{-1}$. HRMS (ESI): m/z calcd for $C_{34}H_{32}BIN^+$ [$M^+$ $H^+$]: 592.1667. Found: 592.1664.

Example 5: Synthesis of a BN Isostere of the Biologically Active PD-1/PD-L1 Inhibitor To show the synthetic utility of this method, first a BN isostere of a PD-1/PD-L1 inhibitor was synthesized, as shown below:

An oven-dried 4 mL vial was charged with azaborine 3ax (0.2 mmol, 1 equiv), $Pd(OAc)_2$ (2.7 mg, 0.012 mmol, 6 mol %), $BuPAd_2$ (di(1-adamantyl)-n-butylphosphine, 8.6 mg, 0.024 mmol, 12 mol %), and HCOONa (68 mg, 1 mmol, 5 equiv) in a nitrogen-filled glovebox. Dry DMF (0.4 mL) was then added. After triethylamine (56 μL, 0.4 mmol, 2 equiv), formic acid (15 μL, 0.4 mmol, 2 equiv) and acetic anhydride (38 μL, 0.4 mmol, 2.0 equiv) were added, the vial was tightly sealed and stirred at 100° C. under nitrogen for 1 h. Upon completion, extra triethylamine (140 μL, 1 mmol, 5 equiv) was added before all the solvent was removed under vacuum. The residue was dissolved with pentane and filtered through a pad of silica gel under nitrogen to give the crude aldehyde.

The crude aldehyde was then dissolved in 1 mL dry THF, followed by the addition of ethanolamine (12 μL, 0.2 mmol) and $Mg_2SO_4$ (36 mg, 0.3 mmol). The reaction mixture was stirred at room temperature for 12 h before sodium borohydride (11.3 mg, 0.3 mmol) was added. The mixture was then stirred at room temperature for 2 h. Upon completion, the mixture was filtered through a pad of Celite, washed with ethyl acetate and concentrated to dryness in vacuo. The crude product was subjected to flash column chromatography (MeOH/DCM=1/100 to 1/10) to give 7 as a light brown oil (19 mg, 30% over two steps). $R_f$=0.2 (DCM/MeOH=9:1). $^1H$ NMR (400 MHz, $C_6D_6$): δ 7.77-7.59 (m, 3H), 7.36 (t, J=7.4 Hz, 2H), 7.31-7.25 (m, 1H), 7.14-7.02 (m, 5H), 6.3¶ (d, J=6.6 Hz, 1H) (aryl CH), 3.47-3.41 (m, 4H) ($CH_2$), 3.18 (s, 3H) ($CH_3$), 2.42 (s, 2H) ($OH_2$). $^{13}C$ NMR (126 MHz, $C_6D_6$): δ 143.4, 133.7, 129.3, 127.9, 114.3 (aryl C), 61.1, 53.2, 51.0 ($CH_2$), 40.0 ($CH_3$). $^{11}B$ NMR (128 MHz, $C_6D_6$): δ 37.3 (br, 1B). IR (KBr, $cm^{-1}$): v 2957, 2918, 2852, 1654, 1598, 1534, 1458, 1448, 1412, 1384, 1250, 1178, 1084, 1027. HRMS (ESI): Calcd for $C_{20}H_{24}BN_2O^+$ [$M^+$ H]$^+$: 319.1976, found: 319.1983.

Starting from imine lax (prepared from the corresponding commercially available ketone and methylamine), the benzannulation with $PhBBr_2$ provided the 1,2-azaborine intermediate (3ax), which then underwent a Pd-catalyzed formylation and reductive amination to deliver the target BN isostere analogue 7. Compound 7 is stable to air and moisture and can be purified via silica gel chromatography.

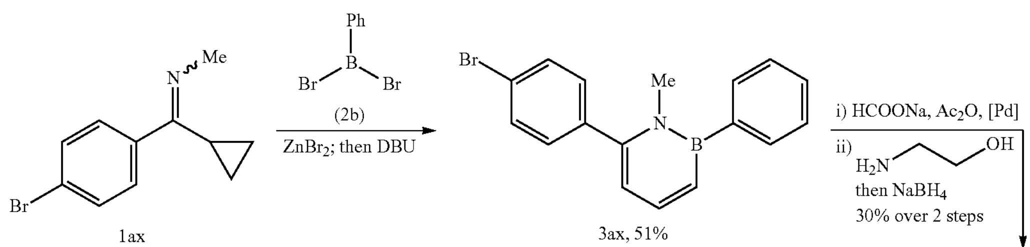

1ax

3ax, 51%

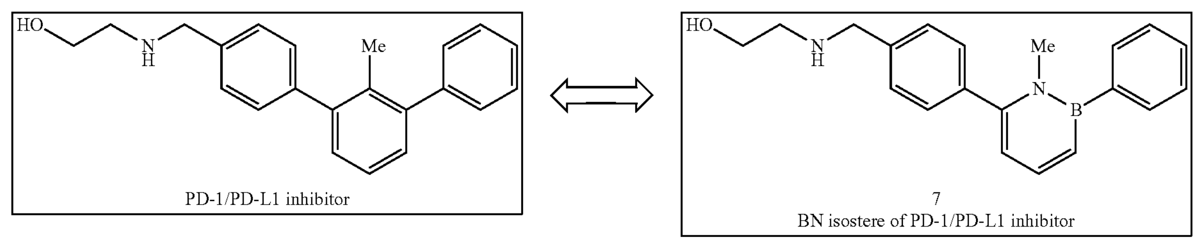

PD-1/PD-L1 inhibitor

7

BN isostere of PD-1/PD-L1 inhibitor

Example 6: Synthesis of a BN Isostere of Bifenthrin

In addition, 1,2-azaborine 3p can be converted to a BN isostere (8) of an insecticide bifenthrin via a boryl diazo intermediate ($3p-CN_2$) in a four-step sequence, shown below:

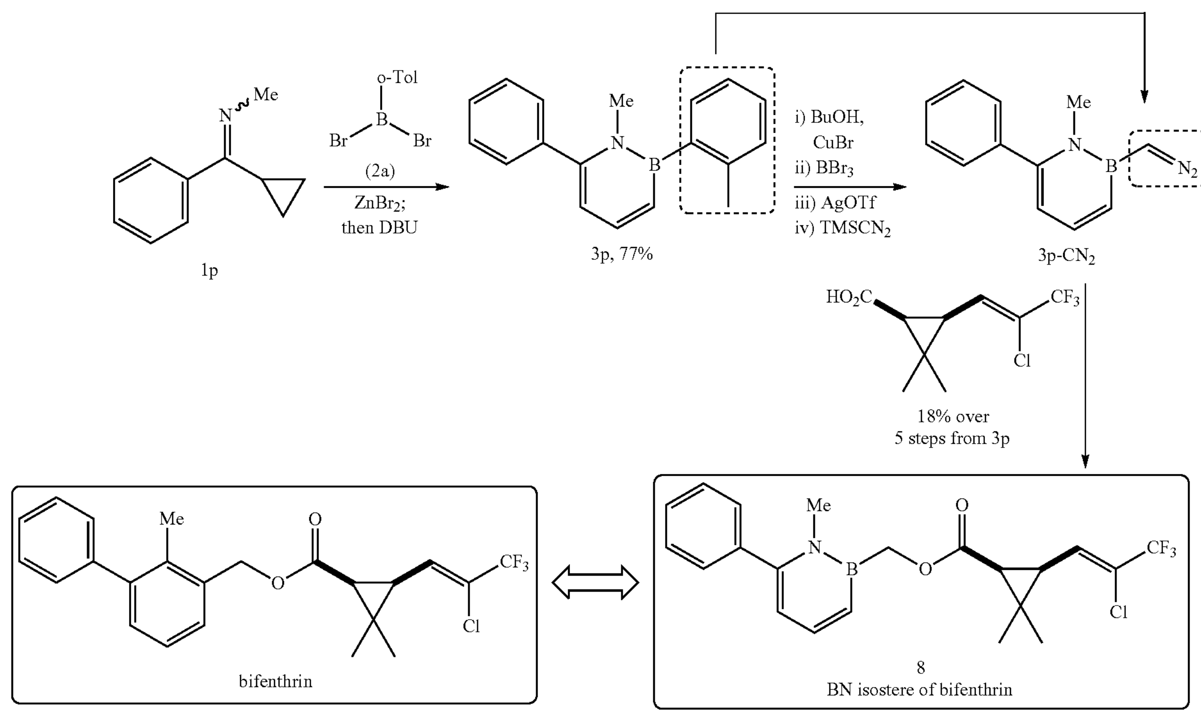

1p 3p, 77%

$3p-CN_2$ bifenthrin

8

BN isostere of bifenthrin

In a nitrogen-filled glovebox, an oven-dried 4 mL vial was charged with azaborine 3p (116 mg, 0.45 mmol, 1 equiv), 1-butanol (45 μL, 0.5 mmol, 1.1 equiv), CuBr (6.7 mg, 0.045 mmol, 10 mol %), pyridine (73 μL, 0.9 mmol, 2 equiv), DTBP (di-tert-butyl peroxide, 82 μL, 0.45 mmol, 1 equiv) and toluene (1.5 mL). The vial was tightly sealed and stirred at 90° C. under nitrogen for 1 h. Upon completion, all the solvent was removed under vacuum. Inside the glovebox, the residue was dissolved with dry pentane, filter d through a pad of silica gel, washed with pentane, and concentrated to dryness to give t e crude 3p-OBu (~0.31 mmol). Then, at −30° C., BBr3 (19 μL, 0.2 mmol) was added slowly to the pentane (5 mL) solution of 3p-OBu, and the reaction mixture was allowed to warm to room temperature and stir for 1 h. Upon completion, the mixture was filtered through a pad of C lite, washed with pentane and concentrated to dryness under vacuum to give crude 3p-Br (~0.3 mmol). To the DCM (3 mL) solution of crude 3p-Br was added AgOTf (77 mg, 0.3 mmol) and the mixture was stirred at room temperature for 4 h. All the solvent was removed under vacuum, and the residue was dissolved with dry pentane, filtered through a pad of Celite, washed with pentane, and concentrated to dryness to give the crude 3p-OTf (~0.2 mmol). Afterwards, to the hexane (2 mL) solution of crude 3p-OTf was added (trimethylsilyl)diazomethane (2 M in hexane, 0.2 mL, 0.4 mmol). After being stirred at room temperature for 5 min, the reaction mixture was further stirred at 40° C. under nitrogen for 2 h. Upon completion, the mixture was filtered through a pad of Celite, washed with pentane and concentrated to dryness under vacuum to give crude 3p-CN2. Then, cis-3-(2-chloro-3,3,3-trifluoroprop-1-en-1-yl)-2,2-dimethylcyclopropanecarboxylic acid (48.5 mg, 0.2 mmol) was added to the pentane solution of crude 3p-CN2, and the mixture was stirred at room temperature for 30 min until the $^{11}B$ NMR showed a main signal at 36.2 ppm. Inside the glovebox, the mixture was filtered through a pad of Celite, washed with pentane, and concentrated to dryness. The resulting crude product was purified by passing through a pipette silica plug (pure pentane to ether/pentane=1/20) to give 8 as a colorless oil (34 mg, 18% over 5 steps). $^1H$ NMR (500 MHz, $C_6D_6$): δ 7.62 (dd, J=11.0, 6.7 Hz, 1H), 7.46-7.39 (m, 1H), 7.13 (dd, J=11.0, 1.6 Hz, 1H), 7.08-7.03 (m, 3H), 6.98-6.90 (m, 2H), 6.20 (dd, J=6.7, 1.6 Hz, 1H) (aryl CH), 4.39 (dd, J=28.5, 16.5, 2H) ($OCH_2$) 2.62 (s, 3H) ($NCH_3$), 2.01-1.96 (m, 2H) (CH), 1.19 (s, 3H), 0.81 (s, 3H) ($CH_3$). $^{13}C$ NMR (126 MHz, $C_6D_6$): δ 171.1 (carbonyl C), 149.9, 143.4, 138.4, 131.6 (q, $^3J_{C-CF3}$=4.4 Hz), 129.2, 128.4, 121.8 (q, $^2J_{C-CF3}$=37.2 Hz) (aryl C and alkenyl C), 121. 5 (q, $^1J_{C-CF3}$=271.1 Hz) ($CF_3$), 113.8 (aryl C), 59.2 ($OCH_2$), 37.0, 33.6, 31.0, 28.4, 28.0, 14.9 (alkyl C). $^{11}B$ NMR (160 MHz, $C_6D_6$): δ 36.2 (br, 1B). $^{11}F$ NMR (470 MHz, $C_6D_6$): δ −68.4 (m, 3F) ($CF_3$). IR (KBr, $cm^{-1}$): v 3061, 3025, 2957, 2925, 2874, 2854, 1719, 1652, 1593, 1531, 1490, 1416, 1384, 1294, 1273, 1239, 1190, 1140, 1084, 1052. HRMS (ESI): Calcd for $C_{21}H_{23}BClF_3NO_2^+$ $[M^+ H]^+$: 424.1457, found: 424.1464.

Example 7: One-Pot Synthesis of 1,2-Azaborine Starting from Cyclopropyl Phenyl Ketone Note that the aryl group on the boron can be easily converted to a more reactive alkoxy group that can be further transformed to other moieties. Bio-evaluation and pharmacological profiling of these BN-isostere analogues will be carried out in the future. Moreover, a one-pot protocol of preparing 1,2-azaborine 3a directly from commercially available cyclopropyl phenyl ketone was realized in good efficiency, as shown below:

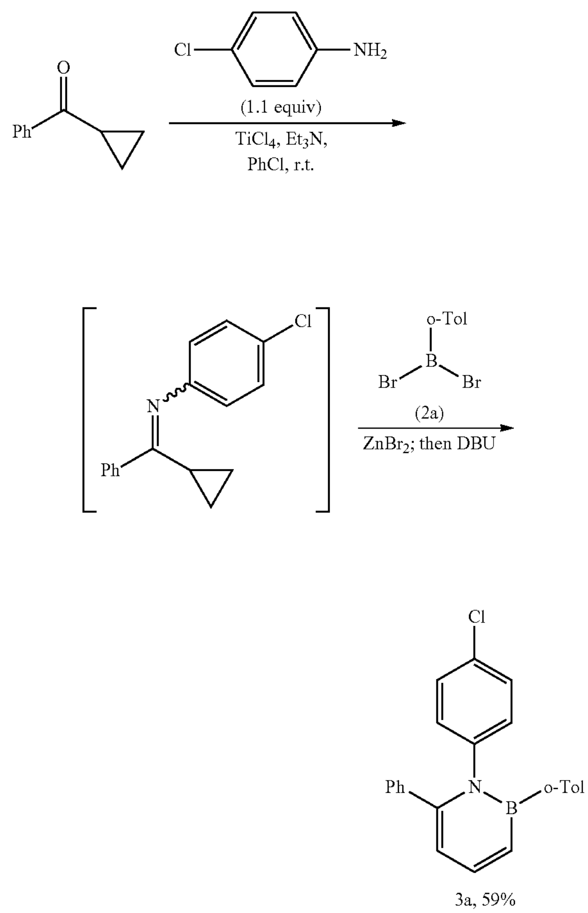

3a, 59%

An oven-dried 4 mL vial was charged with the cyclopropyl phenyl ketone (28 μL, 0.2 mmol, 1 equiv), 4-chloroaniline (28 mg, 0.22 mmol, 1.1 equiv), triethylamine (67 μL, 0.48 mmol, 2.4 equiv) and dry chlorobenzene (1 mL). $TiCl_4$ (13 μL, 0.12 mmol, 0.6 equiv) was then added slowly. After the reaction mixture was stirred at room temperature under nitrogen for 12 h, $ZnBr_2$ (4.5 mg, 0.02 mmol, 10 mol %) and 2a (136 mg, 0.52 mmol, 2.6 equiv) were added, and the vial was tightly sealed and stirred on a pie-block preheated to 60° C. under nitrogen for 4 h. Then, 1, 8-diazabicyclo(5.4.0) undec-7-ene (DBU, 210 μL, 1.4 mmol, 7 equiv) was added and the reaction mixture was stirred at the same temperature under nitrogen for 24 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/20) to give azaborine 3a as a light brown oil (42 mg, 59%).

Example 8: Gram-Scale Reaction

Finally, the synthesis of 1,2-azaborine 3n is readily scalable; good yield can be retained in a gram-scale reaction, as shown in FIG. 1.

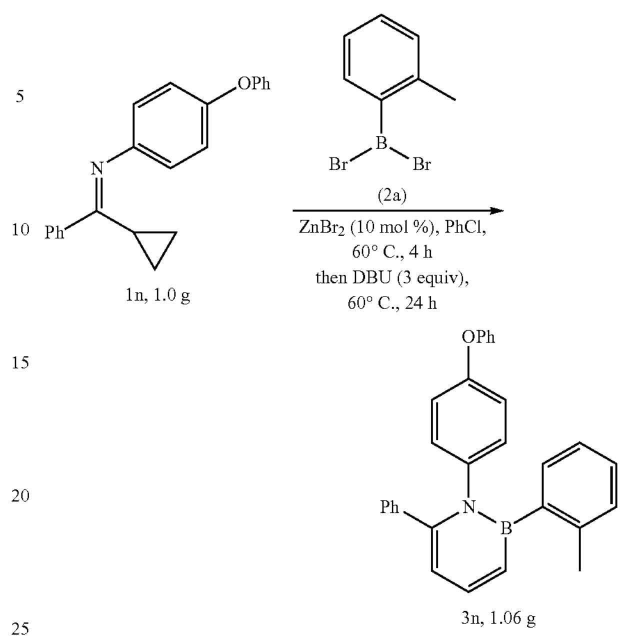

1n, 1.0 g 3n, 1.06 g

An oven-dried 40 mL vial was charged with imine 1n (1.0 g, 3.2 mmol, 1 equiv) and $ZnBr_2$ (72.0 mg, 0.32 mmol, 10 mol %) in a nitrogen-filled glovebox. Dry chlorobenzene (16 mL) was then added. After (o-tolyl)BBr2 (2a, 915.2 mg, 3.52 mmol, 1.1 equiv) was added, the vial was tightly sealed and stirred on a pie-block preheated to 60° C. under nitrogen for 4 h. 1, 8-Diazabicyclo(5.4.0)undec-7-ene (DBU, 1.43 mL, 9.6 mmol, 3 equiv) was then added and the reaction mixture was stirred at the same temperature for 24 h. After cooling to room temperature, the reaction mixture was filtered through a pad of Celite, washed with ethyl acetate and concentrated to dryness in vacuo. The crude product as subjected to flash column chromatography (EtOAc/hexane=1/100 to 1/20) to give azaborine 3n as a pale yellow solid (1.06 g, 80%).

Example 9: Mechanistic Studies. To gain some insights into the reaction mechanism, efforts were first put forth to isolate the intermediates from different reaction stages. After imine 1a reacted with (o-tolyl)$BBr_2$ 2a in the presence of $ZnBr_2$ (without adding DBU), the proposed dibromo intermediate 4a after the C—C cleavage was formed in high yield based on NMR analysis. While 4a was not isolatable, the corresponding hydrolysis product 4a' can be purified and fully characterized, which suggests intermediacy of such an alkyl bromide in the ring-opening stage. This is shown in the schematic below:

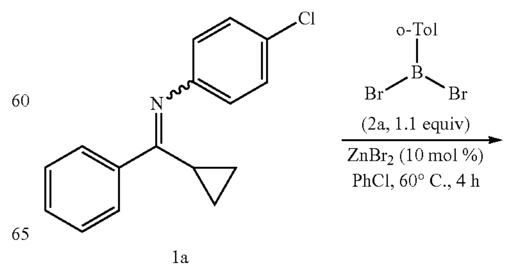

1a

-continued

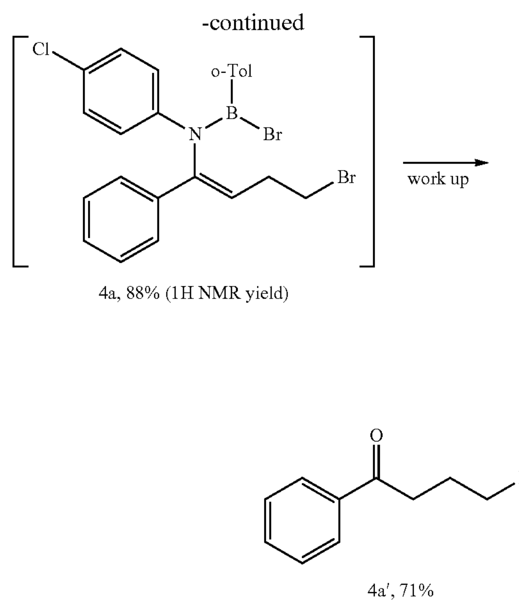

4a, 88% (1H NMR yield)

4a', 71%

An oven-dried 4 mL vial was charged with imine 1a (51 mg, 0.2 mmol, 1 equiv) and $ZnBr_2$ (4.5 mg, 0.02 mmol, 10 mol %) in a nitrogen-filled glovebox. Dry chlorobenzene (1 mL) was then added. After 2a (57 mg, 0.22 mmol, 1.1 equiv) was added, the vial was tightly sealed and stirred on a pie-block preheated to 60° C. under nitrogen for 4 h. After cooling to room temperature, reaction mixture was concentrated to dryness in vacuo. The obtained crude product 4a was analyzed by $^1H$ NMR using dibromomethane as the internal standard. After the addition of water (1 mL) and being stirred at room temperature for 2 h, the mixture was extracted with ethyl acetate (3×5 mL) and the combined organic layers was washed with brine, dried over $MgSO_4$ and concentrated under vacuum. The crude product was subjected to flash column chromatography (EtOAc/hexane=1/20) to give 4a' as a colorless oil (32.0 mg, 71%). $R_f$=0.6 (hexane/ethyl acetate=9:1). $^1H$ NMR (500 MHz, $CDC_3$): δ 7.98 (d, J=7.0 Hz, 2H), 7.62-7.53 (m, 1H), 7.48 (dd, J=8.4, 7.1 Hz, 2H) (phenyl CH), 3.56 (t, J=6.3 Hz, 2H), 3.19 (t, J=6.9 Hz, 2H), 2.35-2.29 (m, 2H) ($CH_2$). $^{13}C$ NMR (126 MHz, $CDC_3$): δ 199.0 (C═O), 136.9, 133.4, 128.8, 128.2 (phenyl C), 36.7, 33.8, 27.0 ($CH_2$). The NMR data match with those reported in literature.

Note that compound 4a is extremely sensitive to oxygen a d moisture, and it was quickly converted to the hydrolyzed product in air. $^1H$ NMR (500 MHz, $C_6D_6$): δ 7.57-7.48 (m, 2H), 7.12-7.09 (m, 2H), 7.03-6.94 (m, 4H), 6.89-6.84 (m, 3H), 6.61 (d, J=8.8 Hz, 2H) (aryl CH), 5.82 (dd, J=7.5, 6.2 Hz, 1H) (olefinic CH), 3.15-3.05 (m, 2H), 2.89-2.73 (m, 2H) ($CH_2$), 2.27 (s, 3H) ($CH_3$). $^{13}C$ NMR (126 MHz, $C_6D_6$): δ 145.9, 143.2, 137.3, 131.5, 130.2, 129.7, 128.9, 128.7, 127.2, 126.9, 125.6, 125.2 (aryl C and olifinic C), 32.6, 31.8, 22.9 ($CH_2$ and $CH_3$). $^{11}B$ NMR (160 MHz, $C_6D_6$): δ 40.3 (br, 1B).

Figure 2:
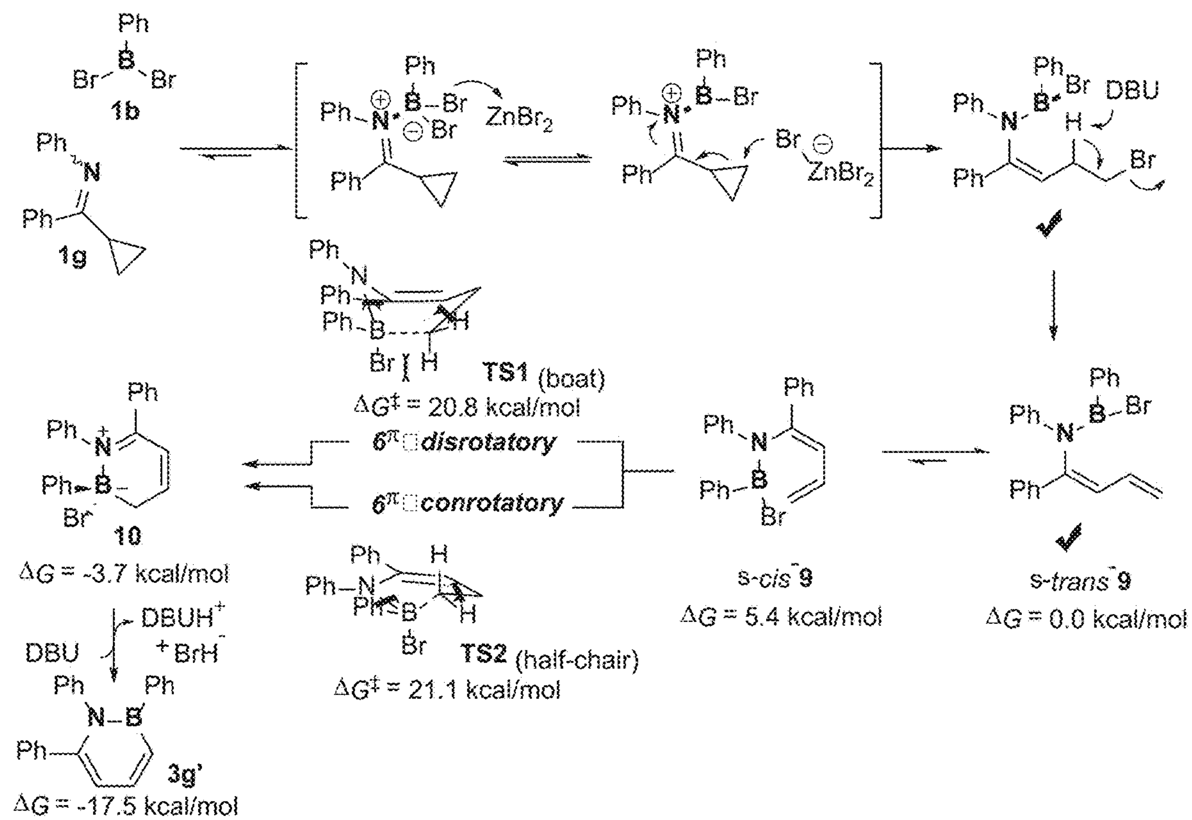
FIG. 2 is a schematic of a proposed mechanism and the energy of the 6π-electrocyclization pathway to form 1,2-azaborines.

This observation is consistent to a Lewis acid-promoted ring-opening pathway for cyclopropyl imines and previous understanding of the bromide anion abstraction/ring-opening process in the $ArBBr_2/ZnBr_2$ system, as shown in FIG. 2. When imine 11 was used as the substrate, shortening the DBU treatment time to 1 h led to isolation of a diene intermediate (51') in 75% yield along with 8% 1,2-azaborine product 31. This reaction is shown in the schematic below:

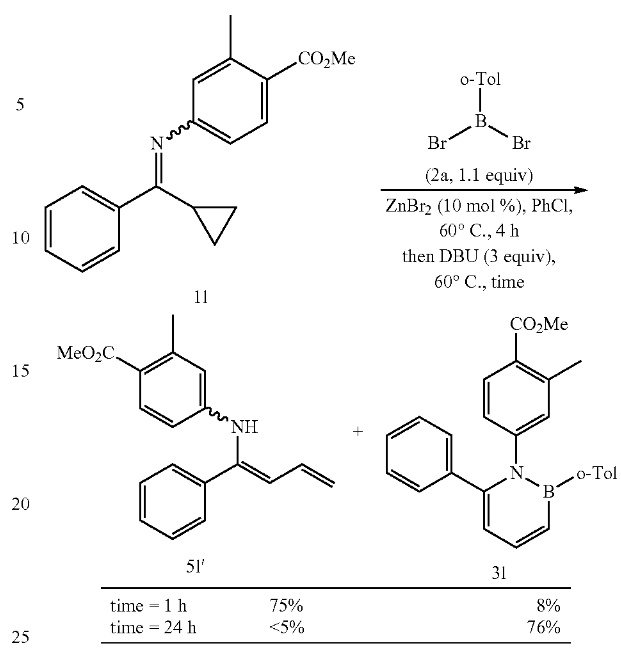

11

51'

31

| | 51' | 31 |
|---|---|---|
| time = 1 h | 75% | 8% |
| time = 24 h | <5% | 76% |

An oven-dried 4 mL vial was charged with imine 11 (0.2 mmol, 1 equiv) and ZnBr2 (4.5 mg, 0.02 mmol, 10 mol %) in a nitrogen-filled glovebox. Dry chlorobenzene (1 mL) was then added. After (o-tolyl)$BBr_2$ (2b, 0.22 mmol, 1.1 equiv) was added, the vial was tightly sealed and stirred on a pie-block preheated to 60° C. under nitrogen for 4 h. 1,8-Diazabicyclo(5.4.0)undec-7-ene (DBU, 90 μL, 0.6 mmol, 3 equiv) was then added and the reaction mixture was stirred at the same temperature for 1 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/10) to give 31 (6 mg, 8%) and 51' (44 mg, 75%).

51'

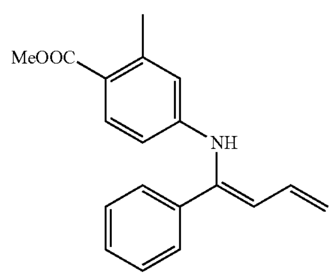

51': Yield: 75%. Light brown oil. $R_f$=0.4 (hexane/ethyl acetate=9:1). $^1H$ NMR (500 MHz, $C_6D_6$): δ 8.03 (d, J=8.4 Hz, 1H), 7.44-7.38 (m, 2H), 7.17-7.13 (m, 2H), 6.66-6.58 (m, 1H), 6.38-6.31 (m, 2H) (aryl CH), 6.20 (d, J=10.8 Hz, 1H), 5.34-5.25 (m, 2H), 5.11 (dd, J=10.2, 2.0 Hz, 1H) (olefinic CH and $CH_2$), 3.58 (s, 3H) ($COOCH_3$), 2.73 (s, 3H) ($CH_3$). $^{13}C$ NMR (126 MHz, $C_6D_6$): δ 167.3 ($COOCH_3$), 148.4, 143.0, 138.3, 138.0, 133.1, 132.9, 128.8, 128.7, 127.1, 120.8, 120.1, 118.3, 117.2, 112.5 (aryl and olefinic C), 50.9 ($COOCH_3$), 22.8 ($CH_3$). IR (KBr, $cm^{-1}$): ν 3362, 3062, 3028, 2949, 2930, 2851, 1709, 1654, 1637, 1606, 1577, 1508, 1491, 1448, 1433, 1384, 1342, 1255, 1189, 1141, 1084, 1028. HRMS (ESI): Calcd for $C_{19}H_{20}NO_2^+$ [M+H]$^+$: 294.1489, found: 294.1491.

In contrast, when the reaction was allowed to stir for 24 h after the addition of DBU, 51' almost fully disappeared and was converted to 1,2-azaborine 31. This observation indicates that a diene intermediate, generated via a base-mediated elimination of HBr, is likely involved in the cyclization stage. As a control experiment, the use of homoallylamine 1ba (mono alkene) as the substrate did not yield any cyclized product under the standard conditions, implying the important role of such a conjugate diene structure in the C—B bond-forming stage. This reaction scheme is shown below:

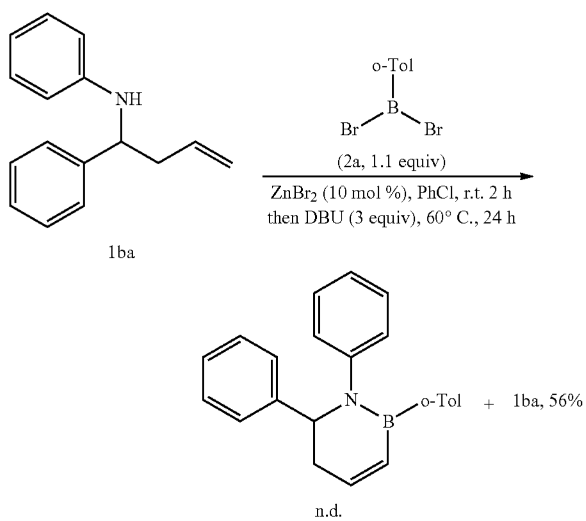

1ba

+ 1ba, 56% n.d.

An oven-dried 4 mL vial was charged with (o-tolyl)BBr2 (2b, 0.22 mmol, 1.1 equiv.) and $ZnBr_2$ (4.5 mg, 0.02 mmol, 10 mol %) in a nitrogen-filled glovebox. Dry chlorobenzene (0.5 mL) was then added. After the slow addition of a chlorobenzene (0.5 mL) solution of amine 1as (44.6 mg, 0.2 mmol, 1 equiv), the vial was tightly sealed and stirred at room temperature under nitrogen for 2 h. 1,8-Diazabicyclo (5.4.0)undec-7-ene (DBU, 90 μL, 0.6 mmol, 3 equiv) was then added and the reaction mixture was stirred at 60° C. under nitrogen for 1 h. After cooling to room temperature, the reaction mixture was filtered through a pad of Celite, washed with ethyl acetate and concentrated to dryness in vacuo. The crude product was subjected to flash column chromatography (EtOAc/hexane=1/100 to 1/10) to recover 1as (25.0 mg, 56%).

DISCUSSION

To understand how 1,2-azaborine is generated from the putative diene intermediate, density functional theory (DFT) calculations were conducted and Torsion energies were calculated.

All density functional theory (DFT) calculations were carried out using Gaussian 16. Geometries of intermediates and transition states were optimized using the M06-2X functional with 6-31G(d) basis set in the gas phase. Vibrational frequency calculations were performed for all the stationary points to confirm if each optimized structure is a local minimum or a transition state structure. Solvation energy corrections were calculated in chlorobenzene solvent with the SMD continuum solvation model based on the gas-phase optimized geometries. The M06-2X functional with 6-311+G(d,p) basis set was used in single-point energy calculations.

Torsion energies (ΔEtorsion) were calculated by comparing the single point energy difference between the freely optimized s-cis conformer of the starting materials (s-cis-9 and s-cis-11) and the s-cis conformer of the starting materials obtained from constrained geometry optimizations with a fixed dihedral angle ($C_1$-N—B—Br or $C_3$-C2-C1-Br) to match the dihedral angle about these bonds in corresponding transition state structures (θ(C1-N—B—Br)=−52.2° for TS1 and θ(C3-C2-C1-Br)=−31.5° for TS3). The M06-2X functional with 6-311+G(d,p) basis set using Hirshfeld population analysis was used in the calculation of molecular orbital coefficients at each atom (with the threshold of the contributions set to 1%). The 3D images of computed structures were prepared using CYLView. Molecular orbital visualizations were prepared using PyMOL software.

Figure 3:
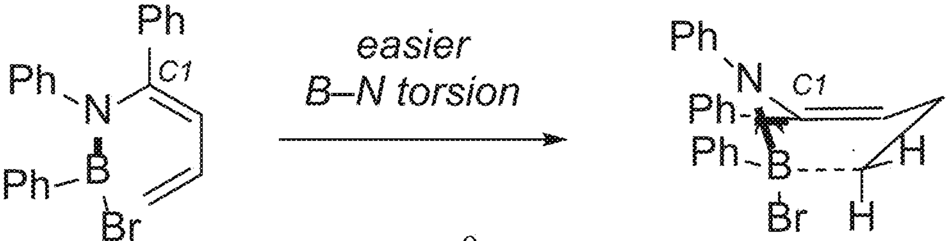
FIG. 3 is a schematic of a torsion-promoted electrocyclizatio of intermediate 9, comparing to a triene substrate 11.
Figure 3:
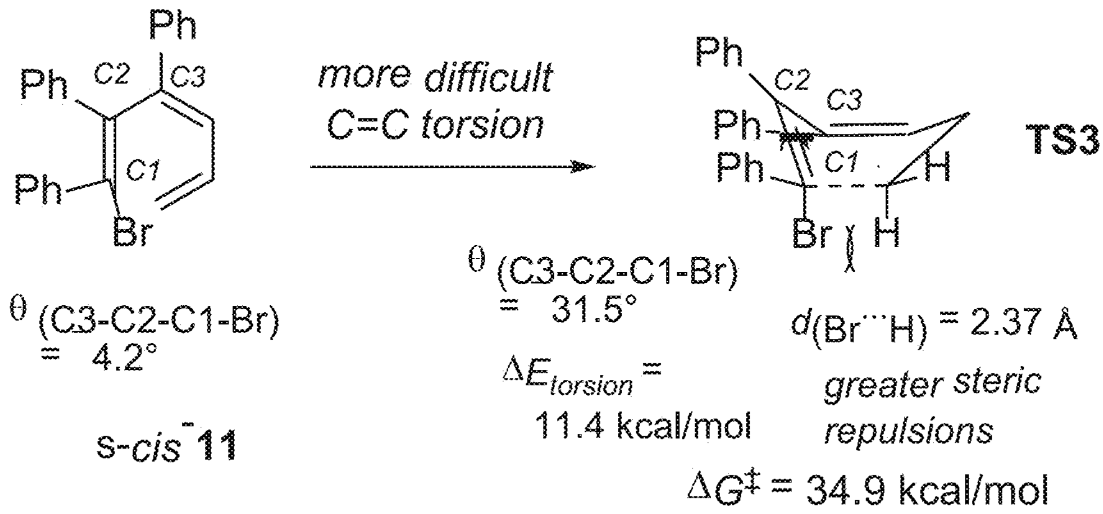

These calculation support an unusual 6π-electrocyclization mechanism, as shown in FIG. 2. The diene intermediate is an isostere of 1,3,5-trienes that are known to undergo 6π-electrocyclization; however, 6π-electrocyclization of unactivated trienes bearing two terminal substituents suffers from relatively low reactivity. For example, the reaction of triene 11, the CC isostere of the BN-diene intermediate (9), requires a relatively high activation free energy of 34.9 kcal/mol, as shown in FIG. 3. By contrast, calculations indicate that diene 9 undergoes a much more facile 6π-electrocyclization via TS1 to form cyclic N-borylat d iminium 10, which upon DBU-mediated elimination of HBr forms azaborine 3g'. The 6π-electrocyclization requires a low activation free energy of 20.8 kcal/mol with respect to the s-trans conformer of 9, which is consistent with the mild reaction conditions observed for the 1,2-azaborine formation. The reactivity of diene 9 is promoted by the polarization of the B—N bond as well as the smaller torsional strain to rotate the B—N bond, compared to the rotation of C═C double bond in 1,3,5-trienes, e.g., 11, as shown in FIG. 3. In TS1, the B—N bond is rotated to a more non-planar geometry, evidenced by the larger dihedral angle of θ(C1-N—B—Br) (−52.2°); for comparison, the corresponding dihedral angle of θ(C3-C2-C1—Br) (−31.5°) in the 67I-electrocyclization transition state of triene 11 is much smaller. The non-planar geometry of the B—N terminus leads to attractive interactions of the electron-rich dienamine moiety with the vacant B orbital on the borane terminus, as well as reduces the steric repulsions between these two termini in the boat-like transition state, as shown in FIG. 3. Notwithstanding the greater rotation, a smaller torsional energy is required to distort the B—N bond in 9 to the corresponding transition state geometry compared to the rotation of the terminal C═C bond in 11 ($\Delta E_{torsion}$=8.8 and 11.4 kcal/mol for 9 and 11, respectively). As a result, the 6π-electrocyclization of diene 9 requires a much lower activation free energy than the corresponding reaction with triene 11 ($\Delta\Delta^{+}$=14.1 kcal/mol).

Figure 4:
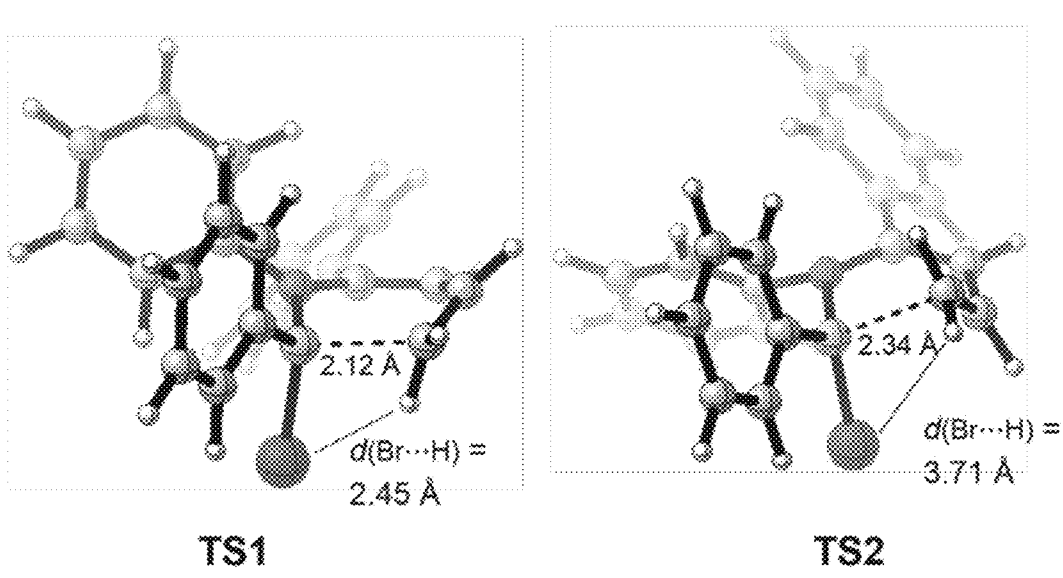
FIG. 4 is a schematic of a transition state structures of TS1 and TS2.
Figure 5:
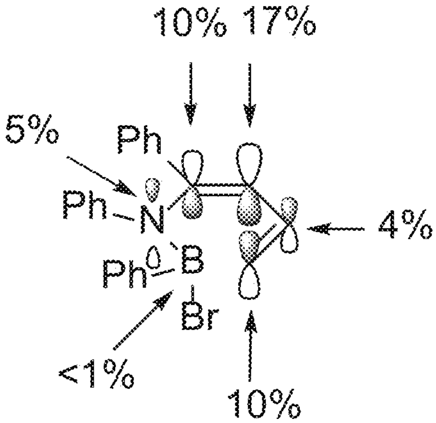
FIG. 5 is a schematic of a unique nodal properties of the π-system of intermediate 9 lead to the small energy difference between the symmetry-allowed (TS1) and forbidden (TS2) electrocyclization pathways. DFT calculations were performed at the M06-2X/6-311+G(d,p)/SMD(chlorobenzene)//M06-2X/6-31G(d) level of theory. All energies are with respect to s-trans-9.
Figure 5:
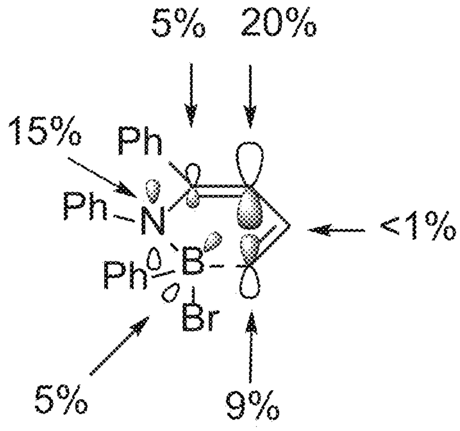
Figure 6:
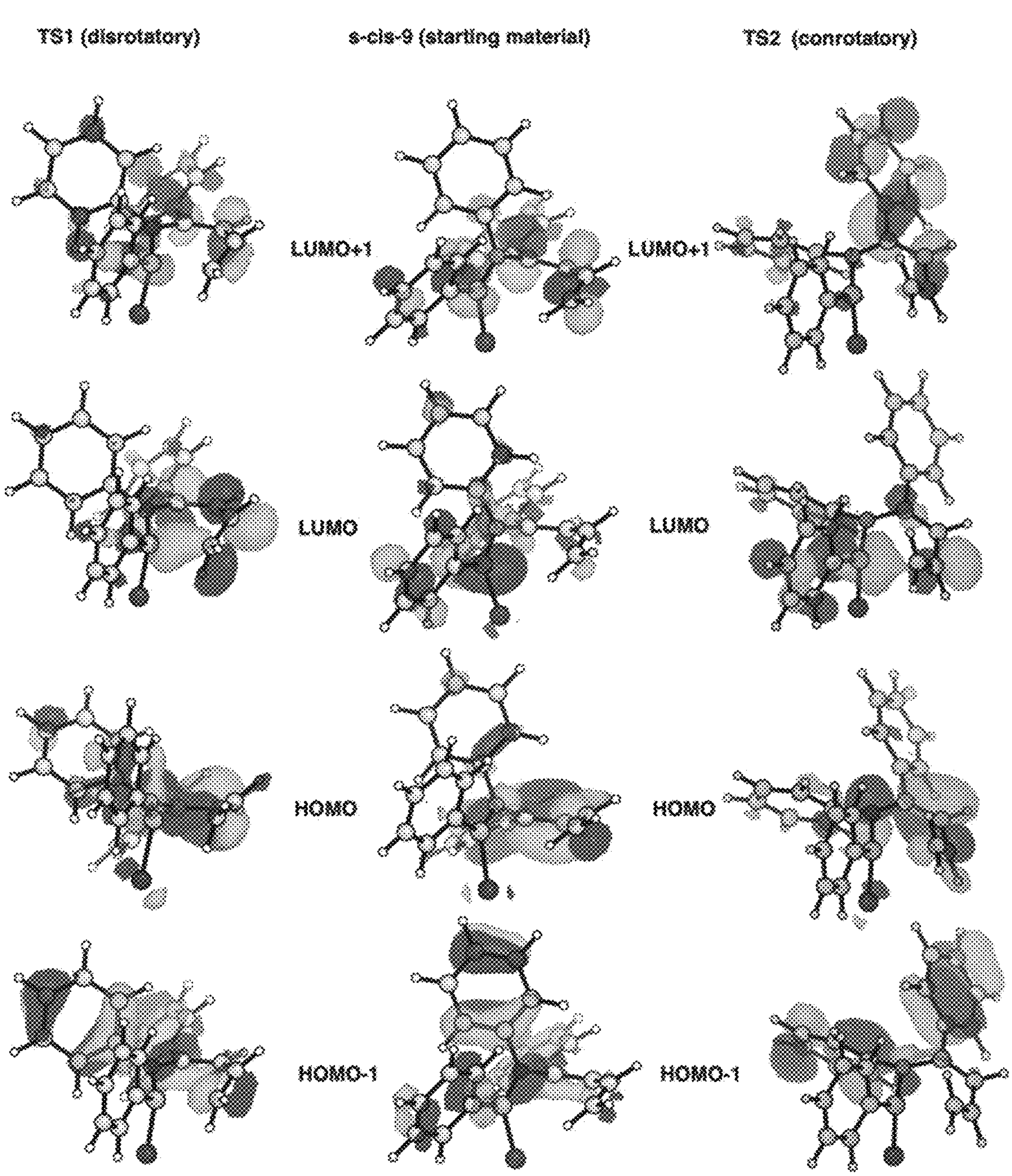
FIG. 6 is an illustration of molecular orbitals of TS1, TS2, ani s-cis-9.

It is also remarkable that the 6π-electrocyclization can occur through either dis- or conrotatory transition states (TS1 and TS2, respectively, and as shown in FIG. 4) that have comparable activation free energies. Based on prior knowledge, there has been no known 6π-electrocyclization that allows both dis- and conrotatory pathways. This finding appears to contradict the Woodward-Hoffmann rules, which predict that for 6π-electrocyclizations the disrotatory transition state barrier should be significantly lower than the barrier for the conrotatory transition state. However, the alteration of the nodal properties of the HOMO shown in FIG. 5 and FIG. 6 indicate that the high polarization of this system eliminates the differences between allowed and forbidden processes, as discussed recently in detail for model systems. The polarization of B—N bond changes the nodal properties of the π-system in 9. The diminished orbital coefficient on the terminal boron atom of the HOMO of s-cis-9 essentially reduces the preference for the allowed disrotatory (TS1) versus the forbidden conrotatory (TS2) electrocyclization. In a normal hydrocarbon triene, the orbital overlap between the termini is favorable for the allowed disrotatory process and unfavorable for the forbidden conrotatory process; when one terminal coefficient, i.e., the one of the boron, is nee rly zero, as shown in the current system, there is no preference.

Example 10: Additional Computational Results and Computational Details

Energy Profile of the Electrophilic Borylation Pathway

Figure 7:
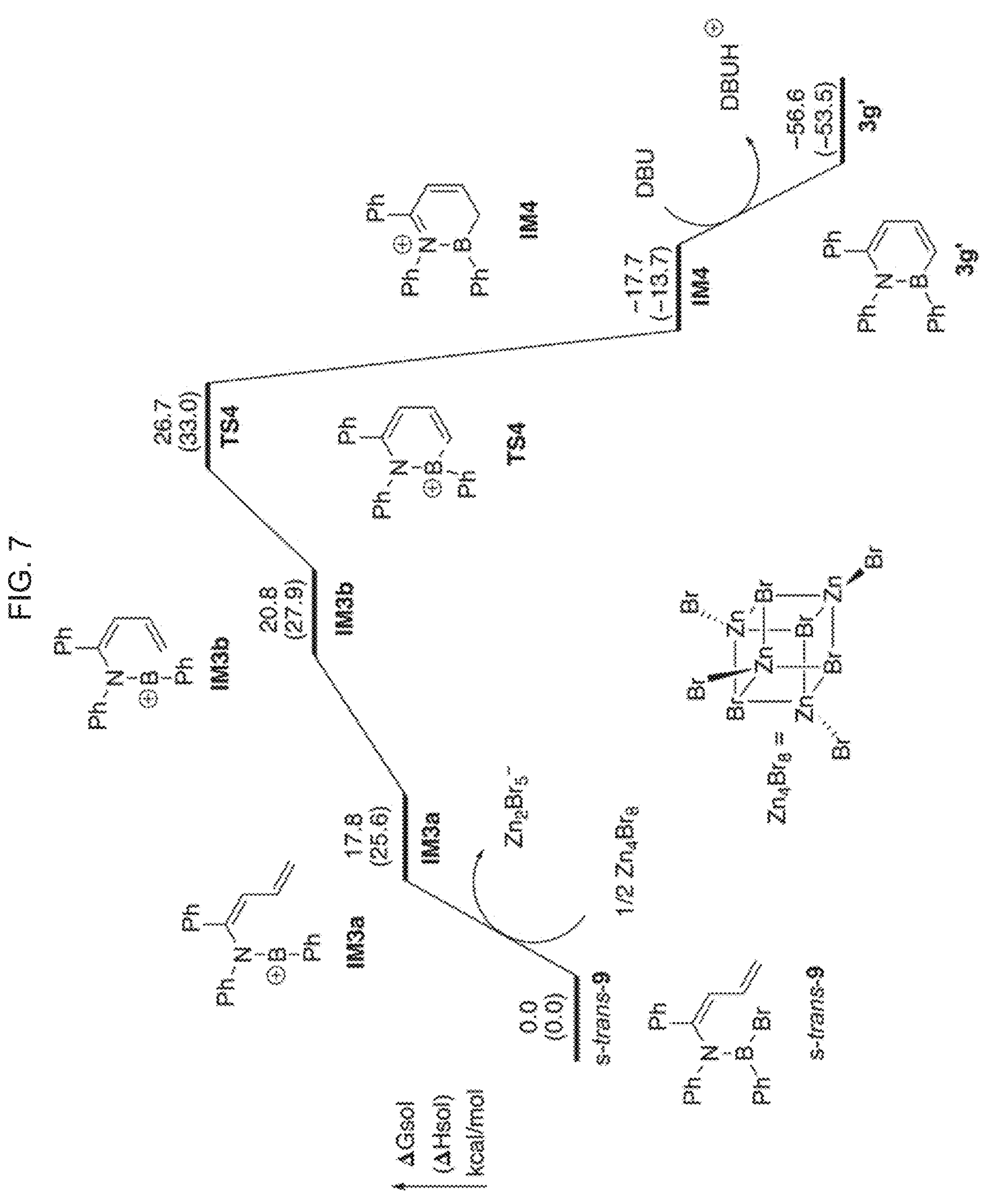
FIG. 7 is an illustration of the calculated reaction free energy profile of the ZnBr2-promoted electrophilic borylation pathway.

An alternative electrophilic borylation mechanism for the formation of azaborine from diene s-trans-9 was investigated (FIG. 7). The reaction begins with the dissociation of a bromide ion facilitated by a tetrameric ZnBr2 to form a two-coordinate borinium ion IM3a. This process is endergonic by 17.8 kcal/mol. Without the ZnBr2, the dissociation of bromide anion from s-trans-9 is highly endergonic by 56.9 kcal/mol. The borinium ion IM3a would then isomerize to the s-cis conformation, IM3b, before undergoing alkene electrophilic cyclization to form borylated iminium cation IM4. The transition state for the electrophilic cyclization (TS4) is 5.9 kcal/mol higher in energy than the low-barrier 6π-electrocyclization transition state TS1 ($\Delta G^{+}$=20.8 kcal/mol). Although the borinium ion itself is highly reactive, its formation is highly endergonic. Therefore, this electrophilic borylation pathway involving borenium can be ruled out. This energy profile is shown in FIG. 7.

Energy Profile of the 6π-Electrocyclization of Triene s-trans-11

Figure 8:
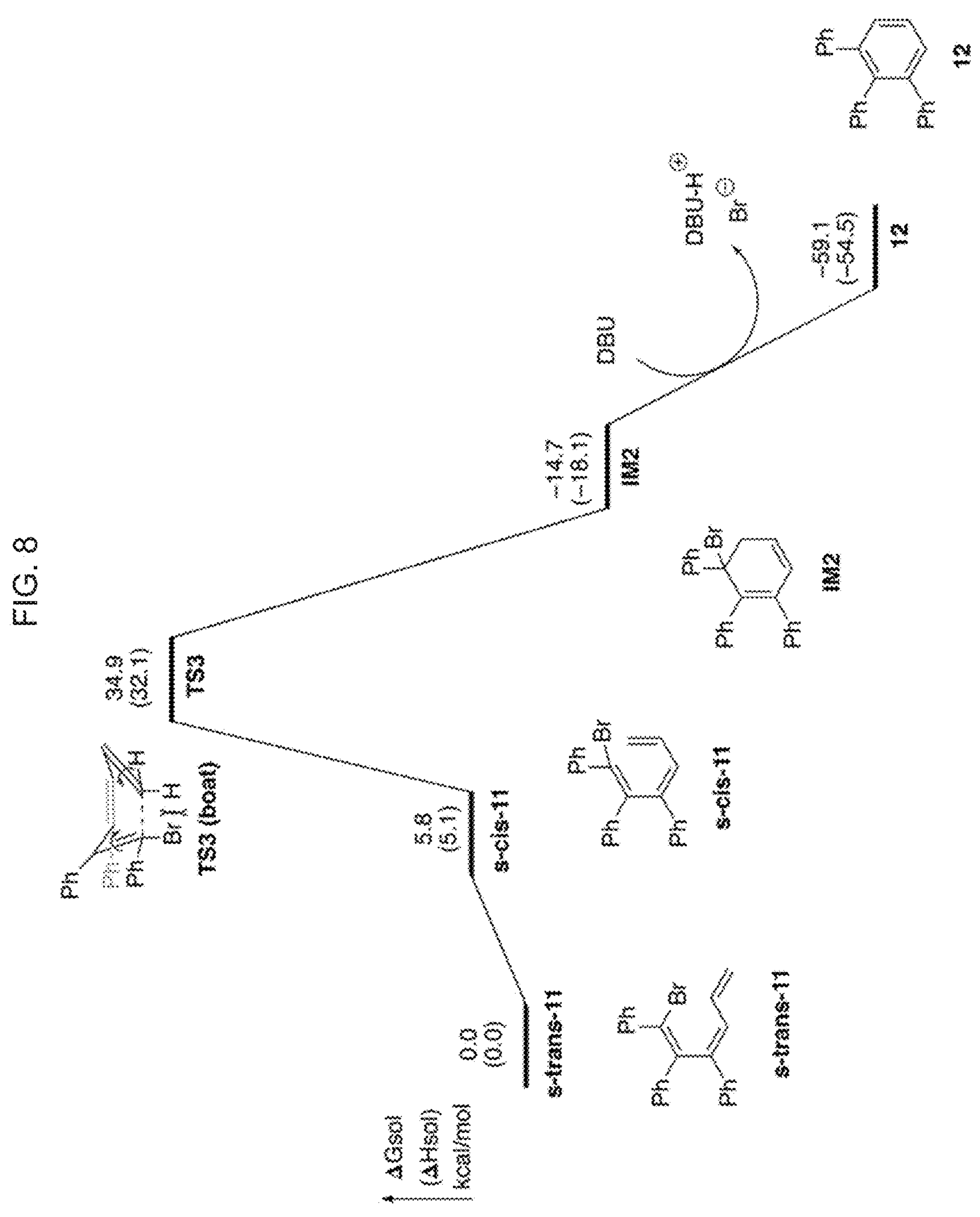
FIG. 8 is an illustration of the calculated energy profile of the π-electrocyclization of a triene analog 11.

In order to better understand factors promoting the azaborine formation via 6π-electrocyclization, the computed 6r-electrocyclization pathway of diene s-trans-9 was compared with the 6r-electrocyclization of a corresponding 1,3,5-hexatriene s-trans-11 (FIG. 8). The energy required to isomerize to the s-cis conformer s-cis-11 is comparable to the corresponding s-trans/s-cis isomerization to form diene s-cis-9. The 6r-electrocyclization of 11 requires an activation free energy of 34.9 kcal/mol with respect to s-trans-11, which is 14.1 kcal/mol higher than the corresponding reaction with diene 9. It is also interesting to note that the cyclized cyclohexadiene intermediate IM2 is 14.7 kcal/mol more stable than s-trans-11, whereas the corresponding intermediate 10 is only 3.7 kcal/mol more stable than diene s-trans-9. This indicates that the high reactivity of diene s-cis-9 is not driven by reaction thermodynamics. This free energy profile is shown in FIG. 8.

Furthermore, the computed barrier to the 6π-electrocyclization of unsubstituted 1,3,5-hexatriene is 30.4 kcal/mol with respect to the s-trans triene ground state. This is 4.5 kcal/mol lower than the barrier to the 6π-electrocyclization of triene 11 via TS3. These results indicated the disubstituted alkenyl terminal of triene 11 further increases the barrier to 67c-electrocyclization due to steric effects.

Optimized Geometries of 6π-Electrocyclization Transition States

Figure 9:
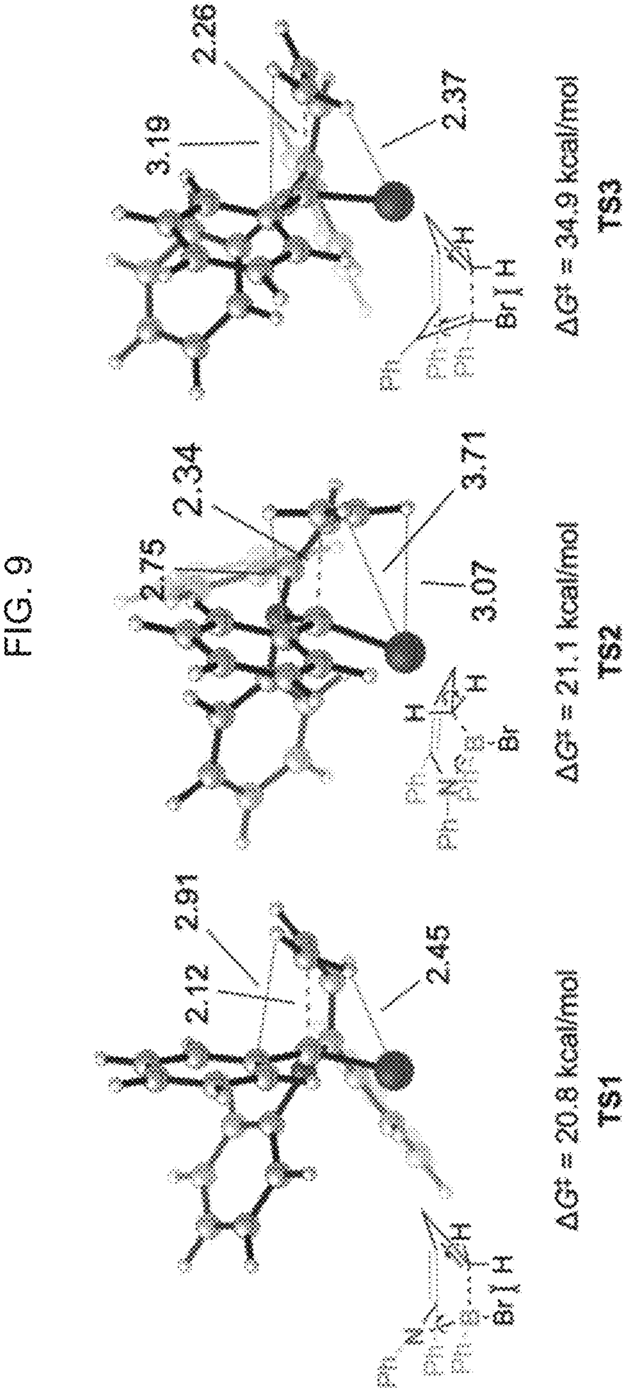
FIG. 9 is an illustration of optimized transition state structures. Distances are in Å.

The optimized geometries of 6π-electrocyclization transition states TS1, TS2, and TS3 are shown in FIG. 9. Although both TS1 and TS3 adopt boat-like geometry, the steric repulsions in these transition states are different. The H . . . Br distances between the two termini in TS1 (2.45 Å) and TS3 (2.37 Å) indicate that the steric repulsions are less significant in TS1, contributing to its lower barrier compared to TS3. A shorter forming C—C bond distance was observed in TS1 (2.12 Å) than in TS3 (2.26 Å). Therefore, the longer H . . . Br distance in TS1 is attributed to the greater degree of rotation about the B—N bond compared to the rotation about the C═C bond in TS3. The symmetry forbidden conrotatory transition state TS2 has a half-chair geometry and the steric repulsion between the two termini is much smaller, evidenced by the much longer H—-—Br distances in TS2 (3.07 and 3.71 Å with the internal and terminal alkenyl C—H bonds, respectively). This optimized transition state structures are shown in FIG. 9.

Molecular Orbitals and Partial Atomic Charges

The highest, and the second-highest occupied molecular orbitals (HOMO, HOMO-1) and the lowest, and the second-lowest unoccupied molecular orbitals (LUMO, LUMO+1) of s-cis-9 and the dis- and conrotatory transition states TS' and TS2 are shown in FIG. S6. The orbitals were computed at the M06-2X/6-311+G(d,p)/SMD(chlorobenzene)//M06-2X/6-31G(d) level of theory. A node exists on the boron center in the HOMO of s-cis-9. The computed orbital coefficients of the HOMO of s-cis-9 indicated a small contribution (<1%) on the boron atom, consistent with the node from the visualized molecular orbitals. The lack of orbital density on boron suggests that there is no preference through symmetry rules for the con- or disrotatory bond formation. The polarization about the B—N bond is responsible for this nodal property.

Figure 10:
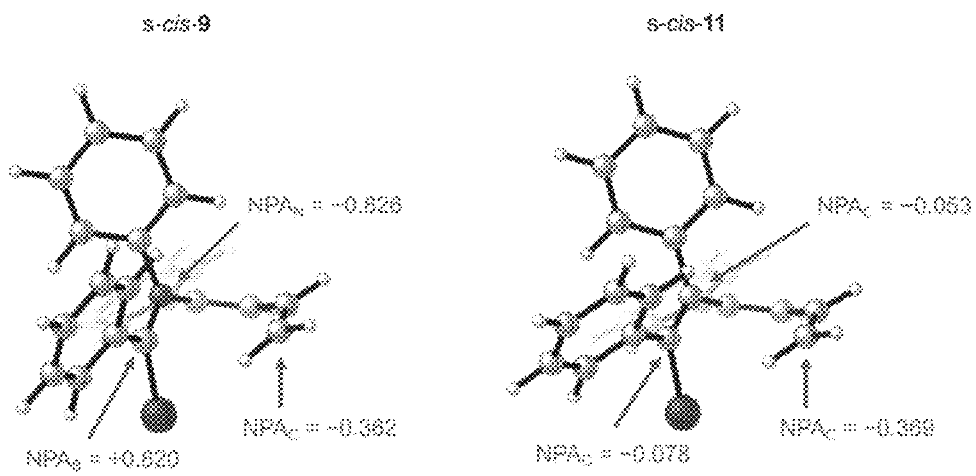
FIG. 10 is an illustration of natural population analysis (NPA) charges of the s-cis conformers of the diene intermediate (s-cis-9) and a 1,3,5-triene analog (s-cis-11)

The natural population analysis (NPA) charges of s-cis-9 and s-cis-11 are shown in FIG. 10. These results indicated the highly polarized B—N bond in s-cis-9, consistent with its enhanced reactivity of s-cis-9 as compared to the triene analog s-cis-11.

Example 11: Synthesis of 1,2,3,4,6-pentasubstituted 1,2-azaborines via the derivatization of 3-iodo-1,2,6-triarylated azaborine The synthesis of 1,2,3,4,6-pentasubstituted azaborines has been very rare. It has been found that such compounds can be prepared via cross couplings of the 3-iodo-1,2, 6-triarylated azaborines 6' to introduce various functional groups at both the $C_3$ and $C_4$ position in a one step process. This reaction scheme is shown below:

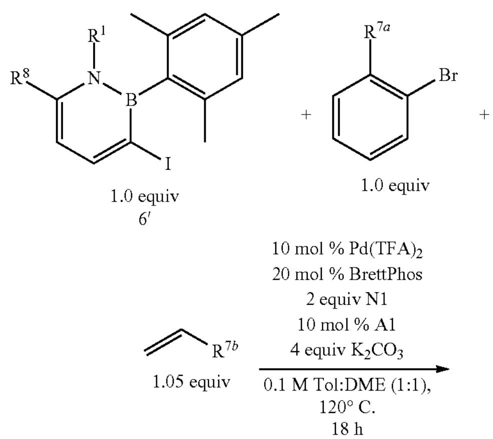

-continued

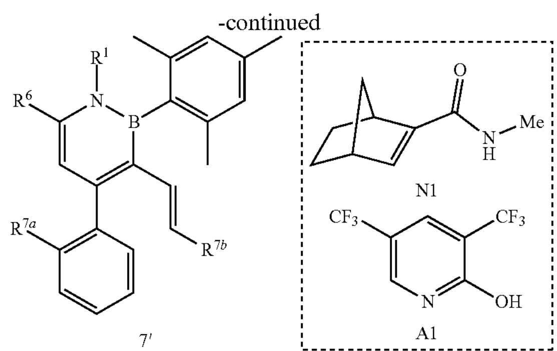

7'

N1

A1

Preparation of pentasubstituted 1,2-azaborines 7a'-7n' (a representative procedure $D_1$ In a flame dried 4 mL vial 1, 6' (0.1 mmol), Ar—Br (0.1 mmol) where $R^{7a}$ is independently selected from $R^7$ as described herein, vinyl reagent (0.105 mmol) where $R^{7b}$ is independently selected from $R^7$ as described herein, N1 (0.2 mmol, 30.2 mg), A1 (10 mol %, 2.3 mg), $K_2CO_3$ (0.4 mmol, 55.3 mg) were added. In a separate vial 2, $Pd(TFA)_2$ (10 mol %, 3.3 mg) and BrettPhos (20 mol %, 10.7 mg) were added. Both vials were brought into the glovebox, and 0.5 mL of DME and 0.5 mL of toluene were added to vial 1 and vial 2, respectively. After stirring for 10 minutes, solution in vial 2 was moved to vial 1. The tightly sealed vial was then placed on a pie-block preheated to 120° C. After 18 h, the reaction mixture was filtered through a pad of celite and washed with ethyl acetate. The crude solution was concentrated to dryness in vacuo, and was subjected to flash column chromatography to give the pentasubstituted 1,2-azaborine 7'.

Characterization

Below are the details of the characterization of compounds 7a'-7n'

7a'

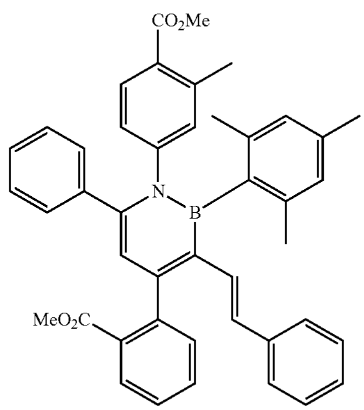

7a': Yield: 73% (mixture of 1:1:1:1 rotamers). Yellow solid, M.p.: 210-212° C. Rr: 0.25 (hexane/ethyl acetate=9:1). $^1$H NMR (400 MHz, $CDCl_3$): δ 7.98 (d, J=7.7 Hz, 1H), 7.58 (t, J=7.5 Hz, 1H), 7.52 (t, J=7.8 Hz, 1H), 7.48-7.39 (m, 2H), 7.14-7.09 (m, 7H), 7.02 (t, J=7.2 Hz, 1H), 6.81-6.77 (m, 4H), 6.73 (d, J=9.4 Hz, 1H), [6.67 (s)+6.64 (s)+6.62 (s)=2H], 6.45 (s, 1H), 5.94 (d, J=16.3 Hz, 1H), 3.78 (s, 3H), 3.65 (s, 3H), [2.30 (s)+2.28 (s)=3H], 2.21 (s, 3H), [2.15 (s)+2.10 (s)=3H], [2.10 (s)+2.06 (s)=3H]. $^{13}$C NMR (101 MHz, $CDC_3$): δ 168.21, 167.50, 153.27, 148.16, 146.16, 143.41, 140.06, 139.21, 138.39, 138.35, 138.31, 136.67, 131.82, 131.79, 131.62, 131.09, 130.88, 130.45, 130.20, 130.09, 129.88, 129.54, 128.28, 127.80, 127.48, 127.26, 127.20, 127.12, 127.05, 126.49, 126.13, 125.68, 125.63, 116.98, 52.04, 51.76, 22.89, 22.45, 21.55, 21.53, 21.30. $^{11}$B NMR (128 MHz, $CDCl_3$): δ 39.61. IR (KBr, $cm^{-1}$): 2948, 1723, 1587, 1570, 1473, 1446, 1434, 1375, 1351, 1291, 1255, 1190, 1166, 1132, 1089, 1031, 968, 850, 773, 751, 539, 699 $cm^{-1}$. HRMS (ESI): m/z calcd for $C_{44}C_{41}BNO_4$+ [$M^+$ $H^+$]: 658.3123. Found: 658.3125.

7b'

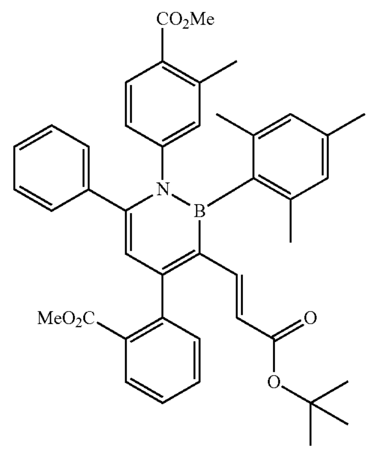

7b': Yield: 62% (mixture of 1:1:1:1 rotamers). Yellow solid, M.p.: 62-64° C. Rr: 0.5 (hexane/dichloromethane=1:4). $^1$H NMR (500 MHz, $CDCl_3$): δ 7.99 (d, i=7.2 Hz, 1H), 7.56 (t, J=7.3 Hz, 1H), 7.51 (t, J=8.3 Hz, 1H), 7.44 (t, J=7.3 Hz, 1H), 7.36 (d, J=6.4 Hz, 1H), 7.32 (d, J=16.0 Hz, 1H), 7.13-7.10 (m, 5H), 6.77-6.73 (m, 1H), 6.72-6.71 (m, 1H), [6.63 (s)+6.60 (s)=2H], 6.46 (s, 1H), 5.07 (d, J=16.5 Hz, 1H), 3.77 (s, 3H), [3.70 (s)+3.69 (s)=3H], (s)+2.27 (s)=3H], 2.16 (s, 3H), [2.09 (s)+2.07 (s)=3H], [2.05 (s)+2.03 (s)=3H], 1.27 (s, 9H). $^{13}$C NMR (126 MHz, $CDCl_3$): δ 167.72, 167.44, 167.42, 157.34, 48.60, 147.73, 145.27, 142.74, 140.15, 138.09, 138.05, 137.95, 137.93, 137.91, 136.94, 131.74, 131.66, 130.62, 130.60, 130.36, 130.26, 129.48, 127.88, 127.84, 127.42, 127.31, 126.72, 125.53, 125.51, 120.58, 116.88, 79.10, 52.07, 51.81, 28.13, 22.86, 22.45, 21.53, 21.51, 21.25. $^{11}$B NMR (128 MHz, $CDCl_3$): δ 39.88. IR (KBr, $cm^{-1}$): 2951, 1716, 1606, 1488, 1435, 1393, 1368, 1256, 1190, 1148, 1084, 848, 777, 700, 668 $cm^{-1}$. HRMS (ESI): m/z calcd for $C_{43}C_{44}BNNaO_6^+$ [$M^+Na^+$]: 704.3154. Found: 704.3152.

7c'

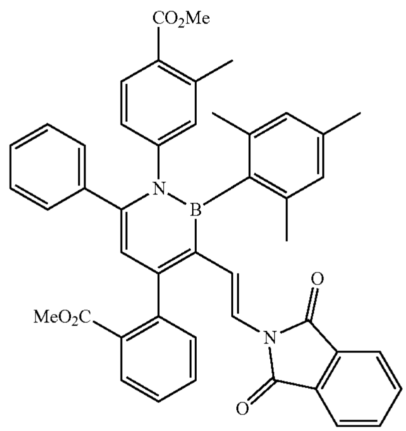

7c': Yield: 48% (mixture of 1:1:1:1 rotamers). Yellow solid, M.p.: 107-109° C. Rr: 0.45 (hexane/ethyl acetate=2:1). $^1$H NMR (500 MHz, $CDCl_3$): δ 8.00 (d, J=7.8 Hz, 1H), 7.66 (dd, J=5.5, 3.0 Hz, 2H), 7.62-7.57 (m, 3H), 7.51 (t, J=8.5 Hz, 1H), 7.48-7.43 (m, 2H), 7.23 (d, J=15.6 Hz, 1H), 7.15-7.09 (m, 5H), 6.80-6.72 (m, 2H), [6.69 (s)+6.66 (s)=2H], 6.44 (s, 1H), 6.25 (d, J=14.7 Hz, 1H), 3.77 (s, 3H), [3.71 (s)+3.70 (s)=3H], [2.30 (s)+2.28 (s)=2H], 2.20 (s, 3H), [2.19 (s)+2.16 (s)=3H], [2.13 (s)+2.11 (s)=3H]. 13C NMR (126 MHz, $CDCl_3$): δ 168.15, 167.50, 166.32, 153.72, 148.09, 146.39, 143.33, 143.31, 140.08, 138.25, 138.17, 138.14, 138.09, 136.94, 134.02, 131.96, 131.79, 131.74, 130.6, 130.61, 130.38, 130.19, 129.55, 127.81, 127.64, 127.52, 127.39, 127.29, 126.50, 125.64, 123.25, 122.90, 118.69, 116.81, 52.09, 51.77, 22.87, 22.45, 21.52, 21.32. $^{11}$B NMR (128 MHz, $CDC_3$): δ 39.65. IR (KBr, $cm^1$): 2928, 2856, 1719, 1605, 1588, 1571, 1474, 1447, 1377, 1290, 1256, 1190, 1132, 1080, 965, 886, 852, 753, 715, 701, 669 $cm^{-1}$. HRMS (ESI): m/z calcd for $C_{46}H_{40}BN_2O_6$+ [$M^+$ $H^+$]: 727.2974. Found: 727.2977.

7d'

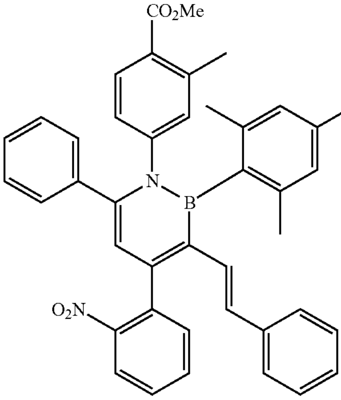

7d': Yield: 27% (mixture of 1:1:1:1 rotamers). Yellow solid, M.p.: 210-212° C. R,: 0.25 (hexane/ethyl acetate=9:1). $^1$H NMR (500 MHz, $CDCl_3$): δ 8.09 (d, J=8.1 Hz, 1H), 7.68 (t, J=7.5 Hz, 1H), 7.54 (tt, J=8.8, 3.3 Hz, 3H), 7.14-7.08 (m, 7H), 7.04 (t, J=7.2 Hz, 1H), 6.78 (q, J=8.5 Hz, 4H), 6.71 (d, J=16.3 Hz, 1H), [6.66 (s)+6.64 (s)+6.62 (s)=2H], 6.41 (s, 1H), 5.97 (d, J=15.7 Hz, 1H), 3.78 (s, 3H), [2.31 (s)+2.18 (s)=3H], 2.20 (s, 3H), [2.15 (s)+2.12 (s)+2.09 (s)+2.06 (s)=6H]. $^{13}$C NMR (126 MHz, $CDC_3$): δ 167.52, 167.48, 149.12, 148.91, 147.93, 146.98, 140.25, 140.06, 138.85, 138.74, 138.72, 138.16, 138.0, 137.97, 136.82, 132.93, 132.17, 131.83, 131.65, 131.04, 130.34, 130.19, 129.58, 129.51, 128.53, 128.34, 127.85, 127.68, 127.42, 127.37, 127.02, 126.96, 126.80, 126.71, 126.66, 126.23, 125.69, 125.49, 124.52, 115.60, 51.80, 22.93, 22.50, 21.55, 21.51, 21.31. $^{11}$B MR (128 MHz, $CDCl_3$): δ 39.54. IR (KBr, $cm^{-1}$): 3057, 3022, 2928, 2856, 1721, 1605, 1586, 15701, 1527, 1496, 1481, 1446, 1437, 1401, 1375, 1351, 1256, 1190, 1166, 1142, 1090, 1030, 967, 915, 883, 857, 809, 786, 770, 749, 738, 700, 675 $cm^{-1}$. HRMS (ESI): m/z calcd for $C_{42}H_{38}B\ _2O_4^+$ [$M^+$ $H^+$]: 645.2919. Found: 645.2925.

7e'

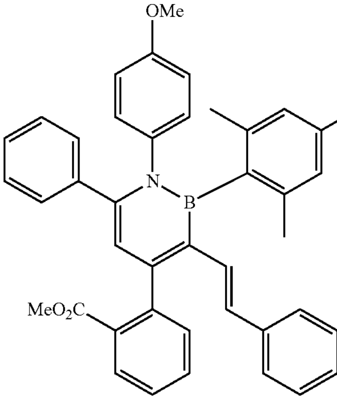

7e': Yield: 64% (mixture of 1:1 rotamers). Yellow solid, M.p.: 90-92° C. Rr: 0.8 (hexane/dichloromethane=1:3). $^1$H NMR (400 MHz, $CDC_3$): δ 7.98 (d, J=7.7 Hz, 1H), 7.57 (t, J=7.1 Hz, 1H), 7.45 (t, J=8.1 Hz, 2H), 7.15-7.07 (m, 8H), 7.03-6.97 (m, 1H), 6.84-6.75 (m, 5H), 6.66 (d, J=10.2 Hz, 2H), 6.44 (t, J=7.2 Hz, 2H), 6.41 (s, 1H), 5.89 (d, J=16.4 Hz, 1H), 3.65 (s, 3H), 3.62 (s, 3H), [2.23 (s)+2.14 (s)=6H], 2.10 (s, 3H). $^{13}$C NMR (101 MHz, $CDCl_3$): δ 168.38, 157.20, 153.13, 147.19, 143.59, 139.38, 138.81, 138.40, 138.09, 136.32, 131.53, 131.19, 130.96, 130.69, 130.04, 129.70, 129.54, 129.03, 129.00, 128.27, 127.66, 127.38, 127.16, 127.13, 127.01, 126.36, 126.11, 116.60, 112.60, 112.55, 55.23, 52.01, 22.94, 22.51, 21.34. $^{11}$B NMR (128 MHz, $CDCl_3$): δ 39.52. IR (KBr, $cm^{-1}$): 2996, 2931, 2856, 2836, 1723, 1609, 1584, 1570, 1474, 1445, 1376, 1352, 1293, 1246, 1181, 1170, 1126, 1078, 1031, 967, 833, 775, 754, 741, 699 $cm^{-1}$. HRMS (ESI): m/z calcd for $C_{42}H_{39}BNO_3^+$ [$M^+$ $H^+$]: 616.3018. Found: 616.3026.

7f'

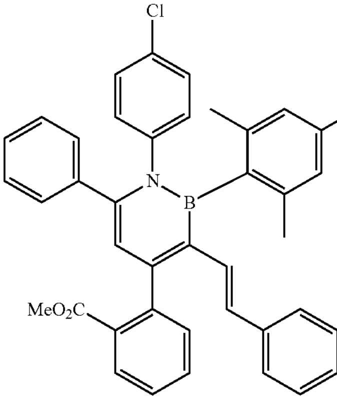

7f': Yield: 73% (mixture of 1:1 rotamers). Yellow solid, M.p.: 194-196° C. Rr: 0.85 (hexane/dichloromethane=1:3). $^1$H NMR (400 MHz, $CDCl_3$): δ 7.98 (d, =7.8 Hz, 1H), 7.57 (t, J=7.5 Hz, 1H), 7.48-7.42 (m, 2H), 7.13 (m, 5H), 7.09 (t, J=7.7 Hz, 2H), 7.02 (t, J=7.1 Hz, 1H), 6.92-6.88 (m, 2H), 6.84 (d, J=8.5 Hz, 1H), 6.81-6.77 (m, 4H), [6.68 (s)+6.55 (s)=2H], 6.44 (s, 1H), 5.91 (d, J=16.4 Hz, 1H), 3.64 (s, 3H), [2.23 (s)+2.12 (s)=6H], 2.08 (s, 3H).

$^{13}$C NMR (101 MHz, $CDCl_3$): δ 168.21, 153.28, 146.40, 143.64, 143.41, 139.22, 138.32, 136.74, 131.62, 131.47, 131.10, 130.89, 130.45, 130.10, 129.85, 129.68, 129.51, 128.30, 127.86, 127.62, 127.50, 127.45, 127.32, 127.17, 126.50, 126.14, 116.95, 52.04, 22.91, 22.47, 21.35. $^{11}$B NMR (128 MHz, $CDCl_3$): δ 39.25. IR (KBr, $cm^{-1}$): 3057, 3022, 2993, 2947, 2855, 1731, 1608, 1587, 1570, 1490, 1446, 1402, 1375, 1351, 1291, 1255, 1190, 1167, 1126, 1113, 1091, 1078, 1015, 967, 851, 833, 774, 761, 734, 699, 677 $cm^1$. HRMS (ESI): m/z c lcd for $C_{41}H_{36}BClNO_2$+[$M^+$ $H^+$]: 620.2522. Found: 620.2515.

7g'

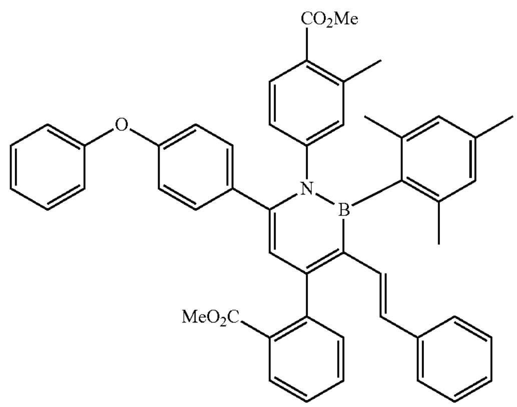

7g': Yield: 68% (mixture of 1:1:1:1 rotamers). Yellow solid, M.p.: 90-92° C. $R_f$: 0.2 (hexane/ethyl acetate=9:1). $^1$H NMR (500 MHz, $CDC_3$): δ 7.99 (d, J=7.7 Hz, 1H), 7.58 (q, J=7.9 Hz, 2H), 7.46 (dd, J=18.6, 7.5 Hz, 2H), 7.30 (t, J=7.1 Hz, 2H), 7.11-7.08 (m, 5H), 7.03 (d, J=7.0 Hz, 1H), 6.88 (d, J=8.3 Hz, 2H), 6.82-6.78 (m, 4H), 6.76 (¶, J=8.5 Hz, 3H), [6.67 (s)+6.65 (s)+6.64 (s)=2H]6.46 (s, 1H), 5.95 (d, J=16.3 Hz, 1H), 3.81 (s, 3H), 3.66 (s, 3H), (s)+2.33 (s)=3H], 2.22 (s, 3H), [2.14 (s)+2.12 (s)+2.11 (s)+2.09 (s)=6H]. $^{13}$C NMR (126 MHz, $CDCl_3$): δ 168.24, 167.48, 157.11, 156.47, 153.27, 148.20, 145.56, 143.41, 140.10, 139.21, 138.36, 138.32, 136.70, 133.44, 131.87, 131.83, 131.63, 131.06, 130.87, 130.45, 130.28, 130.12, 130.09, 129.88, 129.86, 128.30, 127.51, 127.28, 127.2, 127.14, 127.08, 126.59, 126.50, 126.14, 125.75, 125.70, 123.48, 118.87, 118.86, 118.2, 116.77, 52.07, 51.82, 22.90, 22.88, 22.49, 22.46, 21.59, 21.31. $^{11}$B NMR (128 MHz, $CDCl_3$): 539.62. IR (KBr, $cm^{-1}$): 3021, 2997, 2948, 1723, 1589, 1506, 1488, 1457, 1446, 1435, 1374, 1351, 1290, 1271, 1241, 1191, 1167, 1132, 1089, 1078, 1015, 967, 869, 848, 776, 692, 669, 650 $cm^{-1}$. HRMS (ESI): m/z calcd for $C_{50}H_{45}BNO_5^+$ [$M^+$ $H^+$]: 750.3385. Found: 750.3391.

7h'

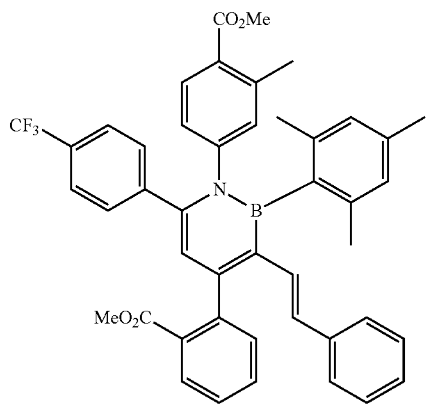

7h': Yield: 44% (mixture of 1:1:1:1 rotamers). Yellow solid, M.p.: 98-100° C. $R_f$: 0.2 (hexane/ethyl acetate=9:1). $^1$H NMR (500 MHz, $CDC_3$): δ 8.00 (d, J=7.8 Hz, 1H), 7.59 (t, J=7.2 Hz, 1H), 7.55 (t, J=7.9 Hz, 1H), 7.48 (t, J=7.6 Hz, 1H), 7.42 (d, J=7.5 Hz, 1H), 7.39 (d, J=8.2 Hz, 2H), 7.28 (d, J=8.1 Hz, 2H), 7.10 (t, J=7.5 Hz, 2H), 7.03 (t, J=7.1 Hz, 1H), 6.82-6.73 (m, 5H), [6.68 (s)+6.66 (s)+6.65 (s)+6.63 (s)=2H], 6.46 (s, 1H), 5.97 (d, J=16.3 Hz, 1H), 3.80 (s, 3H), [3.66 (s)+3.65 (s)=3H], [2.32 (s)+2.30 (s)=3H], 2.22 (s, 3H), (s)+2.12 (s)+2.09 (s)+2.07 (s)=6H]. $^{13}$C NMR (126 MHz, $CDCl_3$): δ 168.01, 167.99, 167.36, 153.02, 147.70, 144.35, 143.16 (d, JC-CF3=2.9 Hz), 141.93, 140.39 (d, JC-CF3=2.3 Hz), 139.03, 138.41, 138.36, 138.31, 138.27, 136.89, 131.76, 131.65, 131.02, 130.81, 130.52, 130.47, 130.17, 130.15, 129.77, 128.33, 127.67, 127.35, 127.28, 127.21, 127.13, 126.93, 126.69, 126.21, 125.57, 125.54, 125.11, 124.85, 124.82, 117.64, 52.10, 51.87, 22.89, 22.86, 22.47, 22.45, 21.58, 21.57, 21.31. $^{11}$B NMR (160 MHz, $CDCl_3$): δ 41.18. 19F NMR (376 MHz, $CDCl_3$): δ −62.61. IR (KBr, $cm^{-1}$): 2950, 2852, 1723, 1597, 1570, 1488, 1435, 1411, 1377, 1351, 1324, 1291, 1255, 1190, 1167, 1128, 1065, 1009, 1018, 968, 842, 777, 693 $cm^{-1}$. HRMS (ESI): m/z calcd for $C_{45}H_{40}BF_3NO_4^+$[$M^+$ $H^+$]: 726.2997. Found: 726.2998.

7i'

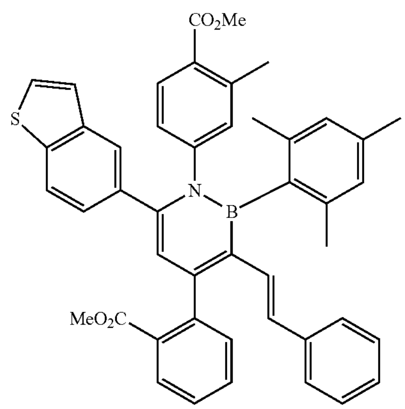

7i': Yield: 52% (mixture of 1:1:1:1 rotamers). Yellow solid, M.p.: 109-111° C. $R_f$: 0.2 (hexane/ethyl acetate=9:1). $^1$H NMR (500 MHz, $CDCl_3$): δ 7.99 (dd, J=7.7, 1.4 Hz, 1H), 7.73 (s, 1H), 7.60-7.55 (m, 2H), 7.52-7.44 (m, 3H), 7.39 (d, J=5.4 Hz, 1H), 7.21 (d, J=5.5 Hz, 1H), 7.09 (t, J=7.5 Hz, 2H), 7.05-7.01 (m, 2H), 6.89-6.75 (m, 5H), [6.69 (s)+6.66 (s)+6.65 (s)+(6.62 (s)=2H], 6.51 (d, J=3.6 Hz, 1H), 5.96 (d, J=16.4 Hz, 1H), 3.75 (s, 3H), [3.67 (s)+3.66 (s)=3H], [2.29 (s)+2.26 (s)=3H], 2.22 (s), [2.19 (s)+2.14 s)=3H], [2.11 (s)+2.07 (s)=3H]. $^{13}$C NMR (126 MHz, $CDCl_3$): δ 168.22, 168.19, 167.45, 153.33, 153.31, 148.19, 146.16, 143.46, 143.43, 140.13, 139.32, 139.24, 138.91, 138.43, 138.36, 138.32, 136.69, 134.70, 131.78, 131.65, 131.15, 131.09, 130.91, 130.87, 130.49, 130.47, 130.31, 130.29, 130.11, 129.90, 128.30, 127.51, 127.28, 127.22, 127.14, 127.06, 126.51, 126.16, 125.76, 125.73, 125.69, 124.55, 123.98, 121.67, 117.47, 52.09, 51.75, 22.95, 22.89, 22.52, 22.46, 21.61, 21.59, 21.32. $^{11}$B NMR (128 MHz, $CDCl_3$): δ 41.14. IR (KBr, $cm^{-1}$): 2947, 1720, 1585, 1571, 1560, 1541, 1474, 1458, 1437, 1375, 1350, 1290, 1254, 1189, 1131, 1089, 1050, 967, 880, 851, 818, 772, 754, 739, 709 $cm^1$. HRMS (ESI): m/z calcd for $C_{46}H_{41}BNO_4S^+$[$M^+$ $H^+$]: 714.2844. Found: 714.2839.

7j'

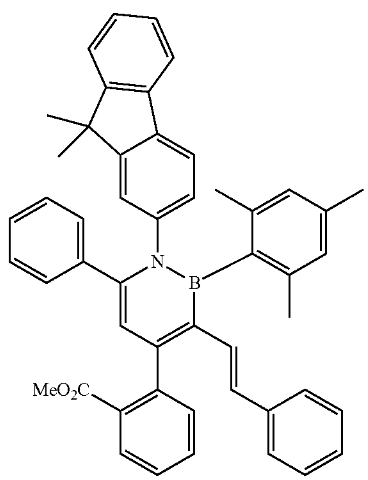

7j': Yield: 56% (mixture of 1:1:1:1 rotamers). Yellow solid, p.: 108-110° C. Rr: 0.3 (hexane/ethyl acetate=9:1). $^{1}$H NMR (500 MHz, $CDCl_3$): δ 8.01-7.99 (m, 1H), 7.59 (t, J=7.5 Hz, 1H), 7.53 (d, J=7.3 Hz, 1H), 7.48 (t, J=7.3 Hz, 2H), 7.33 (d, J=6.8 Hz, 1H), 7.28-7.23 (m, 3H), 7.18 (d, J=8.0 Hz, 2H), 7.11-7.01 (m, 6H), 6.94-6.79 (m, 5H), [6.64 (s)+6.62 (s)+6.60 (s)+6.59 (s)=2H]6.49 (d, J=4.0 Hz, 1H), 6.03 (dd, J=16.3, 2.9 Hz, 1H), 3.68 (s, 3H), [2.21 (s)+2.17 (s)=3H], 2.15 (s, 3H), [2.13 (s)+2.11 (s)=3H], [1.19 (s)+1.17 (s)+1.15 (s)=6H]. $^{13}$C NMR (101 MHz, $CDCl_3$): δ 168.39, 168.29, 153.83, 153.80, 153.18, 153.13, 152.86, 147.00, 146.98, 144.15, 143.64, 143.60, 139.34, 138.94, 138.80, 138.78, 138.41, 138.33, 138.27, 136.40, 136.34, 131.60, 131.56, 131.20, 130.98, 130.74, 130.10, 130.03, 129.72, 129.68, 128.28, 127.65, 127.62, 127.42, 127.17, 127.14, 127.13, 127.10, 127.07, 127.04, 127.02, 126.40, 126.14, 123.27, 123.24, 122.68, 119.97, 119.95, 118.81, 118.79, 116.55, 52.07, 52.05, 46.54, 26.81, 26.79, 26.50, 26.48, 22.94, 22.90, 22.52, 22.50, 21.23. $^{11}$B NMR (160 MHz, $CDCl_3$): δ 38.52. IR (KBr, $cm^{-1}$): 2956, 2920, 2857, 1730, 1585, 1570, 1474, 1460, 1448, 1375, 1352, 1291, 1254, 1127, 1078, 1029, 967, 850, 829, 773, 737, 699 $cm^{-1}$. HRMS (ESI): m/z calcd for $C_{50}H_{45}BNO_2^+$[$M^+$ $H^+$]: 702.3538. Found: 702.3536.

7k'

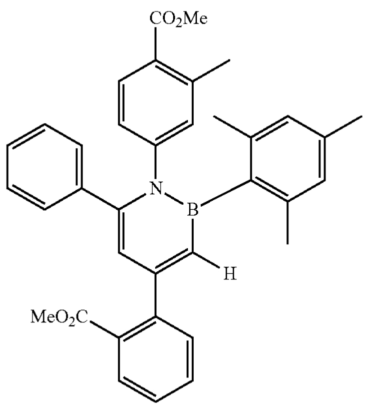

(0.105 mmol of borneol was used instead of vinyl reagent)

7k': Yield: 27% (mixture of 1:1 rotamers). White solid, M.p.: 83-85° C. Rr: 0.25 (hexane/ethyl acetate=9:1). $^{1}$H NMR (500 MHz, $CDC_3$): δ 7.79 (d, J=7.1 Hz, 1H), 7.53-7.51 (m, 3H), 7.40 (ddd, J=7.7, 5.7, 3.1 Hz, 1H), 7.16-7.12 (m, 5H), 6.76 (d, J=2.2 Hz, 1H), 6.73-6.70 (m, 2H), [6.65 (s)+6.64 (s)=2H], 6.53 (d, J=2.2 Hz, 1H), 3.77 (s, 3H), 3.74 (s, 3H), 2.28 (s, 3H), 2.18 (s, 3H), [2.12 (s)+2.10 (s)=6H]. $^{13}$C NMR (126 MHz, $CDCl_3$): δ 169.33, 167.51, 155.52, 148.12, 148.09, 144.16, 140.17, 138.73, 138.57, 136.5, 131.71, 131.33, 130.81, 130.30, 129.91, 129.84, 129.55, 127.87, 127.56, 126.89, 126.86, 126.51, 125.55, 115.69, 52.15, 51.79, 23.20, 23.18, 21.55, 21.23. $^{11}$B NMR (160 MHz, $CDC_3$): δ 37.94. IR (KBr, $cm^{-1}$): 2949, 1723, 1603, 1573, 1505, 1486, 1445, 1434, 1346, 1289, 1255, 1190, 1130, 1086, 1056, 1031, 987, 878, 849, 768, 754, 733, 701 $cm^{-1}$. HRMS (ESI): m/z calcd for $C_{36}C_{35}BNO_4$+[$M^+$ $H^+$]: 556.2654. Found: 556.2659.

7l'

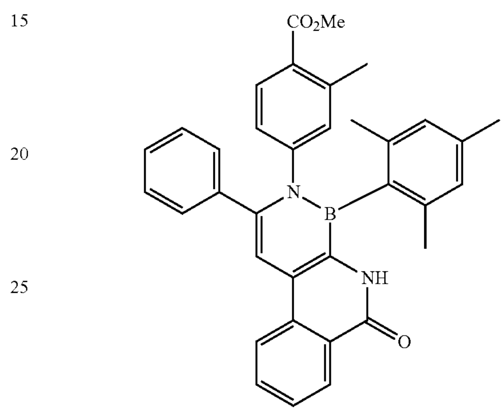

(0.1 mmol 2-bromobenzamide was used instead of Ar—Br and vinyl reagent)

7l': Yield: 25% (mixture of 1:1 rotamers). Off-white solid, M.p.: 114-116° C. Rr: 0.2 (hexane/ethyl acetate=4:1). 1H NMR (500 MHz, $CDCl_3$): δ 8.58 (d, J=8.0 Hz, 1H), 8.34 (s, 1H)f, 8.27 (d, J=8.2 Hz, 1H), 7.83 (t, J=7.8 Hz, 1H), 7.68 (t, J=7.5 Hz, 1H), 7.55 (d, J=8.1 Hz, 1H), 7.30 (s, 1H), 7.24-7.18 (m, 5H), 6.75 (s, 1H), 6.74-6.72 (m, 3H), 3.78 (s, 3H), 2.29 (s, 3H), 2.23 (s, 3H), [2.06 (s)+2.04 (s)=6H]. $^{13}$C NMR (126 MHz, $CDC_3$): δ 167.37, 161.81, 147.69, 143.13, 140.49, 139.54, 138.49, 138.37, 134.55, 132.74, 131.32, 130.58, 129.72, 128.97, 128.57, 128.47, 128.06, 127.88, 127.83, 127.70, 127.01, 125.20, 124.63, 123.13, 108.18, 51.87, 22.76, 21.59, 21.29. $^{11}$B NMR (160 MHz, $CDCl_3$): δ 35.76. IR (KBr, $cm^{-1}$): 3376, 2926, 1722, 1666, 1605, 1569, 1488, 1446, 1335, 1259, 1146, 1089, 1031, 773, 734, 704 $cm^{-1}$. HRMS (ESI): m/z calcd for $C_{35}H_{32}BN_2O_3^+$ [$M^+$ $H^+$]: 539.2500. Found: 539.2507.

7m'

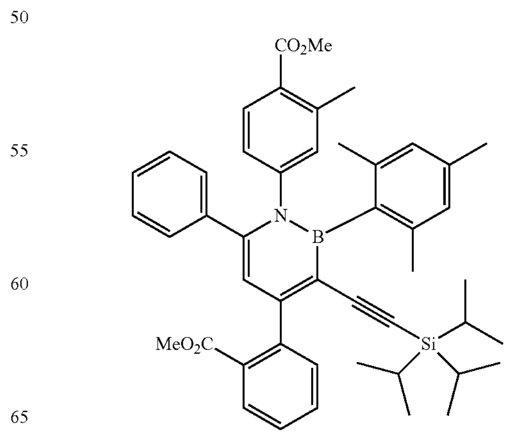

(0.105 mmol of alkyne reagent was used instead of vinyl reagent)

7m': Yield: 59%. Yellow solid, M.p.: 70-72° C. Rr: 0.4 (hexane/ethyl acetate=9:1). $^{1}$H NMR (400 MHz, $CDCl_3$): δ 7.96 (d, J=8.3 Hz, 1H), 7.55-7.52 (m, 2H), 7.47 (d, J=7.0 Hz, 1H), 7.38 (t, J=7.8 Hz, 1H), 7.17-7.11 (m, 5H), 6.78 (s, 1H), 6.77 (d, J=6.7 Hz, 1H), 6.55 (s, 2H), 6.52 (s, 1H), 3.77 (s, 3H), 3.74 (s, 3H), 2.29 (s, 3H), 2.12 (s, 3H), 2.11 (s, 6H), 0.69 (s, 18H). $^{13}$C NMR (126 MHz, $CDCl_3$): δ 167.77, 167.46, 158.84, 147.96, 147.31, 143.38, 140.29, 138.34, 138.13, 136.24, 131.61, 131.55, 130.40, 130.30, 130.06, 130.04, 129.51, 127.89, 127.72, 127.41, 126.75, 126.72, 126.70, 125.39, 116.19, 108.55, 96.98 51.95, 51.78, 22.75, 21.56, 21.16, 18.41, 11.26. $^{11}$B NMR (160 MHz, $CDCl_3$): δ 42.63. IR (KBr, $cm^1$): 2943, 2863, 1725, 1602, 1586, 1573, 1463, 1483, 1463, 1446, 1435, 1377, 1345, 1291, 1255, 1210, 1190, 1166, 1133, 1081, 1066, 1031, 1016, 994, 969, 882, 849, 732, 700, 675, 626 $cm^{-1}$. HRMS (ESI): m/z calcd for $C_{47}C_{55}BNO_4Si^+[M^+ H^+]$: 736.3988. Found: 736.3992.

7n'

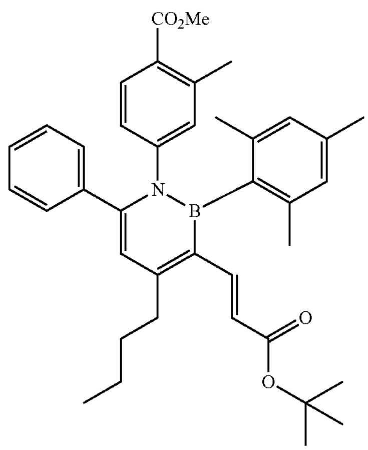

(0.667 mmol of 1-bromobutane was used instead of Ar—Br reagent and 1.06 mmol equiv of $K_2CO_3$ was used)

7n': Yield: 28% (mixture of 1:1 rotamers). Off-white oil. $R_f$: 0.4 (hexane/ethyl acetate=9:1). $^{1}$H NMR (500 MHz, $CDCl_3$): δ 7.84 (d, J=16.0 Hz, 1H), 7.47 (d, J=8.2 Hz, 1H), 7.14-7.10 (m, 5H), 6.66-6.64 (m, 2H), [6.60 (s)+6.57 (s)=2H], 6.43 (s, 1H), 5.23 (d, J=16.0 Hz, 1H), 3.76 (s, 3H), 2.80-2.77 (m, 2H), 2.25 (s, 3H), 2.15 (s, 3H), [2.00 (s)+1.97 (s)=6H], 1.66 (dt, J=15.4, 7.9 Hz, 2H), 1.46 (h, J=7.4 Hz, 2H), 1.40 (s, 9H), 0.98 (t, J=7.3 Hz, 3H). $^{13}$C NMR (126 MHz, $CDCl_3$): δ 167.82, 167.47, 158.26, 148.88, 14'0.86, 144.36, 140.05, 138.32, 138.02, 138.00, 136.70, 131.67, 130.18, 129.42, 127.86, 127.7, 127.23, 127.18, 126.54, 125.52, 120.60, 117.52, 51.77, 34.66, 33.28, 28.32, 23.07, 22.72, 21.49, 21.22, 14.16. $^{11}$B NMR (160 MHz, $CDCl_3$): δ 40.50. IR (KBr, $cm^{-1}$): 2958, 2919, 2856, 1610, 1586, 1571, 1506, 1488, 1472, 1459, 1448, 1421, 1361, 1339, 1297, 1279, 1171, 1155, 1101, 1075, 1028, 995, 847, 828, 761, 738, 698 $cm^{-1}$. HRMS (ESI): m/z calcd for $C_{39}H_{47}BNO_4^+$ $[M^+ H^+]$: 604.3593. Found: 604.3590.

In summary, a general, modular, and straightforward method has been developed to access diverse multi-substituted monocyclic 1,2-azaborines from readily available staring materials. Owing to the relatively mild conditions, the reaction exhibits a broad substrate scope and good functional group compatibility. This method is expected to greatly simplify syntheses of diverse BN-isostere analogues and to be readily adoptable in medicinal chemistry. The mechanistic insights gained here should have broad implications on boron-mediated electrocyclization for preparing other boron-containing heterocycles.

General Information: Unless noted otherwise, all solvents were dried by filtration through a Pure-Solv MD-5 Solvent Purification System (Innovative Technology). The solvents for the azaborine synthesis reactions were freshly distilled from sodium benzophenone ketyl immediately prior to use. All the azaborine synthesis reactions were carried out under nitrogen atmosphere with a stir bar in a sealed vial. Reaction temperatures were reported as the temperatures of the bather surrounding the flasks or vials. Sensitive reagents and solvents were transferred under nitrogen into a nitrogen-¶illed glovebox with standard techniques. Analytical thin-layer chromatography (TLC) was carried out using 0.2 mm commercial silica gel plates (silica gel 60, F254, EMD chemical). Vials (15×45 mm 1 dram (4 mL) with PTFE lined cap attached) were purchased from Qorpak and flame-dried or put in an oven overnight. High resolution mass spectra (HRSM) were obtained on an Agilent G6224A TOF LCMS and are reported as m/z (relative intensity). Accurate masses are reported for the molecular ion $M^+$, $[M^+ H]^+$, $[M^+Na]^+$. Infrared spectra were recorded on a Nicolet 380 FTIR using neat thin film technique. Nuclear magnetic resonance spectra (1H NMR, $^{13}$C NMR, $^{11}$B NMR, $^{19}$F NMR) were recorded with a Bruker Avance 400 instrument (400 MHz, $^{1}$H at 400 MHz, $^{13}$C at 101 MHz, $^{11}$B at 128 MHz, $^{19}$F at 377 MHz) and Bruker Avance 500 instrument (500 MHz, $^{1}$H at 500 MHz, $^{13}$C at 126 MHz, $^{11}$B at 160 MHz, $^{19}$F at 470 MHz). Chemical shifts are reported in parts per million (ppm, δ), downfield from tetramethylsilane (TMS, δ=0.00 ppm) and are referenced to residual solvent ($CDC_3$, 5=7.26 ppm ($^{1}$H) and 77.00 ppm ($^{13}$C); $C_6D_6$, δ=7.16 ppm ($^{1}$H) and 128.06 ppm ($^{13}$C)). All the $^{11}$B chemical shifts were referenced to external $BF_3{\cdot}OEt_2$ (0.00 ppm). All the $^{19}$F chemical shifts were not referenced. Coupling constants were reported in Hertz (Hz). Data for $^{1}$H NMR spectra were reported as follows: chemical shift (ppm, referenced to protium; s=singlet, d=doublet, t=triplet, q=quartet, dd=doublet of doublets, m=multiplet, br=broad, coupling constant (Hz), and integration).

Reagents and Substrates: Compounds N-methoxy-N-methylcyclopropanecarboxamide (Weinreb amide S1)1, PhBBr2 (2b) 2 (hexyl)BBr2 (2d) 3, IpcBBr2 (2e) 4, 1-cyclopropyl-3-phenylpropan-1-one 5, cyclohexyl(cyclopropyl)methanone 6, (E)-1-cyclopropyl-3-phenylprop-2-en-1-one 7 and 1as 8, were prepared according to literature methods. Compounds 2a, 2c, 2f, 1a, 1c, 1d, 1e, 1f, 1g, 1 h, 1i, 1j, 1k, 11, 1m, 1n, 1o, 1t, 1u, 1v, 1w, 1x, 1y, 1z, 1aa, 1ab, 1ac, 1ad, 1ae, 1af, 1ag, 1ak, 1al, 1am, 1an, 1ao and 1ap, used above, were prepared according to the following procedures. The others were commercially available and were used as received.

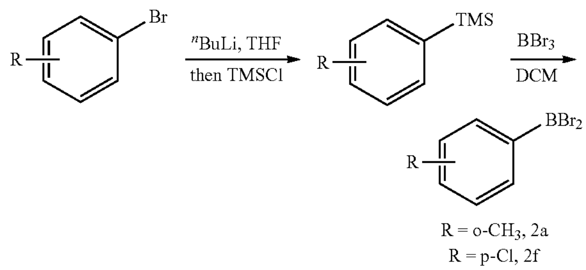

R = o-CH3, 2a
R = p-Cl, 2f

To a dry THE (60 mL) solution of aryl bromide (30 mmol 1 equiv) was added dropwise $^{n}$BuLi (2.5 M in hexane, 12.6 mL, 1.05 equiv) at −78° C. under nitrogen. The mixture was stirred at this temperature for additional 0.5 h followed by the addition of chlorotrimethylsilane (4.0 mL, 31.5 mmol, 1.05 equiv). The mixture was allowed to slowly warm to room temperature and stir for 2 h. Upon completion, the reaction mixture was quenched with water (30 mL) and saturated aqueous $NH_4Cl$ solution (30 mL). The organic phase was separated, and the aqueous layer was extracted with ethyl acetate (3×60 mL). The organic layers were combined, washed with brine, dried over $MgSO_4$, and concentrated under vacuum. The crude product was subjected to flash column chromatography (pure hexane to EtOAc/hexane=1/100) to give the trimethyl(aryl)silane as a colorless oil.

To a solution of tribromoborane (2.0 mL, 21 mmol) in dichloromethane (20 mL) was added trimethyl(aryl)silane (20 mmol) dropwise at 0° C. The mixture was allowed to warm to room temperature and stir overnight. Upon completion, all volatiles were removed under vacuum, and the crude product was distilled under reduced pressure to give $ArBBr_2$.

2a

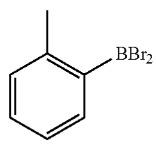

2a: Yield: 74%. Colorless oil. $^{1}$H NMR (500 MHz, $C_6D_6$): δ 7. 5 (dd, J=7.7, 1.5 Hz, 1H), 7.03-6.99 (m, 1H), 6.88 (t, J=7.5 Hz, 1H), 6.79 (d, J=7.6 Hz, 1H) (aryl CH), 2.35 (s, 3H) ($CH_3$). $^{13}$C NMR (126 MHz, $C_6D_6$): δ 143.2, 136.5, 133.4, 131.3, 125.5 (aryl C), 23.9 ($CH_3$). $^{11}$B NMR (160 MHz, $C_6D_6$): δ 58.2 (s, 1B). The NMR data match with those reported in literature.

2f

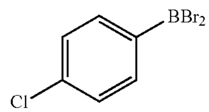

2f: Yield: 70%. Colorless oil. $^{1}$H NMR (500 MHz, $C_6D_6$): δ 7.73 (d, J=8.2 Hz, 2H), 6.93 (d, J=8.3 Hz, 2H) (aryl CH). $^{13}$C NMR (126 MHz, $C_6D_6$): δ 142.5, 139.2, 128.6 (aryl C). $^{11}$B NMR (160 MHz, $C_6D_6$): δ 56.6 (s, 1B). The NMR data match with those reported in literature.

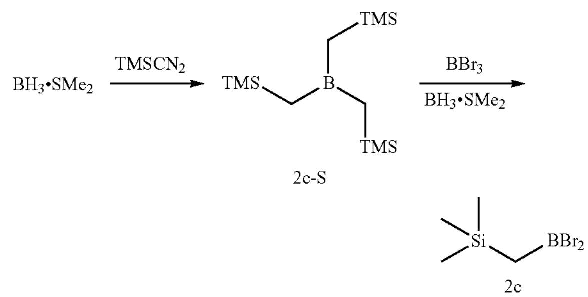

2c-S

2c

An oven-dried, nitrogen-purged 50 mL Schlenk flask was charged with 20 mL dry hexane and (trimethylsilyl)diazomethane (2 M in hexane, 3 mL, 6 mmol). At −78° C., borane dimethyl sulfide complex (316 μL, 3.33 mmol) was added dropwise. After the reaction mixture was allowed to stir and warm to 0° C. over 35 min, the yellow color disappeared. Upon completion, solvent was removed under vacuum to give tris(trimethylsilyl)methylborane 2c-S. Then, dry hexane (4 mL) was added, followed by the addition of boron tribromide (370 μL, 3.9 mmol) at 0° C. After the addiion of borane dimethyl sulfide complex (14 μL, 0.15 mmol), the reaction was allowed to warm to room temperature and stir under nitrogen for 48 h. Upon completion ($^{11}$B NMR only shows a signal at 59 ppm), all volatiles were removed under vacuum, and the crude product was distilled under reduced pressure to give 2c as a colorless oil (860 mg, 56%). $^{1}$H NMR (400 MHz, $C_6D_6$): δ 1.57 (s, 2H) ($CH_2$), −0.01 (s, 9H) ($CH_3$). $^{13}$C NMR (101 MHz, $C_6D_6$): δ 0.2 ($CH_3$)i $^{11}$B NMR (160 MHz, $C_6D_6$): δ 59.3 (s, 1B). The NMR data match with those reported in literature.

Preparation of imines 1α-10, 1ac-1ae, 1aq, 1ak and 1al (a representative procedure)

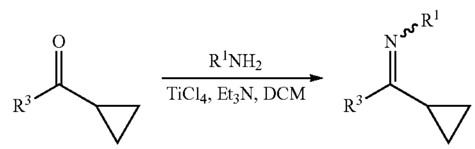

An oven-dried 50 mL Schlenk flask was charged with ketone (5 mmol, 1 equiv), amine (6 mmol, 1.2 equiv) (2.5 mmol, 0.5 equiv for the preparation of imine 1al), triethylamine (1.4 mL, 10 mmol, 2 equiv) and dry dichloromethane (20 mL). $TiCl_4$ (2.5 mL, 1M solution in DCM, 2.5 mmol, 0.5 equiv) was then added dropwise under nitrogen at 0° C. over a period of 15 min. After being stirred at 0° C. for 0.5 h, the reaction mixture was v armed to room temperature and stirred for 12 h. Upon completion, the reaction mixture was quenched with a saturated $K_2CO_3$ solution (2.5 mL) and stirred for 5 min at room temperature. Then, the mixture was filtered through a pad of Celite, washed with dichloromethane and concentrated to dryness under vacuum. The crude product was subjected to flash column chromatography (pure hexane to EtOAc/hexane=1/20) to give the imine. The silica gel for column chromatography was treated with triethylamine (1 mL in 50 mL hexane) for 24 h.

Preparation of Imines 1t-1ab (a Representative Procedure)

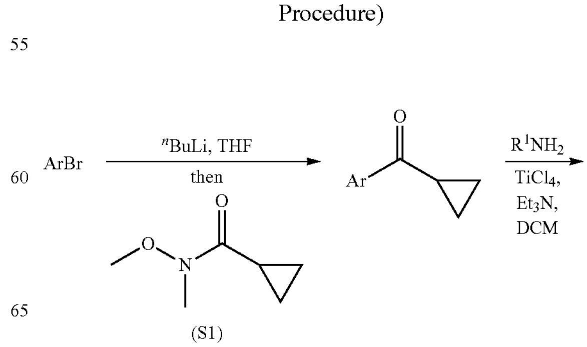

(S1)

-continued

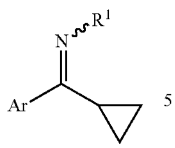

To a dry THE (10 mL) solution of aryl bromide (5 mmol, 1 equiv) was added dropwise $^{n}$BuLi (2.5 M in hexane, 2.1 mL, 1.05 equiv) at −78° C. under nitrogen. The mixture was stirred at this temperature for additional 0.5 h followed by the addition of Weinreb amide S1 (677 mg, 5.25 mmol, 1.05 equiv). The mixture was allowed to warm to room temperature and stir for 2 h. Upon completion, the reaction mixture was quenched with water (5 mL) and saturated aqueous $NH_4Cl$ solution (5 mL). The organic phase was separated, and the aqueous layer was extracted with ethyl acetate (3×10 mL). The organic layers were combined, washed with brine, dried over $MgSO_4$, filtered through a pad of silica gel, and concentrated under vacuum. The obtained ketone was directly used in the next step without further purification.

An oven-dried 50 mL Schlenk flask was charged with the ketone, amine (6 mmol, 1.2 equiv), triethylamine (1.4 mL, 10 mmol, 2 equiv) and dry dichloromethane (20 mL). $TiCl_4$ (2.5 mL, 1M solution in DCM, 2.5 mmol, 0.5 equiv) was then added dropwise under nitrogen at 0° C. over a period of 15 min. After being stirred at 0° C. for 0.5 h, the reaction mixture was warmed to room temperature and stirred for 12 h (the reaction temperature is 50° C. for the preparation of imine lab). Upon completion, the reaction mixture was quenched with a saturated $K_2CO_3$ solution (2.5 mL) and stirred for 5 min at room temperature. Then, the mixture was filtered through a pad of Celite, washed with dichloromethane and concentrated to dryness under vacuum. The crude product was subjected to flash column chromatography (pure hexane to EtOAc/hexane=1/20) to give the imine. The silica gel for column chromatography was treated with triethylamine (1 mL in 50 mL hexane) for 24 h.

Preparation of imine 1af

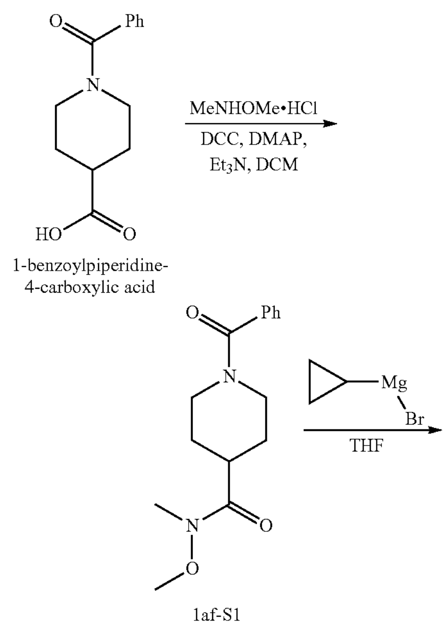

1-benzoylpiperidine-4-carboxylic acid

1af-S1

-continued

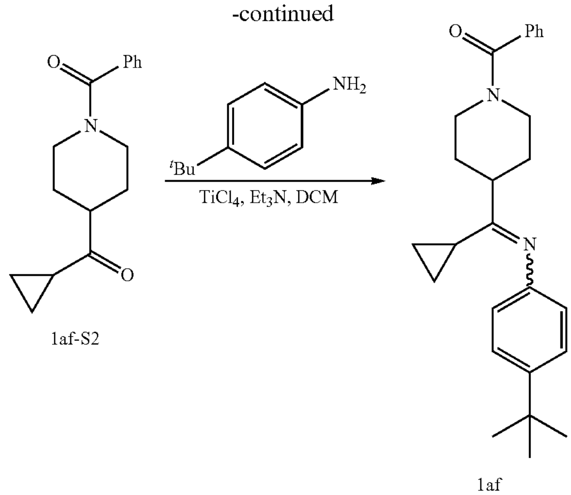

1af-S2

1af

To a solution of 1-benzoylpiperidine-4-carboxylic acid (1.17 g, 5 mmol, 1 equiv) in dichloromethane (10 mL) at 0° C. was added N,O-dimethylhydroxylamine hydrochloride (683 mg, 7 mmol, 1.4 equiv), DCC (N,N'-dicyclohexylcarbodiimide, 1.44 g, 7 mmol, 1.4 eqiuv), DMAP (4-dimethylaminopyridine, 85.4 mg, 0.7 mmol, 0.14 equiv) and triethylamine (934 μL, 7 mmol, 1.4 equiv) sequentially. The reaction mixture was allowed to warm to room temperature and stir for 16 h. Upon completion, the reaction mixture was filtered through a pad of Celite, washed with dichloromethane. The filtrate was washed with saturated aqueous $NaHCO_3$ (10 mL) and brine (10 mL), dried over $MgSO_4$, and concentrated under vacuum. The crude product was subjected to flash column chromatography (E OAc/hexane=1/3 to EtOAc/hexane=1/1) to give Weinreb amide 1af-S1 as a white solid (1.18 g, 86%).

To a solution of the Weinreb amide 1af-S1 (1.18 g, 4.3 mnol, 1.0 equiv) in dry THF (10 mmol) at −78° C. was added cyclopropylmagnesium bromide (10.3 mL, 0.5 M solution in THF, 5.16 mmol, 1.2 equiv) dropwise. The reaction was allowed to warm to room temperature and stir for 12 h. Upon completion, the reaction mixture as quenched with saturated aqueous $NH_4Cl$ solution (20 mL) at 0° C. Then the mixture was extracted with ethyl acetate (3×20 mL) and the combined organic layers was washed with brine, dried over $MgSO_4$ and concentrated under vacuum. The crude product was subjected to flash column chromatography (EtOAc/hexane=1/3) to give ketone 1af-S2 as a white solid (887 mg, 80%).[15]

An oven-dried 50 mL Schlenk flask was charged with the ketone 1af-S2 (514 mg, 2 mmol, 1 equiv), 4-tert-butylaniline (382 μL, 2.4 mmol, 1.2 equiv), triethylamine (0.56 mL, 4 mmol, 2 equiv) and dry dichloromethane (8 mL). $TiCl_4$ (1 mL, 1M solution in DCM, 1 mmol, 0.5 equiv) was then added dropwise under nitrogen at 0° C. over a period of 15 min. After being stirred at 0° C. for 0.5 h, the reaction mixture was warmed to room temperature and stirred for 12 h. Upon completion, the reaction mixture was quenched with a saturated $K_2CO_3$ solution (1 mL) and stirred for 5 min at room temperature. Then, the mixture was filtered through a pad of Celite, washed with dichloromethane and concentrated to dryness under vacuum. The crude product was subjected to flash column chromatography (EtOAc/hexane=1/10 to EtOAc/hexane=1/3) to give imine 1af as a pale yellow solid (566 mg, 73%). The silica gel for column chromatography was treated with triethylamine (1 mL in 50 mL hexane) for 24 h.

Preparation of imine 1an

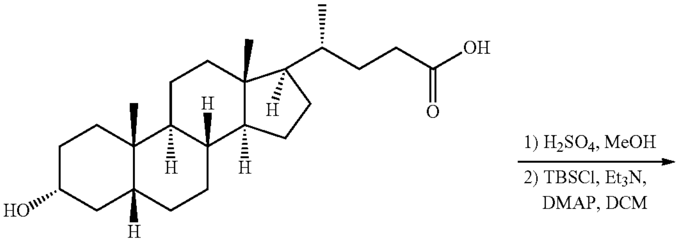

Lithocholic acid

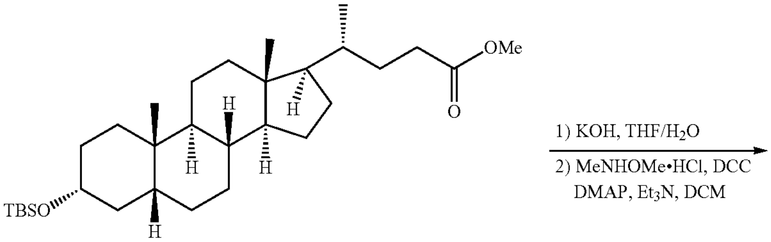

1an-S1

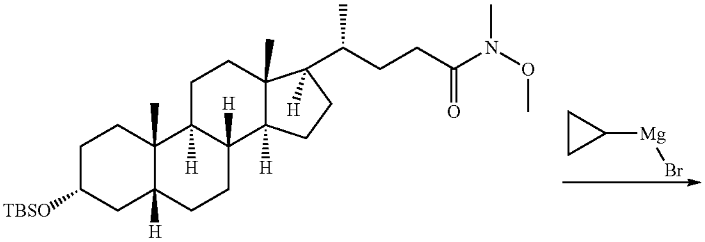

1an-S2

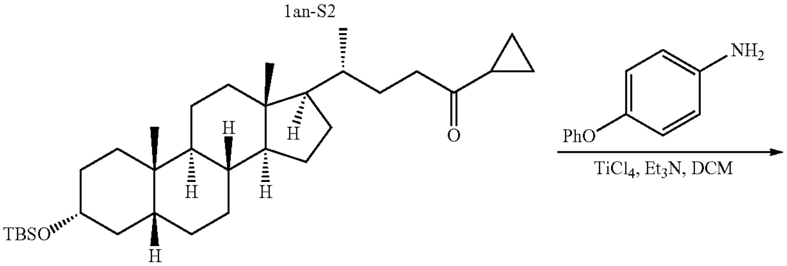

1an-S3

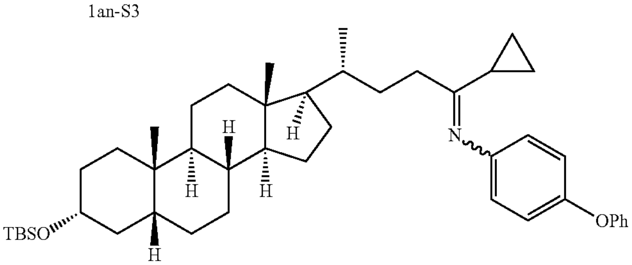

1an

To a solution of lithocholic acid (1.88 g, 5 mmol, 1 equiv.) i methanol (25 mL) was added sulfuric acid (0.625 mL), and the mixture was then stirred for 5 hours at reflux. After removing the volatiles, the crude was extracted with DCM (3×50 mL). The combined organic phase was dried over $MgSO_4$, filtered, and concentrated to dryness in vacuo. The resulting solid was dissolved in DCM (20.0 ml). Triethylamine (1.05 mL, 7.5 mmol), DMAP (122 mg, 1.0 mmol) and TBSCl (tert-butyldimethylsilyl chloride, 825 mg, 5.5 mmol, 1.1 equiv.) were then added, and the mixture was stirred at room temperature for 12 h. Upon completion, the reaction mixture was quenched with a saturated aqueous solution of $NH_4Cl$ (30 mL), and the mixture was extracted with DCM (3×50 mL), dried over $MgSO_4$, filtered and concentrated under vacuum. The crude product was subjected to flash column chromatography (EtOAc/hexane=1/20) to give 1an-S1 (2.17 g, 86% over two steps) as a white solid.

To a solution of 1an-S1 (4.3 mmol, 2.17 g) in THF (20 mL) was added KOH (2.0 M aqueous solution, 4.3 mL, 8.6 mmol, 2 equiv) dropwise. The reaction was stirred at room temperature for 2 h. Upon completion, the reaction was poured into water (100 mL) and HCl (1 M aqueous solution) was added to acidify the solution to pH=2-3. The mixture was extracted with ethyl acetate (3×50 mL), and the combined organic layers were washed with brine, dried over $MgSO_4$ and concentrated to dryness under vacuum to give the acid as a white solid. To a solution of the obtained acid in dichloromethane (10 mL) at 0° C. was added N,O-dimethylhydroxylamine hydrochloride (585 mg, 6 mmol, 1.4 equiv), DCC (N,N-dicyclohexylcarbodiimide, 1.23 g, 6 mmol, 1.4 eqiuv), DMAP (4-dimethylaminopyridine, 73.2 mg, 0.6 mmol, 0.14 equiv) and triethylamine (835 μL, 6 mmol, 1.4 equiv) sequentially. The reaction mixture was allowed to warm to room temperature and stir for 16 h. Upon completion, the reaction mixture was filtered through a pad of Celite, washed with dichloromethane. The filtrate was washed with saturated aqueous $NaHCO_3$ (10 mL) and brine (10 mL), dried over $MgSO_4$, and concentrated under vacuum. The crude product was subjected to flash column chromatography (EtOAc/hexane=1/20 to EtOAc/hexane=1/5) to give Weinreb amide 1an-S2 as a white solid (1.76 g, 77% over two steps).

To a solution of the Weinreb amide 1an-S2 (1.60 g, 3 mmol, 1 equiv) in dry THE (10 mmol) at −78° C. was added cyclopropylmagnesium bromide (7.2 mL, 0.5 M solution in THF, 3.6 mmol, 1.2 equiv) dropwise. The reaction was allowed to warm to room temperature and stir for 12 h. Upon completion, the reaction mixture was quenched with saturated aqueous $NH_4Cl$ solution (15 mL) at 0° C. Then the mixture was extracted with ethyl acetate (3×20 mL) and the combined organic layers was washed with brine, dried over $MgSO_4$ and concentrated under vacuum. The crude product was subjected to flash column chromatography (EtOAc/hexane=1/10) to give ketone 1an-S3 as a white solid (971 mg, 63%).

An oven-dried 50 mL Schlenk flask was charged with the ketone 1an-S3 (514 mg, 1 mmol, 1 equiv), 4-phenoxyaniline (222 mg, 1.2 mmol, 1.2 equiv), triehylamine (0.28 mL, 2 mmol, 2 equiv) and dry dichloromethane (5 mL). $TiCl_4$ (0.5 mL, 1M solution in DCM, 0.5 mmol, 0.5 equiv) was then added dropwise under nitrogen at 0° C. over a period of 15 min. After being stirred at 0° C. for 0.5 h, the reaction mixture was warmed to room temperature and stirred for 12 h. Upon completion, the reaction mixture was quenched with a saturated $K_2CO_3$solution (0.5 mL) and stirred for 5 min at room temperature. Then, the mixture was filtered through a pad of Celite, washed with dichloromethane and concentrated to dryness under vacuum. The crude product was subjected to flash column chromatography (pure hexane to EtOAc/hexane=1/20) to give imine Ian as a pale yellow solid (415 mg, 61%). The silica gel for column chromatography was treated with triethylamine (1 mL in 50 mL hexane) for 24 h.

Preparation of imine 1am and 1ao

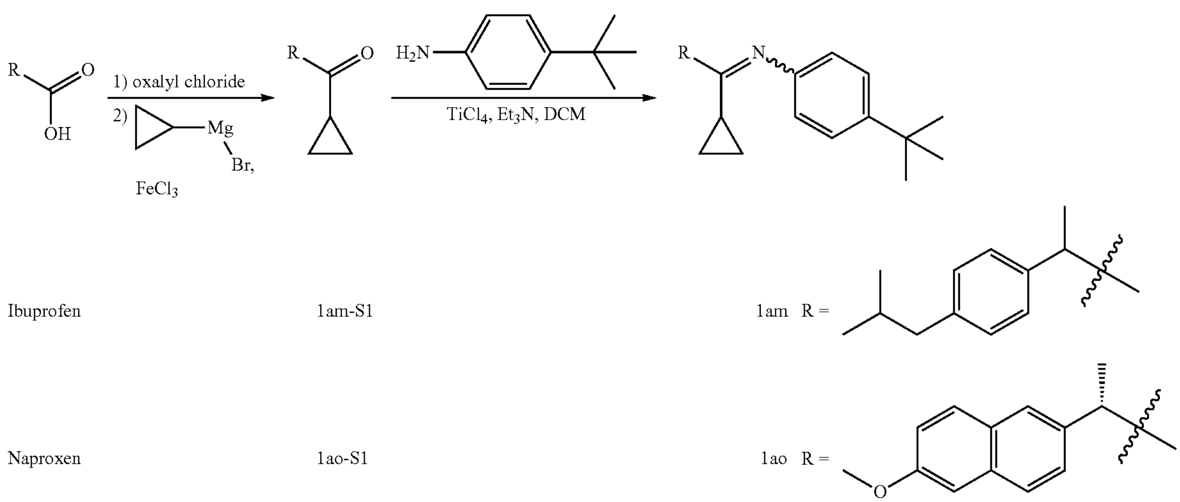

Ibuprofen

1am-S1

1am R =

Naproxen

1ao-S1

1ao R =

To a solution of carboxylic acid (10 mmol, 1 equiv) in dry DCM (20 mL) was added DMF (3-4 drops) and oxalyl chloride (1.03 mL, 1.2 equiv) dropwise. The resulting mixture was stirred at room temperature for 2 h. Upon completion, all volatiles were removed under vacuum to give the acyl chloride. To the THE solution of the obtained acyl chloride was added anhydrous $FeCl_3$ (8.1 mg, 0.5 mmol, 5 mol %). At −78° C., cyclopropylmagnesium bromide (24 mL, 0.5 M solution in THF, 12 mmol, 1.2 equiv) was added dropwise. The reaction mixture was stirred at −78° C. for 1 h before being slowly warmed to room temperature and stirred for 12 h. Upon completion, the reaction mixture was quenched with saturated aqueous $NH_4Cl$ solution (30 mL) at 0° C. Then the mixture was extracted with ethyl acetate (3×40 mL) and the combined organic layers was washed with brine, dried over $MgSO_4$ and concentrated under vacuum. The crude product was subjected to flash column chromatography (EtOAc/hexane=1/10) to give ketone 1am-S1 (1.48 g, 64%) or 1ao-S1 (2.26 g, 89%).

An oven-dried 50 mL Schlenk flask was charged with ketone 1am-S1 or 1ao-S1 (2 mmol, 1 equiv), 4-tert-butylaniline (382 μL, 2.4 mmol, 1.2 equiv), triethylamine (0.56 mL, 4 mmol, 2 equiv) and dry dichloromethane (8 mL). $TiCl_4$ (1 mL, 1M solution in DCM, 1 mmol, 0.5 equiv) was then added dropwise under nitrogen at 0° C. over a period of 15 min. After being stirred at 0° C. for 0.5 h, the reaction mixture was warmed to room temperature and stirred for 12 h. Upon completion, the reaction mixture was quenched with a saturated $K_2CO_3$ solution (1 mL) and stirred for 5 min at room temperature. Then, the mixture was filtered through a pad of Celite, washed with dichloromethane and concentrated to dryness under vacuum. The crude product was subjected to flash column chromatography (pure hexane to EtOAc/hexane=1/20) to give imine lam or 1ao. The silica gel for column chromatography was treated with triethylamine (1 mL in 50 mL hexane for 24 h.

Preparation of Imine Lap

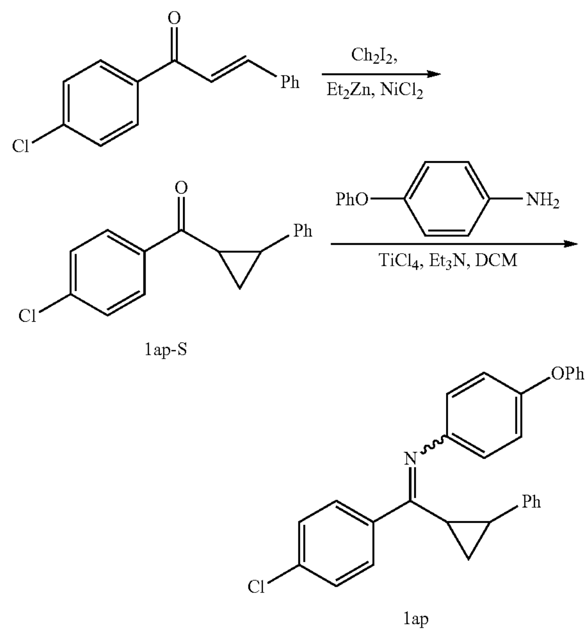

1ap-S

1ap

To a mixture of 4-chlorochalcone (1.21 g, 5 mmol, 1 equiv.), $NiCl_2$ (13.0 mg, 0.1 mmol, 2 mol %) and $CH_2I_2$ (5.36 g, 20 mmol, 4 equiv.) in 20 mL DCM at 40° C. was added slowly $Et_2Zn$ (10 mL, 1M in hexane, 10 mmol, 2 equiv.) over 20 min under nitrogen. After the addition, the reaction was stirred for 10 min before diluted with DCM und quenched with saturated aqueous $NH_4Cl$ solution (30 mL). Then the mixture was extracted with DCM (3×40 mL) and the combined organic layers was washed with brine, dried over $MgSO_4$ and concentrated under vacuum. The crude product was subjected to flash column chromatography (EtOAc/hexane=1/20) to give ketone 1ap-S (0.92 g, 72%).

An oven-dried 50 mL Schlenk flask was charged with the ketone 1ap-S (512 mg, 2 mmol, 1 equiv.), 4-phenoxyaniline (444 mg, 2.4 mmol, 1.2 equiv.), triethylamine (0.56 mL, 4 mmol, 2 equiv) and dry dichloromethane (10 mL). $TiCl_4$ (1 mL, 1M sol tion in DCM, 1 mmol, 0.5 equiv) was then added dropwise under nitrogen at 0° C. over a period of 15 min. After being stirred at 0° C. for 0.5 h, the reaction mixture was warmed to room temperature and stirred for 12 h. Upon completion, the reaction mixture was quenched with a saturated $K_2CO_3$ solution (1 mL) and stirred for 5 min at room temperature. Then, the mixture was filtered through a pad of Celite, washed with dichloromethane and concentrated to dryness under vacuum. The crude product was subjected to flash column chromatography (pure hexane to EtOAc/hexane=1/20) to give imine lap as a yellow oil (643 mg, 76%). The silica gel for column chromatography was treated with triethylamine (1 mL in 50 mL hexane) for 24 h.

1a

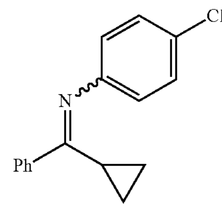

1a: Yield: 90%. Light yellow oil. $R_f$=0.5 (hexane/ethyl acetate=9:1). $^1H$ NMR (500 MHz, $CDCl_3$, a mixture of geometrical isomers in ~2:1 ratio): δ 7.82-7.73 (m, 0.66H), 7.45-7.44 (m, 1H), 7.39-7.31 (m, 0.66H), 7.27-7.26 (m, 2H), 7.22-7.13 (m, 1.33H), 7.08 (dd, J=8.4, 1.6 Hz, 1.32H), 6.99-6.89 (m, 0.67H), 6.56 (d, J=8.7 Hz, 1.32H) (aryl CH), 2.07-2.02 (m, 0.67H), 1.87-1.84 (m, 0.33H) (CH), 1.24-1.17 (m, 1.33H), 1.07-1.04 (m, 1.34H), 0.86 (dd, J=8.6, 2.1 Hz, 0.67H), 0.63 (dd, J=5.7, 1.9 Hz, 0.66H) ($CH_2$). $^{13}C$ NMR (126 MHz, CDCl): δ 174.0, 171.7 (C=N), 149.7, 137.6, 129.7, 128.9, 28.7, 128.6, 128.2, 128.1, 128.1, 128.0, 128.0, 122.4, 121.6 (aryl C), 20.2, 14.1 (CH), 10.0, 8.0 ($CH_2$). IR (KBr, $cm^{-1}$): ν 3464, 3372, 3217, 3083, 3060, 3026, 3008, 1667, 1631, 1599, 1578, 1494, 1483, 1448, 1417, 1384, 1290, 1226, 1191, 1173, 1092, 1061, 1040, 1027, 1012. HRMS (ESI): Calcd for $C_{16}H_{15}ClN^+[M^+ H]^+$: 256.0888, found: 256.0894.

1c

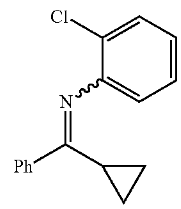

1c: Yield: 82%. Light yellow oil. $R_f$=0.5 (hexane/ethyl acetate=9:1). $^1H$ NMR (400 MHz, $CDCl_3$, a mixture of geometrical isomers in ~2:1 ratio): δ 7.69 (d, J=5.8 Hz, 0.64H), 7.31-7.31 (m, 1.32H), 7.14-7.09 (m, 4.33H), 6.91-6.80 (m, 1.34H), 6.68 (t, J=7.6 Hz, 0.68H), 6.36 (d, J=7.9 Hz, 0.66H) (aryl CH), 1.97-1.90 (m, 0.67H), 1.70-1.63 (m, 0.33H) (CH), 1.19-1.17 (m, 1.37H), 0.96-0.91 (m, 1.34H), 0.67-0.65 (m, 0.66H), 0.53-0.51 (m, 0.64H) ($CH_2$). $^{13}C$ NMR (126 MHz, $CDCl_3$): δ 174.9, 172.7 (C=N), 148.5, 148.2, 138.1, 138.1, 129.7, 129.4, 128.8, 128.1, 128.0, 127.3, 127.2, 126.9, 124.9, 124.1, 123.6, 121.6, 120.9 (aryl C), 19.8, 14.7 (CH), 10.5, 7.2 ($CH_2$). IR (KBr, $cm^{-1}$): ν 3082, 3060, 3007, 1637, 1600, 1586, 1490, 1467, 1445, 1384, 1315, 1296, 1281, 1262, 1233, 1179, 1157, 1126, 1101, 1055, 1040, 1032, 1008. HRMS (ESI): Calcd for $C_{16}H_{15}ClN^+[M^+ H]^+$: 256.0888, found: 256.0899.

1d

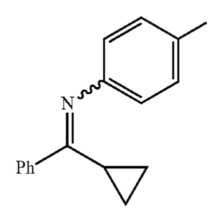

1d: Yield: 91%. Light yellow oil. $R_f$=0.4 (hexane/ethyl acetate=9:1). $^1H$ NMR (500 MHz, $C_6D_6$, a mixture of geometrical isomers in ~2.6:1 ratio): δ 7.95-7.92 (m, 0.56H), 7.20-7.17 (m, 0.73H), 7.04-6.98 (m, 1.46H), 6.96-6.81 (m, 2.74H), 6.76-6.69 (m, 0.56H), 6.64-6.57 (m, 1.45H), 6.48-6.41 (m, 1.44H) (aryl CH), 1.76-1.71 (in, 0.72H), 1.44-1.35 (m, 0.28H) (CH), 1.33-1.28 (m, 1.44H), 0.75-0.71 (m, 1.47H), 0.40-0.33 (m, 0.54H), 0.27-0.25 (m, 0.54H) ($CH_2$). $^{13}C$ NMR (126 MHz, $C_6D_6$): δ 172.9, 167.0 (=N), 159.8 (d, $^1J_{C-F}$=242 Hz), 159.4 (d, $^1J_{C-F}$=242 Hz), 147.8 (d, $^4J_{C-F}$=2.8 Hz), 147.7 (d, $^4J_{C-F}$=2.8 Hz), 139.3, 138.6, 129.9, 128.6, 128.5, 128.3, 128.3, 122.6 (d, $^3J_{C-F}$=7.9 Hz), 121.9 (d, $^3J_{C-F}$=7.7 Hz), 115.6 (d, $^2J_{C-F}$=22.2 Hz), 115.5 (d, $^2J_{C-F}$=22.3 Hz), 20.2, 13.6 (CH), 10.3, 8.2 ($CH_2$). $^{19}F$ NMR (377 MHz, $CDCl_3$): δ −121.06, −121.57 (m, 1F). IR (KBr, $cm^1$): v 3319, 3086, 3060, 3008, 1669, 1629, 1598, 1578, 1499, 1449, 1384, 1226, 1151, 1125, 1092, 1040, 1027, 1012. HRMS (ESI): Calcd for $C_{16}H_{15}FN^+[M^+ H]^+$: 240.1183, found: 240.1189.

1e

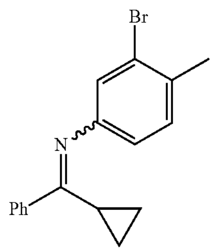

1e: Yield: 86%. Light yellow oil. $R_f$=0.5 (hexane/ethyl acetate=9:1). $^1H$ NMR (500 MHz, $CDCl_3$, a mixture of geometrical isomers in ~1.6:1 ratio): δ 7.75 (dd, J=6.7, 3.0 Hz, 0.73H), 7.50-7.37 (m, 1.14H), 7.33-7.12 (m, 3.89H), 7.00-6.8 (m, 1.55H), 6.43 (dd, J=7.9, 2.1 Hz, 0.60H) (aryl CH), 2.43 (s, 1.17H), 2.28 (s, 1.90H) ($CH_3$), 2.06-2.01 (m, 0.62H), 1.91-1.86 (m, 0.38H) (CH), 1.20-1.19 (m, 1.25H), 1.06-1.02 (m, 1H), 0.90-0.85 (m, 1H), 0.67-0.63 (m, 1H) ($CH_2$). $^{13}C$ NMR (126 MHz, $CDCl_3$): δ 174.1, 172.0 (C=N), 150.0, 149.9, 138.3, 137.6, 132.3, 131.7, 130.8, 130.5, 129.6, 128.7, 128.2, 128.1, 128.1, 128.0, 124.9, 124.8, 124.5, 123.8, 120.0, 119.5 (aryl C), 22.4, 22.2 ($CH_3$), 20.2, 14.2 (CH), 9.9, 8.0 ($CH_2$). IR (KBr, $cm^{-1}$): v 3082, 3056, 3028, 3005, 2979, 2948, 2920, 2859, 1629, 1597, 1576, 1548, 1482, 1445, 1384, 1295, 1273, 1231, 1188, 1158, 1097, 1074, 1057, 1031, 1009. HRMS (ESI): Calcd for $C_{17}H_{17}BrN^+[M^+ H]^+$: 314.0539, found: 314.0550.

1f

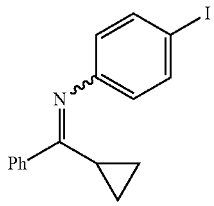

if: Yield: 84%. Light yellow oil. $R_f$=0.5 (hexane/ethyl acetate=9:1). $^1H$ NMR (400 MHz, $CDCl_3$, a mixture of geometrical isomers in ~1.9:1 ratio): o 7.76-7.74 (m, 0.69H), 7.65 (d, J=8.1 Hz, 0.71H), 7.42-7.38 (m, 2.4H), 7.26-7.19 (m, 1.85H), 7.17-7.14 (m, 1.29H), 6.74 (d, J=8.1 Hz, 0.69H), 6.37 (d, J=8.2 Hz, 1.26H) (aryl CH), 2.04-1.98 (m, 0.65H), 1.86-1.79 (m, 0.35) (CH), 1.2-1.16 (m, 1.28H), 1.04-0.99 (n, 1.27H), 0.87-0.80 (m, 0.72H), 0.63-0.58 (t, J=5.7 Hz, 0.68H) ($CH_2$). $^{13}C$ NMR (101 MHz, $CDCl_3$): δ 173.8, 171.5 (C=N), 150.8, 150.6, 137.7, 137.4, 129.6, 128.7, 128.1, 128.0, 28.0, 128.0, 128.0, 123.2, 122.4, 86.8, 86.2 (aryl C), 20.2, 14.1 (CH), 10.0, 8.0 ($CH_2$). IR (KBr, $cm^{-1}$): v 3467, 3382, 3082, 3056, 3022, 3006, 1629, 1577, 1487, 1476, 1445, 1419, 1384, 1295, 1229, 1191, 1172, 1097, 1057, 1040, 1027, 1009. HRMS (ESI): Calcd for $C_1H_{15}N^+[M^+ H]^+$: 348.0244, found: 348.0249.

1g

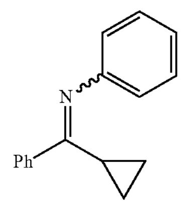

1g: Yield: 90%. Light yellow oil. $R_f$=0.5 (hexane/ethyl acetate=9:1). $^1H$ NMR (500 MHz, $CDCl_3$, a mixture of geometrical isomers in ~1.7:1 ratio): o 7.84-7.76 (m, 0.74H), 7.48-7.45 (m Hz, 1H), 7.41 (t, J=7.8 Hz, 0.76H), 7.28-7.20 (m, 3.17H), 7.18-7.09 (m, 1.65H), 7.06-6.99 (m, 0.74H), 6.96-6.87 (m, 0.62H), 6.69-6.61 (m, 1.25H) (aryl CH), 2.10-2.04 (m, 0.63H), 1.93-1.87 (m, 0.37H) (CH), 1.26-1.24 (m, 1.27H), 1.09-1.04 (m, 1.27H), 0.87-0.82 (m, 1H), 0.68-0.62 (m, 1H) ($CH_2$). $^{13}C$ NMR (126 MHz, $CDCl_3$): δ 172.9, 171.2 (C=N), 151.1, 151.0, 138.5, 137. 9, 129.4, 128.8, 128.5, 128.4, 128.1, 128.1, 128.0, 127.9, 123.3, 122.7, 121.0, 120.2 (aryl C), 20.1, 14.1 (CH), 9.7, 7.8 ($CH_2$). IR (KBr, $cm^{-1}$): v 3078, 3059, 3027, 3017, 1669, 1630, 1593, 1577, 1484, 1446, 1416, 1383, 1295, 1233, 1170, 1096, 1072, 1040, 1026, 1010. HRMS (ESI): Calcd for $C_{16}H_{16}N^+ [M^+ H]^+$: 222.1277, found: 222.1298.

1h

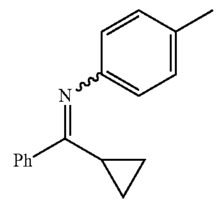

1h: Yield: 92%. Light yellow oil. $R_f$=0.5 (hexane/ethyl acetate=9:1). $^1H$ NMR (500 MHz, $CDCl_3$, a mixture of geometrical isomers in ~1.6:1 ratio): δ 7.85-7.77 (m, 0.76H), 7.48-7.46 (m, 1.18H), 7.30-7.22 (m, 3.79H), 6.96 (dd, J=8.1, 2.1 Hz, 2.04H), 6.57 (d, J=8.4 Hz, 1.23H) (aryl CH), 2.43 (s, 1.18H), 2.27 (s, 1.85H) ($CH_3$), 2.10-2.05 (m, 0.61H), 1.97-1.91 (m, 0.39H) (CH), 1.26-1.23 (m, 1.26H), 1.08-1.04 (m, 1.28H), 0.89-0.85 (m, 1H), 0.70-0.66 (m, 1H) ($CH_2$). $^{13}C$ NMR (126 MHz, $CDCl_3$): δ 172.6, 171.0 (C=N), 148.4, 148.4, 138.1, 132.0, 129.4, 129.3, 129.1, 128.3, 128.1, 128.1, 128.00, 127.9, 120.9, 120.2, 77.4, 77.2, 76.9 (aryl C), 21.0, 20.8 ($CH_3$), 20.2, 14.1 (CH), 9.5, 7.8 ($CH_2$). IR (KBr, $cm^{-1}$): v 3081, 3052, 3022, 2920, 2864, 1630, 1576, 1504, 1445, 1383, 1294, 1232, 1191, 1173, 1109, 1074, 1040, 1027, 1009. HRMS (ESI): Calcd for $C_{17}H_{18}N^+[M^+ H]^+$: 236.1434, found: 236.1456.

1i

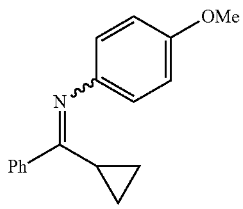

1i: Yield: 81%. Pale yellow solid. M.p.=48-50° C. $R_f$=0 3 (hexane/ethyl acetate=9:1). $^1$H NMR (400 MHz, $CDC_3$, a mixture of geometrical isomers i ~1.6:1 ratio): δ 7.74-7.54 (m, 0.74H), 7.34-7.27 (m, 1.04H), 7.18-7.02 (m, 3H), 6.98-6.64 (m, 1.69H), 6.62-6.50 (m, 1.24H), 6.50-6.30 (m, 1.25H) (aryl CH), 3.73 (s, 1.12H), 3.60 (s, 1.83H) ($OCH_3$), 1.96-1.83 (m, 0.62H), 1.83-1.75 (m, 0.38H) (CH), 1.09-1.05 (m, 1.21H), 0.92-0.86 (m, 1.22H), 0.76-0.68 (m, 0.73H), 0.52-0.42 (m, 0.74H) ($CH_2$). $^{13}$C NMR (101 MHz, $CDC_3$): δ 172.8, 170.9 (C=N), 156.1, 155.6, 144.2, 144.1, 138.9, 138.2, 129.3, 12.8.3, 128.2, 128.1, 128.1, 128.0, 122.3, 121.7, 114.1, 113.8 (aryl C), 55.5, 55.4 ($OCH_3$), 20.3, 14.0 (CH), 9.4, 8.1 ($CH_2$). IR (KBr, $cm^{-1}$): v 3080, 3058, 3034, 3001, 2948, 2932, 2908, 2833, 1628, 1576, 1502, 1465, 1443, 1383, 1288, 1241, 1179, 1104, 1037, 1011. HRMS (ESI): Calcd for $C_{17}H_{18}NO^+[M^+ H]^+$: 252.1383, found: 252.1398.

1j

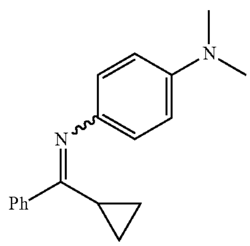

1j: Yield: 82%. Pale yellow solid. M.p.=82-84° C. $R_f$=0.15 (hexane/ethyl acetate=9:1). $^1$H NMR (400 MHz, $CDC_3$, a mixture of geometrical isomers in ~1.4:1 ratio): δ 7.70-7.61 (m, 0.81H), 7.26-7.24 (m, 1.17H), 7.13-7.01 (m, 3H), 6.86 (d, =8.8 Hz, 0.84H), 6.64 (d, J=8.9 Hz, 0.85H), 6.47-6.32 (m, 2.39H) (aryl CH), 2.81 (s, 2.47H), 2.68 (s, 2.54H) ($N(CH_3)_2$), 1.89-1.76 (m, 1H) (CH), 1.06-1.00 (m, 1.16H), 0.85-0.79 (m, 1.17H), 0.74-0.66 (m, 0.82H), 0.44 (dd, J=5.8, 1.8 Hz, 0.82H) ($CH_2$). $^{13}$C NMR (101 MHz, $CDCl_3$): δ 171.3, 169.6 (C=N), 147.5, 147.1, 141.0, 140.8, 139.2, 138.6, 129.1, 128.2, 128.2, 128.1, 128.0, 128.0, 122.6, 122.1, 113.2, 113.2 (aryl C), 41.2, 41.1 ($N(CH_3)_2$), 20.4, 14.0 (CH), 9.1, 8.2 ($CH_2$). IR (KBr, $cm^{-1}$): v 3079, 3031, 3003, 2924, 2885, 2853, 2800, 2363, 2345, 1623, 1575, 1560, 1508, 1487, 1457, 1442, 1412, 1384, 1346, 1241, 1219, 1168, 1156, 1128, 1057, 1038, 1024, 1004. HRMS (ESI): Calcd for $C_{18}H_{21}N_2^+$ $[M^+ H]^+$: 265.1699, found: 265.1722.

1k

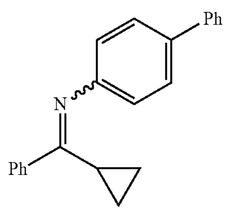

1k: Yield: 89%. Pale yellow solid. M.p.=65-67° C. $R_f$=0.4 (hexane/ethyl acetate=9:1). $^1$H NMR (400 MHz, $CDCl_3$, a mixture of geometrical isomers in ~1.6:1 ratio): δ 7.77 (dd, J=6.8, 3.1 Hz, 0.77H), 7.63 (dd, J=12.6, 7.8 Hz, 1.62H), 7.54-7.31 (m, 6.22H), 7.28-7.26 (m, 0.62H), 7.25-7.20 (m, 3H), 7.05 (d, J=8.0 Hz, 0.76H), 6.67 (d, J=8.3 Hz, 1.24H) (aryl CH), 2.07-2.01 (m, 0.62H), 1.94-1.89 (m, 0.38H) (CH), 1.23-1.19 (m, 1.25H), 1.06-1.01 (m, 1.27H), 0.89-0.79 (m, 0.77H), 0.66-0.64 (in, 0.75H) ($CH_2$). $^{13}$C NMR (101 MHz, $CDCl_3$): δ 173.2, 171.4 (C=N), 150.5, 150.3, 141.1, 140.9, 138.6, 138.0, 136.2, 135.4, 129.5, 128.9, 128.8, 128.6, 128.2, 128.2, 128.1, 128.1, 127.5, 127.2, 127.0, 126.9, 126.8, 126.7, 121.5, 120.8 (aryl C), 20.2, 14.3 (CH), 9.8, 8.0 ($CH_2$). IR (KBr, $cm^{-1}$): v 3082, 3056, 3027, 3003, 1629, 1601, 1576, 1514, 1483, 1446, 1383, 229, 1174, 1107, 1075, 1057, 1040, 1027, 1009. HRMS (ESI): Calcd for $C_{22}H_{20}N^+[M^+ H]^+$: 298.1590, found: 298.1608.

1l

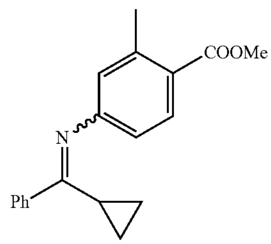

1l: Yield: 87%. Light yellow oil. $R_f$=0.3 (hexane/ethyl acetate=9:1). $^1$H NMR (500 MHz, $CDC_3$, a mixture of geometrical isomers in ~2:1 ratio): δ 8.00-7.91 (m, 0.33H), 7.79-7.69 (m, 1.32H), 7.42-7.11 (m, 4.36H), 6.79 (br, 0.69H), 6.59-6.29 (m, 1.33H) (aryl CH), 3.85-3.76 (m, 3H) ($COOCH_3$), 2.68-2.37 (m, 3H) ($CH_3$), 1.98 (br, 0.68H), 1.91-1.69 (m, 0.32H) (CH), 1.28-1.07 (m, 1.36H), 1.05-0.92 (m, 1.37H), 0.86-0.50 (m, 1.28H) ($CH_2$). $^{13}$C NMR (126 MHz, $CDCl_3$): δ 173.3, 170.8, 167.5 (C=N and COOMe), 154.6, 141.5, 137.9, 137.4, 131.7, 128.7, 128.0, 127.8, 123.7, 123.2, 122.7, 117.7, 117.1 (aryl C), 51.3 ($COOCH_3$), 21.9 ($CH_3$), 19.8, 14.3 (CH), 10.1, 7.8 ($CH_2$). IR (KBr, $cm^{-1}$): v 3379, 3088, 3056, 3028, 3004, 2949, 2928, 2840, 1717, 1635, 1596, 1559, 1491, 1435, 1383, 1261, 1189, 1139, 1101, 1080, 1040, 1028, 1008. HRMS (ESI): Calcd for $C_{19}H_{20}NO_2^+[M^+ H]^+$: 294.1489, found: 294.1492.

1m

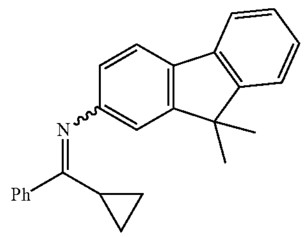

1m: Yield: 89%. Light yellow oil. $R_f$=0.4 (hexane/ethyl aceate=20:1). $^1$H NMR (400 MHz, $CDC_3$, a mixture of geometrical isomers in ~2:1 ratio): δ 7.87 (dd, J=6.6, 3.0 Hz, 0.66H), 7.75 (dd, J=7.8, 2.3 Hz, 0.65H), 7.66-7.59 (m, 0.68H), 7.55-7.44 (m, 2H), 7.41-7.20 (m, 6H), 7.12 (d, J=1.9 Hz, 0.34H), 7.01 (dd, J=7.9, 1.9 Hz, 0.34H), 6.75-6.60 (m, 1.31H) (aryl CH), 2.13-2.07 (m, 0.66H), 2.02-1.94 (m, 0.34H) (CH), 1.57 (s, 2H), 1.34 (s, 4H) ($CH_3$), 1.34-1.27 (m, 1.31H), 1.11-1.07 (m, 1.33H), 0.89-0.85 (m, 0.67H), 0.71-0.63 (m, 0.64H) ($CH_2$). $^{13}C$ NMR (101 MHz, $CDC_3$): δ 173.2, 170.7 (C=N), 154.7, 154.3, 153.5, 153.5, 150.6, 150.4, 139.4, 138.7, 138.1, 134.7, 134.0, 129.6, 128.4, 128.2, 128.2, 128.1, 127.9, 127.1, 126.9, 126.6, 126.4, 122.6, 122.5, 120.3, 120.3, 120.1, 119.5, 119.4, 119.3, 115.9, 115.1 (aryl C), 46.9, 46.6 ($C(CH_3)_2$), 27.3, 27.1 ($CH_3$), 20.1, 14.3 (CH), 9.8, 8.2 ($CH_2$). IR (KBr, $cm^{-1}$): v 3082, 3059, 3036, 3007, 2959, 2921, 2898, 2859, 1625, 1605, 1576, 1490, 1470, 1459, 1445, 1420, 1383, 1360, 1298, 1273, 1230, 1180, 1156, 1127, 1087, 1071, 1057, 1040, 1025, 1009. HRMS (ESI): Calcd for $C_{25}H_{24}N^+$ $[M^+ H]^+$: 338.1903, found: 338.1929.

1n

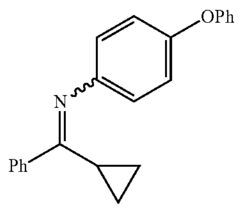

In: Yield: 88%. Light yellow oil. $R_f$=0.4 (hexane/ethyl acetate=9:1). $^1H$ NMR (400 MHz, $C_6D_6$, a mixture of geometrical isomers in ~2.3:1 ratio): δ 7.98-7.93 (m, 0.60H), 7.22-7.16 (m, 0.73H), 7.13-6.92 (m, 6.71H), 6.91-6.85 (m, 2.31H), 6.84-6.79 (m, 0.73H), 6.73 (d, J=8.7 Hz, 1.41H), 6.58 (d, J=8.7 Hz, 1.40H) (aryl CI—), 1.81-1.75 (m, 0.70H), 1.56-1.49 (m, 0.30H) (CH), 1.35-1.29 (m, 1.39H), 0.77-0.73 (m, 1.40H), 0.48-0.39 (m, 0.61H), 0.37-0.28 (m, 0.59H) ($CH_2$). $^{13}C$ NMR (101 MHz, $C_6D_6$): δ 172.5, 168.7 (C=N), 158.7, 158.6, 153.4, 152.8, 147.5, 147.4, 139.4, 138.8, 130.1, 129.9, 129.8, 128.6, 128.5, 128.4, 128.3, 128.2, 123.0, 122.8, 122.7, 122.1, 120.0, 119.9, 118.6, 118.5 (aryl C), 20.3, 13.8 (CH), 10.3, 8.3 ($CH_2$). IR (KBr, $cm^{-1}$): v 3084, 3060, 3037, 3008, 1669, 1629, 1588, 1488, 1445, 1414, 1384, 1333, 1231, 1164, 1097, 1073, 1058, 1040, 1026, 1012. HRMS (ESI): Calcd for $C_{22}H_{20}NO^+$ $[M^+ H]^+$: 314.1539, found: 314.1549.

1o

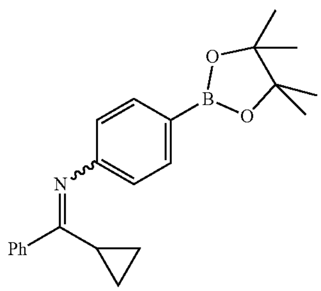

10: Yield: 85%. Pale yellow solid. M.p.=119-121° C. $R_f$ 0.35 (hexane/ethyl acetate=9:1). $^1H$ NMR (500 MHz, $CDCl_3$, a mixture of geometrical isomers in ~1.7:1 ratio): δ 7.93-7.62 (m, 1.48H), 7.62-7.28 (m, 2.46H), 7.24-7.08 (m, 3H), 6.95 (d, J=7.7 Hz, 0.74H), 6.59 (d, J=7.7 Hz, 1.26H) (aryl CH), 2.04-1.98 (m, 0.63H), 1.85-1.75 (m, 0.37H) (CH), 1.36-1.30 (m, 12H) ($CH_3$), 1.21-1.12 (m, 1.3H), 1.02-1.00 m, 1.3H), 0.79-0.77 (m, 0.74H), 0.61-0.59 (m, 0.73H) ($CH_2$). $^{13}C$ NMR (101 MHz, $CDCl_3$) δ 172.8, 170.9 (C=N), 154.0, 138.3, 137.7, 135.6, 135.3, 129.5, 128.5, 128.5, 128.1, 128.0, 20.2, 119.4 (aryl C), 83.5 ($CMe_2$), 25.0 ($CH_3$), 20.0, 14.3 (CH), 9.8, 7.8 ($CH_2$). IR (KBr, $cm^{-1}$): v 3030, 2995, 2978, 2931, 1639, 1599, 1445, 1396, 1384, 1358, 1317, 1265, 1235, 1143, 1099, 1086, 1041, 1027, 1016, 1008. HRMS (ESI): Calcd for $C_{22}H_{27}BNO_2^+[M^+ H]^+$: 348.2129, found: 348.2151.

1t

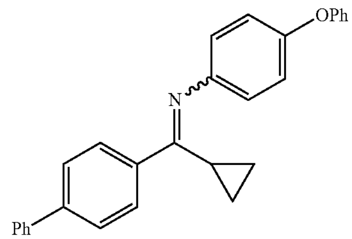

it: Yield: 86%. Light yellow oil. $R_f$=0.4 (hexane/ethyl acetate=9:1). $^1H$ NMR (400 MHz, $C_6D_6$, a mixture of geometrical isomers in ~2:1 ratio): δ 8.09 (d, J=8.4 Hz, 0.65H), 7.58-7.45 (m, 1.36H), 7.35-7.30 (m, 1.36H), 7.28-7.20 (m, 2H), 7.19-7.14 (m, 3.36H), 7.13-6.96 (m, 4H), 6.93-6.87 (m, 2H), 6.83-6.72 (m, 2H), 6.68-6.60 (m, 1.3H) (aryl CH), 1.86-1.79 (m, 0.67H), 1.56-1.49 (m, 0.33H) (CH), 1.42-1.38 (m, 1.31H), 0.81-0.76 (m, 1.36H), 0.49-0.42 (m, 0.64H), 0.40-0.33 (m, 0.62H) ($CH_2$). $^{13}C$ NMR (101 MHz, $C_6D_6$): δ 172.0, 168.0 (C=N), 158.7, 158.5, 153.5, 153.0, 147.6, 147.4, 142.9, 141.6, 141.0, 140.6, 138.5, 137.5, 130.1, 129.9, 129.2, 129.1, 129.1, 127.5, 127.4, 127.0, 127.0, 123.0, 122.9, 122.7, 122.2, 120.1, 120.0, 118.7, 118.6 (aryl C), 20.3, 13.7 (CH), 10.5, 8.5 ($CH_2$). IR (KBr, $cm^{-1}$): v 3062, 3032, 3009, 1624, 1603, 1589, 1559, 1487, 1448, 1404, 1384, 1332, 1234, 1163, 1097, 1074, 1035, 1006. HRMS (ESI): Calcd for $C_{28}H_{24}NO^+$ $[M^+ H]^+$: 390.1852, found: 390.1857.

1u

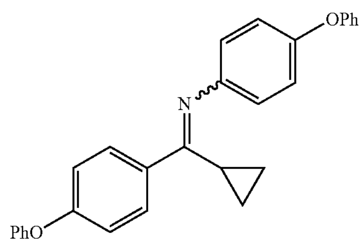

1u: Yield: 84%. Light yellow oil. $R_f$=0.4 (hexane/ethyl acetate=9:1). $^1H$ NMR (400 MHz, $C_6D_6$, a mixture of geometrical isomers in ~1.8:1 ratio): δ 8.00 (d, J=8.8 Hz, 0.73H), 7.11-6.97 (m, 8H), 6.93-6.77 (m, 6.73H), 6.74-6.69 (m, 1.28H), 6.59 (d, J=8.7 Hz, 1.29H) (aryl CH), 1.79-1.73 (m, 0.64H), 1.49-1.42 (m, 0.36H) (CH), 1.37-1.34 (m, 1.28H), 0.80-0.70 (m, 1.27H), 0.47-0.40 (m, 0.71H), 0.34-0.30 (, 0.73H) ($CH_2$). $^{13}C$ NMR (101 MHz, $C_6D_6$): δ 171.5, 167.1 (C=N), 159.5, 158.7, 158.7, 158.2, 157.2, 156.7, 153.3, 152.8, 147.7, 147.3, 134.5, 133.1, 130.4, 130.3, 130.2, 130.2, 130.1, 129.9, 124.1, 124.0, 123.0, 122.8, 122.6, 122.2, 120.1, 120.0, 119.9, 119.8, 118.6, 118.5, 118.1, 117.8 (aryl C), 20.2, 13.6 (CH), 10.4, 8.5 ($CH_2$). IR (KBr, $cm^{-1}$): v 3068, 3038, 3009, 1624, 1588, 1488, 1384, 1236, 1165, 1098, 1035, 1021. HRMS (ESI): Calcd for $C_{28}H_{24}NO_2^+[M^+ H]$: 406.1802, found: 406.1812.

1v

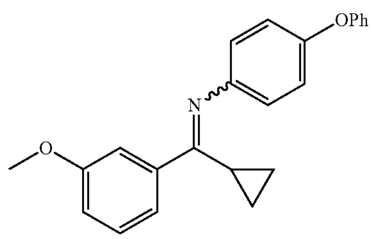

iv: Yield: 82%. Light yellow oil. $R_f$=0.3 (hexane/ethyl acetate=9:1). $^1$H NMR (500 MHz, $CDCl_3$, a mixture of geometrical isomers in ~1.9:1 ratio): δ 7.40-7.30 (m, 1.71H), 7.26 (t, J=7.8 Hz, 1.29H), 7.17 (t, J=7.9 Hz, 0.67H), 7.10-6.95 (m, 3.37H), 6.89 (d, J=8.1 Hz, 1.3H), 6.82-6.78 (m, 2.63H), 6.70 (s, 0.63H), 6.60 (d, J=8.4 Hz, 1.32H) (aryl CH), 3.85 (s, 1.04H), 3.67 (s, 1.98H) ($OCH_3$), 2.05-1.99 (m, 0.66H), 1.94-1.76 (m, 0.34H) (CH), 1.23-1.19 (m, 1.32H), 1.03-0.99 (m, 1.33H), 0.87-0.82 (m, 0.69H), 0.64-0.61 (m, 0.69H) ($CH_2$). $^{13}$C NMR (126 MHz, $CDC_3$): δ 173.1, 170.8 (C=N), 159., 159.1, 158.2, 158.0, 152.8, 152.1, 147.1, 140.0, 139.2, 129.7, 129.6, 129.1, 129.1, 122.8, 122.5, 122.2, 121.6, 120.6, 120.5, 119.9, 119.8, 118.2, 117.8, 115.5, 114.2, 113.8, 113.1 (aryl C), 55.3, 55.1 ($OCH_3$), 20.0, 14.0 (CH), 9.8, 8.2 ($CH_2$). IR (KBr, $cm^{-1}$): v 3066, 3037, 3005, 2958, 2938, 2910, 2834, 1625, 1587, 1487, 1428, 1384, 1320, 1288, 1266, 1237, 1164, 1097, 1073, 1034. HRMS (ESI): Calcd for $C_{23}H_{22}NO_2^+$[$M^+$ H]$^+$: 344.1645, found: 344.1665.

1w

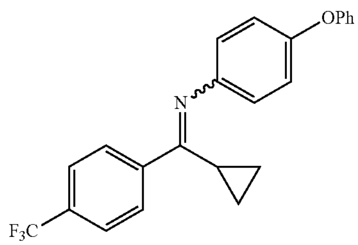

1w: Yield: 89%. Pale yellow solid. M.p.=96-98° C. $R_f$=0.4 (hexane/ethyl acetate=9:1). $^1$H NMR (400 MHz, $CDC_3$, a mixture of geometrical iso ers in ~1.5:1 ratio): δ 8.00 (d, J=8.1 Hz, 0.81H), 7.73 (d, J=8.2 Hz, 0.81H), 7.56 (d, J=8.1 Hz, 1.18H), 7.42-7.27 (m, 3.18H), 7.15-7.03 (m, 3.41H), 6.99-6.89 (m, 1.19H), 6.85 (d, J=8.8 Hz, 1.19H), 6.62 (d, J=8.7 Hz, 1.19H) (aryl CH), 2.07-1.92 (m, 1H) (CH), 1.34-1.25 (m, 1.19H), 1.11-1.06 (m, 1.19H), 0.95-0.89 (m, 0.82H), 0.66-0.58 (m, 0.80H) ($CH_2$). $^{13}$C NMR (101 MHz, $CDCl_3$): δ 172.0, 169.1 (C=N), 157.9, 157.9, 153.3, 152.6, 146.4, 145.9, 142.1, 141.7, 131.2 (q, $^2J_{C-CF3}$=35.2 Hz), 130.3 (q, $^2J_{C-CF3}$=36.3 Hz), 129.7, 129.6, 128.4, 128.3, 125.0 (q, $^3J_{C-CF3}$=3.3 Hz), 125.0 (q, $^3J_{C-CF3}$=3.3 Hz) (aryl C), 124.1 (q, $^1J_{C-CF3}$=273.7 Hz), 123.9 (q, $^1J_{C-CF3}$=272.7 Hz) ($CF_3$), 122.9, 122.7, 122.2, 121.7, 119.7, 119.6, 118.3, 117.9 (aryl C), 20.0, 13.7 (CH), 10.0, 8.1 ($CH_2$). $^{19}$F NMR (377 MHz, $C_6D_6$): δ −62.6 (m, 3F) ($CF_3$). IR (KBr, $cm^{-1}$): v 3068, 3040, 3011, 2959, 2932, 2872, 1676, 1627, 1589, 1508, 1488, 1457, 1410, 1383, 1325, 1237, 1167, 1128, 1067, 1036, 1021, 1012. HRMS (ESI): Calcd for $C_{23}H_{19}$F3NO$^+$ [$M^+$ H]$^+$: 382.1413, found: 382.1427.

1x

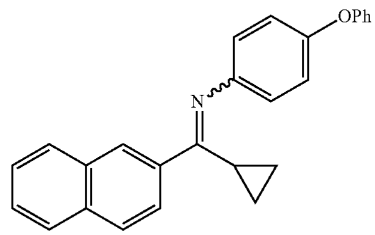

1x: Yield: 80%. Light yellow oil. $R_f$=0.4 (hexane/ethyl acetate=9:1). $^1$H NMR (400 MHz, $CDCl_3$, a mixture of geometrical isomers in ~1.7:1 ratio): δ 8.37 (s, 0.36H), 8.04-7.90 (m, 1.48H), 7.83-7.80 (m, 1.88H), 7.72 (d, J=8.5 Hz, 0.62H), 7.60-7.48 (m, 2H), 7.41-7.37 (m, 0.74H), 7.29-7.25 (m, 2H), 7.18-6.96 (m, 3.26H), 6. 2-6.85 (m, 1.26H), 6.81 (d, J=8.7 Hz, 1.26H), 6.67 (d, J=8.7 Hz, 1.25H) (aryl CH), 2.20-2.13 (m, 0.63H), 2.08-2.01 (m, 0.37H) (CH), 1.34-1.30 (m, 1.25H), 1.14-1.09 (m, 1.26H), 0.99-0.92 (m, 0.74H), 0.73-0.64 (m, 0.73H) ($CH_2$). $^{13}$C NMR (101 MHz, $CDCl_3$): δ 173.3, 170.5 (C=N), 158.3, 158.2, 153.0, 152.2, 147.1, 146.7, 136.2, 135.6, 134.0, 133.0, 132.9, 132.8, 129.8, 129.6, 128.8, 128.4, 128.2, 128.0, 127.8, 127.8, 127.6, 127.0, 126.9, 126.5, 126.4, 125.7, 125.3, 122.9, 122.5, 122.5, 121.8, 120.0, 119.9, 118.3, 117.8 (aryl C), 20.3, 14.1 (CH), 10.0, 8.4 ($CH_2$). IR (KBr, $cm^{-1}$): v 3038, 3009, 2926, 2852, 1666, 1623, 1588, 1488, 1414, 1384, 1333, 1274, 1239, 1181, 1164, 1128, 1098, 1072, 1058, 1034, 1023, 1013. HRMS (ESI): Calcd for $C_{26}H_{22}NO^+$ [$M^+$ H]$^+$: 364.1696, found: 364.1706.

1y

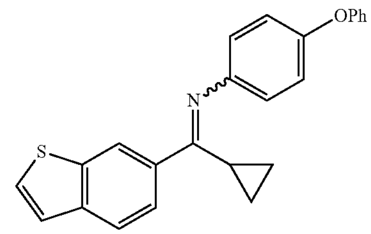

1z

1y: Yield: 81%. Light yellow oil. $R_f$=0.35 (hexane/ethyl acetate=9:1). $^1$H NMR (400 MHz, $CDCl_3$, a mixture of geometrical isomers in ~1.6:1 ratio): δ 8.36 (s, 0.36H), 7.97-7.88 (m, 0.75H), 7.80-7.70 (m, 1.23H), 7.51-7.25 (m, 4H), 7.21-7.00 (m, 4H), 6.94-6.87 (m, 1.22H), 6.86-6.79 (m, 1.24H), 6.70-6.62 (m, 1.24H) (aryl CH), 2.15-2.09 (m, 0.62H), 2.04-1.97 (m, 0.38H) (CH), 1.34-1.27 (m, 1.24H), 1.12-1.05 (m, 1.24H), 0.96-0.88 (m, 0.77H), 0.76-0.57 (m, 0.78H) ($CH_2$). $^{13}$C NMR (101 MHz, $CDCl_3$): δ 173.2, 170.5 (C=N), 158.2, 158.1, 152.8, 152.1, 147.1, 146.7, 141.0, 139.8, 139.4, 139.1, 135.1, 134.1, 129.7, 129.6, 127.3, 127.2, 124.3, 124.2, 124.0, 124.0, 123.5, 123.5, 122.8, 122.5, 122.4, 122.1, 122.0, 121.7, 119.9, 119.8, 118.2, 117.8 (aryl C), 20.4, 14.1 (CEF), 9.9, 8.3 ($CH_2$). IR (KBr, $cm^{-1}$): v 3067, 3037, 3007, 1624, 1588, 1544, 1487, 1457, 1436, 1421, 1383, 1359, 1324, 1276, 1235, 1195, 1164, 1095, 1072, 1053, 1033, 1015. HRMS (ESI): Calcd for $C_{24}H_{20}NOS^+$ [$M^+$ H]$^+$: 370.1260, found: 370.1271.

1z

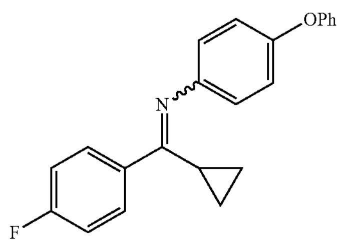

1z: Yield: 86%. Light yellow oil. $R_f$=0.4 (hexane/ethyl acetate=9:1). $^1H$ NMR (400 MHz, $CDCl_3$, a mixture of geometrical isomers in ~1.5:1 ratio): δ 7.71 (dd, J=8.7, 5.6 Hz, 0.8H), 7.18-7.07 (m, 2H), 7.05-6.97 (m, 1.2H), 6.94-6.72 (m, 6.6H), 6.67-6.61 (m, 1.2H), 6.45-6.35 (m, 1.2H) (aryl CH), 1.83-1.77 (m, 0.6H), 1.74-1.66 (m, 0.4H) (CH), 1.09-1.02 (m, 1.2H), 0.86-0.82 (m, 1.2H), 0.70-0.64 (m, 0.8H), 0.42-0.34 (m, 0.8H) ($CH_2$). $^{13}C$ NMR (101 MHz, $CDC_3$): δ 172.0, 168.9 (C=N), 163.7 (d, $^{1}J_{C-F}$=249.5 Hz), 162.3 (d, $^1J_{C-F}$=249.0 Hz), 158.0, 158.0, 152.9, 152.2, 146.8, 146.3, 134.9 (d, $^4J_{C-F}$=3.2 Hz), 133.9 (d, $^4J_{C-F}$=3.5 Hz), 130.1 (d, $^3J_{C-F}$=8.2 Hz), 130.0 (d, $^3J_{C-F}$=8.4 Hz), 129.7, 129.6, 122.8, 122.6, 122.2, 121.6, 119.7, 119.7, 118.1, 117.9, 115.0 (d, $^2J_{C-F}$=21.5 Hz), 115.0 (d, $^2J_{C-F}$=21.6 Hz) (aryl C), 20.0, 13.7 (CH), 9.8, 8.2 ($CH_2$). $^1F$ NMR (377 MHz, $CDCl_3$): δ −111.08, −111.47 (m, 1F). IR (KBr, $cm^{-1}$): v 3068, 3039, 3010, 1670, 1625, 1601, 1589, 1507, 1488, 1410, 1383, 1334, 1291, 1230, 1157, 1098, 1073, 1035, 1011. HRMS (ESI): Calcd for $C_{22}H_{19}FNO^+[M^+\ H]^+$: 332.1445, found: 332.1480.

1aa

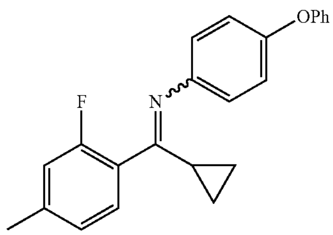

1aa: Yield: 79%. Light yellow oil. $R_f$=0.4 (hexane/ethyl ac tate=9:1). $^1H$ NMR (400 MHz, $CDC_3$, a mixture of geometrical isomers in ~5:1 ratio): δ 7.31 (dd, J=8.8, 7.1 Hz, 0.35H), 7.25-7.20 (m, 1.67H), 7.08-6.96 (m, 2.18H), 6.94-6.84 (m 2.68H), 6.83-6.72 (m, 3.36H), 6.70-6.64 (m, 1.66H) (aryl CH), 2.34 (s, 0.5H), 2.23 (s, 2.5H) i$CH_3$), 2.07-1.95 (m, 1H) (CH), 1.16-1.13 (m, 1.65H), 1.00-0.95 (m, 1.65H), 0.84-0.74 (n, 0.34H), 0.74-0.62 (m, 0.33H) ($CH_2$). $^{13}C$ NMR (101 MHz, $CDCl_3$): δ 171.0, 169.6 (d, $^4J_{C-F}$==2.6 Hz) (C=N), 159.4 (d, $^1J_{C-F}$=247.0 Hz), 158.1 (d, $^1J_{C-F}$=246.6 Hz), 157.8, 157.7, 152.9, 152.3, 146.8, 146.1, 141.0 (d, $^3J_{C-F}$=7.9 Hz), 140.8 (d, $^3J_{C-F}$=7.7 Hz), 129.8 (d, $^4J_{C-F}$=4.1 Hz), 129.5, 129.4, 129.0 (d, $^4J_{C-F}$=5.0 Hz), 124.5 (d, $^4J_{C-F}$=2.9 Hz), 124.4 (d, $^4J_{C-F}$=2.9 Hz), 122.7, 122.6 (d, $^2J_{C-F}$=16.5 Hz), 122.4, 122.3 (d, $^2J_{C-F}$=18.7 Hz), 121.4, 120.3, 119.6, 119.2, 118.1, 117.8, 116.0 (d, $^2J_{C-F}$=21.5 Hz), 115.9 (d, $^2J_{C-F}$=21.6 Hz) (aryl C), 20.9 (d, $^4J_{C-F}$=1.5 Hz), 20.9 (d, $^4J_{C-F}$=1.6 Hz) ($CH_3$), 20.4, 15.2 (CH), 8.9, 7.2 ($CH_2$). $^{19}F$ NMR (377 MHz, $CDCl_3$): δ −112.73, −115.62 (m, 1F). IR (KBr, $cm^{-1}$): v 3090, 3060, 3038, 3010, 2923, 1626, 1589, 1488, 1456, 1414, 1383, 1333, 1290, 1277, 1239, 1164, 1153, 1124, 1097, 1073, 1056, 1033, 1013. HRMS (ESI): Calcd for $C_{23}H_{21}FNO^+[M^+\ H]^+$: 346.1602, found: 346.1602.

1ab

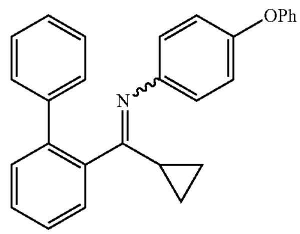

lab: Yield: 69%. Light yellow oil. $R_f$=0.4 (hexane/ethyl acetate=9:1). $^1H$ NMR (400 MHz, $CDCl_3$, a mixture of geometrical isomers in ~3.3:1 ratio): δ 7.66 (d, J=7.4 Hz, 0.48H), 7.50-7.29 (m, 9H), 7.26-7.22 (m, 1.46H), 7.16-7.01 (m, 2H), 7.00-6.94 (m, 2H), 6.75-6.57 (m, 1.55H), 6.17 (d, J=8.5 Hz, 1.54H) (aryl CH), 2.02-1.96 (m, 0.77H), 1.65-1.57 (m, 0.23H) (CH), 1.29 (br, 1.54H), 1.12-0.94 (m, 1.54H), 0.610.40 (m, 0.93H) ($CH_2$).

$^{13}C$ NMR (101 MHz, $CDCl_3$): δ 176.0, 173.4 (C=N), 158.3, 158.0, 152.9, 152.0, 146.6, 145.8, 141.2, 140.6, 140.3, 139.5, 138.1, 136.4, 130.1, 129.9, 129.7, 129.7, 129.6, 128.9, 128.8, 128.8, 128.8, 128.7, 128.2, 128.1, 127.3, 127.3, 127.0, 127.0, 122.9, 122.5, 122.5, 121.2, 119.9, 119.3, 118.4, 117.8 (aryl C), 21.0, 15.5, 7.6 (CH and $CH_2$). IR (KBr, $cm^{-1}$): v 3086, 3059, 3037, 3022, 3007, 1672, 1630, 1588, 1488, 1450, 1435, 1414, 1379, 1241, 1220, 1163, 1098, 1074, 1057, 1032, 1007. HRMS (ESI): Calcd for $C_{28}H_{24}NO^+\ [M^+\ H]^+$: 390.1852, found: 390.1865.

1ac

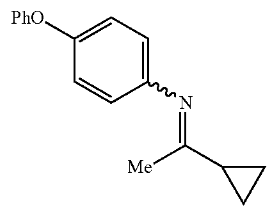

lac: Yield: 91%. Light yellow oil. $R_f$=0.25 (hexane/ethyl acetate=9:1). $^1H$ NMR (500 MHz, $C_6D_6$, a mixture of geometrical isomers in ~4.6:1 ratio): δ 7.12-7.04 (m, 2H), 7.04-6.94 (m, 2.35H), 6.94-6.90 (m, 1.64H), 6.88-6.80 (m, 1.37H), 6.58-6.52 (m, 1.64H) (aryl CH), 1.55 (s, 0.54H) ($CH_3$), 1.54-1.51 (m, 2.65H) (CH and $CH_3$), 1.46-1.40 (m, 0.82H) (CH), 1.04-1.00 (m, 1.66H), 0.61-0.57 (m, 1.67H), 0.46-0.43 (m, 0.37H), 0.30-0.20 (m, 0.36H) ($CH_2$). $^{13}C$ NMR (126 MHz, $C_6D_6$): δ 171.7, 171.2 (=N), 158.8, 152.9, 152.8, 148.2, 148.1, 130.0, 130.0, 122.9, 122.8, 121.6, 121.3, 120.4, 120.4, 118.5, 118.4 (aryl C), 20.3, 19.9, 19.1, 15.1 (CH and $CH_3$), 8.8, 6.6 ($CH_2$). IR (KBr, $cm^{-1}$), v 3090, 3064, 3037, 3008, 2963, 2918, 1653, 1589, 1488, 1456, 1414, 1385, 1333, 1235, 1200, 1176, 1096, 1072, 1024. HRMS (ESI): Calcd for $C_{17}H_{18}NO^+\ [M^+\ H]^+$: 252.1383, found: 252.1401.

1ad

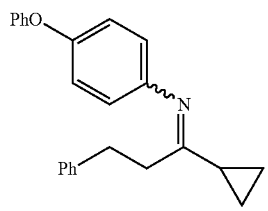

1ad: Prepared starting from 1-cyclopropyl-3-phenylpropan-1-one. Yield: 88%. Light yellow oil. $R_f$=0.4 (hexane/ethyl acetate=9:1). $^1$H NMR (400 MHz, $C_6D_6$, a mixture of geometrical isomers in ~1.8:1 ratio): δ 7.14-6.95 (m, 8.73H), 6.89-6.78 (m, 4H), 6.36-6.27 (m, 1.28H) (aryl CH), 3.12-2.97 (m, 0.71H), 2.61 (t, J=7.8 Hz, 0.29H), 2.38-2.29 (m, 1.29H), 1.97 (dd, J=8.3, 7.1 Hz, 0.72H) ($CH_2$), 1.52-1.46 (m, 0.36), 1.36-1.30 (m, 0.64H) (CH), 1.18-1.14 (m, 1.29H), 0.64-0.59 (m, 1.28H), 0.38-0.34 (m, 0.72H), 0.18-0.12 (m, 0.72H) ($CH_2$). $^{13}$C NMR (101 MHz, $C_6D_6$): δ 174.4, 172.6 (C=N), 159.0, 158.9, 152.9, 152.6, 148.2, 147.8, 142.6, 141.1, 130.0, 123.0, 129.0, 128.8, 128.7, 128.7, 126.5, 126.2, 122.9, 122.8, 121.5, 121.0, 120.5, 120.4, 118.5, 118.3 (aryl C), 36.6, 33.9, 33.6, 32.6 ($CH_2$), 17.4, 14.9 (CH), 10.0, 6.3 ($CH_2$). IR (KBr, $cm^{-1}$): v 3086, 3062, 3027, 3003, 1961, 2927, 2861, 1879, 1700, 1647, 1588, 1488, 1454, 1414, 1385, 1333, 1234, 1198, 1164, 123, 1096, 1085, 1070, 1024, 1011. HRMS (ESI): Calcd for $C_{24}H_{24}NO^+$ [$M^+$ H]$^+$: 342.1852, found: 342.1870.

1ae

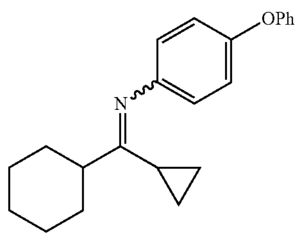

1ae

1ae: Prepared starting from cyclohexyl(cyclopropyl) methanon e. Yield: 86%. Light yellow oil. $R_f$=0.5 (hexane/ethyl acetate=9:1). $^1$H NMR (500 MHz, $CDCl_3$, a mixture of geometrical isomers in ~1.4:1 ratio): δ 7.32-7.26 (m, 2H), 7.14-6.86 (m, 5H), 6.76 (d, J=8.3 Hz, 0.84H), 6.56 (d, J=8.4 Hz, 1.18H) (aryl CH), 2.58-2.52 (m, 0.58H), 1.81-1.54 (m, 9.38H), 1.22-1.09 (m, 2H), 0.99-0.96 (m, 1.19H), 0.82-0.78 (m, 2.1H), 0.76-0.74 (m, 0.84H) (CH and $CH_2$). $^{13}$C NMR (101 MHz, $CDCl_3$): δ 179.5, 178.6 (C=), 158.4, 158.3, 152.1, 151.9, 147.6, 147.3, 129.6, 122.5, 122.5, 121.2, 120.6, 120.1, 120.1, 117.9, 117.9 (aryl C), 43.1, 39.2, 31.7, 30.1, 26.4, 26.0, 25.9, 25.6, 13.8, 13.4, 9.3, 6.5 (CH and $CH_2$). IR (KBr, $cm^{-1}$): v 3064, 3037, 3006, 2928, 2853, 1695, 1637, 1607, 1589, 1488, 1449, 1414, 1385, 1352, 1332, 1237, 1201, 1179, 1164, 1124, 1096, 1073, 1055, 1024, 1011. HRMS (ESI): Calcd for $C_{22}H_{25}BNNaO^+$[$M^+$ Na]$^+$: 342.1828, found: 342.1852.

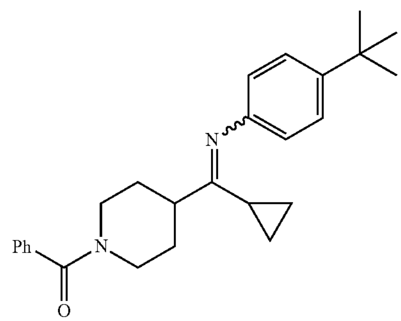 [SMILES: CC(C)(C)c1ccc(N=C(C2CC2)C2CCN(C(=O)c3ccccc3)CC2)cc1]

1af

1af: Yield: 73%. Pale yellow solid. M.p.=161-163° C. $R_f$=0.1 (hexane/ethyl acetate=3:1). $^1$H NMR (500 MHz, $C_6D_6$, a mixture of geometrical isomers in ~1.3:1 ratio): 6 7.40-7.33 (m, 2.87H), 7.28 (d, J=8.3 Hz, 1.12H), 7.13-7.02 (m, 3H), 6.89 (d, J=8.1 Hz, 0.88H), 6.62 (d, J=8.1 Hz, 1.22H) (aryl CH), 4.82 (br, 1H), 3.64 (br, 11H) ($NCH_2$), 2.77-2.69 (m, 0.55H), 2.53-2.47 (m, 0.90H), 2.06-1.98 (m, 1.12H), 1.93-1.85 (m, 0.88H), 1.55-1.47 (m, 1.57H), 1.37-1.10 (m, 13.12H), 0.61-0.59 (m, 1.11H), 0.43-0.31 (m, 0.88H), 0.26-0.19 (m, 0.87H) (CH and $CH_2$). $^{13}$C NMR (126 MHz, $C_6D_6$): δ 175.8, 175.1 (C=N), 169.8, 169.5, 149.6, 149.1, 145.5, 145.4, 137.4, 137.1, 129.6, 129.3, 128.5, 127.7, 127.6, 126.2, 126.1, 119.8, 119.4 (aryl C), 41.0, 37.8, 34.3, 31.7, 31.7, 31.2, 14.0, 13.7, 9.8, 6.4 (CH and $CH_2$). IR (KBr, $cm^{-1}$): v 3088, 3056, 3030, 3001, 2960, 2902, 2863, 1636, 1603, 1578, 1503, 1433, 1384, 1372, 1310, 1278, 1252, 1209, 1179, 1146, 1134, 1092, 1026. HRMS (ESI): Calcd for $C_{26}H_{33}N_2O^+$ [$M^+$ H]$^+$: 389.2587, found: 389.2610.

1ag

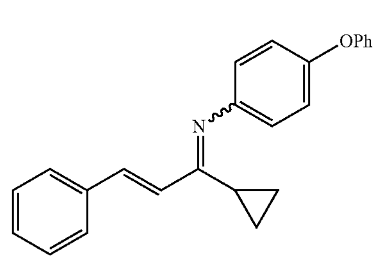

1ag: Prepared starting from (E)-1-cyclopropyl-3-phenylprop-2-en-1-one. Yield: 82%. Light yellow oil. $R_f$=0.4 (hexane/ethyl acetate=9:1). $^1$H NMR (500 MHz, $C_6D_6$, a mixture of geometrical isomers in ~1.3:1 ratio): δ 7.57 (d, J=16.1 Hz, 0.35H), 7.24-7.13 (m, 3H), 7.13-6.80 (m, 9H), 6.77-6.66 (m, 1.64H) (alkenyl CH and aryl CH), 1.92-1.87 (m, 0.66H), 1.82-1.77 (m, 0.34H) (CH), 1.35-1.32 (m, 1.33H), 1.21-1.18 (m, 0.66H), 0.78-0.75 (m, 1.32H), 0.61-0.57 (m, 0.66H) ($CH_2$). $^{13}$C NMR (126 MHz, $C_6D_6$): δ 198.4 (C=N), 167.7, 158.4, 153.5, 147.2, 141.5, 137.8, 136.4, 135.2, 130.2, 130.0, 19.3, 129.1, 129.0, 128.5, 127.7, 127.0, 123.0, 122.8, 122.4, 120.0, 118.8 (alkenyl C and aryl C), 19.7, 15.0 (CH), 11.1, 9.3 ($CH_2$). IR (KBr, $cm^{-1}$): v 3086, 3064, 3038, 3008, 1679, 1647, 1625, 1589, 1488, 1449, 1385, 1333, 1275, 1238, 1207, 1180, 1164, 1087, 1024. HRMS (ESI): Calcd for $C_{24}H_{21}NO^+$ [M]$^+$: 339.1618, found: 339.1618.

1ak

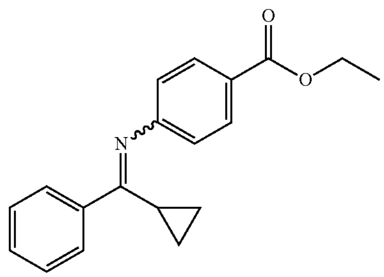

1ak: Yield: 81%. Light yellow oil. $R_f$=0.3 (hexane/ethyl acetate=9:1). $^1$H NMR (500 MHz, $C_6D_6$, a mixture of geometrical isomers in ~3:1 ratio): δ 8 17 (br, 0.5H), 8.00-7.81 (m, 2H), 7.22-6.84 (m, 5H), 6.58 (br, 1.5H) (aryl CH), 4.19-4.04 (m, 2H) ($OCH_2$), 1.77 (br, 0.75H), 1.63-1.42 (m, 0.25H) (CH), 1.24 (br, 1.51H) ($CH_2$), 1.10-0.97 (m, 3H) ($CH_3$), 0.77 (br, 1.51H), 0.42-0.30 (m, 1H) ($CH_2$). $^{13}$C NMR (126 MHz $C_6D_6$): δ 173.32, 169.12 (C=N), 166.1, 156.2, 138.0, 130.8, 129.0, 128.3, 128.3, 125.3, 120.8, 120.1, 120.1 (aryl C), 60.5 ($OCH_2$), 20.1, 14.4, 10.8, 8.2 (CH, $CH_2$ and $CH_2$). IR (KBr, $cm^{-1}$): v3406, 3082, 3057, 2981, 2936, 2904, 2872, 1721, 1708, 1636, 1598, 1577, 1500, 1477, 1446, 1412, 1384, 1367, 1305, 1269, 1167, 1099, 1058, 1040, 1016. HRMS (ESI): Calcd for $C_{19}NO_2$+[M]$^+$: 293.1410, found: 293.1412.

1al

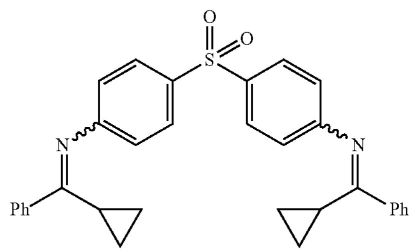

1al: Yield: 62%. Pale yellow solid. M.p.=157-159° C. $R_f$=0.3 (hexane/ethyl acetate=3:1). $^1$H NMR (500 MHz, $CDC_3$, a mixture of geometrical isomers in ~2.4:1 ratio): δ 8.27-6.28 (m, 18H) (aryl CH), 2.15-1.64 (m, 2H) (CH), 1.42-0.35 (m, 8H) ($CH_2$). $^{13}$C NMR (126 MHz, $CDCl_3$): δ 174.7 (C=N), 155.7, 137.0, 135.5, 129.2, 128.4, 128.2, 128.0, 121.1 (aryl C), 20.0, 14.6 (CH), 10.6, 8.1 ($CH_2$). IR (KBr, $cm^{-1}$): v 3428, 3005, 2924, 1646, 1631, 1583, 1483, 1444, 1384, 1316, 1284, 1227, 1155, 1106, 1086, 1038, 1026, 1004. HRMS (ESI): Calcd for $C_{32}H_{29}N_2O_2S^+$[$M^+$ H]$^+$: 505.1944, found: 505.1948.

1am

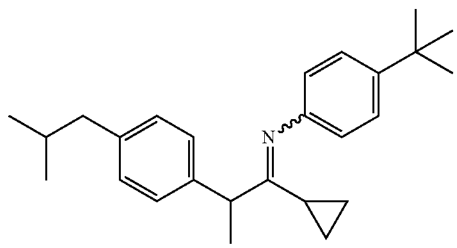

1am: Yield: 72%. Light yellow oil. $R_f$=0.6 (hexane/ethyl acetate=9:1). $^1$H NMR (400 MHz, $C_6D_6$, a mixture of geometrical isomers in ~2.7:1 ratio): δ 7.36 (t, J=8.0 Hz, 1.26H), 7.28 (d, J=8.4 Hz, 1.47H), 7.17 (d, J=5.7 Hz, 1.28H), 7.08-7.02 (m, 2H), 6.97 (d, J=8.4 Hz, 0.54H), 6.82 (d, J=8.4 Hz, 1.47H) (aryl CH), 4.23 (q, J=7.1 Hz, 0.73H), 3.16 (q, J=6.8 Hz, 0.27H) (CH), 2.39-2.36 (m, 2H) ($CH_2$), 1.84-1.74 (m, 1H) (CH), 1.62-1.56 (m, 1.09H) ($CH_3$ and CH), 1.41-1.37 (m, 0.74H) (CH), 1.33 (d, J=7.1 Hz, 2.18H) ($CH_3$), 1.30-1.26 (m, 9H) ($^t$Bu), 1.14-1.09 (m, 0.73H), 0.88-0.85 (m, 6.55H), 0.6-0.58 (m, 1.47H), 0.46-0.40 (m, 0.74H), 0.27-0.22 (m, 0.25H), 0.13-0.08 (m, 0.25H) ($C_3$ and $CH_2$). $^{13}$C NMR (101 MHz, $C_6D_6$): δ 176.7, 174.5 (C=N), 150.0, 149.6, 145.3, 145.2, 139.9, 139.9, 139.3, 129.7, 129.5, 127.7, 126.2, 126.0, 119.9, 119.6 (aryl C), 45.4, 45.3, 420, 41.6, 34.4, 34.3, 31.8, 31.7, 30.5, 30.5, 22.7, 22.6, 22.6, 22.6, 17.1, 15.2, 14.3, 11.3, 93, 6.9, 6.9 (alkyl C). IR (KBr, $cm^{-1}$): v 3086, 3052, 3030, 3005, 2962, 2932, 2908, 2868, 1647, 1605, 1506, 1460, 1415, 1385, 1364, 1268, 1233, 1202, 1167, 1113, 1085, 1056, 1037, 1023. HRMS (ESI) Calcd for $C_{26}H_{36}N^+$[$M^+$ H]$^+$: 362.2842, found: 362.2845.

1an

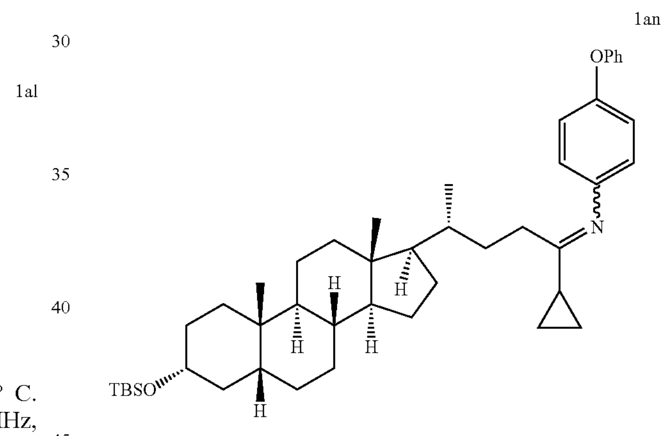

1an: Yield: 61%. Pale yellow solid. M.p.=56-58° C. $R_f$=0.4 (hexane/ethyl acetate=9:1). $^1$H NMR (400 MHz, $C_6D_6$, a mixture of geometrical isomers in ~3.2:1 ratio): δ 7.12-7.06 (m, 2H), 7.04-6.92 (m, 4H), 6.91-6.80 (m, 1.48H), 6.62 (d, J=8.6 Hz, 1.52H) (aryl CH), 3.67-3.61 (m, 1H) (OCH), 2.30-2.24 (m, 0.78H), 2.20-2.13 (m, 0.76H), 1.99-1.96 (m, 1.24H), 1.82-1.63 (m, 6H), 1.54-1.48 (m, 4.51H), 1.35-1.3 (m, 9.52H), 1.16-1.10 (m, 2H), 1.04-1.03 (m, 10.25H), 1.00-0.90 (m, 9H), 0.80-0.79 (m, 2.54H), 0.73-0.68 (m, 2H), 0.56 (s, 2H), 0.36-0.31 (m, 0.52H), 0.14 (d, J=2.1 Hz, 6H) (alkyl H). $^{13}$C NMR (101 MHz, $C_6D_6$): δ 176.2, 173.9 (C=N), 159.1, 159.0, 152.8, 152.6, 148.4, 148.2, 130.0, 130.0, 122.8, 122.7, 121.5, 121.2, 120.5, 118.5, 118.3 (aryl C), 73.0, 72.9, 56.4, 56.2, 56.2, 55.5, 43.0, 42.9, 42.6, 42.5, 40.6, 40.6, 40.3, 40.2, 37.4, 36.1, 36.0, 35.9, 35.9, 34.8, 34.7, 33.8, 33.3, 31.6, 31.0, 28.4, 27.7, 26.7, 26.2, 24.5, 24.5, 23.7, 23.7, 21.2, 21.2, 18.8, 18.4, 17.8, 14.8, 12.3, 10.3, 10.2, 9.9, 9.8, 6.7, 6.6, −4.2, −4.3 (alkyl C). IR (K r, $cm^{-1}$): v 2928, 2884, 2860, 1647, 1589, 1488, 1471, 1385, 1238, 1200, 1164, 1095, 1079, 1023. HRMS (ESI): Calcd for $C_{45}He_8NO_2Si^+$[$M^+$ H]$^+$: 682.5014, found: 682.5015.

1ao

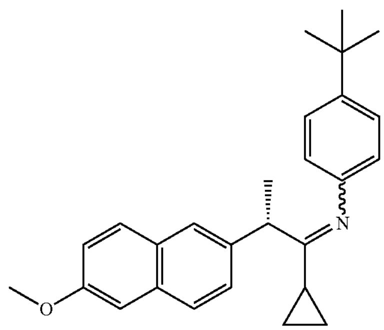

1ao: Yield: 71%. White solid. M.p.=113-115° C. $R_f$=0.4 (hexane/ethyl acetate=9:1). $^1$H NMR (400 MHz, $CDCl_3$, a mixture of geometrical isomers in ~2.7:1 ratio): δ 7.87-7.75 (m, 3H), 7.68 (dd, J=8.5, 1.8 Hz, 0.27H), 7.52-7.45 (m, 2H), 0.41 (dd, J=8.5, 1.9 Hz, 0.73H), 7.30-7.21 (m, 2H), 6.99 (d, J=8.4 Hz, 0.55H), 6.88 (d, J=8.4 Hz, 1.46H) (aryl CH), 4.41 (q, J=7.0 Hz, 0.73H) (CH), 3.98 (s, 3H) ($OCH_3$), 3.56 (q, J=6.9 Hz, 0.27H) (CH), 1.83-1.76 (m, 0.28H) (CH), 1.74 (d, J=7.1 Hz, 2.18H), 1.68 (d, J=6.9 Hz, 0.82H) ($CH_3$), 1.65-1.61 (m, 0.73H) (CH), 1.467-1.45 (m, 9H) ($CH_3$), 1.20-1.09 (in, 1.45H), 1.04-0.97 (m, 0.28H), 0.95-0.78 (m, 1.28H), 0.70-0.57 (m, 1H) ($CH_2$). $^{13}$C NMR (101 MHz, $CDCl_3$): δ 177.0, 174.9 (C=N), 157.6, 157.5, 149.0, 148.6, 145.4, 145.4, 139.5, 136.7, 133.5, 133.4, 129.3, 129.3, 129.2, 129.0, 127.2, 127.1, 126.9, 126.7, 125.9, 125.8, 125.7, 125.3, 119.5, 119.1, 118.9, 118.8, 105.7, 105.6 (aryl C), 55.3, 42.1, 41.3, 34.3, 34.3, 31.6, 31.6, 22.1, 17.1, 14.9, 13.9, 11.0, 9.1, 7.1, 6.9 (alkyl C). IR (KBr, $cm^{-1}$): v3054, 3028, 3002, 2963, 2904, 2868, 2840, 1644, 1606, 1504, 1484, 1462, 1415, 1391, 1363, 1265, 1217, 1164, 1120, 1034. HRMS (ESI): Calcd for $C_{27}H_{32}NO^+$ [$M^+$ H]$^+$: 386.2478, found: 386.2499.

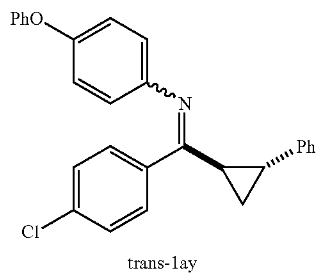

trans-1ay trans-lay: Yield: 76%. Light yellow oil. $R_f$=0.4 (hexane/ethyl acetate=9:1). $^1$H NMR (500 MHz, $CDCl_3$, a mixture of geometrical isomers in ~1.4:1 ratio): 6.02 (d, J=8.5 Hz, 0.84H), 7.48 (d, J=8.6 Hz, 0.82H), 7.44-7.25 (m, 7.48H), 7.22 (d, J=8.5 Hz, 1H), 7.19-7.12 (m, 1.16H), 7.10-6.99 (m, 4.43H), 6.95 (d, J=8.7 Hz, 1.17H), 6.73 (d, J=8.7 Hz, 1.16H), 2.83-2.80 (m, 0.58H), 2.37-2.34 (m, 0.59H), 2.28-0.24 (m, 0.42H), 2.14-2.10 (m, 0.59H), 2.06-1.93 (m, 0.42H), 1.61-1.56 (m, 0.58H), 1.49-1.33 (m, 0.42H), 1.23-1.19 (m, 0.42H). $^{13}$C NMR (126 MHz, $CDCl_3$): δ 169.9, 166.1, 157.9, 157.8, 153.1, 152.6, 146.4, 146.0, 141.3, 140.5, 137.1, 136.2, 136.2, 134.6, 129.7, 129.6, 129.5, 129.5, 128.5, 128.5, 128.4, 126.3, 126.0, 125.5, 122.8, 122.7, 122.2, 121.6, 119.8, 118.2, 118.1, 31.7, 29.2, 26.1, 25.1, 19.0, 18.1. IR (KBr, $cm^{-1}$): v3086, 3062, 3034, 2965, 2928, 1625, 1607, 1589, 1566, 1487, 1457, 1401, 1385, 1334, 1277, 1235, 1176, 1163, 1092, 1054, 1031, 1013. HRMS (ESI): Calcd for $C_{28}H_{23}ClNO^+$[$M^+$ H]$^+$: 424.1463, found: 424.1460.

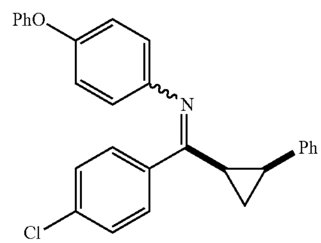

cis-1ay cis-lay: Yield: 47%. Light yellow oil. $R_f$=0.4 (hexane/ethyl acetate=9:1). $^1$H NMR (500 MHz, $C_6D_6$, a mixture of geometrical isomers in ~2:1 ratio): δ 7.73 (d, J=8.6 Hz, 0.67H), 7.24 (d, J=7.3 Hz, 1.34H), 7.14-7.05 (m, 3.36H), 7.04-6.97 (m, 2.67H), 6.93-6.79 (m, 4.67H), 6.74-6.70 (m, 2H), 6.67-6.61 (m, 2H), 6.15 (d, J=8.7 Hz, 1.31H), $^2$0.46-2.40 (m, 0.66H), 2.39-2.34 (m, 0.66H), 2.08-2.03 (m, 0.66H), 1.88-1.79 (m, 0.67H), 1.10-1.06 (m, 0.67H), 0.92-0.87 (m, 0.33H), 0.80-0.76 (m, 0.34H). $^{13}$C NMR (126 MHz, $C_6D_6$): δ 165.0, 162.8, 158.7, 158.4, 153.7, 153.2, 146.9, 146.7, 138.7, 138.0, 137.1, 137.1, 136.2, 134.6, 130.1, 129.9, 129.8, 129.7, 129.6, 128.4, 128.4, 128.0, 128.0, 127.0, 126.7, 126.3, 123.1, 123.0, 122.2, 122.1, 119.9, 119.8, 118.7, 30.1, 28.6, 25.8, 23.2, 14.7, 10.2. IR (KBr, $cm^{-1}$): v 3035, 2925, 2851, 2427, 1942, 1881, 1588, 1567, 1456, 1399, 1381, 1332, 1236, 1164, 1091, 1024, 1011. HRMS (ESI): Calcd for $C_{28}H_{23}ClNO^+$[$M^+$ H]$^+$: 424.1463, found: 424.1451.

Additional aspects of the disclosure are provided by the following enumerated embodiments, which may be combined in any number and in any combination that is not logically or technically inconsistent.

Embodiment 1. A compound having the structure

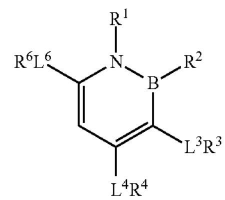

or a pharmaceutically-acceptable salt thereof, or a solvate thereof, wherein $R^1$ is a carbon-linked substituent having no more than 40 non-H atoms;

$R^2$ is a carbon-linked substituent having no more than 40 non-H atoms;

$R^3$ is H or a substituent having no more than 40 non-H atoms, and $L^3$ is selected from the group consisting of a bond, —C(O)—, —S—, —S(O)$_{1-2}$—, —O—, —NR$^7$—, —C(O)NR$^7$—, —NR$^7$C(O)—, —C(S)NR$^7$—, —NR$^7$C(S)—, —C(O)O—, —OC(O)—, —C(O)S—, —SC(O)—, —C(S)O—, —OC(S)—, —C(S)S—, —SC(S)—, —S(O)$_{1-2}$O—, —OS(O)$_{1-2}$—, —S(O)$_{1-2}$NR$^7$— and —NR$^7$S(O)$_{1-2}$—, or -$L^3$-$R^3$ is halo (e.g., chloro, fluoro or bromo), nitro, or cyano;

$R^4$ is H or a substituent having no more than 40 non-H atoms, a d $L^4$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{1-2}NR^7$— and —$NR^7S(O)_{1-2}$—, or -$L^4$-$R^4$ is halo (e.g., chloro, fluoro or bromo), nitro, or cyano;

$R^6$ is H or a substituent having no more than 40 non-H atoms, and $L^6$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}$O—, —O$S(O)_{1-2}$—, —$S(O)_{1-2}NR^7$— and —$NR^7S(O)_{1-2}$—, or -$L^6$-$R^6$ is halo (e.g., chloro, fluoro or bromo), nitro, or cyano;

wherein each $R^6$ is independently selected from the group consisting of hydrogen, $C_1$-$C_3$ alkyl and —C(O)($C_1$-$C_3$ alkyl).

Embodiment 2. The compound of embodiment 1, wherein $R^1$ is an optionally-substituted $C_1$-$C_{24}$ alkyl, an optionally-substituted $C_2$-$C_{24}$ alkenyl, or an optionally-substituted $C_1$-$C_{24}$ alkynyl.

Embodiment 3. The compound of embodiment 1, wherein $R^1$ is a optionally-substituted $C_6$-$C_{24}$ aryl or an optionally-substituted $C_5$-$C_{24}$ heteroaryl.

Embodiment 4. The compound of embodiment 1, wherein $R^1$ is a optionally-substituted $C_3$-$C_{24}$ cycloalkyl or an optionally-substituted $C_3$-$C_{24}$ heterocycloalkyl.

Embodiment 5. The compound of any of embodiments 1-4, wherein $R^2$ is an optionally-substituted $C_1$-$C_{24}$ alkyl, an optionally-substituted $C_2$-$C_{24}$ alkenyl, or an optionally-substituted $C_1$-$C_{24}$alkynyl.

Embodiment 6. The compound of any of embodiments 1-4, wherein $R^2$ is an optionally-substituted $C_6$-$C_{24}$ aryl or an optionally-substituted $C_5$-$C_{24}$ heteroaryl.

Embodiment 7. The compound of any of embodiments 1-4, wherein $R^2$ is optionally-substituted $C_3$-$C_{24}$ cycloalkyl or an optionally-substituted $C_3$-$C_{24}$ heterocycloalkyl.

Embodiment 8. The compound of any of embodiments 1-7, wherein $R^3$ is H.

Embodiment 9. The compound of any of embodiments 1-7, wherein, $R^3$ is an optionally-substituted $C_1$-$C_{24}$ alkyl, an optionally-substituted $C_2$-$C_{24}$ alkenyl, or an optionally-substituted $C_1$-$C_{24}$alkynyl.

Embodiment 10. The compound of any of embodiments 1-7, wherein $R^3$ is an optionally-substituted $C_6$-$C_{24}$ aryl or an optionally-substituted $C_5$-$C_{24}$ heteroaryl.

Embodiment 11. The compound of any of embodiments 1-7, wherein $R^3$ is optionally-substituted $C_3$-$C_{24}$ cycloalkyl or an optionally-substituted $C_3$-$C_{24}$ heterocycloalkyl.

Embodiment 12. The compound of any of embodiments 1-11, wherein $L^3$ is a bond.

Embodiment 13. The compound of any of embodiments 1-11, wherein $L^3$ is selected from the group consisting of a bond, —C(O)—, —S—, —$S(O)_{1-2}$—, —O—, and —$NR^7$—.

Embodiment 14. The compound of any of embodiments 1-7, wherein -$L^3$-$R^3$ is halo (e.g., chloro, fluoro or bromo), nitro, or cyano.

Embodiment 15. The compound of any of embodiments 1-14, wherein $R^4$ is H.

Embodiment 16. The compound of any of embodiments 1-14, wherein $R^4$ is an optionally-substituted $C_1$-$C_{24}$ alkyl, an optionally-substituted $C_2$-$C_{24}$ alkenyl, or an optionally-substituted $C_1$-$C_{24}$alkynyl.

Embodiment 17. The compound of any of embodiments 1-14, wherein $R^4$ is an optionally-substituted $C_6$-$C_{24}$ aryl or an optionally-substituted $C_5$-$C_{24}$ heteroaryl.

Embodiment 18. The compound of any of embodiments 1-14, wherein $R^4$ is optionally-substituted $C_3$-$C_{24}$ cycloalkyl or an optionally-substituted $C_3$-$C_{24}$ heterocycloalkyl.

Embodiment 19. The compound of any of embodiments 1-18, wherein $L^4$ is a bond.

Embodiment 20. The compound of any of embodiments 1-18, wherein $L^4$ is is selected from the group consisting of a bond, —C(O)—, —S—, —$S(O)_{1-2}$—, —O—, and —$NR^7$—.

Embodiment 21. The compound of any of embodiments 1-14, wherein -$L^4$-$R^4$ is halo (e.g., chloro, fluoro or bromo), nitro, or cyano.

Embodiment 22. The compound of any of embodiments 1-21, wherein $R^6$ is H.

Embodiment 23. The compound of any of embodiments 1-21, wherein $R^6$ is an optionally-substituted $C_1$-$C_{24}$ alkyl, an optionally-substituted $C_2$-$C_{24}$ alkenyl, or an optionally-substituted $C_1$-$C_{24}$alkynyl.

Embodiment 24. The compound of any of embodiments 1-21, wherein $R^6$ is an optionally-substituted $C_6$-$C_{24}$ aryl or an optionally-substituted $C_5$-$C_{24}$ heteroaryl.

Embodiment 25. The compound of any of embodiments 1-21, wherein $R^6$ is optionally-substituted $C_3$-$C_{24}$ cycloalkyl or an optionally-substituted $C_3$-$C_{24}$ heterocycloalkyl.

Embodiment 26. The compound of any of embodiments 1-25, wherein $L^6$ is a bond.

Embodiment 27. The compound of any of embodiments 1-25, wherein $L^6$ is is selected from the group consisting of a bond, —C(O)—, —S—, —$S(O)_{1-2}$—, —O—, and —$NR^7$—.

Embodiment 28. The compound of any of embodiments 1-21, wherein -$L^6$-$R^6$ is halo (e.g., chloro, fluoro or bromo), nitro, or cyano.

Embodiment 29. The compound of any of embodiments 1-28, wherein optionally-substituted groups are independently optionally-substituted by one or more of each $R^7$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^8$, —($C_0$-$C_6$ alkyl)-$NR^{10}R^9$, —($C_0$-$C_6$ alkyl)-$OR^{11}$, —($C_0$-$C_6$ alkyl)-C(O)$R^{11}$, —($C_0$-$C_6$ alkyl)-$S(O)_{0-2}R^{11}$, -halogen, —$NO_2$ and —CN, wherein each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O) $R^9$—, —$NR^9$C(S)—, —$S(O)_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —S C(S)O—, —OC(S)S—, —$NR^9$C($NR^2$)$NR^9$—, —$NR^9SO_2$—, —$SO_2$NR - and —$NR^9SO_2NR^9$—, each $R^8$, $R^{10}$ and $R^{11}$ is independently selected from H, —($C_0$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl) and —($C_0$-$C_6$ alkyl)-$S(O)_{0-2}$—($C_0$-$C_6$ alkyl), each $R^9$ is independently selected from —H, —($C_1$-$C_4$ alkyl), —C(O)—($C_1$-$C_4$ alkyl) and —C(O)O—($C_1$-$C_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

Embodiment 30. An N-substituted 1-cyclopropyl imine compound having the structure

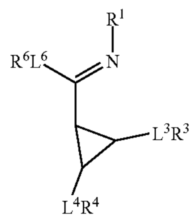

wherein the substituents are as described in any of embodiments 1-29 above.

Embodiment 31. A method for making a 1,2-disubstituted azaborine, the method comprising:

combining a Lewis acid, an N-substituted 1-cyclopropyl imine and a B-substituted dihaloborane and allowing them to react to form an B-substituted, N-substituted, 1-halo-N-(6-halohex-3-enyl)boranamineB-substituted, N-substituted, 1-halo-N-(6-halohex-3-enyl)boranamine; then treating the B-substituted, N-substituted, 1-halo-N-(6-halohex-3-enyl)boranamineB-substituted, N-substituted, 1-halo-N-(6-halohex-3-enyl)boranamine with abase to provide the 1,2-disubstituted azaborine.

Embodiment 32. The method of embodiment 31, wherein the Lewis acid is $ZnBr_2$, $Zn(OTf)_2$ or $BF_3$.

Embodiment 33. The method of embodiment 31 or embodiment 32, wherein the N-substituted 1-cyclopropyl imine has the structure

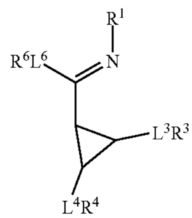

wherein the substituents are as described in any of embodiments 1-29 above.

Embodiment 34. The method of any of embodiments 31-33, wherein the dihaloborane is a dibromoborane.

Embodiment 35. The method of any of embodiments 31-34, wherein the B-substituted dihaloborane has the structure

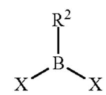

wherein $R^2$ is as described in any of embodiments 1-29 above, and X is halo.

Embodiment 36. The method of any of embodiments 31-35, wherein the B-substituted, N-substituted, 1-halo-N-(6-halohex-3-enyl)boranamineB-substituted, N-substituted, 1-halo-N-(6-halohex-3-enyl)boranamine has the structure

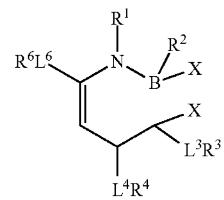

wherein the substituents are as described in any of embodiments 1-29 above.

Embodiment 37. The method of any of embodiments 31-36, wherein the Lewis acid is present in amount of 10 mol % of the N-substituted 1-cyclopropyl imine and the B-substituted dihaloborane, whichever is provided in lesser molar amount.

Embodiment 38. The method of any of embodiment 31-37, wherein a molar ratio of the B-substituted dihaloborane to the N-substituted 1-cyclopropyl imine is in the range of 0.7-1.5, e.g., 0.8-1.25, or 0.9-1.1.

Embodiment 39. The method of any of embodiments 31-37, wherein a molar ratio of the B-substituted dihaloborane to the N-substituted 1-cyclopropyl imine is in the range of 0.95-1.5, e.g., 0.95-1.25, or 0.95-1.15, or 1.05-1.5, or 1.05-1.25, or 1.05-1.15.

Embodiment 40. The method of any of embodiments 31-39, wherein the Lewis acid, the N-substituted 1-cyclopropyl imine and the B-substituted dihaloborane are allowed to react at a temperature in the range of 40-100 C, e.g., 40-80 C, or 40-70 C, or 40-65 C, or 50-100 C, or 50-80 C, or 50-70 C, or 50-65 C, or 55-100 C, or 55-80 C, or 55-70 C, or 5-65 C.

Embodiment 41. The method of any of embodiments 31-40, wherein the the Lewis acid, the N-substituted 1-cyclopropyl imine and the B-substituted dihaloborane are allowed to react for a time of at least 1 h, e.g., at least 2 h, or at least 3 h.

Embodiment 42. The method any of embodiments 31-41, wherein the reaction is performed in a solvent, e.g., chlorobenzene.

Embodiment 43. The method of any of embodiments 31-42, wherein the base is an amine base (e.g., a hindered amine base).

Embodiment 44. The method of embodiment 43, wherein the amine base has a conjugate acid pKa in water of at least 12, e.g., at least 12.5 or at least 13.

Embodiment 45. The method of any of embodiments 43-44, wherein the amine base is 1,8-diazabicyclo(5.4.0)undec-7-ene (DBU).

Embodiment 46. The method of any of embodiments 31-45, wherein the B-substituted, N-substituted, 1-halo-N-(6-halohex-3-enyl)boranamineB-substituted, N-substituted, 1-halo-N-(6-halohex-3-enyl)boranamine is treated with the base in the reaction mixt re of the previous step.

Embodiment 47. The method of any of embodiments 31-46, wherein the B-substituted dihaloborane is generated (e.g., in situ) by reaction of a trihaloborane with a substituted silane.

Embodiment 48. The method of any of embodiments 31-47, wherein the 1,2-disubstituted azaborine is a compound of any of embodiments 1-29.

Embodiment 49. A method for making a 3-halo-1,2-disubstituted azaborine, the method comprising:

combining a Lewis acid, an N-substituted 1-cyclopropyl imine and a B-substituted dihaloborane and allowing them to react to form an B-substituted, N-substituted, 1-halo-N-(6-halohex-3-enyl)boranamine; then treating the B-substituted, N-substituted, 1-halo-N-(6-halohex-3-enyl)boranamine with a base to provide the 1,2-disubstituted azaborine; and then halogenating the 1,2-disubstituted azaborine to provide a 3-halo-1,2-disubstituted azaborine; wherein the N-substituted 1-cyclopropyl imine has the structure:

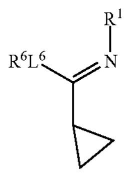

wherein $L^6$ and $R^6$ are as described in any of embodiments 1-29 above.

Embodiment 50. The method of embodiment 49, wherein the Lewis acid is $ZnBr_2$, $Zn(OTf)_2$ or $BF_3$.

Embodiment 51. The method of any of embodiments 49-50, wherein the dihaloborane is a dibromoborane.

Embodiment 52. The method of any of embodiments 49-51, wherein the B-substituted dihaloborane has the structure

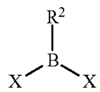

wherein $R^2$ is as described in any of embodiments 1-29 above, and X is halo.

Embodiment 53. The method of any of embodiments 49-52, wherein the B-substituted, N-substituted, 1-halo-N-(6-halohex-3-enyl)boranamine has the structure

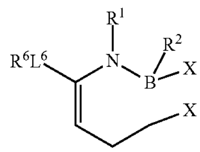

wherein the substituents are as described in any of embodiments 1-29 above.

Embodiment 54. The method of any of embodiments 49-53, wherein the Lewis acid is present in amount of 10 mol % of the N-substituted 1-cyclopropyl imine and the B-substituted dihaloborane, whichever is provided in lesser molar amount.

Embodiment 55. The method of any of embodiment 49-54, wherein a molar ratio of the B-substituted dihaloborane to the N-substituted 1-cyclopropyl imine is in the range of 0.7-1.5, e.g., 0.8-1.25, or 0.9-1.1.

Embodiment 56. The method of any of embodiments 49-55, wherein a molar ratio of the B-substituted dihaloborane to the N-substituted 1-cyclopropyl imine is in the range of 0.95-1.5, e.g., 0.95-1.25, or 0.95-1.15, or 1.05-1.5, or 1.05-1.25, or 1.05-1.15.

Embodiment 57. The method of any of embodiments 49-56, wherein the Lewis acid, the N-substituted 1-cyclopropyl imine and the B-substituted dihaloborane are allowed to react at a temperature in the range of 40-100 C, e.g., 40-80 C, or 40-70 C, or 40-65 C, or 50-100 C, or 50-80 C, or 50-70 C, or 50-65 C, or 55-100 C, or 55-80 C, or 55-70 C, or 55-65 C.

Embodiment 58. The method of any of embodiments 49-57, wherein the Lewis acid, the N-substituted 1-cyclopropyl imine and the B-substituted dihaloborane are allowed to react for a time of at least 1 h, e.g., at least 2 h, or at least 3 h.

Embodiment 59. The method any of embodiments 49-58, wherein the reaction is performed in a solvent, e.g., chlorobenzene.

Embodiment 60. The method of any of embodiments 49-59, wherein the base is an amine base (e.g., a hindered amine base).

Embodiment 61. The method of embodiment 60, wherein the amine base has a conjugate acid pKa in water of at least 12, e.g., at least 12.5 or at least 13.

Embodiment 62. The method of any of embodiments 60-61, wherein the amine base is 1,8-diazabicyclo(5.4.0)undec-7-ene (DBU).

Embodiment 63. The method of any of embodiments 49-62, wherein the B-substituted, N-substituted, 1-halo-N-(6-halohex-3-enyl)boranamine is treated with the base in the reaction mixture of the previous step.

Embodiment 64. The method of any of embodiments 49-63, wherein the B-substituted dihaloborane is generated (e.g., in situ) by reaction of a trihaloborane with a substituted silane.

Embodiment 65. The method of any of embodiments 49-54, wherein halogenating comprising contacting the 1,2-azaborine with a halogenating agent (e.g., a brominating agent or an iodinating agent).

Embodiment 66. The method of embodiment 65, wherein the halogenating agent is bromine.

Embodiment 67. The method of embodiment 65, wherein the halogenating agent is 1,3-Diiodo-5,5-Dimethylhydantoin (DIH).

Embodiment 68. The method any of embodiments 49-67, wherein the halogenating is performed in a solvent (e.g., dichloromethane).

Embodiment 69. The method of any of embodiments 49-68, wherein the halogenating is conducted at a temperature in the range of 0° C. to 60° C. (e.g., in the range of 10-60° C., or 10-50° C., or 10-40° C., or 20-60° C., or 20-50° C., or 20-40° C.).

Embodiment 70. The method of any of embodiments 49-69, wherein the halogenating is conducted for a time sufficient to provide the 3-halo-1,2-disubstituted azaborine (e.g., at least 1 hour, at least 2 hours, at least 3 hours, or at least 4 hours).

Embodiment 71. The method of any of embodiments 49-70, wherein the 3-halo-1,2-disubstituted azaborine is a compound of any of embodiments 1-29.

Embodiment 72. The method of any of embodiments 49-71, wherein the method further comprising cross-coupling the 3-halo-1,2-disubstituted azaborine to provide a 1,2,3-trisubstituted azaborine.

Embodiment 73. The method of embodiment 72, wherein the 3-halo-1,2-disubstituted azaborine is a 3-bromo-1,2-disubstituted azaborine.

Embodiment 74. The method of embodiment 72 or 73, wherein the 3-halo-1,2-disubstituted has the structure:

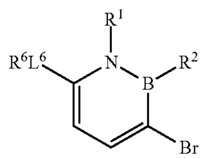

wherein the substituents are as described in any of embodiments 1-29 above.

Embodiment 75. The method of any of embodiments 72-74 wherein 1,2,3-trisubstituted azaborine is a compound of any of embodiments 1-29.

Embodiment 76. A method for making a 1,2,3,4,6-pentasubstituted azaborine, the method comprising:

providing a 3-halo-1,2-disubstituted azaborine; and combining the 3-halo-1,2-disubstituted azaborine, a bromo-containing compound, and a vinyl or alkyne reagent in the presence of palladium catalyst system, a carboxamide, a pyridinol, and a base and allowing them to react to form the 1,2,3,4,6-pentasubstituted azaborine.

Embodiment 77. The method of embodiment 76, wherein the 3-ha o-1,2-disubstituted azaborine is a 3-iodo-1,2-disubstituted azaborine.

Embodiment 78. The method of embodiment 76 or 77, wherein the 3-halo-1,2-disubstituted azaborine has the structure:

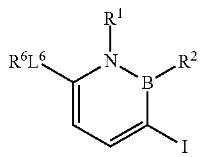

wherein the substituents are as described in any of embodiments 1-29 above.

Embodiment 79. The method of any of embodiments 76-78, wherein the 3-halo-1,2-disubstituted azaborine is prepared by the method as described in any of embodiments 49-71.

Embodiment 80. The method of any of embodiments 76-79, wherein the bromo-containing compound is an optionally substituted aryl-bromo compound or an optionally substituted alkyl-bromo compound.

Embodiment 81. The method of any of embodiments 76-80, wherein the 3-halo-1,2-disubstituted azaborine and a bromo-containing compound are combined with a vinyl reagent.

Embodiment 82. The method of any of embodiments 76-81, wherein the 3-halo-1,2-disubstituted azaborine and a bromo-containing compound are combined with an alkyne reagent.

Embodiment 83. The method of any of embodiments 76-82, wherein the palladium catalyst system comprises $Pd(TFA)_2$ and 2-(Dicyclohexylphosphino)3,6-dimethoxy-2',4',6'-triisopropyl-1,1'-biphenyl (BrettPhos reagent).

Embodiment 84. The method of any of embodiments 76-83, the carboxamide is (1S,4R)-N-methylbicyclo[2.2.1]hept-2-ene-2-carboxamide.

Embodiment 85. The method of any of embodiments 76-84, wherein the pyridinol is 3,5-bis(trifluoromethyl)pyridin-2-ol.

Embodiment 86. The method of any of embodiments 76-85, where in the base is selected from a hydroxide, carbonate, or phosphate.

Embodiment 87. The method of any of embodiments 76-85, wherein the base is a carbonate (e.g. potassium carbonate).

Embodiment 88. The method of any of embodiments 76-87, wherein the 3-halo-1,2-disubstituted azaborine, a bromo-containing compound, and a vinyl or alkyne reagent are present in a molar ratio of at least 1:1:1 (e.g., at least 1:1:1.05).

Embodiment 89. The method of any of embodiments 76-88, wherein the palladium catalyst system is present in an amount of at least 10 mol % (e.g., at least 20 mol %, or at least 30 mol %).

Embodiment 90. The method of any of embodiments 76-89, wherein the carboxamide and 3-halo-1,2-disubstituted azaborine are present in molar ratio of at least 1:1 (e.g., at least 1.5:1, or 2:1).

Embodiment 91. The method of any of embodiments 76-90, wherein the pyridinol is present in an amount of at least 5 mol % (e.g., at least 10 mol %).

Embodiment 92. The method of any of embodiments 76-91, wherein the base and 3-halo-1,2-disubstituted azaborine present in a molar ratio of at least 1:1 (e.g., at least 2:1, at least 3:1, or at least 4:1).

Embodiment 93. The method of any of embodiments 76-92, wherein the reaction is performed in a solvent (e.g., toluene: dimethyl ether (1:1)).

Embodiment 94. The method of any of embodiments 76-93, wherein the 3-halo-1,2-disubstituted azaborine, a bromo-containing compound, and a vinyl or alkyne reagent in the presence of palladium catalyst system, a carboxamide, a pyridinol, and a base are allowed to react at a temperature in the range of 100-150° C. (e.g., in the range of 100-140° C., or 100-130° C., or 100-120° C., or 110-150° C., or 110-140° C., or 110-130° C., or 110-120° C.).

Embodiment 95. The method of any of embodiments 76-94, wherein the 3-halo-1,2-disubstituted azaborine, a bromo-containing compound, and a vinyl or alkyne reagent in the presence of palladium catalyst system, a carboxamide, a pyridinol, and a base are allowed to react for a time sufficient to provide the 1,2,3,4,6-pentasubstituted azaborine (e.g., at least 12 hours, at least 14 hours, at least 16 hours, or at least 18 hours).

Embodiment 96. The method of any of embodiments 76-95, wherein the 1,2,3,4,6-pentasubstituted azaborine is a compound of any of embodiments 1-29.

It is understood that the examples and embodiments described herein are for illustrative purposes only and that various modifications or changes in light thereof will be suggested to persons skilled in the art and are to be incorporated within the spirit and purview of this application and scope of the appended claims. All publications, patents, and patent applications cited herein are hereby incorporated herein by reference for all purposes.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the di closure. In this regard, no attempt is made to show structural details of the disclosure in more detail than is necessary for the fundamental understanding of the disclosure, the description taken with the drawings and/or examples making apparent to those skilled in the art how the several forms of the disclosure may be embodied in practice. Thus, before the disclosed processes and devices are described, it is to be understood that the aspects described herein are not limited to specific embodiments, apparatuses, or configurations, and as such can, of course, vary. It is also to be understood that the terminology used herein is for the purpose of describing particular aspects only and, unless specifically defined herein, is not intended to be limiting.

The terms "a," "an," "the" and similar referents used in the context of describing the disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. It will be further understood that the endpoints of each of the ranges are significant both in relation to the other endpoint, and independently of the other endpoint.

All methods described herein can be performed in any suitable order of steps unless otherwise indicated herein or otherwise clearly contradicted by context. The use of any and all examples, or exemplary language (e.g., "such as") provided herein is in ended merely to better illuminate the disclosure and does not pose a limitation on the scope of the disclosure otherwise claimed. No language in the specification should be construed as indicting any non-claimed element essential to the practice of the disclosure.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to". Words using the singular or plural number also include the plural and singular number, respectively. Additionally, the words "herein," "above," and "below" and words of similar import, when used in this application, shall refer to this application as a whole and not to any particular portions of the application.

As will be understood by one of ordinary skill in the art, each embodiment disclosed herein can comprise, consist essentially of or consist of its particular stated element, step, ingredient or component. As used herein, the transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment.

Unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical value, however, inherently contains certain errors necessarily resulting from the standard deviation found in their respective testing measurements.

Groupings of alternative elements or embodiments of the disclosure disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When a y such inclusion or deletion occurs, the specification is deemed to contain the group as modified thus fulfilling the written description of all Markush groups used in the appended claims.

Some embodiments of this disclosure are described herein, including the best mode known to the inventors for carrying out the disclosure. Of course, variations on these described embodiments will become apparent to those of ordinary skill in the art upon reading the foregoing description. The inventor expects skilled artisans to employ such variations as appropriate, and the inventors intend for the disclosure to be practiced otherwise than specifically described herein. Accordingly, this disclosure includes all modifications and equivalents of the subject matter recited in the claims appended hereto as permitted by applicable law. Moreover, any combination of the above-described elements in all possible variations thereof is encompassed by the disclosure unless otherwise indicated herein or otherwise clearly contradicted by context.

Furthermore, it is to be understood that the embodiments of he disclosure disclosed herein are illustrative of the principles of the present disclosure. Other modifications that may be employed are within the scope of the disclosure. Thus, by way of example, but not of limitation, alternative configurations of the present disclosure may be utilized in accordance with the teachings herein. Accordingly, the present disclosure is not limited to that precisely as shown and described.

We claim:

1. A method for making a 1,2-disubstituted azaborine having the structure:

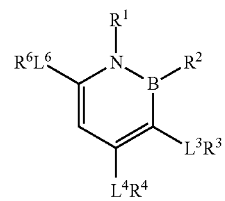

or a pharmaceutically-acceptable salt thereof, or a solvate thereof, wherein $R^1$ is a carbon-linked substituent having no more than 40 non-H atoms;

$R^2$ is a carbon-linked substituent having no more than 40 non-H atoms;

$R^3$ is H or a substituent having no more than 40 non-H atoms, and $L^3$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)

S—, —SC(S)—, —$S(O)_{1-2}O$—, —$OS(O)_{1-2}$—, —$S(O)_{1-2}NR^7$—, and —$NR^7S(O)_{1-2}$—, or -$L^3$-$R^3$ is halo, nitro, or cyano;

$R^4$ is H or a substituent having no more than 40 non-H atoms, and $L^4$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{12}O$—, —$OS(O)_{1-2}$—, —$S(O)_{1-2}NR^7$—, and —$NR^7S(O)_{1-2}$—, or -$L^4$-$R^4$ is halo, nitro, or cyano;

$R^6$ is H or a substituent having no more than 40 non-H atoms, and $L^6$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}O$—, —$OS(O)_{1-2}$—, —$S(O)_{1-2}NR^7$—, and —$NR^7S(O)_{1-2}$—, or -$L^6$-$R^6$ is halo, nitro, or cyano:

wherein each $R^7$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^8$, —($C_0$-$C_6$ alkyl)-$NR^{10}R^9$, —($C_0$-$C_6$ alkyl)-$OR^{11}$, —($C_0$-$C_6$ alkyl)-C(O)$R^{11}$, —($C_0$-$C_6$ alkyl)-$S(O)_{0-2}R^{11}$, -halogen, —$NO_2$, and —CN, wherein each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —$S(O)_{0-2}$—, —$C(O)_0$, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9$C($NR^2$)$NR^9$—, —$NR^9SO_2$—, —$SO_2NR^9$—, and —$NR^9SO_2NR^9$—, each $R^8$, $R^{10}$, and $R^{11}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-$S(O)_{0-2}$—($C_0$-$C_6$ alkyl), each $R^9$ is independently selected from —H, —($C_1$-$C_4$ alkyl), —C(O)—($C_1$-$C_4$ alkyl), and —C(O)O—($C_1$-$C_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted, the method comprising:

combining a Lewis acid, an N-substituted 1-cyclopropyl imine, and a B-substituted dihaloborane and allowing them to react to form a B-substituted, N-substituted, 1-halo-N-(6-halohex-3-enyl)boranamine; then treating the B-substituted, N-substituted, 1-halo-N-(6-halohex-3-enyl)boranamine with a base to provide the 1,2-disubstituted azaborine.

2. The method of claim 1, wherein the Lewis acid is $ZnBr_2$, $Zn(OTf)_{21}$ or $BF_3$, and wherein the dihaloborane is a dibromoborane.

3. The method of claim 1, wherein the N-substituted 1-cyclopropyl imine has the structure

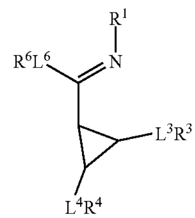

wherein $R^1$ is a carbon-linked substituent having no more than 40 non-H atoms;

$R^3$ is H or a substituent having no more than 40 non-H atoms, and $L^3$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}O$—, —$OS(O)_{1-2}$—, —$S(O)_{1-2}NR^7$—, and —$NR^7S(O)_{1-2}$—, or -$L^3$-$R^3$ is halo, nitro, or cyano;

$R^4$ is H or a substituent having no more than 40 non-H atoms, and $L^4$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}O$—, —$OS(O)_{1-2}$—, —$S(O)_{1-2}NR^7$—, and —$NR^7S(O)_{1-2}$—, or -$L^4$-$R^4$ is halo, nitro, or cyano;

$R^6$ is H or a substituent having no more than 40 non-H atoms, and $L^6$ is selected from the group consisting of a bond, —C(O)—, —S—, —$S(O)_{1-2}$—, —O—, —$NR^7$—, —C(O)$NR^7$—, —$NR^7$C(O)—, —C(S)$NR^7$—, —$NR^7$C(S)—, —C(O)O—, —OC(O)—, —C(O)S—, —SC(O)—, —C(S)O—, —OC(S)—, —C(S)S—, —SC(S)—, —$S(O)_{1-2}O$—, —$OS(O)_{1-2}$—, —$S(O)_{1-2}NR^7$—, and —$NR^7S(O)_{1-2}$—, or -$L^6$-$R^6$ is halo, nitro, or cyano;

wherein each $R^7$ is independently selected from —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-$R^8$, —($C_0$-$C_6$ alkyl)-$NR^{10}R^9$, —($C_0$-$C_6$ alkyl)-$OR^{11}$, —($C_0$-$C_6$ alkyl)-C(O)$R^{11}$, —($C_0$-$C_6$ alkyl)-$S(O)_{0-2}R^{11}$, -halogen, —$NO_2$, and —CN, wherein each L is independently selected from —$NR^9$C(O)O—, —OC(O)$NR^9$—, —$NR^9$C(O)—$NR^9$—, —$NR^9$C(O)S—, —SC(O)$NR^9$—, —$NR^9$C(O)—, —C(O)—$NR^9$—, —$NR^9$C(S)O—, —OC(S)$NR^9$—, —$NR^9$C(S)—$NR^9$—, —$NR^9$C(S)S—, —SC(S)$NR^9$—, —$NR^9$C(S)—, —C(S)$NR^9$—, —SC(O)$NR^9$—, —$NR^9$C(S)—, —$S(O)_{0-2}$—, —C(O)O, —OC(O)—, —C(S)O—, —OC(S)—, —C(O)S—, —SC(O)—, —C(S)S—, —SC(S)—, —OC(O)O—, —SC(O)O—, —OC(O)S—, —SC(S)O—, —OC(S)S—, —$NR^9C(NR^2)NR^9$—, —$NR^9SO_2$—, —$SO_2NR^9$—, and —$NR^9SO_2NR^9$—, each $R^8$, $R^{10}$, and $R^{11}$ is independently selected from H, —($C_1$-$C_6$ alkyl), —($C_1$-$C_6$ haloalkyl), —($C_0$-$C_6$ alkyl)-Ar, —($C_0$-$C_6$ alkyl)-Het, —($C_0$-$C_6$ alkyl)-Cak, —($C_0$-$C_6$ alkyl)-Hca, —($C_0$-$C_6$ alkyl)-L-($C_0$-$C_6$ alkyl), —($C_0$-$C_6$ alkyl)-$NR^9$—($C_0$-$C_6$ alkyl), —($C_0$-$C_6$ alkyl)-O—($C_0$-$C_6$ alkyl), —($C_0$-$C_6$ alkyl)-C(O)—($C_0$-$C_6$ alkyl), and —($C_0$-$C_6$ alkyl)-$S(O)_{0-2}$—($C_0$-$C_6$ alkyl), each $R^9$ is independently selected from —H, —($C_1$-$C_4$ alkyl), —C(O)—($C_1$-$C_4$ alkyl), and —C(O)O—($C_1$-$C_4$ alkyl), each Ar is an optionally substituted aryl, each Het is an optionally substituted heteroaryl, each Cak is an optionally substituted cycloalkyl, each Hca is an optionally substituted heterocycloalkyl, and each alkyl is optionally substituted.

4. The method of claim 1, wherein the Lewis acid is present in an amount of 10 mol % of the N-substituted 1-cyclopropyl imine and the B-substituted dihaloborane, whichever is provided in lesser molar amount.

5. The method of claim 1, wherein a molar ratio of the B-substituted dihaloborane to the N-substituted 1-cyclopropyl imine is in a range of 0.7-1.5.

6. The method of claim 1, wherein the Lewis acid, the N-substituted 1-cyclopropyl imine, and the B-substituted dihaloborane are allowed to react at a temperature in a range of 40-100° C. for at least one hour.

7. The method of claim 1, wherein the base is 1,8-diazabicyclo(5.4.0)undec-7-ene (DBU).

8. The method of claim 1, wherein $R^1$ is an optionally-substituted $C_1$-$C_{24}$ alkyl, an optionally-substituted $C_2$-$C_{24}$ alkenyl, an optionally-substituted $C_1$-$C_{24}$ alkynyl, an optionally-substituted $C_6$-$C_{24}$ aryl, an optionally-substituted $C_5$-$C_{24}$ heteroaryl, an optionally-substituted $C_3$-$C_{24}$cycloalkyl, or an optionally-substituted $C_3$-$C_{24}$ heterocycloalkyl; or wherein $R^2$ is an optionally-substituted $C_1$-$C_{24}$ alkyl, an optionally-substituted $C_2$-$C_{24}$ alkenyl, an optionally-substituted $C_1$-$C_{24}$ alkynyl, an optionally-substituted $C_6$-$C_{24}$ aryl, an optionally-substituted $C_5$-$C_{24}$ heteroaryl, an optionally-substituted $C_3$-$C_{24}$ cycloalkyl, or an optionally-substituted $C_3$-$C_{24}$ heterocycloalkyl.

9. The method of claim 1, wherein $R^3$ is an optionally-substituted $C_1$-$C_{24}$ alkyl, an optionally-substituted $C_2$-$C_{24}$ alkenyl, an optionally-substituted $C_1$-$C_{24}$ alkynyl, an optionally-substituted $C_6$-$C_{24}$ aryl, an optionally-substituted $C_5$-$C_{24}$ heteroaryl, an optionally-substituted $C_3$-$C_{24}$cycloalkyl, or an optionally-substituted $C_3$-$C_{24}$ heterocycloalkyl.

10. The method of claim 4, wherein $L^3$ is selected from the group consisting of a bond, —C(O)—, —S—, —$S(O)_{1-2}$—, —O—, and —$NR^7$—.

11. The method of claim 1, wherein -$L^3$-$R^3$ is halo, nitro, or cyano.

12. The method of claim 1, wherein $R^4$ is an optionally-substituted $C_1$-$C_{24}$ alkyl, an optionally-substituted $C_2$-$C_{24}$ alkenyl, an optionally-substituted $C_1$-$C_{24}$ alkynyl, an optionally-substituted $C_6$-$C_{24}$ aryl, an optionally-substituted $C_5$-$C_{24}$ heteroaryl, an optionally-substituted $C_3$-$C_{24}$ cycloalkyl, or an optionally-substituted $C_3$-$C_{24}$ heterocycloalkyl.

13. The method of claim 1, wherein $L^4$ is selected from the group consisting of a bond, —C(O)—, —S—, —$S(O)_{1-2}$—, —O—, and —$NR^7$—.

14. The method of claim 1, wherein -$L^4$-$R^4$ is halo, nitro, or cyano.

15. The method of claim 1, wherein $R^6$ is an optionally-substituted $C_1$-$C_{24}$ alkyl, an optionally-substituted $C_2$-$C_{24}$ alkenyl, an optionally-substituted $C_1$-$C_{24}$ alkynyl, an optionally-substituted $C_6$-$C_{24}$ aryl, an optionally-substituted $C_5$-$C_{24}$ heteroaryl, an optionally-substituted $C_3$-$C_{24}$ cycloalkyl, or an optionally-substituted $C_3$-$C_{24}$ heterocycloalkyl.

16. The method of claim 1, wherein $L^6$ is selected from the group consisting of a bond, —C(O)—, —S—, —$S(O)_{1-2}$—, —O—, and —$NR^7$—.

17. The method of claim 1, wherein -$L^6$-$R^6$ is halo, nitro, or cyano.

* * * * *